US010316060B2

(12) United States Patent
Tovar et al.

(10) Patent No.: US 10,316,060 B2
(45) Date of Patent: Jun. 11, 2019

(54) ENERGY TRANSFER WITHIN PI-CONJUGATED PEPTIDE HETEROSTRUCTURES IN AQUEOUS ENVIRONMENTS

(71) Applicant: THE JOHNS HOPKINS UNIVERSITY, Baltimore, MD (US)

(72) Inventors: John D. Tovar, Baltimore, MD (US); Howard E. Katz, Owings Mills, MD (US); Herdeline Ann M. Ardona, Baltimore, MD (US); Allix Sanders, Baltimore, MD (US); Kalpana Besar, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/950,603

(22) Filed: Nov. 24, 2015

(65) Prior Publication Data

US 2016/0145305 A1    May 26, 2016

Related U.S. Application Data

(60) Provisional application No. 62/083,761, filed on Nov. 24, 2014.

(51) Int. Cl.
| | |
|---|---|
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 7/06* | (2006.01) |
| *H01L 29/49* | (2006.01) |
| *H01L 29/06* | (2006.01) |
| *C07K 5/062* | (2006.01) |
| *H01L 51/00* | (2006.01) |

(52) U.S. Cl.
CPC ............ *C07K 7/06* (2013.01); *C07K 5/06026* (2013.01); *C07K 5/06052* (2013.01); *H01L 29/0665* (2013.01); *H01L 29/49* (2013.01); *H01L 51/00* (2013.01)

(58) Field of Classification Search
None
See application file for complete search history.

(56) References Cited

U.S. PATENT DOCUMENTS 9,334,304 B2 *   5/2016   Tovar ................. A61K 49/0056

OTHER PUBLICATIONS

Shao et al. "Self-Assembly of 1-D n-Type Nanostructures Based on Naphthalene Diimide-Appended Dipeptides" J. Am. Chem. Soc. 131:16374-16376. Published Oct. 23, 2009.*

Sanders et al. "Peptide-Based Supramolecular Semiconductor Nanomaterials via Pd-Catalyzed Solid-Phase "Dimerizations"" ACS Macro Letters 1:1326-1329. Published Oct. 30, 2012.*
Bheemaraju A "Effect of Side Chains on Organic Donor (D) and Acceptor (A) Complexes and Photophysical Properites of D-A Dyads" Dissertation. Sep. 1, 2011.*
Sanders et al. "Photoinduced Electron Transfer within Supramolecular Donor-Acceptor Peptide Nanostructures under Aqueous Conditions" J. Am. Chem. Soc. 138:3362-3370. Published Feb. 22, 2016. (Year: 2016).*
Sanders A and Tovar J "Solid Phase Pd-catalysed cross-coupling methods for the construction of pi-conjugated peptide nanomaterials" Suprmolecular Chemistry, 26:259-266. Published online Nov. 22, 2013. (Year: 2013).*
Polander et al. "Solution-Processed Molecular Bis(Naphthalene Diimide) Derivatives with High Electron Mobility" Chemistry of Materials 23:3408-3410. (Year: 2011).*
Imahori, H.; Tamaki, K.; Guldi, D. M.; Luo, C.; Fujitsuka, M.; Ito, O.; Sakata, Y.; Fukuzumi, S. J. Am. Chem. Soc. 2001, 123 (11), 2607-2617.
Ivnitski, D.; Amit, M.; Rubinov, B.; Cohen-Luria, R.; Ashkenasy, N.; Ashkenasy, G. Chem. Commun. 2014, 50 (51), 6733.
Jahnke, E.; Lieberwirth, I.; Severin, N.; Rabe, J. P.; Frauenrath, H. Topochemical Polymerization in Supramolecular Polymers of Oligopeptide-Functionalized Diacetylenes. Angew. Chem. Int. Ed. 2006, 45, 5383-5386.
Jatsch, A.; Schillinger, E. K.; Schmid, S.; Baeuerle, P., Biomolecule Assisted Self-Assembly of Pi-Conjugated Oligomers J. Mater. Chem. 2010, 20, 3563-3578.
Jones, G.; Vullev, V.; Braswell, E. H.; Zhu, D. J. Am. Chem. Soc. 2000, 122 (2), 388-389.
Jurchescu, O. D.; Hamadani, B. H.; Xiong, H. D.; Park, S. K.; Subramanian, S.; Zimmerman, N. M.; Anthony, J. E.; Jackson, T. N.; Gundlach, D. J. Correlation Between Microstructure, Electronic Properties and Flicker Noise in Organic Thin Film Transistors. Appl. Phys. Lett. 2008, 92, 132103.
Kasha, M.; Rawls, H. R.; El-Bayoumi, M. A. Pure Appl. Chem. 1965, 11, 371-392.
Kawano, S.; Fujita, N.; Shinkai, S. Quater-, Quinque-, and Sexithiophene Organogelators: Unique Thermochromism and Heating-Free Sol-Gel Phase Transition. Chem.-Eur. J. 2005, 11, 4735-4742.
Kim, S. H.; Parquette, J. R. A Model for the Controlled Assembly of Semiconductor Peptides. Nanoscale 2012, 4, 6940-6947.
Kline, R. J.; McGehee, M. D.; Kadnikova, E. N.; Liu, J. S.; Frechet, J. M. J.; Toney, M. F., Dependence of Regioregular Poly(3-hexylthiophene) Film Morphology and Field-Effect Mobility on Molecular Weight. Macromolecules 2005, 38, 3312-3319.
Korevaar, P. A.; Newcomb, C. J.; Meijer, E. W.; Stupp, S. I. J. Am. Chem. Soc. 2014, 136, 8540-8543.
Kraus, M.; Richter, S.; Opitz, A.; Bruetting, W.; Haas, S.; Hasegawa, T.; Hinderhofer, A.; Schreiber, F., High-mobility copper-phthalocyanine field-effect transistors with tetratetracontane passivation layer and organic metal contacts. J. Appl. Phys. 2010, 107, 094503.

(Continued)

*Primary Examiner* — Zachary J Miknis
(74) *Attorney, Agent, or Firm* — Casimir Jones, S.C.; Jeffrey W. Childers

(57) ABSTRACT

Nanostructures comprising Π-conjugated peptides for energy migration in aqueous environments are disclosed. Conductive material comprising these nanostructures, and supramolecular assemblies comprising covalently-bound electron donor-acceptor chromophores for photoinduced electron transfer also are disclosed.

4 Claims, 52 Drawing Sheets

(56) References Cited

OTHER PUBLICATIONS

Krieg, E.; Weissman, H.; Shimoni, E.; Bar On (Ustinov), A.; Rybtchinski, B. J. Am. Chem. Soc. 2014, 136, 9443-9452.

Kuciauskas, D.; Lin, S.; Seely, G. R.; Moore, A. L.; Moore, T. A; Gust, D.; Drovetskaya, T.; Reed, C. A.; Boyd, P. D. W. J. Phys. Chem. 1996, 100 (39), 15926-15932.

Kuciauskas, D.; Liddell, P. A.; Lin, S.; Johnson, T. E.; Weghorn, S. J.; Lindsey, J. S.; Moore, A. L.; Moore, T. A.; Gust, D. J. Am. Chem. Soc. 1999, 121 (37), 8604-8614.

Kumar, R. J.; MacDonald, J. M.; Singh, T. B.; Waddington, L. J.; Holmes, A. B. Hierarchical Self-Assembly of Semiconductor Functionalized Peptide Alpha-Helices and Optoelectronic Properties. J. Am. Chem. Soc. 2011, 133, 8564-8573.

Kwiatkowski, J. J.; Frost, J. M.; Nelson, J., The Effect of Morphology on Electron Field-Effect Mobility in Disordered C60 Thin Films. Nano Lett. 2009, 9, 1085-1090.

Lap, D. V; Grebner, D.; Rentsch, S. J. Phys. Chem. A 1997, 101 (2), 107-112.

Liddell, P. A.; Sumida, J. P.; Macpherson, A. N.; Noss, L.; Seely, G. R.; Clark, K. N.; Moore, A. L.; Moore, T. A.; Gust, D. Photochem. Photobiol. 1994, 60 (6), 537-541.

Liddell, P. A.; Kodis, G.; Moore, A. L.; Moore, T. A.; Gust, D. J. Am. Chem. Soc. 2002, 124 (26), 7668-7669.

Lim, J. M.; Kim, P.; Yoon, M.C.; Sung, J.; Dehm, V.; Chen, Z.; Würthner, F.; Kim, D. Chem. Sci. 2013, 4, 388-397.

Lin, Y. A.; Ou, Y. C.; Cheetham, A. G.; Cui, H. G. Supramolecular Polymers Formed by ABC Miktoarm Star Peptides. ACS Macro Letters 2013, 2, 1088-1094.

Malachowski, M. J.; Zmija, J. Organic Field-Effect Transistors. Opto-Electron. Rev. 2010, 18, 121-136.

Marciel, A. B.; Tanyeri, M.; Wall, B. D.; Tovar, J. D.; Schroeder, C .M.; Wilson, W. L. Adv. Mater. 2013, 25, 6398-6404.

Martinez-Hardigree, J. F.; Katz, H. E. Through Thick and Thin: Tuning the Threshold Voltage in Organic Field-Effect Transistors. Acc. Chem. Res. 2014, 47, 1369-1377.

Matmour, R.; De Cat, I.; George, S. J.; Adriaens, W.; Leclere, P.; Bomans, P. H. H.; Sommerdijk, N. A. J. M.; Gielen, J. C.; Christianen, P. C. M.; Heldens, J. T.; van Hest, J. C. M.; Lowik, D. W. P. M.; De Feyter, S.; Meijer, E. W.; Schenning, A. P. H. J. Oligo(p-phenylenevinylene)-Peptide Conjugates: Synthesis and Self-Assembly in Solution and at the Solid-Liquid Interface. 2008, 130, 14576-14583.

Mawad, D.; Stewart, E.; Officer, D. L.; Romeo, T.; Wagner, P.; Wagner, K.; Wallace, G. G. Adv. Funct. Mater. 2012, 22 (13), 2692-2699.

Morris, K. L.; Chen, L.; Raeburn, J.; Sellick, O. R.; Cotanda, P.; Paul, A.; Griffiths P. C.; King, S. M.; O'Reilly, R. K.; Serpell, L. C.; Adams, D. J. Nat. Commun. 2013, 4, 1480.

Nakashima, T.; Kimizuka, N. Adv. Mater. 2002, 14, 1113-1116.

Nalluri, S. K. M.; Ulijn, R. V., Discovery of Energy Transfer Nanostructures Using Gelation-Driven Dynamic Combinatorial Libraries. Chem. Sci. 2013, 4, 3699-3705.

Neuteboom, E. E.; Beckers, E. H. A.; Meskers, S. C. J.; Meijer, E. W.; Janssen, R. A. J. Org. Biomol. Chem. 2003, 1, 198-203.

Nishinari, K.; Shibuya, N.; Kainuma, K., Dielectric-relaxation in solid dextran and pullulan. Macromol. Chem. Phys. 1985, 186, 433-438.

Noriega, R.; Rivnay, J.; Vandewal, K.; Koch, F. P. V.; Stingelin, N.; Smith, P.; Toney, M. F.; Salleo, A. A General Relationship Between Disorder, Aggregation and Charge Transport in Conjugated Polymers. Nat. Mater. 2013, 12, 1038-1044.

Prasanthkumar, S.; Gopal, A.; Ajayaghosh, A. Self-Assembly of Thienylenevinylene Molecular Wires to Semiconducting Gels with Doped Metallic Conductivity. J. Am. Chem. Soc. 2010, 132, 13206-13207.

Praveen, V. K.; Ranjith, C.; Bandini, E.; Ajayaghosh, A.; Armaroli, N. Chem. Soc. Rev. 2014, 43, 4222.

Reches, M.; Gazit, E., Casting Metal Nanowires Within Discrete Self-Assembled Peptide Nanotubes. Science 2003, 300, 625-627.

Rogers, J. E.; Weiss, S. J.; Kelly, L. A. J. Am. Chem. Soc. 2000, 122 (3), 427-436.

Roncali, J. Macromol. Rapid Commun. 2007, 28, 1761-1775.

Rose, A.; Tovar, J. D.; Yamaguchi, S.; Nesterov, E. E.; Zhu, Z.; Swager, T. M. Philos. Trans. R. Soc. Math. Phys. Eng. Sci. 2007, 365, 1589-1606.

Rybtchinski, B; Sinks, L. E.; Wasielewski, M. R. J. Am. Chem. Soc. 2004, 126, 12268.

Sakai, N.; Mareda, J.; Vauthey, E.; Matile, S. Chem. Commun. 2010, 46 (24), 4225.

Sakakibara, K.; Chithra, P.; Das, B.; Mori, T.; Akada, M.; Labuta; J.; Tsuruoka, T.; Maji, S.; Furumi, S.; Shrestha, L. K.; Hill, J. P.; Acharya, S.; Ariaga, K.; Ajayaghosh, A. J. Am. Chem. Soc. 2014, 136, 8548-8551.

Sanders, A. M.; Dawidczyk, T. J.; Katz, H. E.; Tovar, J. D., Peptide-Based Supramolecular Semiconductor Nanomaterials via Pd-Catalyzed Solid-Phase "Dimerizations". ACS Macro Lett. 2012, 1, 1326-1329.

Sanders, A. M.; Tovar, J. D., Solid-Phase Pd-Catalysed Cross-coupling Methods for the Construction of Pi-Conjugated Peptide Nanomaterials. Supramol. Chem. 2014, 26 (3-4), 259-266.

Schenning, A. P. H. J.; Herrikhuyzen, J. V.; Jonkheijm, P.; Chen, Z.; Würthner, F.; Meijer, E. W. J. Am. Chem. Soc. 2002, 124, 10252-10253.

Schillinger, E.-K.; Mena-Osteritz, E.; Hentschel, J.; Borner, H. G.; Bauerle, P. Adv. Mater. 2009, 21, 1562-1567.

Schmid, S.; Mena-Osteritz, E.; Kopyshev, A.; Bäuerle, P. Self-Assembling Carbohydrate-Functionalized Oligothiophenes Org. Lett. 2009, 11, 5098-5101.

Schmid, S. A.; Abbel, R.; Schenning, A. P. H. J.; Meijer, E. W.; Herz, L. M. Philos. Trans. R. Soc. Math. Phys. Eng. Sci. 2012, 370, 3787-3801.

Schmidt, C. E.; Shastri, V. R.; Vacanti, J. P.; Langer, R. Proc. Natl. Acad. Sci. U. S. A. 1997, 94 (17), 8948-8953.

Schulze, J.; Torbjörnsson, M.; Kuhn, O.; Pullerits, T. New J. Phys. 2014, 16, 045010.

Seeman, N. C. DNA in a Material World. Nature 2003, 421, 427-431.

Serin, J. M.; Brousmiche, D. W.; Frechet, J. M. J. Chem. Commun. 2002, 2605-2607.

Sessler, J. L.; Brown, C. T.; O'Connor, D.; Springs, S. L.; Wang, R.; Sathiosatham, M.; Hirose, T. J. Org. Chem. 1998, 63 (21), 7370-7374.

Shao, H.; Nguyen, T.; Romano, N. C.; Modarelli, D. A.; Parquette, J. R. Self-Assembly of 1-D n-Type Nanostructures Based on Naphthalene Diimide-Appended Dipeptides. J. Am. Chem. Soc. 2009, 131, 16374-16376.

Sherwood, G. A.; Cheng, R.; Smith, T. M.; Werner, J. H.; Shreve, A. P.; Peteanu, L. A.; Wilderman, J. J. Phys. Chem. C 2009, 113, 18851-18862.

Sirringhaus, H.; Brown, P. J.; Friend, R. H.; Nielsen, M. M.; Bechgaard, K.; Langeveld-Voss B. M. W.; Spiering, A. J. H.; Janssen, R. A. J.; Meijer, E. W.; Herwig, P.; de Leeuw, D. M. Nature. 1999, 401, 685-688.

Spano, F. C. J. Chem. Phys. 2002, 116, 5877.

Stone, D. A.; Hsu, L.; Stupp, S. I. Self-Assembling Quinquethiophene-Oligopeptide Hydrogelators. Soft Matter 2009, 5, 1990-1993.

Sugiyasu, K.; Kawano, S.; Fujita, N.; Shinkai, S. Chem. Mater. 2008, 20, 2863-2865.

Sugiyasu, K.; Fujita, N.; Shinkai, S. Angew. Chem. Int. Ed. 2004, 43, 1229-1233.

Sun, Y.; Jiang, L.; Schuermann, K. C.; Adriaens, W.; Zhang, L.; Boey, F. Y. C.; De Cola, L.; Brunsveld, L.; Chen, X. Semiconductive, One-Dimensional, Self-Assembled Nanostructures Based on Oligopeptides with Pi-Conjugated Segments. Chem-Eur. J. 2011, 17, 4746-4749.

Traina, C. A.; Bakus II, R. C.; Bazan, G. C. J. Am. Chem. Soc. 2011, 133 (32),12600-12607.

Tsai, W.-W.; Tevis, I. D.; Tayi, A. S.; Cui, H.; Stupp, S. I. Semiconducting Nanowires from Hairpin-Shaped Self Assembling Sexithiophenes. J. Phys.Chem. B 2010, 114, 14778-14786.

Vadehra, G. S.; Wall, B. D.; Diegelmann, S. R.; Tovar, J. D. Chem. Commun. 2010, 46, 3947-3949.

(56) References Cited

OTHER PUBLICATIONS

Van Hal, P. A.; Beckers, E. H. A.; Meskers, S. C. J.; Jousselme, B.; Blanchard, P.; Roncali, J. Chem. Eur. J. 2002, 8 (23), 5415-5429.

Vijayakumar, C.; Praveen, V. K.; Kartha, K. K.; Ajayaghosh, A. Phys. Chem. Chem. Phys. 2011, 13, 4942-4949.

Wall, B. D.; Diegelmann, S. R.; Zhang, S.; Dawidczyk, T. J.; Wilson, W. L.; Katz, H. E.; Mao, H.-Q.; Tovar, J. D. Aligned Macroscopic Domains of Optoelectronic Nanostructures Prepared via Shear-Flow Assembly of Peptide Hydrogels. Adv.Mater. 2011, 23, 5009-5014.

Wall, B. D.; Zacca, A. E.; Sanders, A. M.; Wilson, W. L.; Ferguson, A. L.; Tovar, J. D. Supramolecular Polymorphism: Tunable Electronic Interactions within pi-Conjugated Peptide Nanostructures Dictated by Primary Amino Acid Sequence. Langmuir 2014, 30 (20) 5946-5956.

Wang, Y.; Corbitt, T. S.; Jett, S. D.; Tang, Y.; Schanze, K. S.; Chi, E. Y.; Whitten, D.G. Langmuir 2012, 28(1), 65-70.

Wasielewski, M. R. Chem. Rev. 1992, 92 (3), 435-461.

Wasielewski, M. R. Acc. Chem. Res. 2009, 42, 1910.

Wong, J. Y.; Langer, R.; Ingber, D. E. Proc. Natl. Acad. Sci. U. S. A. 1994, 91 (8), 3201-3204.

Wong, L. Y.; Png, R. Q.; Silva, F. B. S.; Chua, L. L.; Repaka, D. V. M.; Shi, C.; Gao, X. Y.; Ke, L.; Chua, S. J.; Wee, A. T. S.; Ho, P. K. H. Interplay of Processing, Morphological Order, and Charge-Carrier Mobility in Polythiophene Thin Films Deposited by Different Methods: Comparison of Spin-Cast, Drop-Cast, and Inkjet-Printed Films. Langmuir 2010, 26, 15494-15507.

Zelzer, M.; Ulijn, R. V. Chem. Soc. Rev. 2010, 39, 3351-3357.

Zhao, H.; Zhu, B.; Sekine, J.; Luo, S. C.; Yu, H. H. ACS Appl. Mater. Interfaces 2012, 4 (2), 680-686.

Zhou, J.; Yu, W.; Bragg, A. E. J. Phys. Chem. Lett. 2015, 6, 3496-3502.

Abidian, M. R.; Corey, J. M.; Kipke, D. R.; Martin, D. C. Conducting-Polymer Nanotubes Improve Electrical Properties, Mechanical Adhesion, Neural Attachment, and Neurite Outgrowth of Neural Electrodes. Small 2010, 6, 421-429.

Aida, T.; Meijer, E. W.; Stupp, S. I. Science 2012, 335, 813-817.

Ajayaghosh, A.; Praveen, V. K.; Vijayakumar, C.; George, S. J. Angew. Chem. Int. Ed. 2007, 46, 6260-6265.

Ahrens, M. J.; Sinks, L. E.; Tybtchinski, B.; Liu, W.; Jones, B. A.; Giaimo, J. M.; Gusev, A. V.; Goshe, A. J.; Tiede, D. M.; Wasielewski, M. R. J. Am. Chem. Soc. 2004, 126, 8284.

Amit, M.; Appel, S.; Cohen, R.; Cheng, G.; Hamley, I. W.; Ashkenasy, N., Hybrid Proton and Electron Transport in Peptide Fibrils. Adv. Funct. Mater. 2014, 24, 5873-5880.

Ardoña, H. A. M.; Besar, K.; Togninalli, M.; Katz, H. E.; Tovar, J. D. Sequence-Dependent Mechanical, Photophysical and Electrical Properties of Pi-Conjugated Peptide Hydrogelators. J. Mater. Chem. C 2015, 3, 6505-6514.

Ardoña, H. A. M.; Tovar, J. D., Energy Transfer within Responsive Pi-Conjugated Coassembled Peptide-Based Nanostructures in Aqueous Environments. Chem. Sci. 2015, 6, 1474-1484.

Ashkenasy, N.; Home, W. S.; Ghadiri, M. R. Design of Self-Assembling Peptide Nanotubes with Delocalized Electronic States. Small 2006, 2, 99-102.

Beckers, E. H. A.; Meskers, S. C. J.; Schenning, A. P. H. J.; Chen, Z.; Würthner, F.; Marsal, P.; Belionne, D.; Cornil, J.; Janssen, R. A. J. J. Am. Chem. Soc. 2006, 128, 649-657.

Benincori, T.; Bongiovanni, G.; Botta, C.; Cerullo, G.; Lanzani, G.; Mura, A.; Rossi, L.; Sannicolò, F.; Tubino, R. Phys. Rev. B 1998, 58 (14), 9082-9086.

Bheemaraju, A.; Pourmand, M.; Yang, B.; Surampudi, S. K.; Benanti, T. L.; Achermann, M.; Barnes, M. D.; Venkataraman, D. J. Macromol. Sci, Pure Appl. Chem. 2011, 48, 986-993.

Bhosale, S. Science 2006, 313 (5783), 84-86.

Bhosale, S. V; Jani, C. H.; Langford, S. J. Chem. Soc. Rev. 2008, 37 (2), 331-342.

Boekhoven, J; Stupp, S. I. Adv. Mater. 2014, 6, 1642-1659.

Botelho, A. L.; Shin, Y.; Liu, J.; Lin, X. PLoS ONE 2014, 9, e86370, doi: 10.1371/journal.pone.0086370.

Bradford, V. J.; Iverson, B. L. J. Am. Chem. Soc. 2008, 130, 1517-1524.

Braga, D.; Horowitz, G., High-Performance Organic Field-Effect Transistors. Adv. Mater. 2009, 21, 1473-1486.

Choi, M.-S.; Aida, T.; Yamazaki, T.; Yamazaki, I. A. Angew. Chem. Int. Ed. 2001, 40, 3194-3198.

Channon, K. J.; Devlin, G. L.; MacPhee, C. E. Efficient Energy Transfer within Self-Assembling Peptide Fibers: A Route to Light-Harvesting Nanomaterials. J. Amer. Chem. Soc. 2009, 131, 12520-12521.

Channon, K. J.; Devlin, G.L.; Magennis, S.W.; Finlayson, C.E.; Tickler, A.K.; Silva, C.; MacPhee, C.E. J. Am. Chem. Soc. 2008, 130, 5487-5491.

Chen, L.; Revel, S.; Morris, K.; Adams, D. J., Energy Transfer in Self-Assembled Dipeptide Hydrogels. Chem. Commun. 2010, 46, 4267-4269.

Chworos, A.; Severcan, I.; Koyfman, A. Y.; Weinkam, P.; Oroudjev, E.; Hansma, H. G.; Jaeger, L. Building Programmable Jigsaw Puzzles with RNA. Science 2004, 306, 2068-2072.

Cipriano, T.; Knotts, G.; Laudari, A.; Bianchi, R. C.; Alves, W. A.; Guha, S. Bioinspired Peptide Nanostructures for Organic Field-Effect Transistors. ACS Appl. Mater. Interfaces 2014, 6, 21408-21415.

Cornil, J.; Beljonne, D.; Calbert, J.-P.; Brédas, J.-L. Adv. Mater. 2001, 13, 1053-1067.

Diegelmann, S. R.; Gorham, J. M.; Tovar, J. D. One-Dimensional Optoelectronic Nanostructures Derived from the Aqueous Self-Assembly of Pi-conjugated Oligopeptides. J. Am. Chem. Soc. 2008, 130, 13840-13841.

Diegelmann, S. R.; Hartman, N.; Markovic, N.; Tovar, J. D. Synthesis and Alignment of Discrete Polydiacetylene-Peptide Nanostructures. J. Amer. Chem. Soc. 2012, 134, 2028-2031.

Draper, E. R.; Walsh, J. J.; McDonald, T. O.; Zwijnenburg, M. A.; Cameron, P. J.; Cowan, A. J.; Adams, D. J., Air-stable photoconductive films formed from perylene bisimide gelators. J. Mater. Chem. C 2014, 2, 5570-5575.

Fassioli, F.; Dinshaw, R.; Arpin, P. C.; Scholes, G. D. J. R. Soc. Interface 2013, 11, 20130901-20130901.

Fei, Z.; Pattanasattayavong, P.; Han, Y.; Schroeder, B. C.; Yan, F.; Kline, R. J.; Anthopoulos, T. D.; Heeney, M., Influence of Side-Chain Regiochemistry on the Transistor Performance of High-Mobility, All-Donor Polymers. J. Am. Chem. Soc. 2014, 136, 15154-15157.

Forciniti, L.; Guimard, N. K.; Lee, S.; Schmidt, C. E. J. Mater. Chem. 2010, 20 (40), 8865.

Fox, M. A.; Galoppini, E. J. Am. Chem. Soc. 1997, 119, 5277.

Frischmann, P. D.; Mahata, K.; Würthner, F. Chem. Soc. Rev. 2013, 42, 1847-1870.

Gallaher, J. K.; Aitken, E. J.; Keyzers, R. A.; Hodgkiss, J. M. Chem. Commun. 2012, 48 (64), 7961.

Galoppini, E.; Fox, M. A. J. Am. Chem. Soc. 1996, 118, 2299.

Gao, M.; Paul, S.; Schwieters, C. D.; You, Z.-Q.; Shao, H.; Herbert, J. M.; Parquette, J. R.; Jaroniec, C. P. J. Phys. Chem. C 2015, 119 (24), 13948-13956.

Generali, G.; Dinelli, F.; Capelli, R.; Toffanin, S.; di Maria, F.; Gazzano, M.; Barbarella, G.; Muccini, M., Correlation among Morphology, Crystallinity, and Charge Mobility in OFETs Made of Quaterthiophene Alkyl Derivatives on a Transparent Substrate Platform. J. Phys. Chem.C 2011, 115, 23164-23169.

Ghadiri, M. R.; Granja, J. R.; Milligan, R. A.; McRee, D. E.; Khazanovich, N. Self-Assembling Organic Nanotubes Based of a Cyclic Peptide Architecture. Nature 1994, 366, 324-327.

Guarino, V.; Alvarez-Perez, M. A.; Borriello, A.; Napolitano, T.; Ambrosio, L. Adv. Healthc. Mater. 2013, 2 (1), 218-227.

Gumus, A.; Califano, J. P.; Wan, A. M. D.; Huynh, J.; Reinhart-King, C. A.; Malliaras, G. G. Soft Matter 2010, 6 (20), 5138.

Guo, X.; Watson, M. D. Org. Lett. 2008, 10, 5333-5336.

Gust, D.; Moore, T. A.; Moore, A. L. Acc. Chem. Res. 2001, 34, 40-48.

Haycock, R. A.; Yartsev, A.; Michelsen, U.; Sundström, V.; Hunter, C. A. Angew. Chem. Int. Ed. 2000, 39, 3616-3619.

(56) References Cited

OTHER PUBLICATIONS

Herz, L.; Daniel, C.; Silva, C.; Hoeben, F.J.M., Schenning, A.P.H.J.; Meijer, E.W.; Friend, R.H.; Phillips, R.T. Phys. Rev. B 2003, 68, 045203.

Himmelberger, S.; Vandewal, K.; Fei, Z. P.; Heeney, M.; Salleo, A., Role of Molecular Weight Distribution on Charge Transport in Semiconducting Polymers. Macromolecules 2014, 47 (20), 7151-7157.

Hirst, A. R.; Roy, S.; Arora, M.; Das, A. K.; Hodson, N.; Murray, P.; Marshall, S.; Javid, N.; Sefcik, J.; Boekhoven, J.; van Esch, J. H.; Santabarbara, S.; Hunt, N. T.; Ulijn, R. V. Nat. Chem. 2010, 2, 1089-1094.

Hoeben, F. J. M.; Schenning, A. P. H. J.; Meijer, E. W. ChemPhysChem 2005, 6, 2337-2342.

Hoeben, F. J. M.; Herz, L.M.; Daniel, C.; Jonkheijm, P.; Schenning, A.P.H.J; Silva, C.; Meskers, S.C.J.; Beljonne, D.; Philips, R.T.; Friend, R.H.; Meijer, E.W. Angew. Chem. Int. Ed. 2004, 116, 2010-2013.

Horne, W. S.; Ashkenasy, N.; Ghadiri, M. R. Chem. Eur. J. 2005, 11 (4), 1137-1144.

Horowitz, G. Organic Field-Effect Transistors. Adv. Mater. 1998, 10, 365-377.

Imahori, H.; Guldi, D. M.; Tamaki, K.; Yoshida, Y.; Luo, C.; Sakata, Y.; Fukuzumi, S. J. Am. Chem. Soc. 2001, 123 (27), 6617-6628.

\* cited by examiner

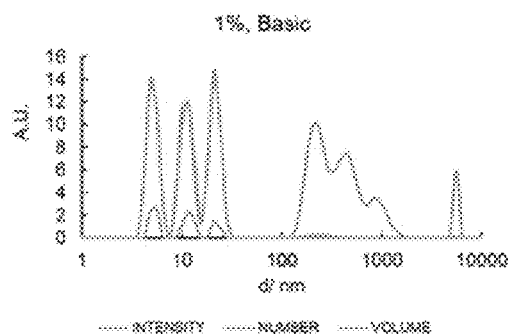
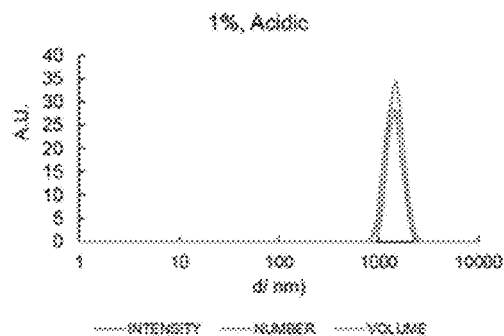
*Fig. 4A*  *Fig. 4B*
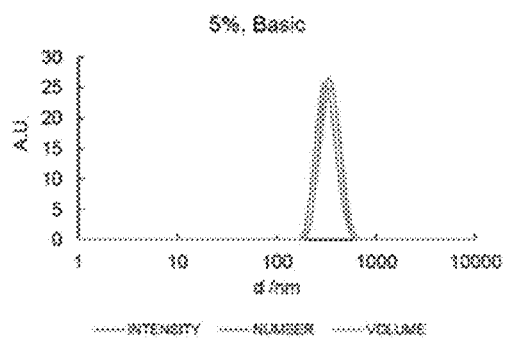
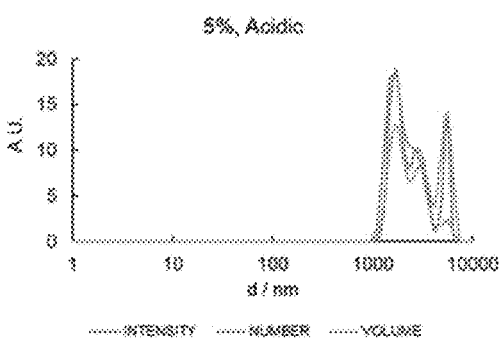
*Fig. 4C*  *Fig. 4D*
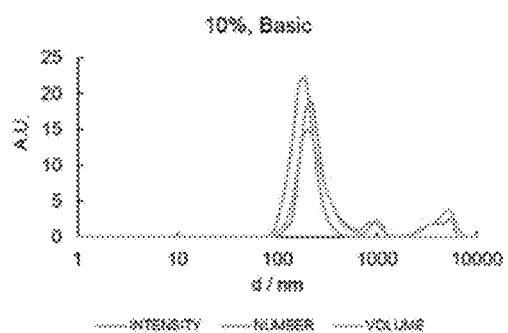
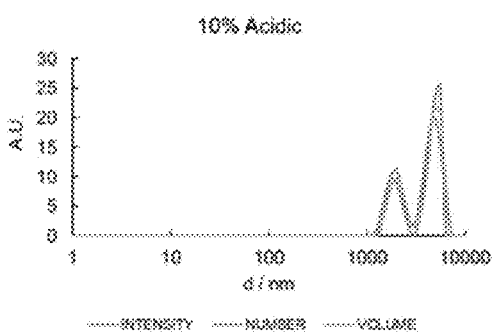
*Fig. 4E*  *Fig. 4F*

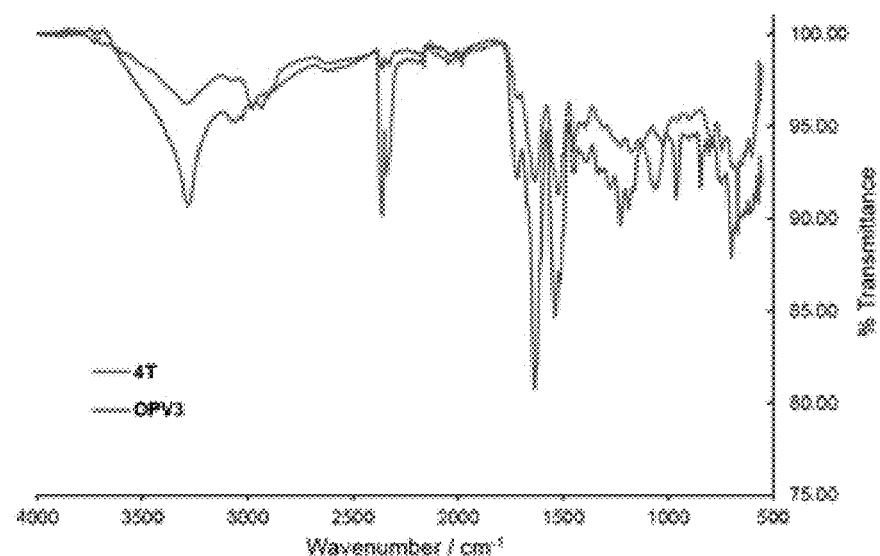
*Fig. 6A*
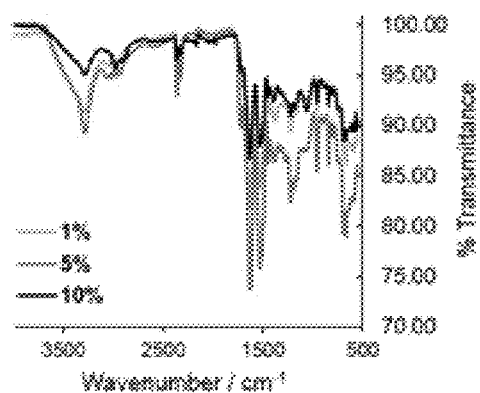  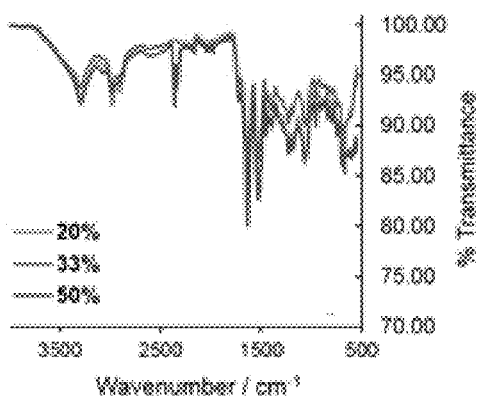
*Fig. 6B*  *Fig. 6C*

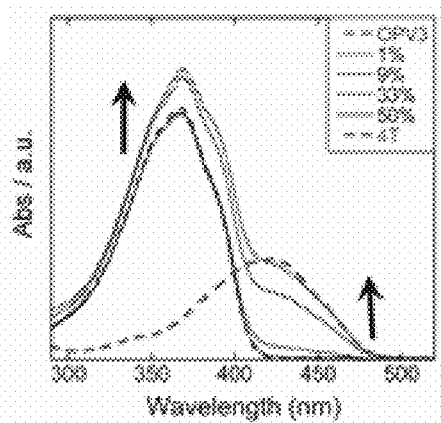 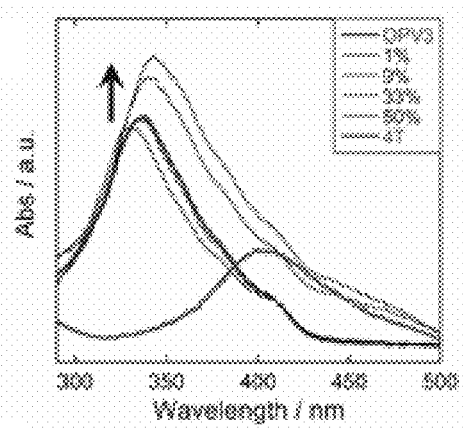
Fig. 7A                Fig. 7B
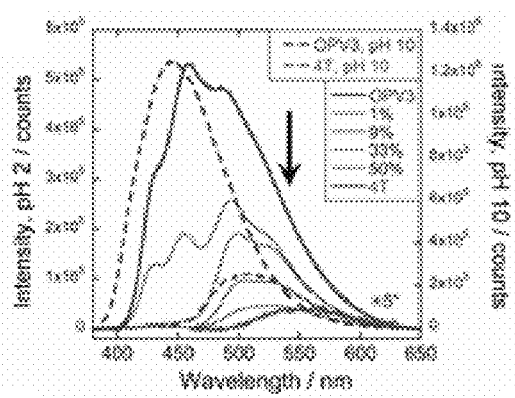 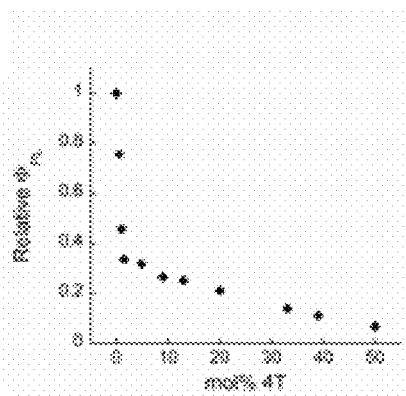
Fig. 7C                Fig. 7D

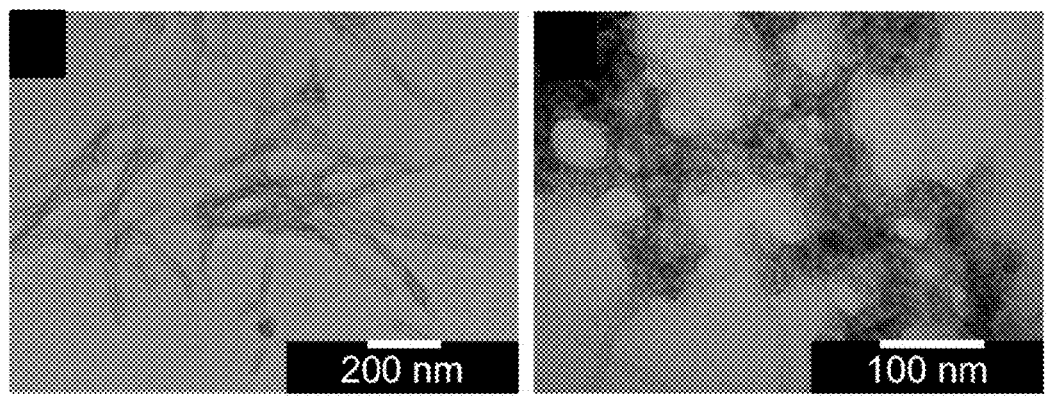
*Fig. 10A*　　*Fig. 10B*

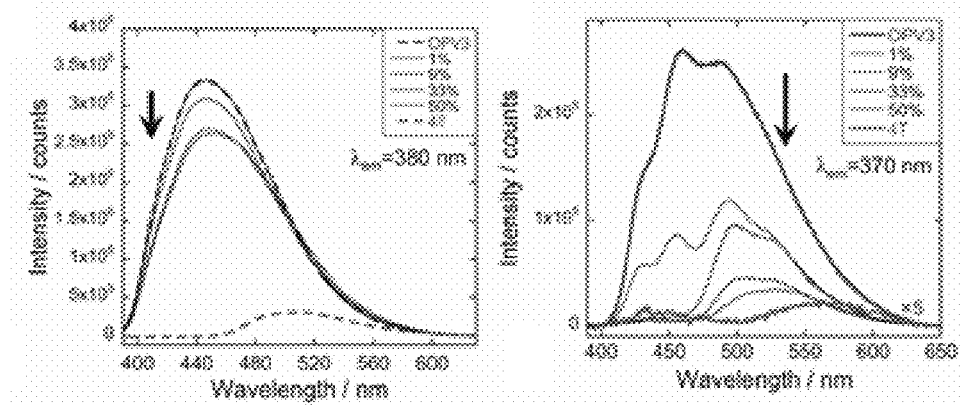
*Fig. 11A*  *Fig. 11B*
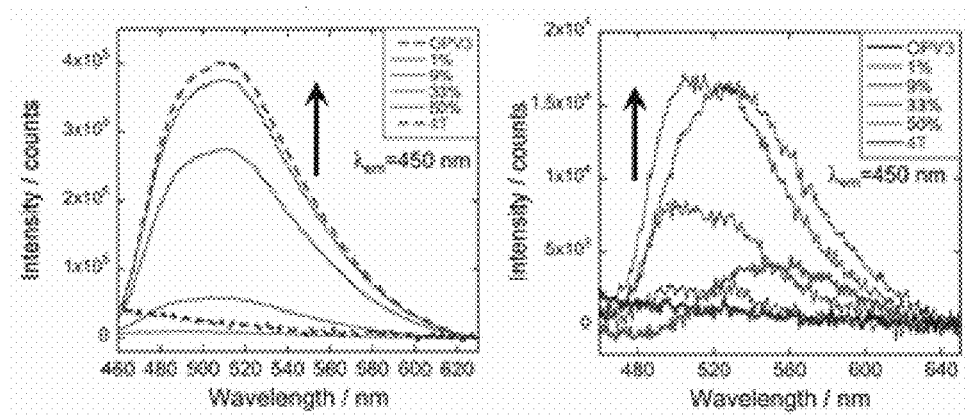
*Fig. 11C*  *Fig. 11D*

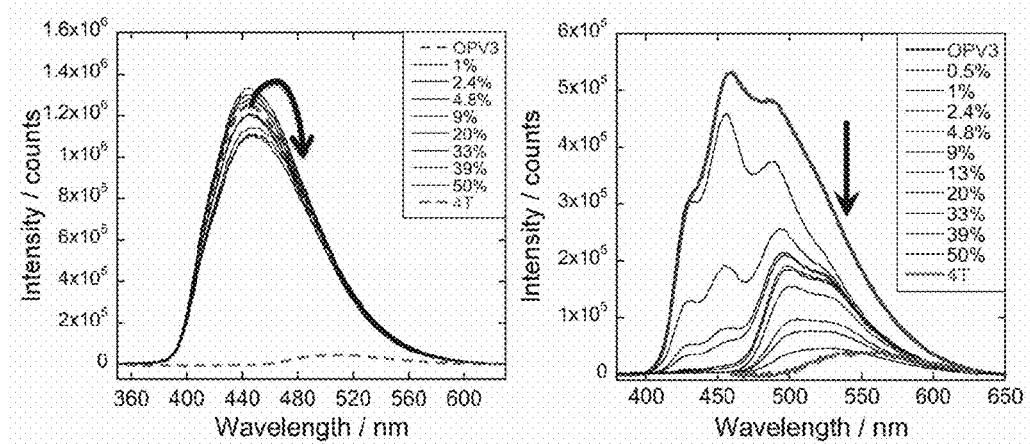
*Fig. 12A*     *Fig. 12B*
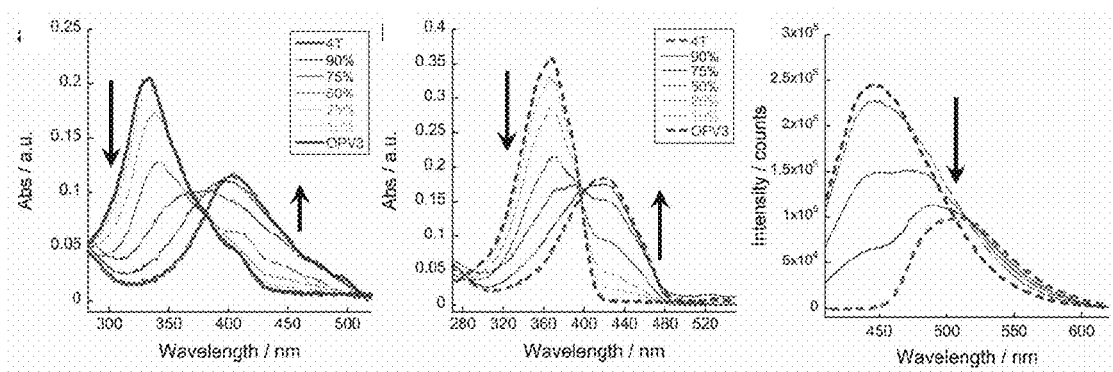
*Fig. 12C*     *Fig. 12D*     *Fig. 12E*

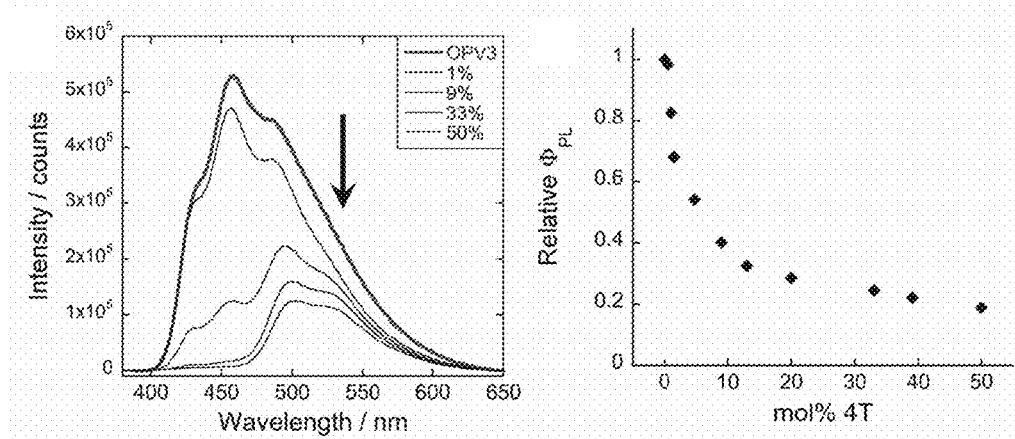
*Fig. 14A*    *Fig. 14B*
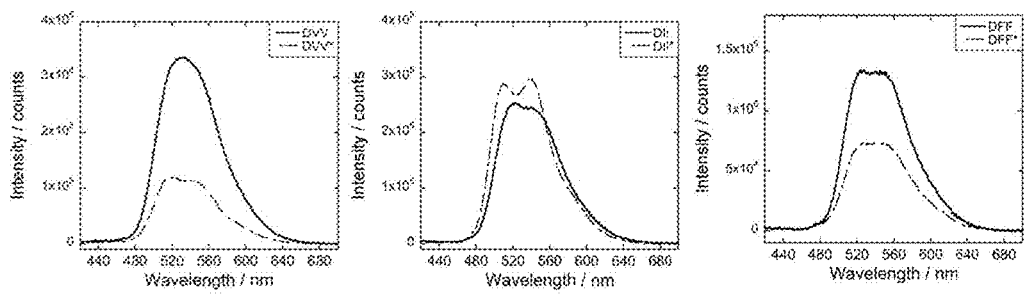
*Fig. 14C*    *Fig. 14D*    *Fig. 14E*

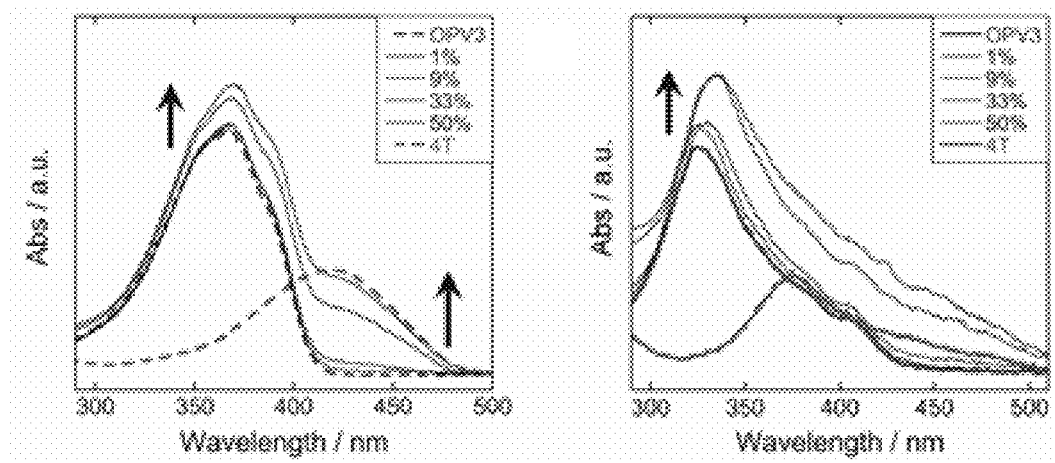
*Fig.15A*  *Fig.15B*
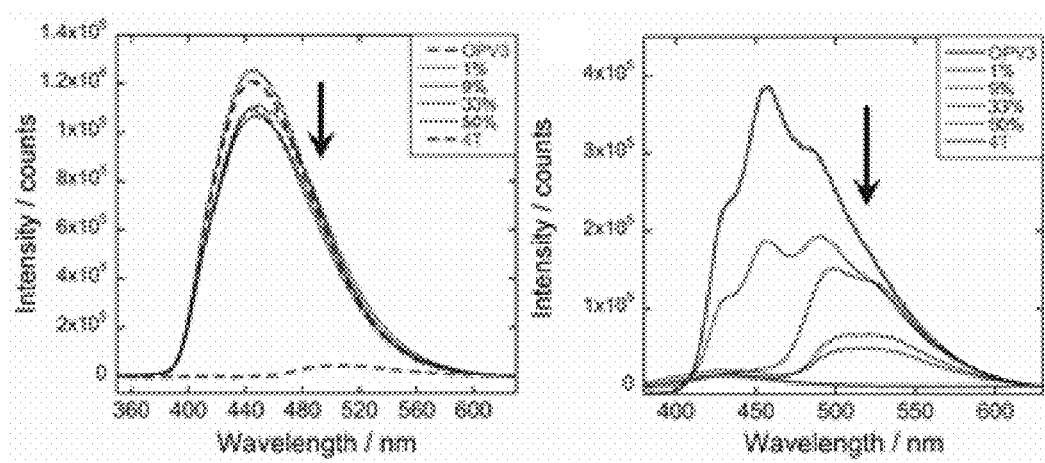
*Fig.15C*  *Fig.15D*

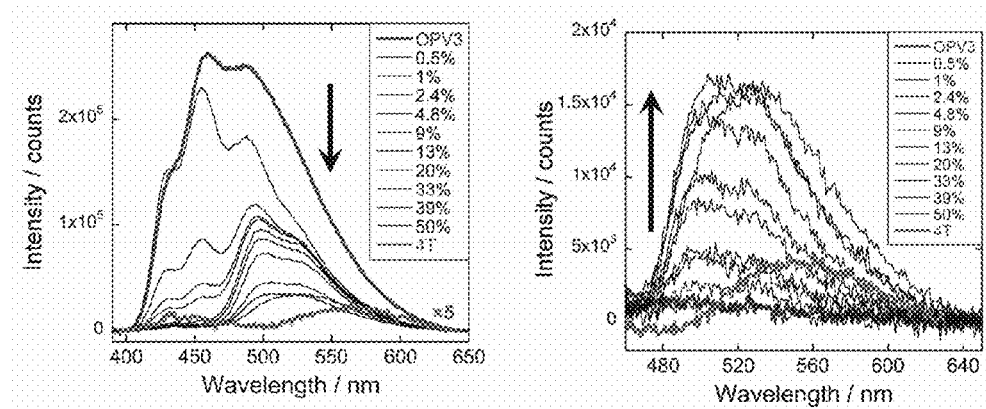
*Fig.16A*            *Fig.16B*
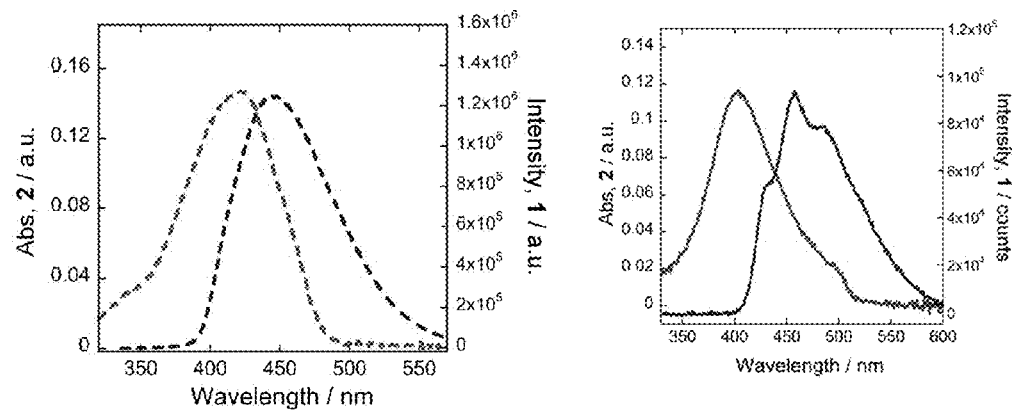
*Fig.16C*            *Fig.16D*

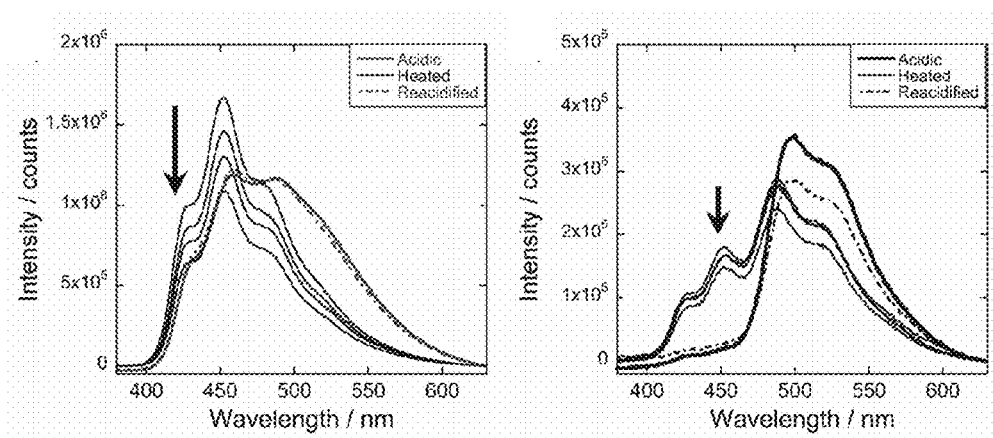
*Fig.17A*  *Fig.17B*
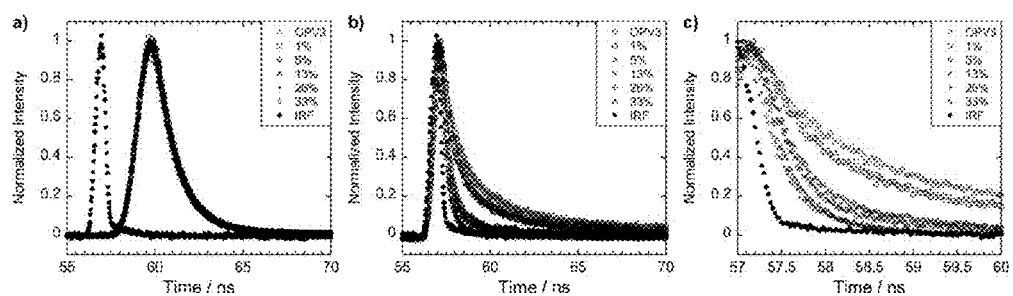
*Fig. 17C*  *Fig. 17D*  *Fig. 17E*

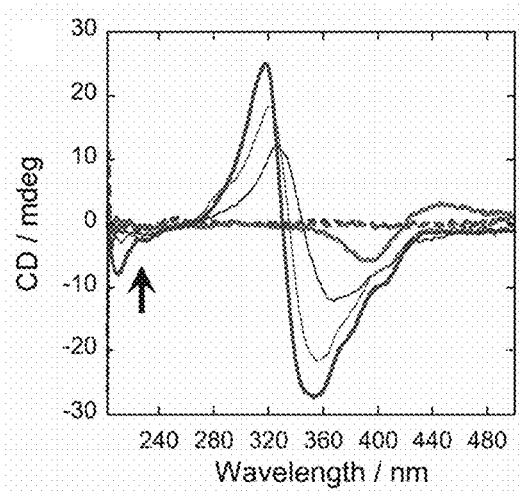
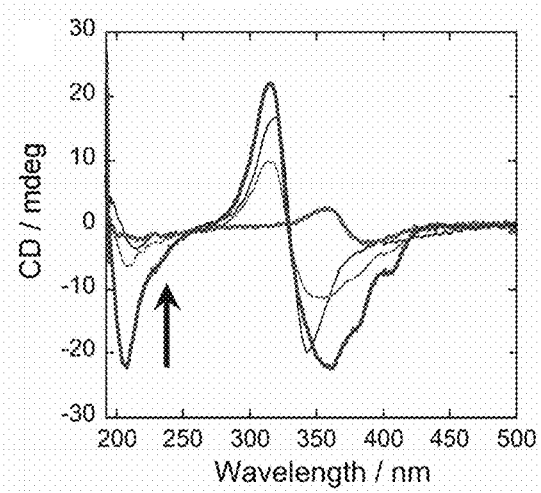
*Fig. 18A*  *Fig. 18B*
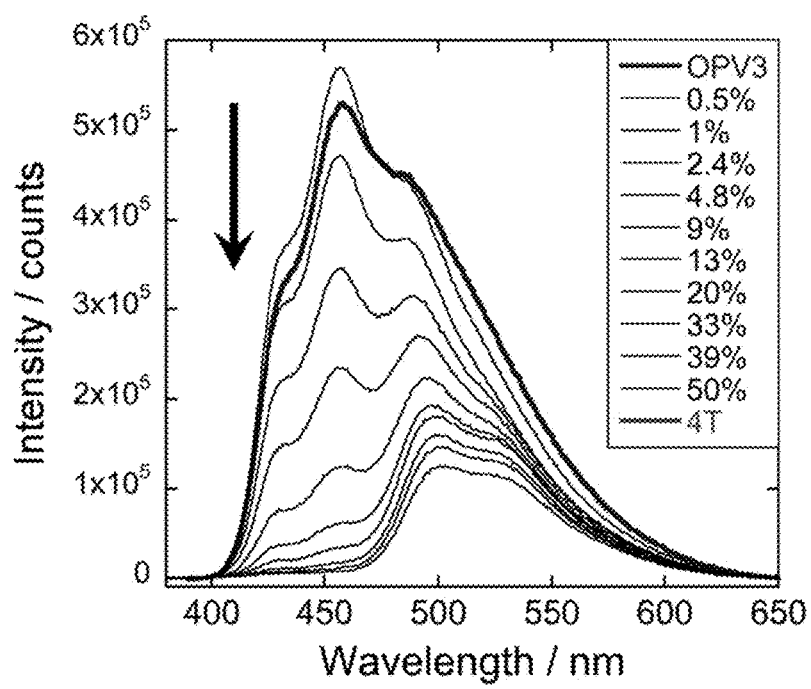
*Fig. 18C*

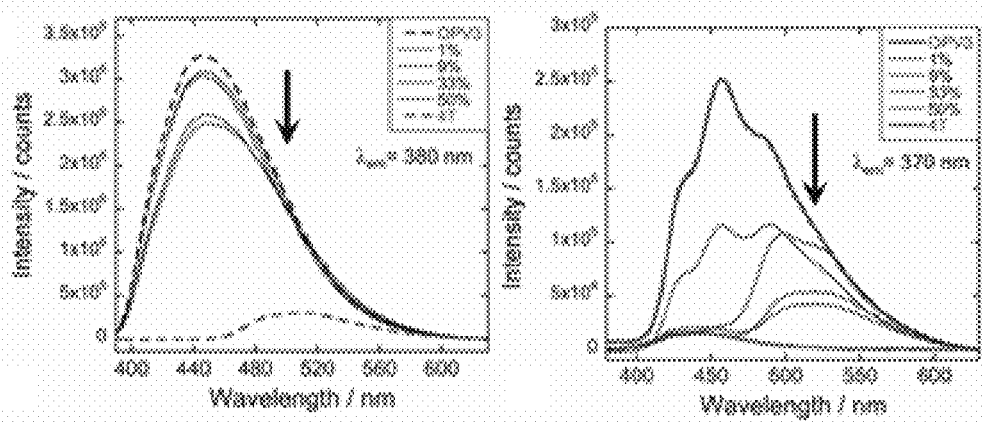
*Fig.19A*    *Fig.19B*
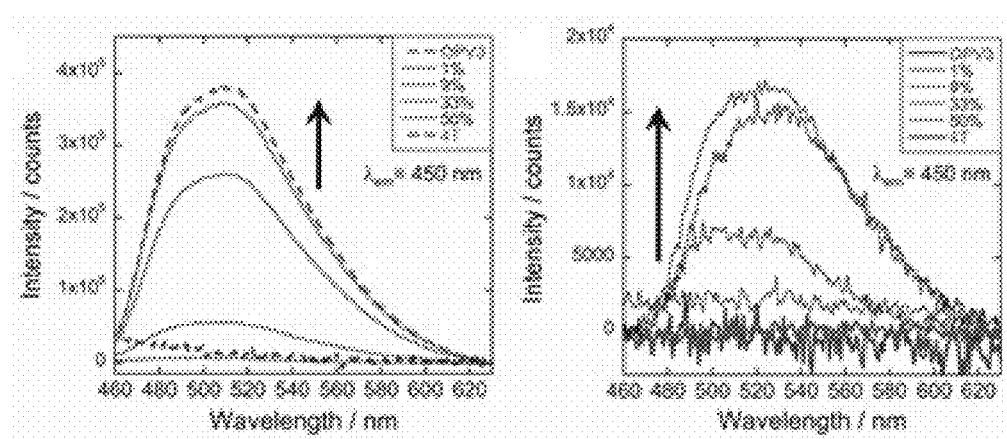
*Fig.19C*    *Fig.19D*

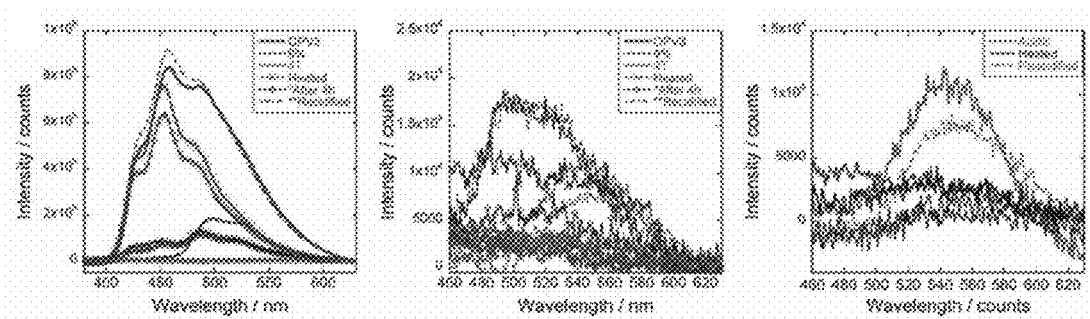
*Fig. 21A*  *Fig. 21B*  *Fig. 21C*

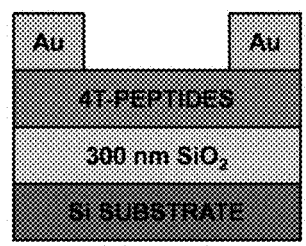
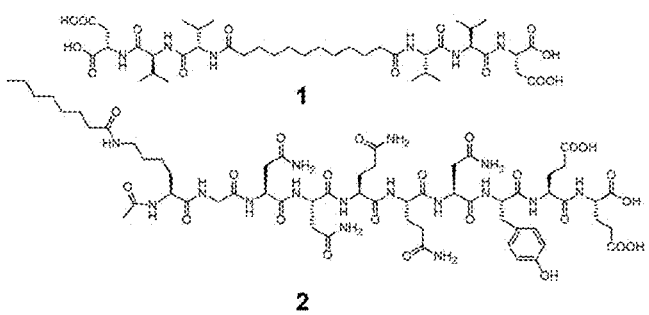
*Fig.23A*  *Fig.23B*
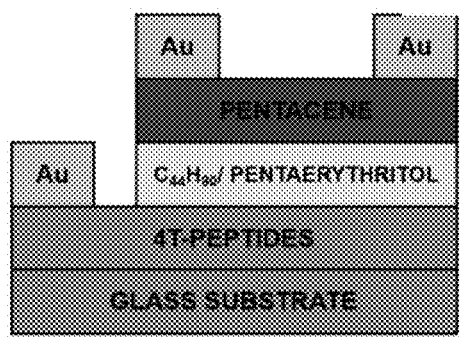
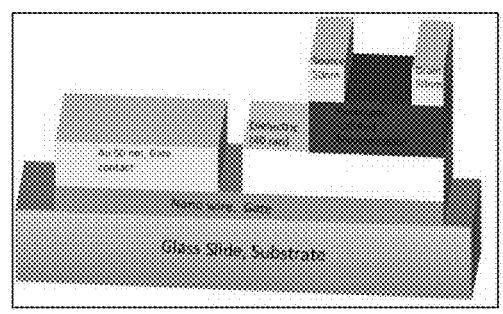
*Fig.23C*  *Fig.23D*

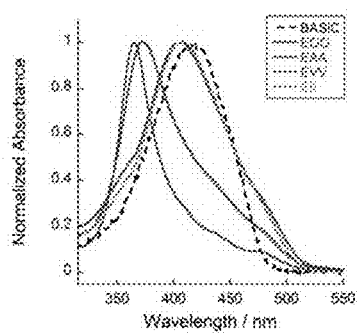 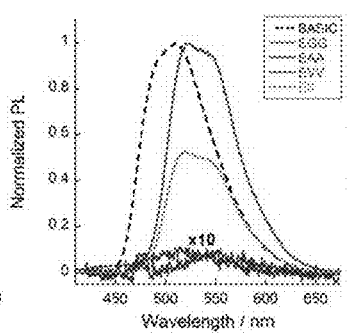 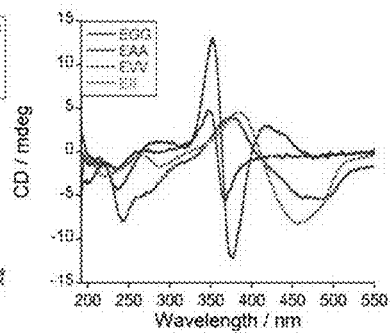
*Fig. 25A*    *Fig. 25B*    *Fig. 25C*

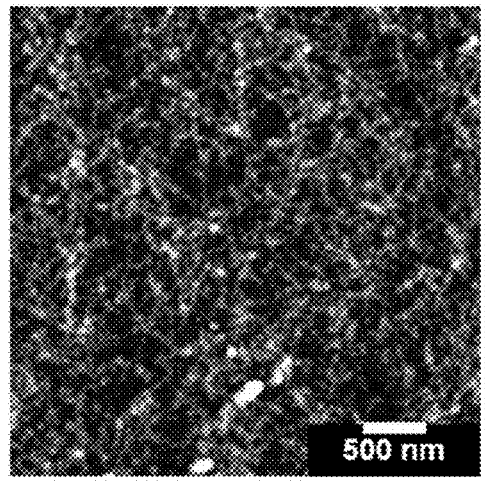 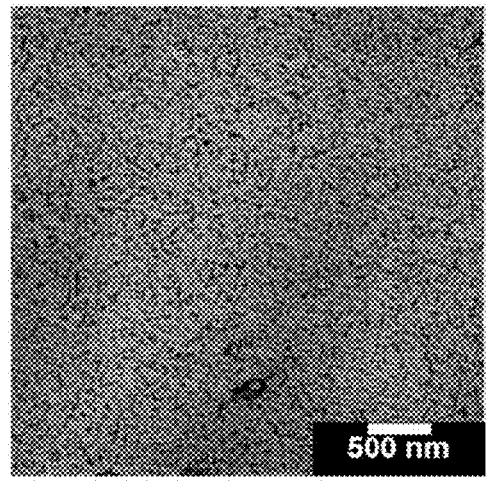
*Fig. 31A*  *Fig. 31B*
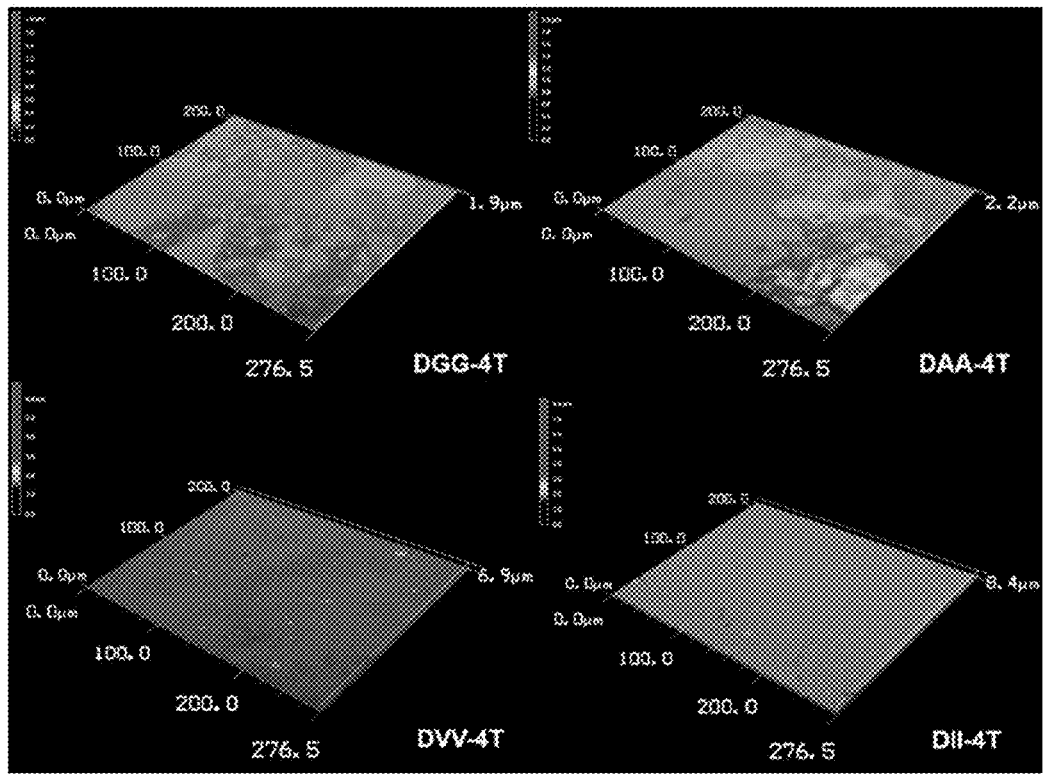
*Fig. 31C*

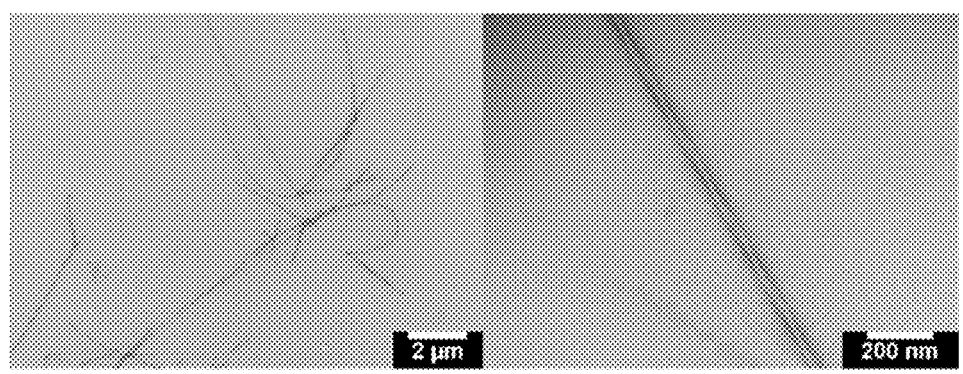
*Fig. 33A*
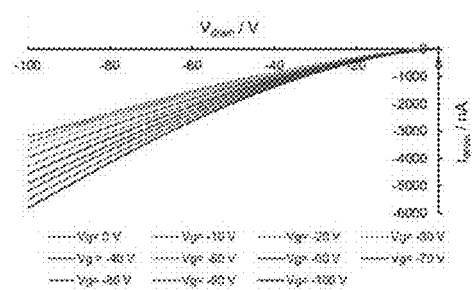 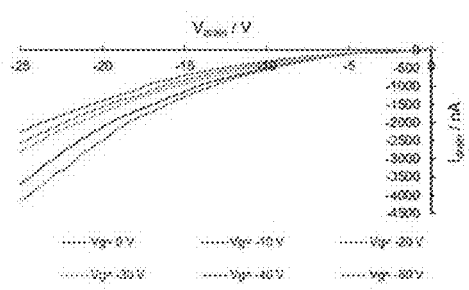
*Fig. 33B*     *Fig. 33C*

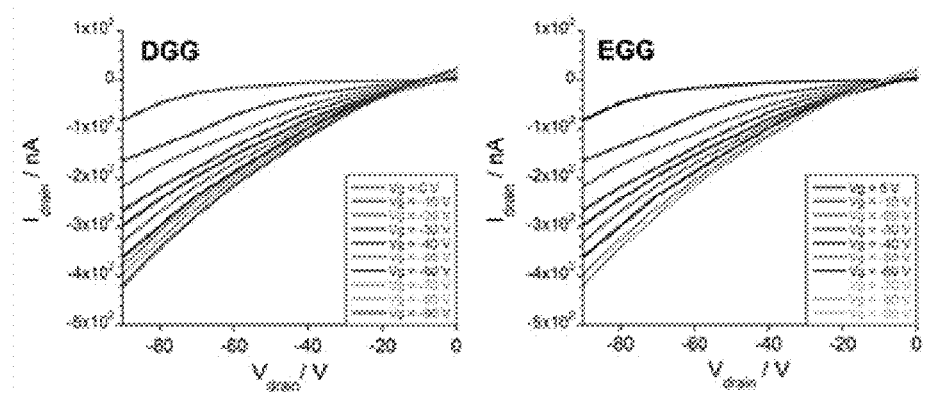
*Fig. 34A*    *Fig. 34B*
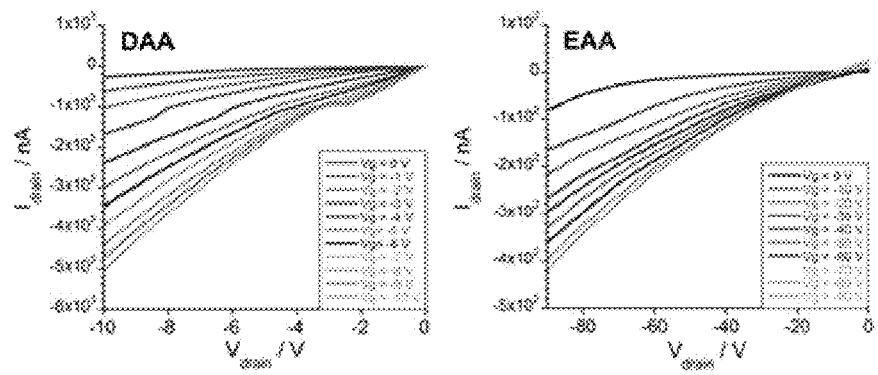
*Fig. 34C*    *Fig. 34D*
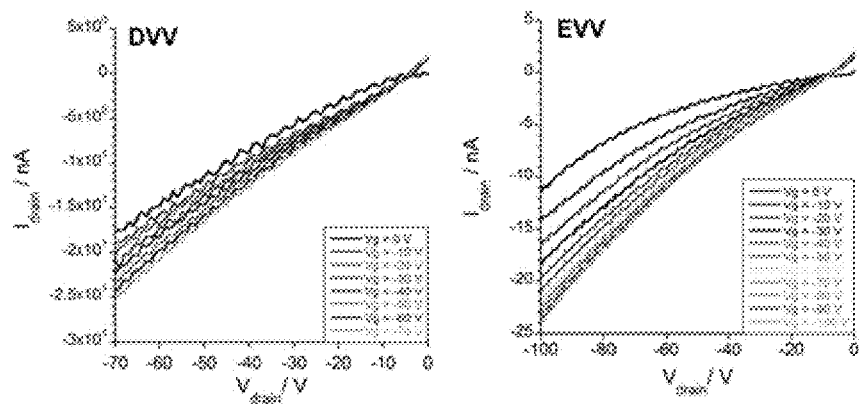
*Fig. 34E*    *Fig. 34F*

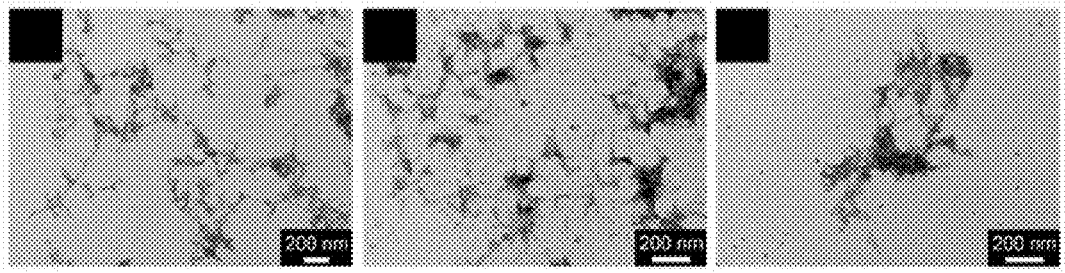
*Fig. 38A*   *Fig. 38B*   *Fig. 38C*
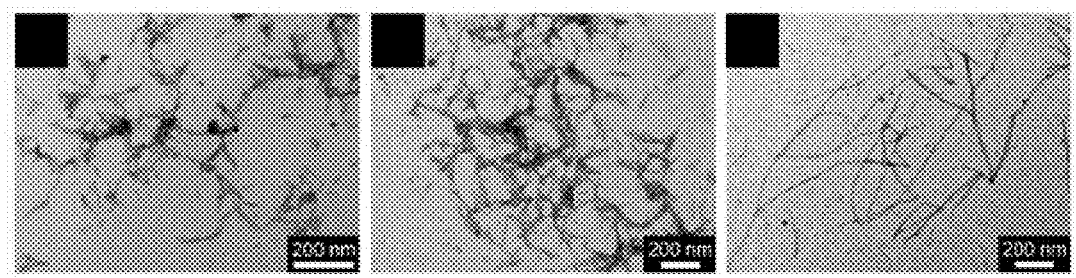
*Fig. 38D*   *Fig. 38E*   *Fig. 38F*
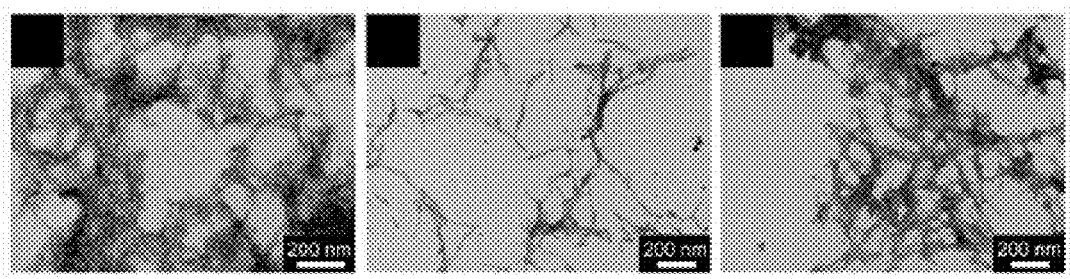
*Fig. 38G*   *Fig. 38H*   *Fig. 38I*

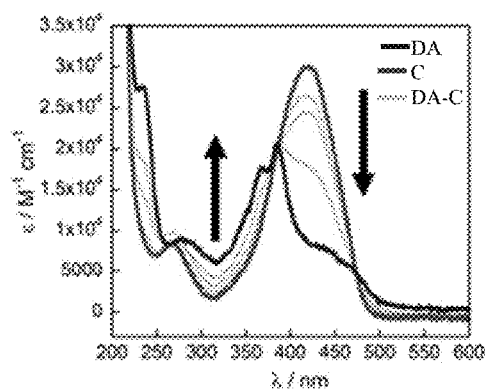
FIG. 40A
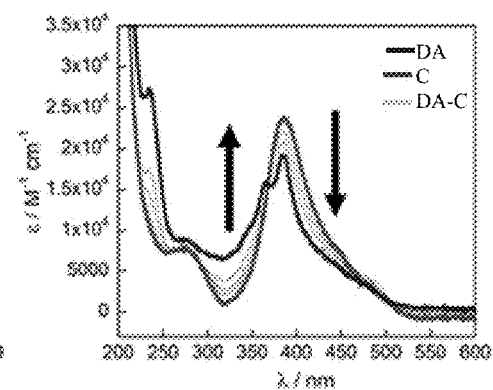
FIG. 40B
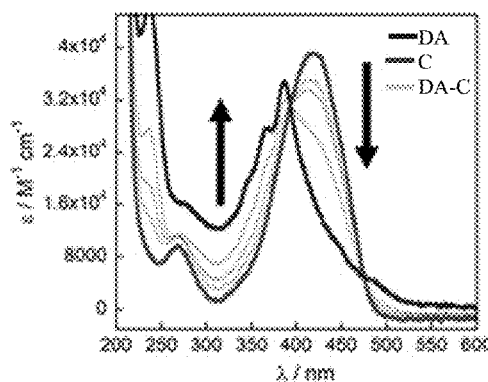
FIG. 40C
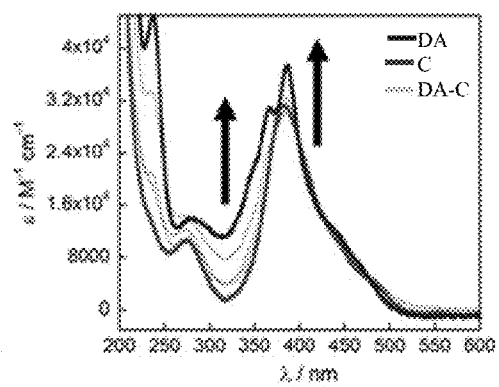
FIG. 40D
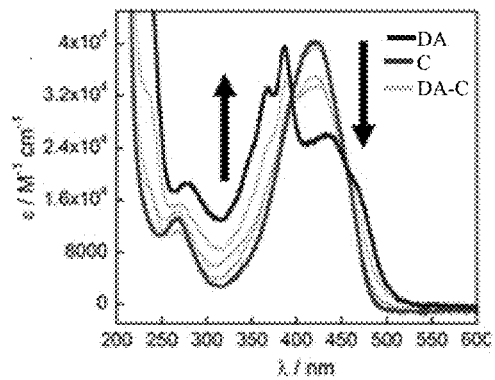
FIG. 40E
FIG. 40F

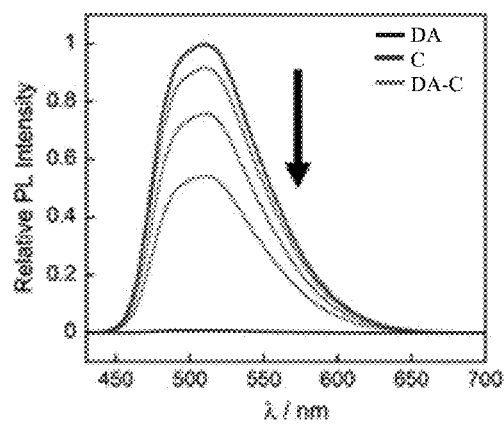
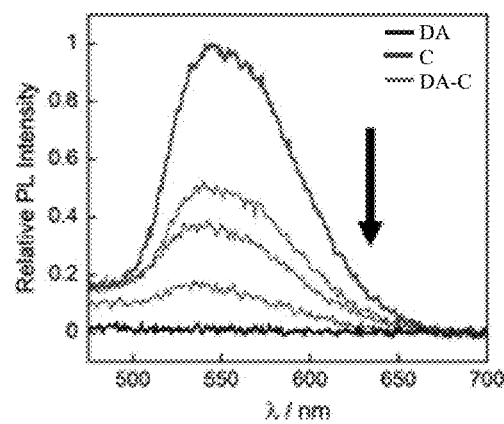
*FIG. 41E*  *FIG. 41F*
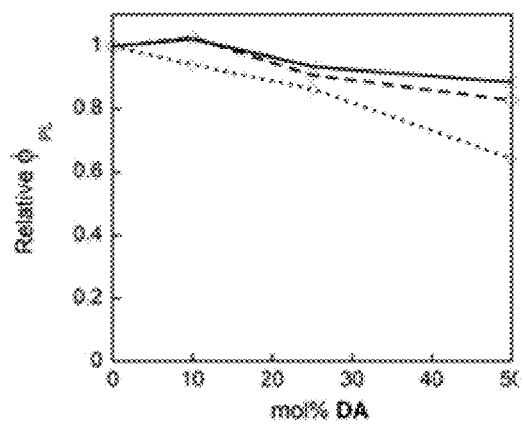
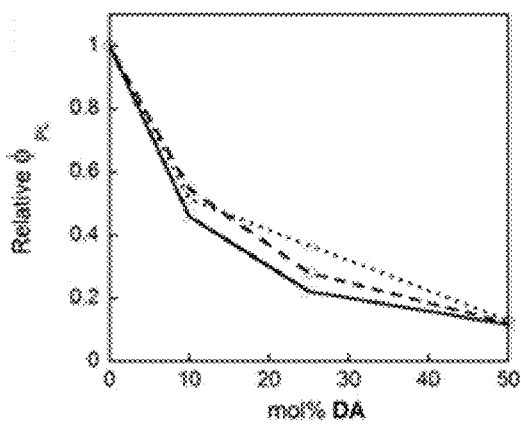
*FIG. 41G*  *FIG. 41H*

ENERGY TRANSFER WITHIN PI-CONJUGATED PEPTIDE HETEROSTRUCTURES IN AQUEOUS ENVIRONMENTS

CROSS-REFERENCE TO RELATED APPLICATIONS

This application claims the benefit of U.S. Provisional application No. 62/083,761, filed Nov. 24, 2014, which is incorporated herein by reference in its entirety.

FEDERALLY SPONSORED RESEARCH OR DEVELOPMENT

This invention was made with government support under DE-SC0004857 awarded by the Department of Energy (DOE) and DMR-1407493 awarded by the National Science Foundation. The government has certain rights in the invention.

BACKGROUND

Supramolecular assembly is a recurring theme in nature that plays a significant role in the function of biological assemblies and is a widely used strategy to organize molecular components in organic electronic devices. Aida, T., et al., *Science* 2012, 335, 813-817; Boekhoven, J; Stupp, S. I. *Adv. Mater.* 2014, 6, 1642-1659; Sirringhaus, H., et al., *Nature*. 1999, 401, 685-688. In both photosynthetic complexes and in most optoelectronic devices, excitation energy transfer process plays a central role. Praveen, V. K., et al., *Chem. Soc. Rev.* 2014, 43, 4222; Hoeben, F. J. M., et al., *Angew. Chem. Int. Ed.* 2004, 116, 2010-2013; Sakakibara, K., et al., *J. Am. Chem. Soc.* 2014, 136, 8548-8551; Ajayaghosh, A., et al., *Angew. Chem. Int. Ed.* 2007, 46, 6260-6265. This excitation energy transfer process generally occurs via diffusion of excitons, electronically excited states of molecules that are created by light absorption or other electron transfer processes.

These transport processes are highly dependent on ordering effects, Sirringhaus, H., et al., *Nature*. 1999, 401, 685-688, whereby the direction and degree of intermolecular organization of $\pi$-conjugated assemblies are key factors that determine the efficiency of energy transduction. Cornil, J., et al., *Adv. Mater.* 2001, 13, 1053-1067; Roncali, *J. Macromol. Rapid Commun.* 2007, 28, 1761-1775; Botelho, A. L., et al., *PLoS ONE* 2014, 9, e86370. The peptide-driven mesoscale organization of the chromophores in the photosynthetic membrane allows fast directional migration of excitation energy within the chromophore assemblies before being transferred to the reaction center (the final destination of the collected energy), which is crucial to the biological light-harvesting process. Schulze, J., et al., *New J. Phys.* 2014, 16, 045010; Hoeben, F. J. M., et al., *Chem Phys Chem* 2005, 6, 2337-2342; Vijayakumar, C., et al., *Phys. Chem. Chem. Phys.* 2011, 13, 4942-4949; Nakashima, T.; Kimizuka, N. *Adv. Mater.* 2002, 14, 1113-1116. To maximize the harvesting capacity of pigments, an exciton funneling system is involved in the overall photosynthetic process, wherein different antenna complexes with distinctive transition energies are used to expand the spectral light absorption. Fassioli, F., et al., *J. R. Soc. Interface* 2013, 11, 20130901-20130901.

Multicomponent synthetic materials exhibiting supramolecular ordering and/or exciton migration, thus making good candidates for light-harvesting antenna mimics, have received considerable attention. Wasielewski, M. R. *Chem. Rev.* 1992, 92, 435-461; Gust, D., et al., *Acc. Chem. Res.* 2001, 34, 40-48; Choi, M.-S., et al., *Angew. Chem. Int. Ed.* 2001, 40, 3194-3198; Frischmann, P. D., et al., *Chem. Soc. Rev.* 2013, 42, 1847-1870. Multichromophoric dendrimers, Serin, J. M., et al., *Chem. Commun.* 2002, 2605-2607, and ring-like harvesting units, Haycock, R. A., et al., *Angew. Chem. Int. Ed.* 2000, 39, 3616-3619, are two among many molecular and other supramolecular forms that have been comprehensively studied in solution or in solid state (i.e., as hydrogels or organogels) Nakashima, T.; Kimizuka, N. *Adv. Mater.* 2002, 14, 1113-1116; Sugiyasu, K., et al., *Angew. Chem. Int. Ed.* 2004, 43, 1229-1233, demonstrating the prospects for directional and near quantitative energy transfer in synthetic systems.

Over the past decade, Meijer and co-workers reported exciton migration leading to energy transfer within supramolecular columnar stacks of oligo(p-phenylenevinylene) (OPV) in dodecane, Hoeben, F. J. M., et al., *Chem. Int. Ed.* 2004, 116, 2010-2013, and hydrogen-bonded dimers between OPV-perylene bisimide in toluene. Neuteboom, E. E., et al., *Org. Biomol. Chem.* 2003, 1, 198-203. Functionalized OPVs that act as hydrogelators also were extensively studied for exciton funneling by Ajayaghosh and co-workers, showing that confining the acceptor units within an organogel made of molecular wires results into a more efficient energy transfer. Ajayaghosh, A., et al., *Angew. Chem. Int. Ed.* 2007, 46, 6260-6265.

Currently, studies involving 1D-nanostructures or molecular wires composed of $\pi$-stacked monomers are of particular interest due to their generally superior carrier transport along the stacking axis, which is beneficial for nanoscale optoelectronic devices. Lim, J. M., et al., *Chem. Sci.* 2013, 4, 388-397. Most studies of electronically responsive supramolecular analogs of biological structures are conducted in organic media. Oshovsky, G. V., et al., *Angew. Chem. Int. Ed.* 2007, 46, 2366-2393; Ponnuswamy, N., et al., *Science* 2012, 338, 783-785; Bradford, V. J.; Iverson, B. L. *J. Am. Chem. Soc.* 2008, 130, 1517-1524. Therefore, it is of interest to explore aqueous supramolecular systems that could more efficiently mimic important bioenergetic processes under native conditions.

Further, while biopolymers, such as DNA (Seeman, 2003), RNA (Chworos et al., 2004) and other biological scaffolds, such as carbohydrates (Schmid et al., 2009) and steroids (Kawano et al., 2005) have been widely used as self-assembling systems for the construction of semiconducting and optoelectronic nanostructures, the vast majority of bio-inspired organic electronic research has utilized peptide-based architectures derived from natural amino acids (Reches et al., 2003; Ashkenasy et al., 2006; Gharidi et al., 1994; Jatsch et al., 2010; Diegelmann et al., 2008; Shao et al., 2009; Matmour et al., 2008; Jahnke et al., 2006; Stone et al., 2009; Abidian et al., 2010; Kim et al., 2012; Kumar et al., 2011), building blocks that are considered attractive for new materials design because of the scalability, ease of standard solid-phase peptide synthesis and the wide variety of side chains that can be used to alter molecular and supramolecular properties (Cipriano et al., 2014). Oligopeptides have been attached to $\pi$-conjugated components in order to form one-dimensional (1D) nanostructures with photophysical and electronic properties that show promise for functional materials, including materials for electronic stimulation of cells. Among the advantages of these types of platforms for organizing $\pi$-conjugated oligomers are allowance for a controlled assembly of heterogeneous mixtures of donor and acceptor containing materials (Ardona et al., 2015; Channon et al., 2009; Chen et al., 2010; Nalluri et al., 2013) and addition of reactive groups for further functionality (Diegelmann et al., 2012). The general organic semiconductor field is rich with examples of solubilizing (and electrically insulating) alkyl side chains that also promote crystalline self-assembly in the solid-state thereby improving charge transport. Interestingly, attaching semiconducting units to self-assembling amide substituents that result in organogel formation has led to measurable charge mobilities upon incorporation in organic field-effect transistors (OFETs) (Tsai et al., 2010; Jurchescu et al., 2008; Prasanthkumar et al., 2010). However, utilizing longer oligopeptide assembling subunits limits the charge transport properties because of the large volume fraction of "insulating" peptide moieties, thus making it challenging to build electronic devices and directly characterize conductivity of more biologically relevant constructs (Kumar et al., 2011; Sun et al., 2011).

Pi-conjugated systems have been a mainstay of cutting-edge flexible electronics applications over the past decade, but more recently, attention has turned to their prospects in biological environments. Semiconducting, biocompatible materials based on organic electronic polymers and oligomers have been used to create a variety of bioelectronics devices that can be used for sensing/signaling (Forciniti et al., 2010; Wang et al., 2012; Traina et al., 2011), controlling cell growth (Wong et al., 1994; Zhao et al., 2012), migration (Gumus et al., 2010), and differentiation (Abidian et al., 2011; Guarino et al., 2013; Schmidt et al., 1997; Mawad et al., 2012). However, the conductivity of the materials, i.e. the ability to create charge-carriers and generate electric fields, typically relies on chemical doping and/or the use of external electronics. The next crucial step in the development of these materials for biomedical applications is to investigate the creation of such fields and carriers in the absence of chemical doping and external electronics.

Donor-acceptor systems capable of photoinduced charge transfer represent one possibility to generate electric fields. Nature uses photoinduced electron transfer to perform redox reactions, particularly in the process of photosynthesis, whereby initial excitations harvested by the photosynthetic pigments are transferred to a reaction center. Several synthetic mimics have been synthesized and studied to understand this process, typically involving the design of covalently bound donor-acceptor dyads, triads, and tetrads ((Wasielwski, 2012; Imahori, Guldi, et al., 2001; Imahori, Tamaki, et al., 2001; Liddel et al., 1994; Kuciasukas et al., 1996; Liddell et al., 1997; Kuciasukas et al., 1999; Liddel et al., 2002). The covalent connection of complementary redox-active chromophores allows for charge transfer to not be limited by diffusion. Furthermore, the self-assembly of these donor-acceptor systems into supramolecular arrays encourages more rapid electron transfer kinetics (Beckers et al., 2006; Wasielwski, 2009; Ahrens et al., 2004; Rybtchinski et al., 2004; Schenning et al., 2002). These examples illustrate that supramolecular assemblies of covalently-bound donor-acceptor chromophores, including those that rely on peptide assembly (Home et al., 2005; Jones et al., 2000; Fox et al., 1997; Galoppini et al., 1996), can be used to facilitate charge transfer and induce polar charge-separated states with low-energy photonic inputs.

SUMMARY

In some aspects, the presently disclosed subject matter provides a nanostructure comprising two or more π-conjugated peptide units that upon self-assembly exhibits energy transport in a completely aqueous or physiological medium, wherein the energy transport can be photonic or electrical in nature.

In particular aspects, the two or more π-conjugated peptides have a structure of peptide-[(organic electronic unit)-peptide], wherein each peptide can be the same or different and comprises from 2 to 15 naturally occurring amino acid residues or a variant thereof.

In yet more particular aspects, the two or more π-conjugated peptide units are selected from the group consisting of:

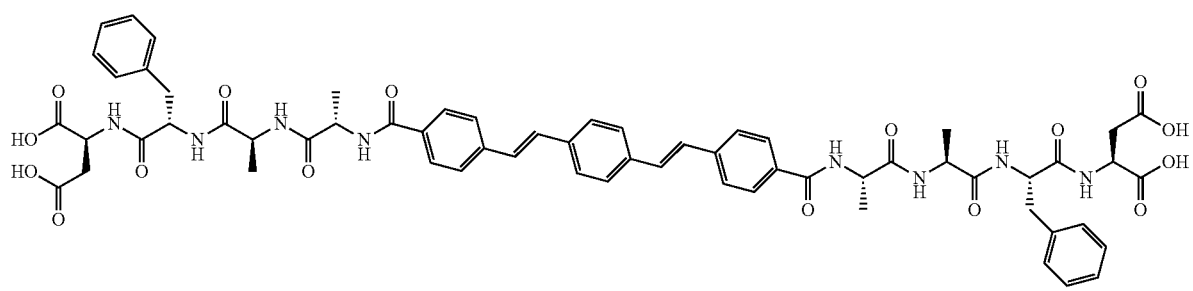

OPV3

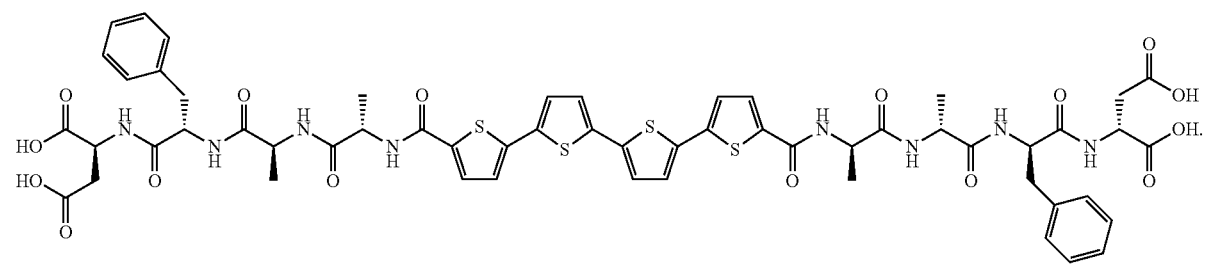

4T

In other aspects, the presently disclosed subject matter provides a conductive material comprising the nanostructure disclosed hereinabove.

In particular aspects, the π-conjugated peptides units have the following structure:

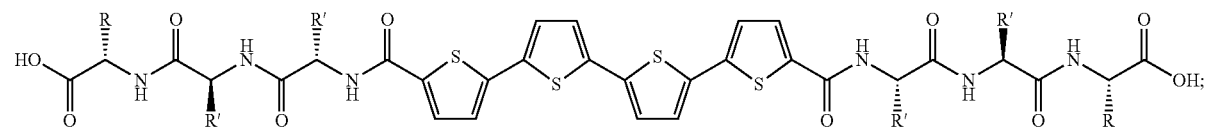

wherein R is —(CH$_2$)$_m$—COR$_1$, m is an integer selected from the group consisting of 0, 1, 2, 3, and 4, and R$_1$ is selected from the group consisting of —OH and —NH$_2$; R' is selected from the group consisting of H, straight-chain alkyl, branched alkyl, and benzyl.

In yet more particular aspects, the π-conjugated peptides units are selected from the group consisting of:

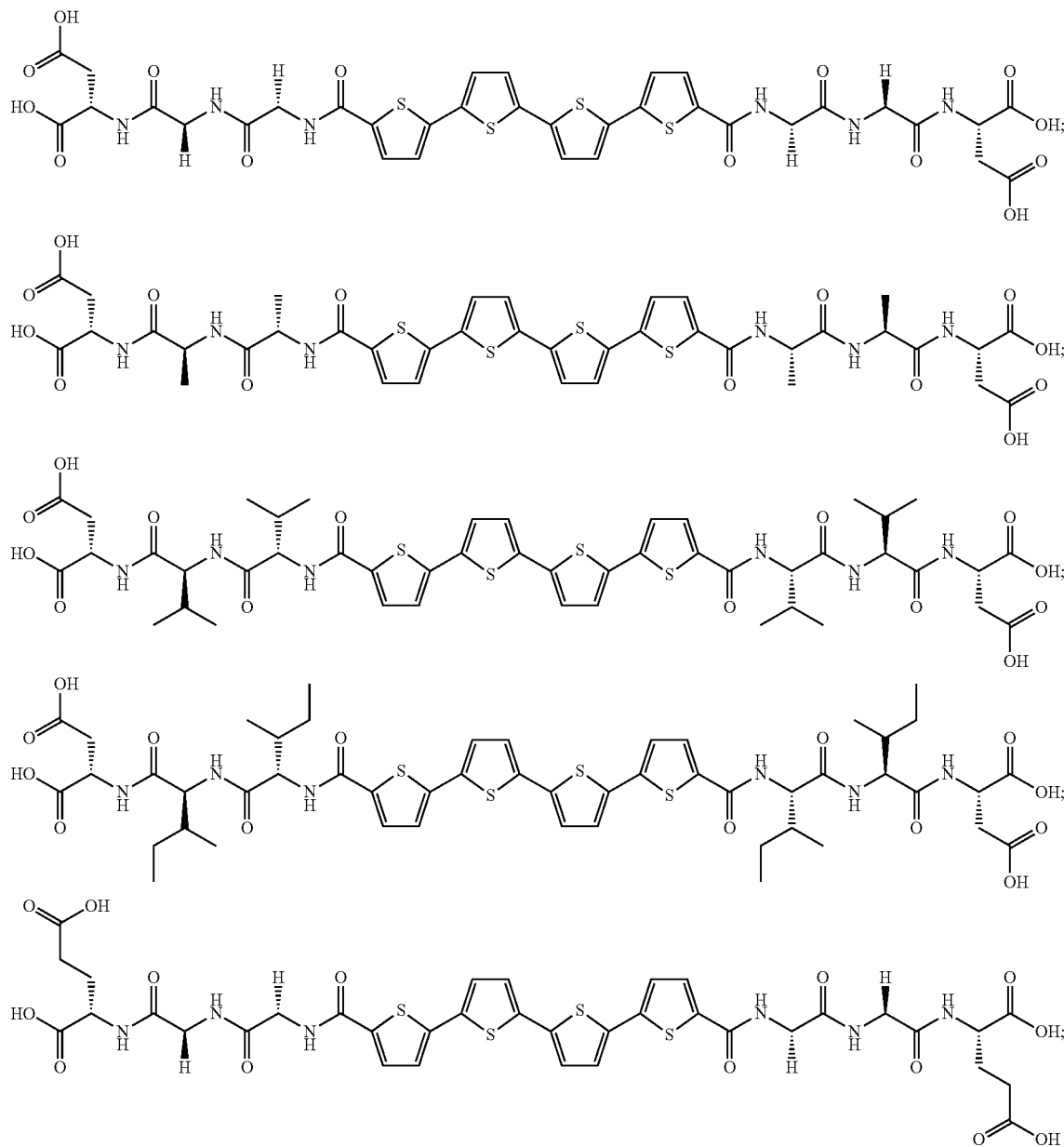

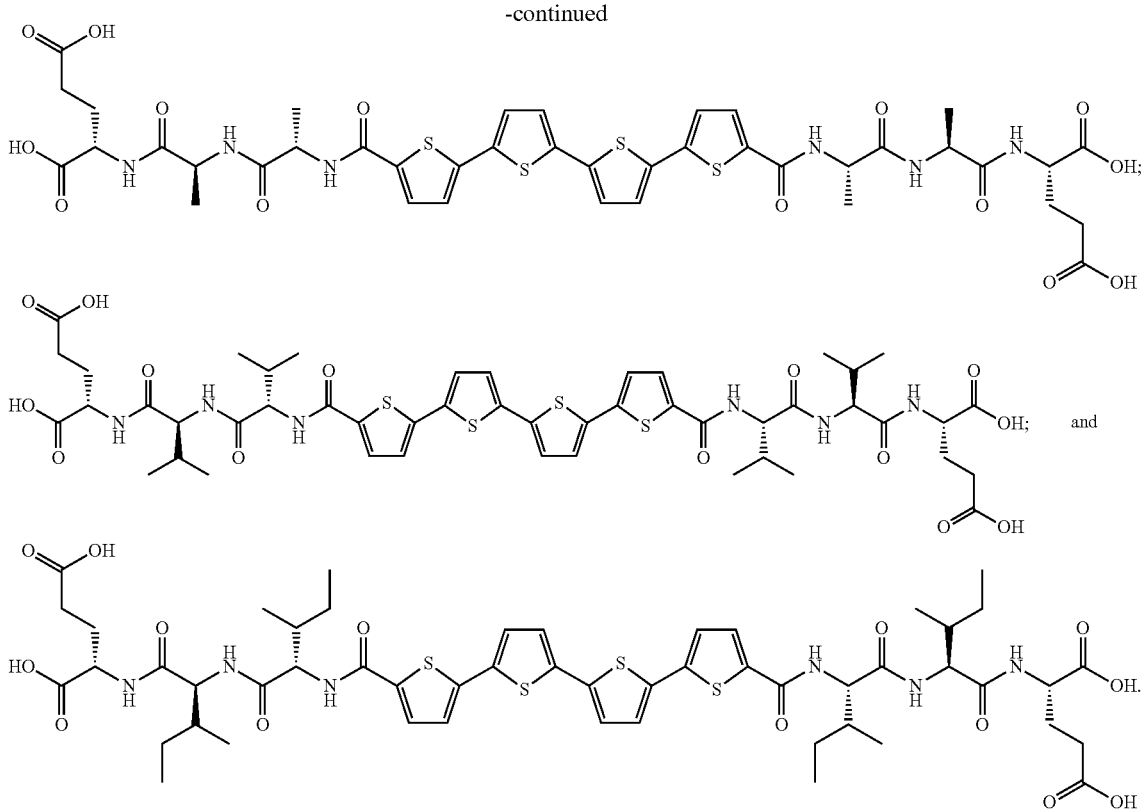

In other aspects, the presenting disclosed subject matter provides a supramolecular assembly comprising covalently-bound electron donor-acceptor chromophores in which either electron acceptor semiconducting π-units are incorporated into amino acid side chains on peptides embedded with an electron donor semiconducting π-unit or electron donor semiconducting π-units are incorporated into amino acid side chains on peptides embedded with an electron acceptor semiconducting π-unit.

In particular aspects, the π-conjugated peptides units have the following structures:

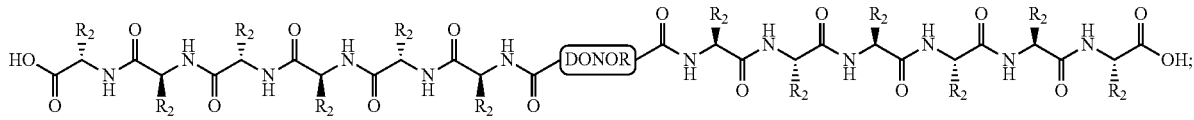

wherein each $R_2$ is independently selected from the group consisting of H, straight-chain alkyl, branched alkyl, benzyl, $-(CH_2)_n$-A and $-(CH_2)_p-COR_3$, wherein A is an electron acceptor, n is an integer selected from the group consisting of 2, 3, and 4, p is an integer selected from the group consisting of 0, 1, 2, 3, and 4, and $R_3$ is selected from the group consisting of $-OH$ and $-NH_2$; or

wherein each $R_2$ is independently selected from the group consisting of H, straight-chain alkyl, branched alkyl, benzyl, —$(CH_2)_n$-D and —$(CH_2)_p$—$COR_3$, wherein D is an electron donor, n is an integer selected from the group consisting of, 2, 3, and 4, p is an integer selected from the group consisting of 0, 1, 2, 3, and 4, and $R_3$ is selected from the group consisting of —OH and —$NH_2$.

In yet more particular aspects, the π-conjugated peptides units are selected from the group consisting of:

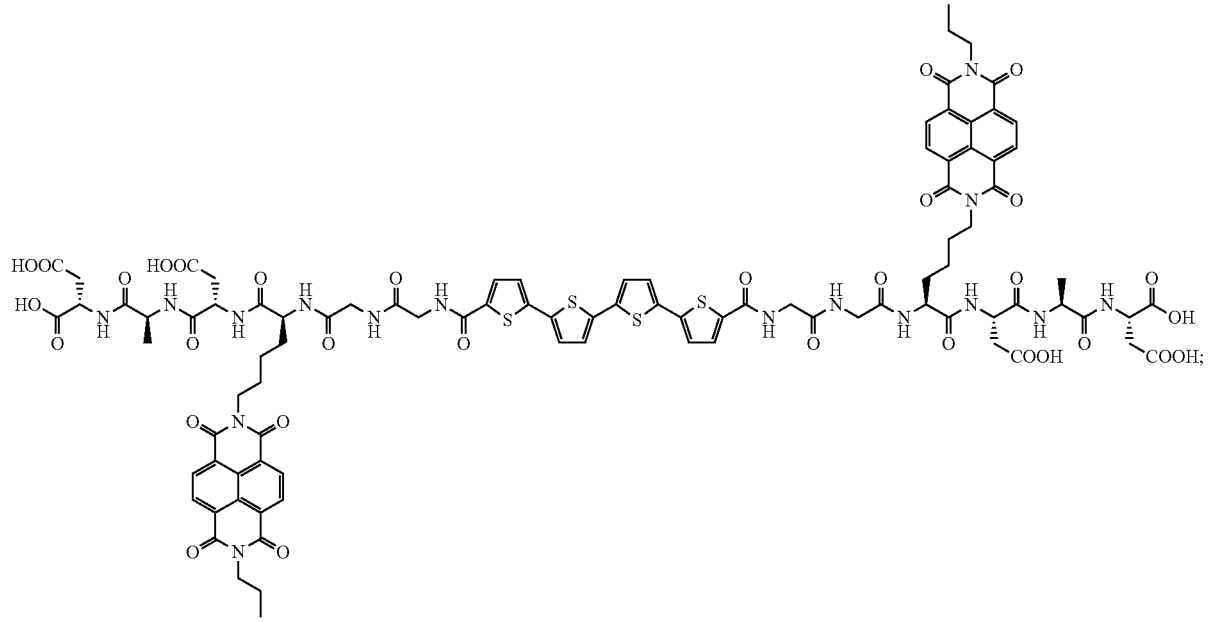

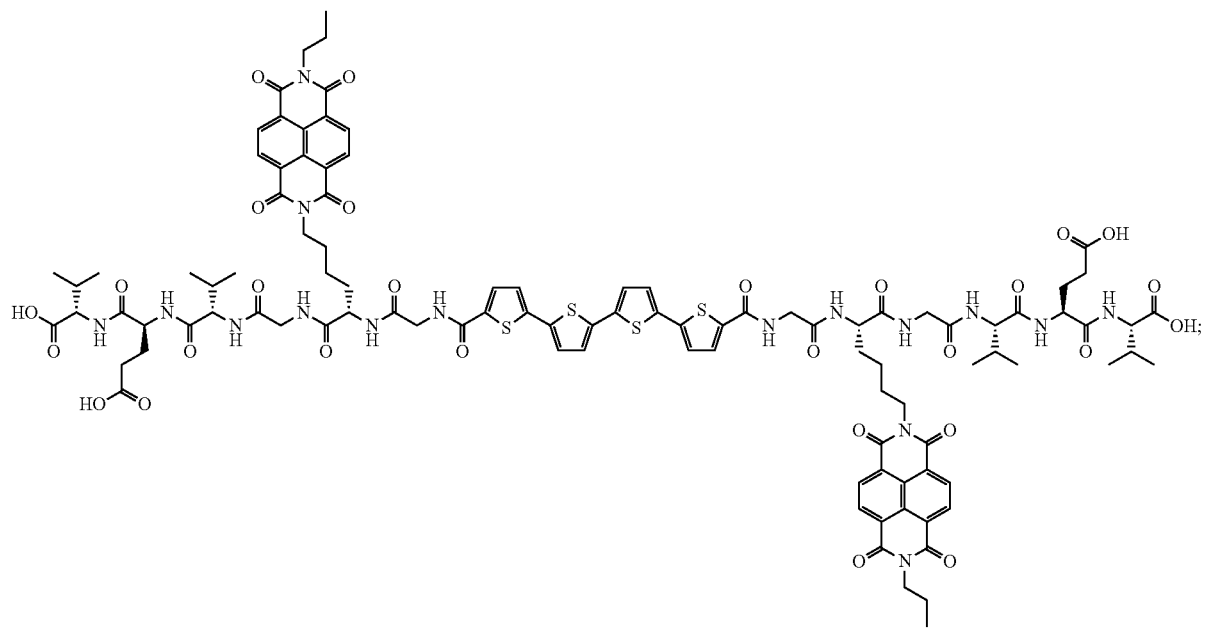

DA-2

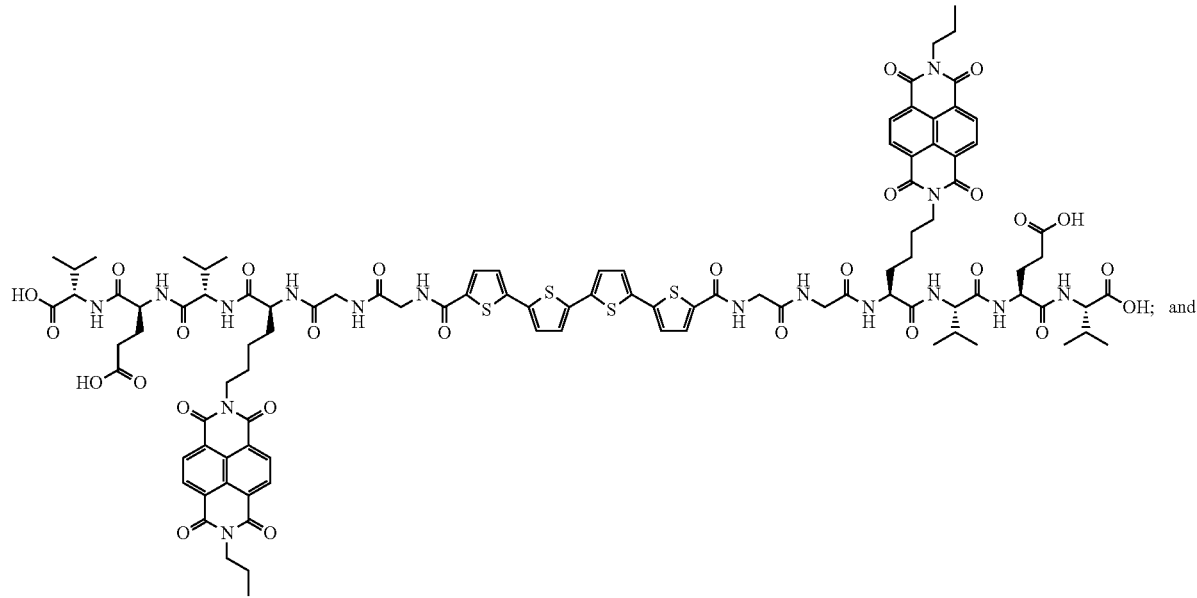

DA-3

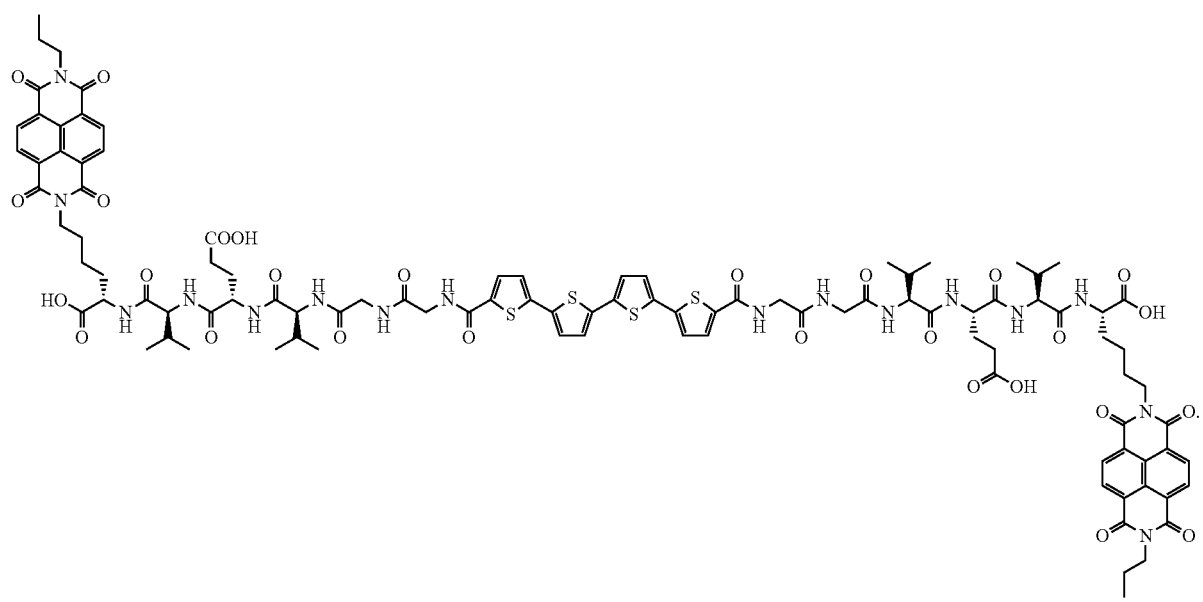

DA-6

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
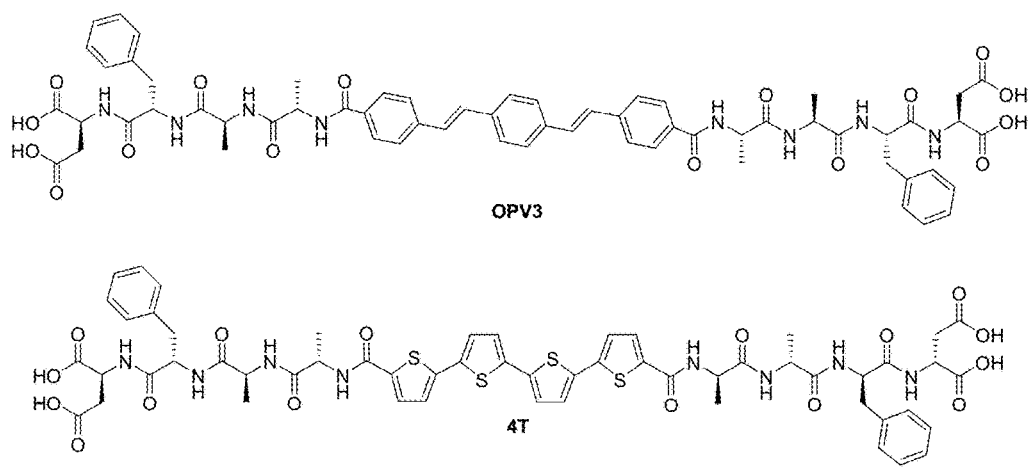
Figure 2A:
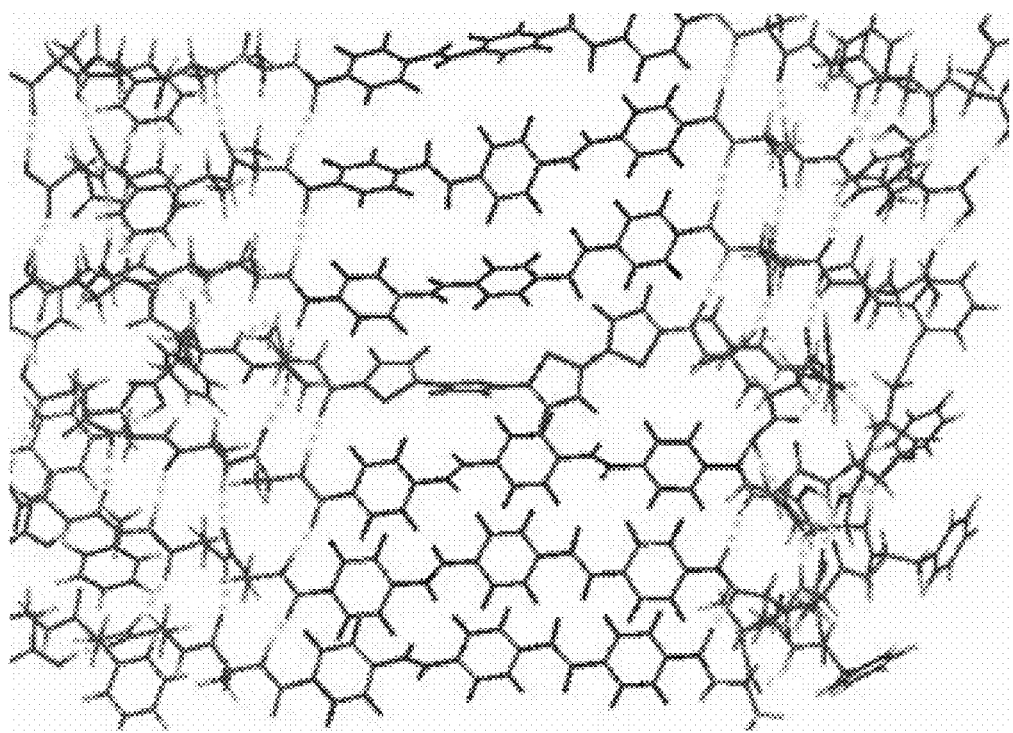
Figures 2B, 2C:
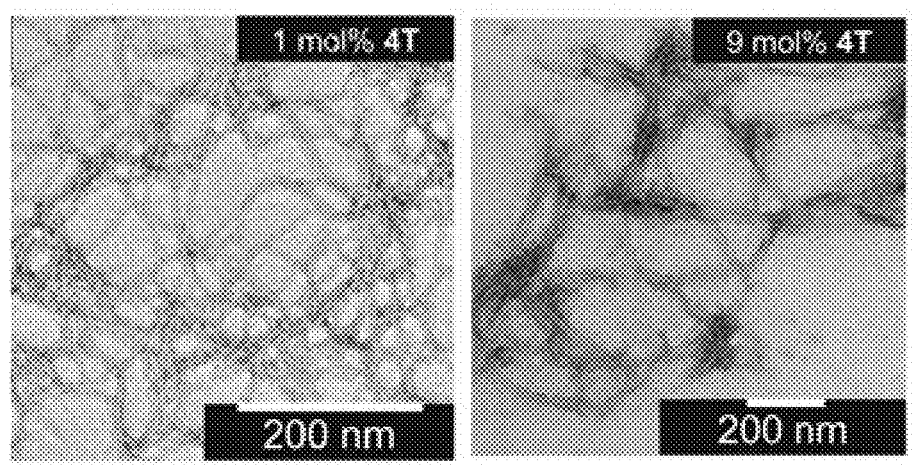
Figure 3A:
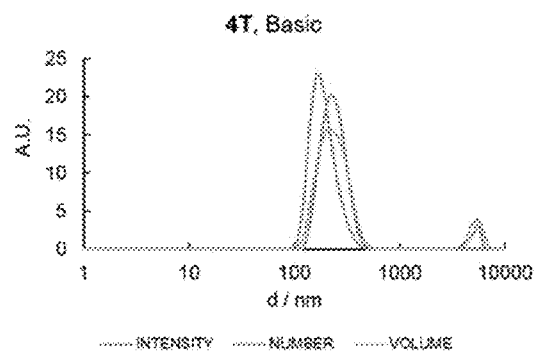
Figure 3B:
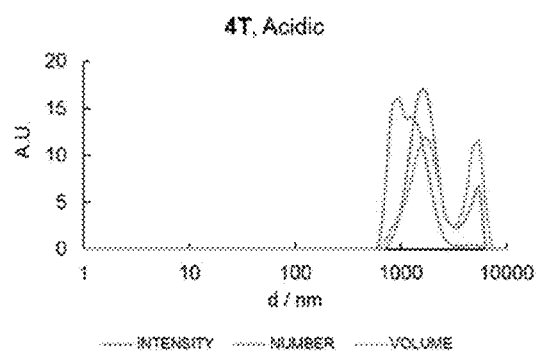
Figure 3C:
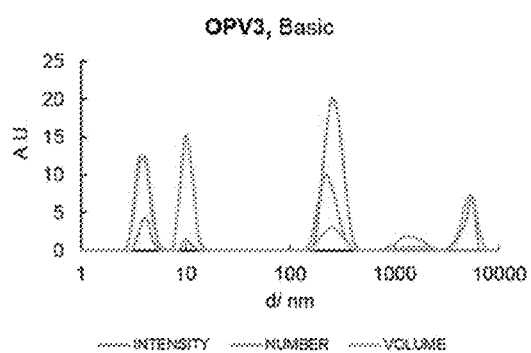
Figure 3D:
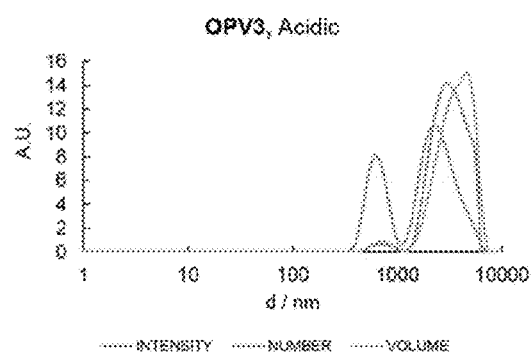
Figure 4G:
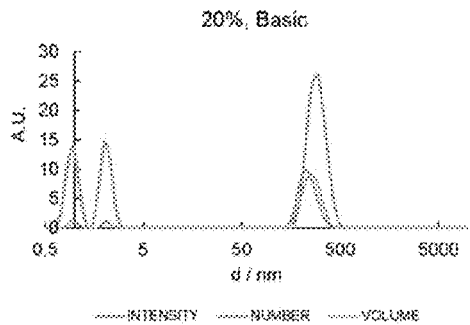
Figure 4H:
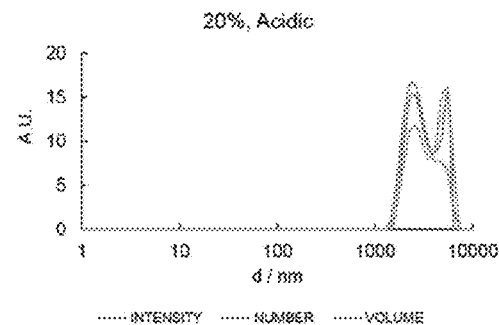
Figure 4I:
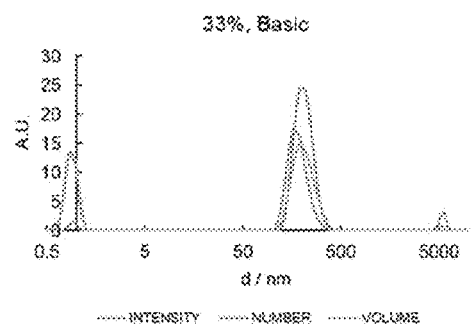
Figure 4J:
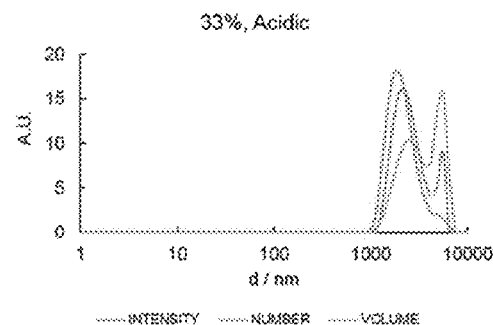
Figure 4K:
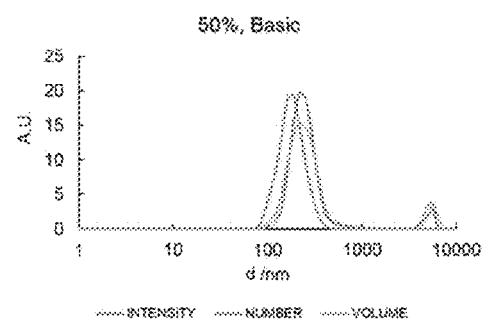
Figure 4L:
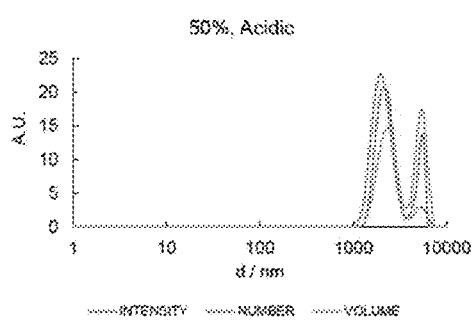
Figure 5A:
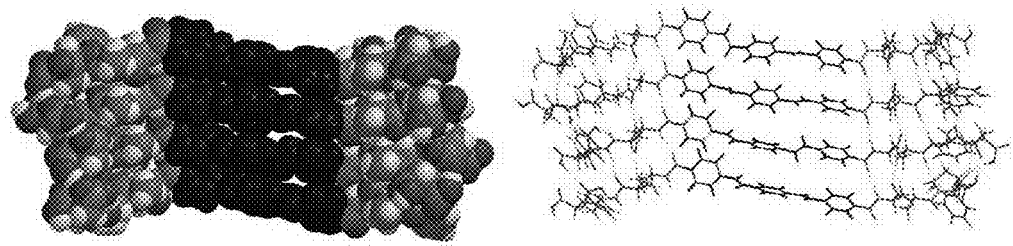
Figure 5B:
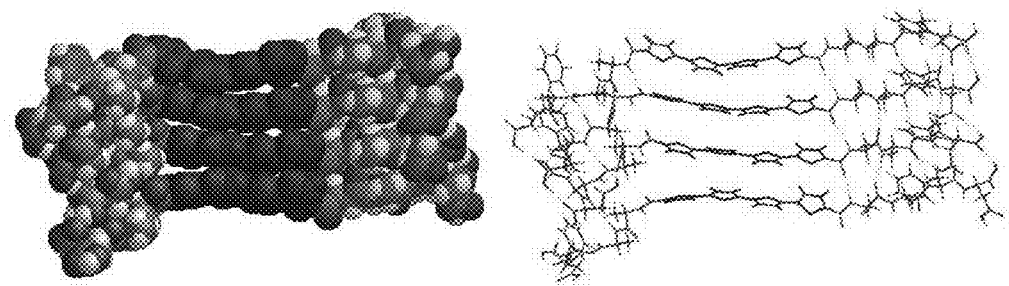
Figure 5C:
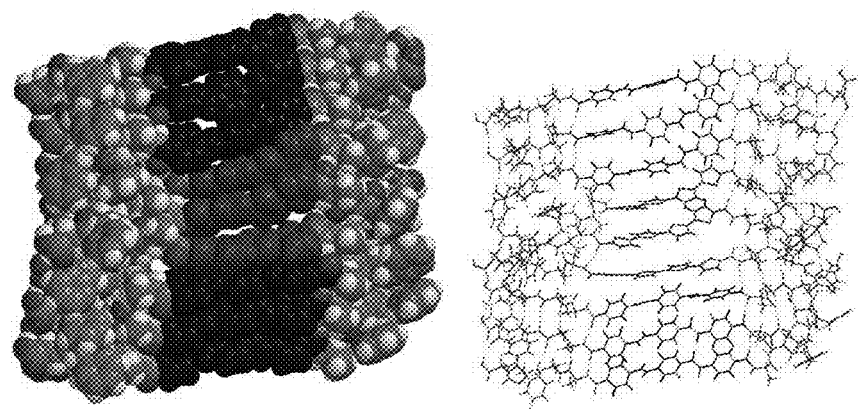
Figure 8A:
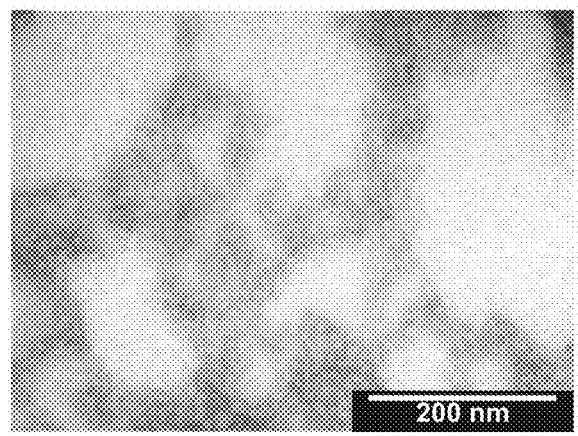
Figure 8B:
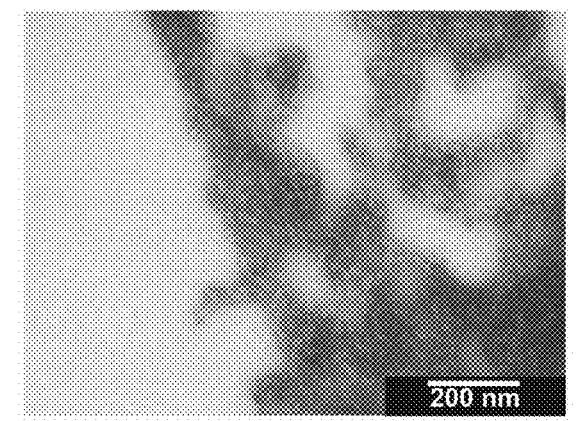
Figure 9A:
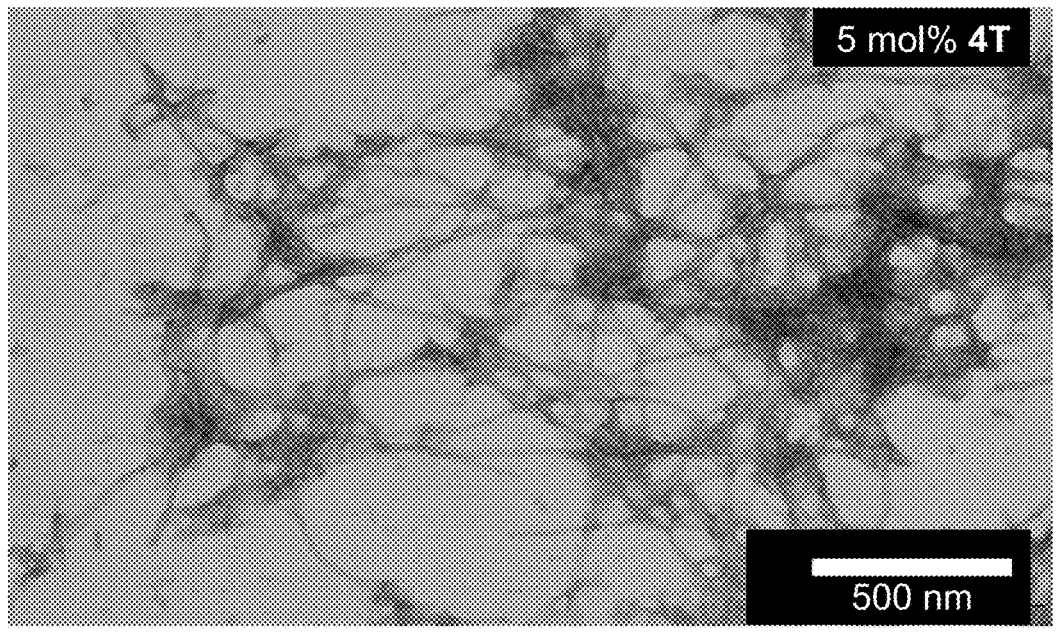
Figure 9B:
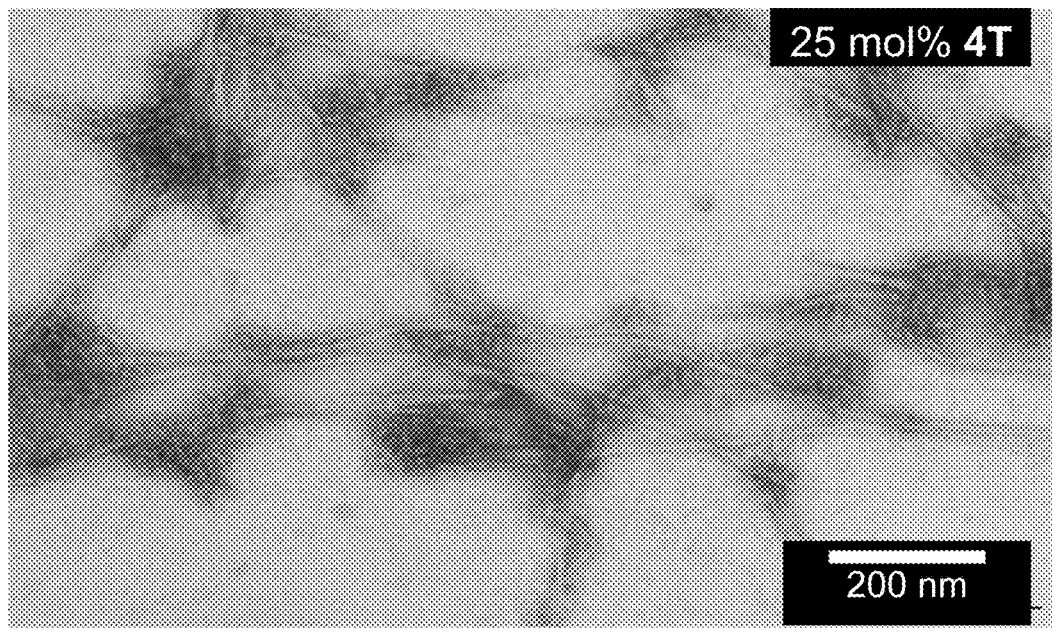
Figure 13:
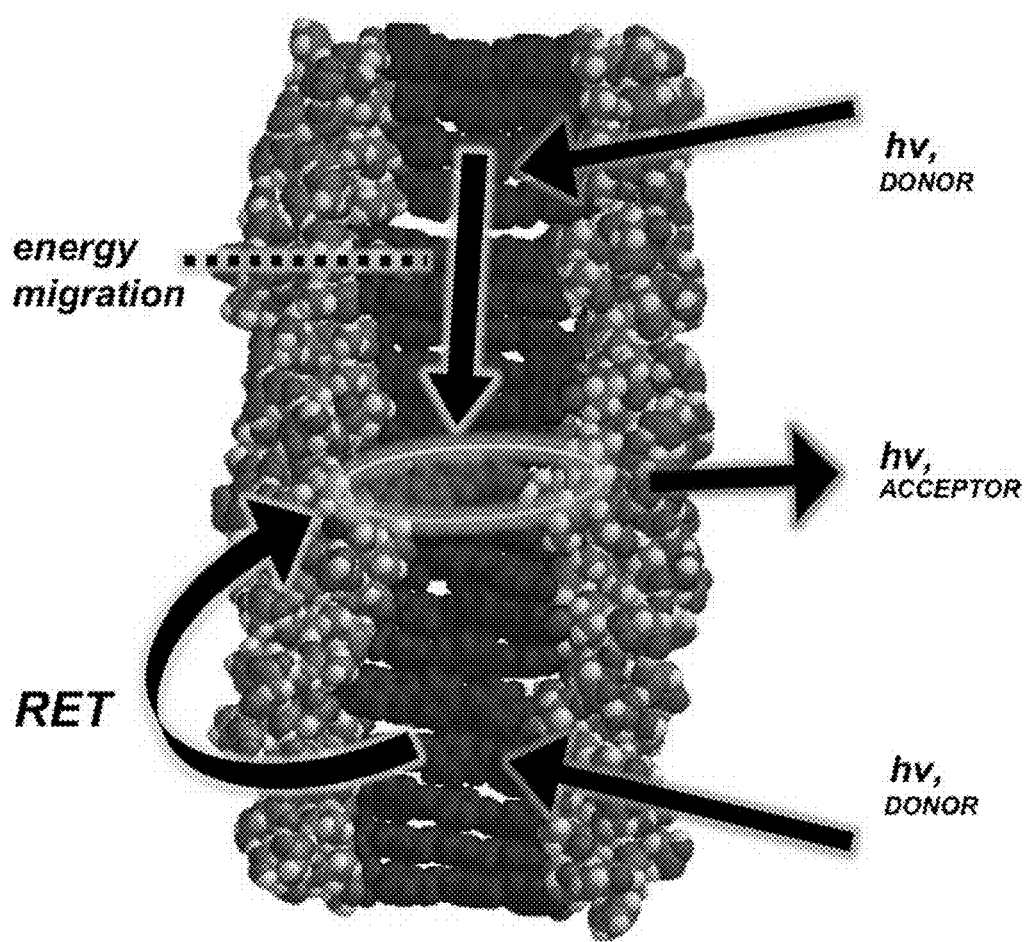
Figure 20:
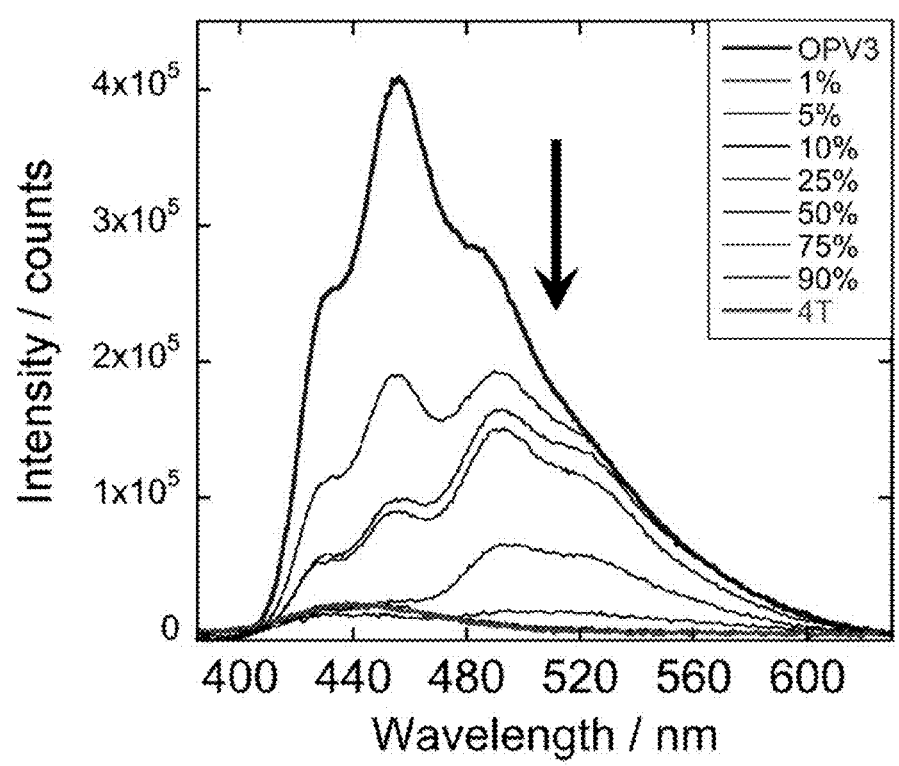
Figure 22A:
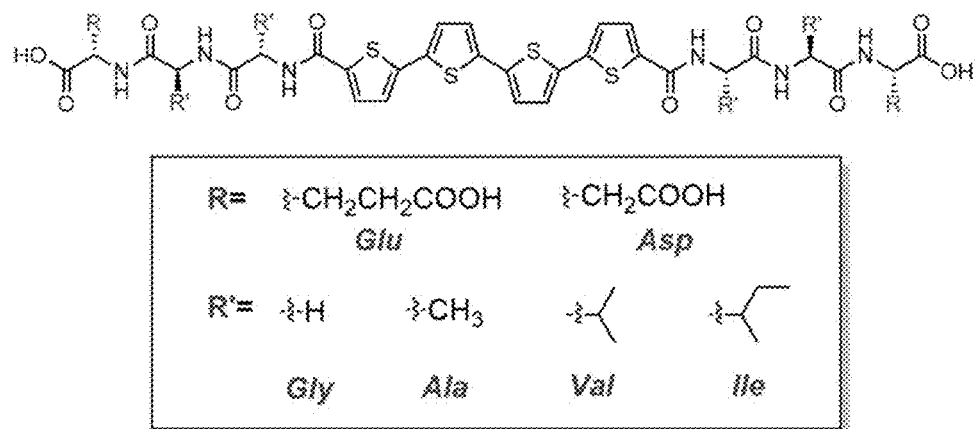
Figure 22B:
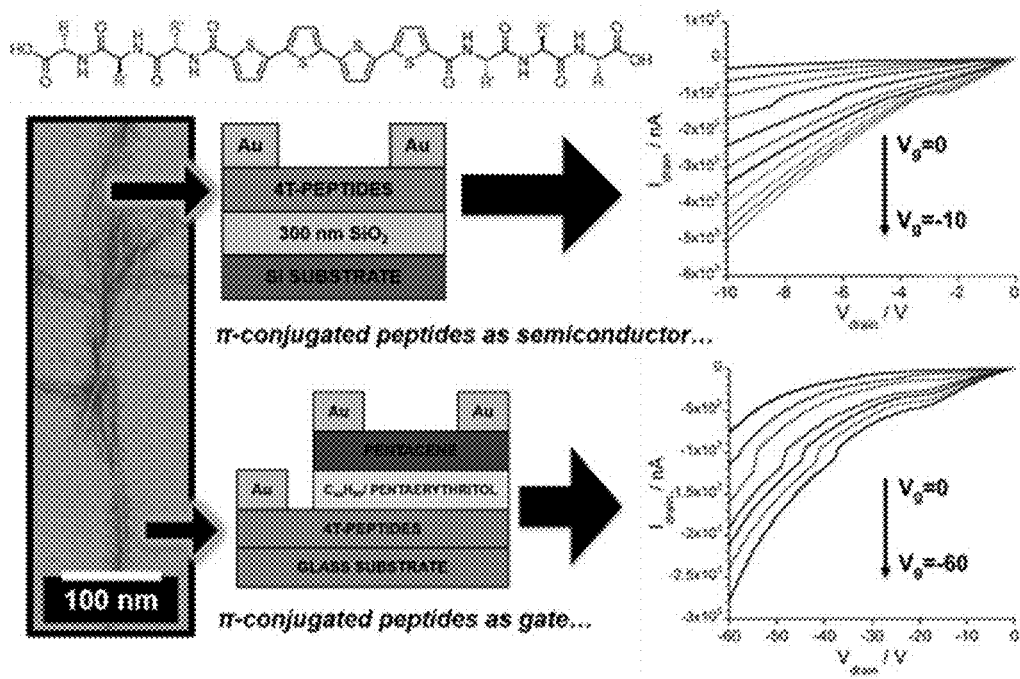
Figure 24A:
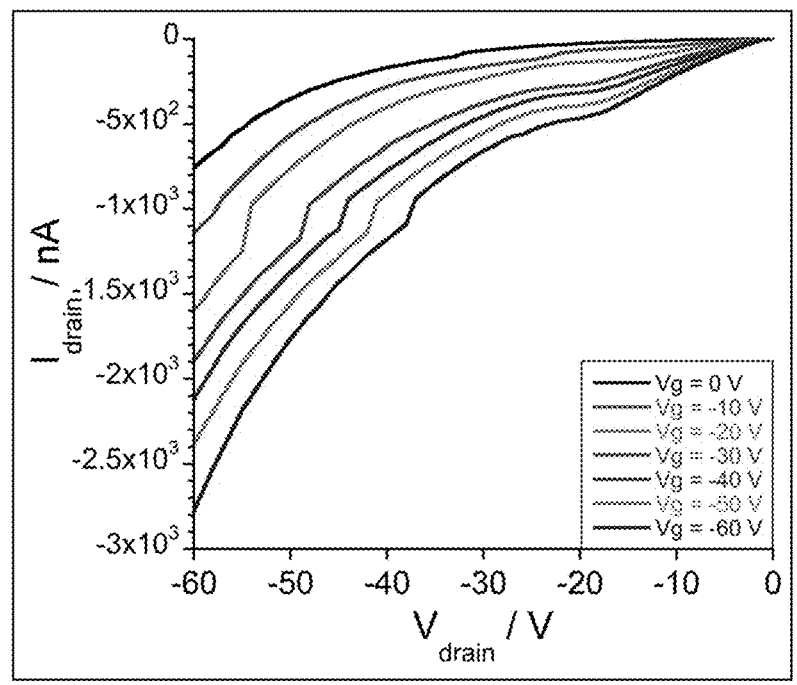
Figure 24B:
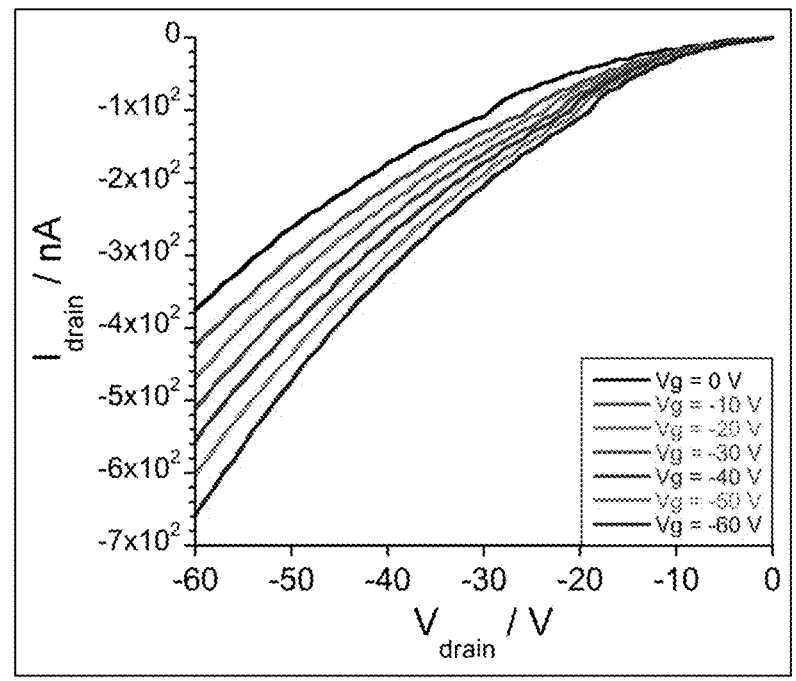
Figure 27A:
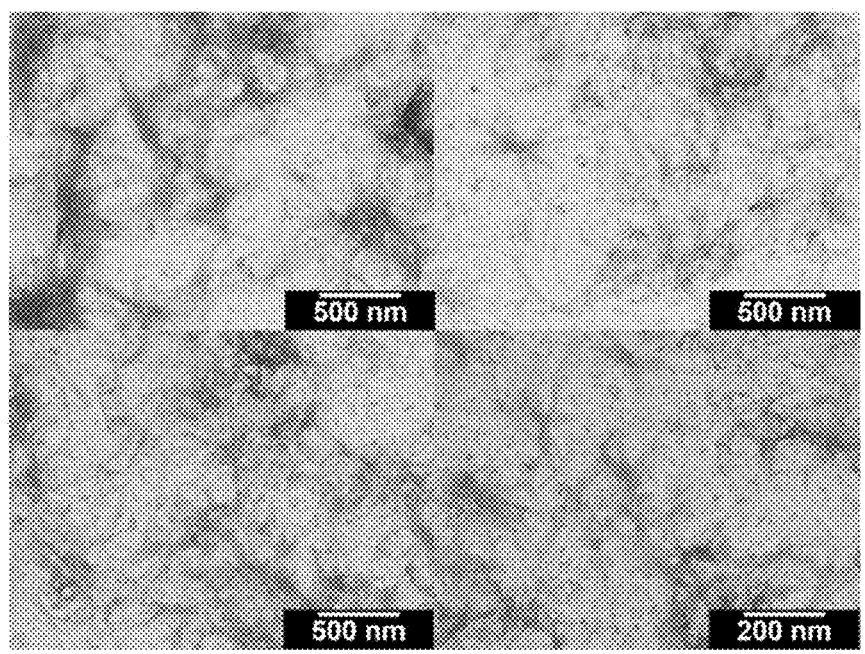
Figure 27B:
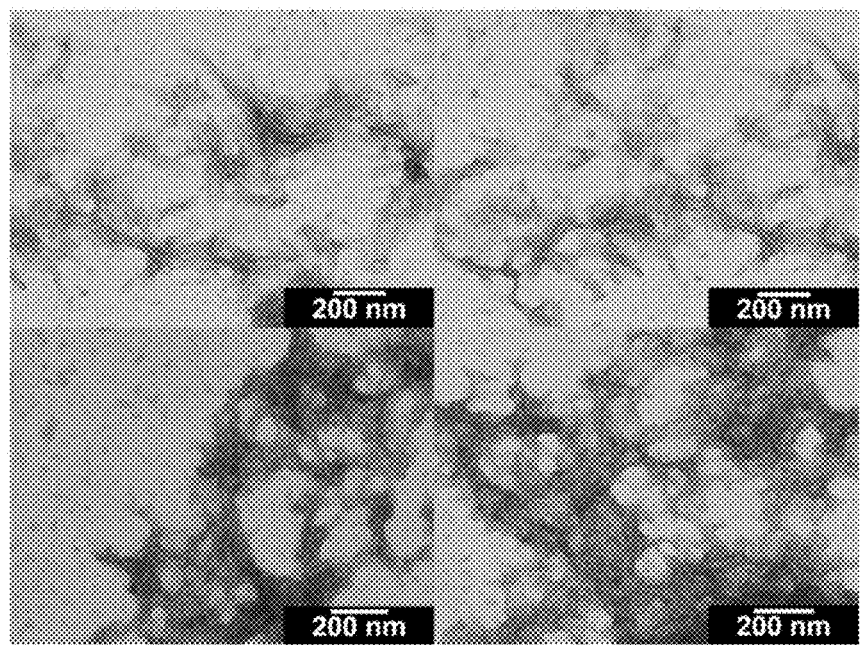
Figure 28A:
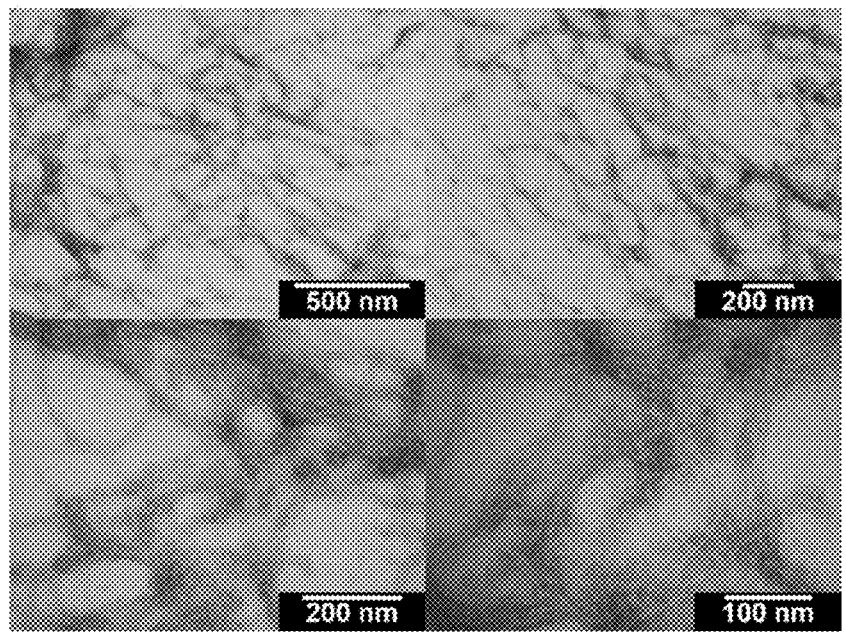
Figure 28B:
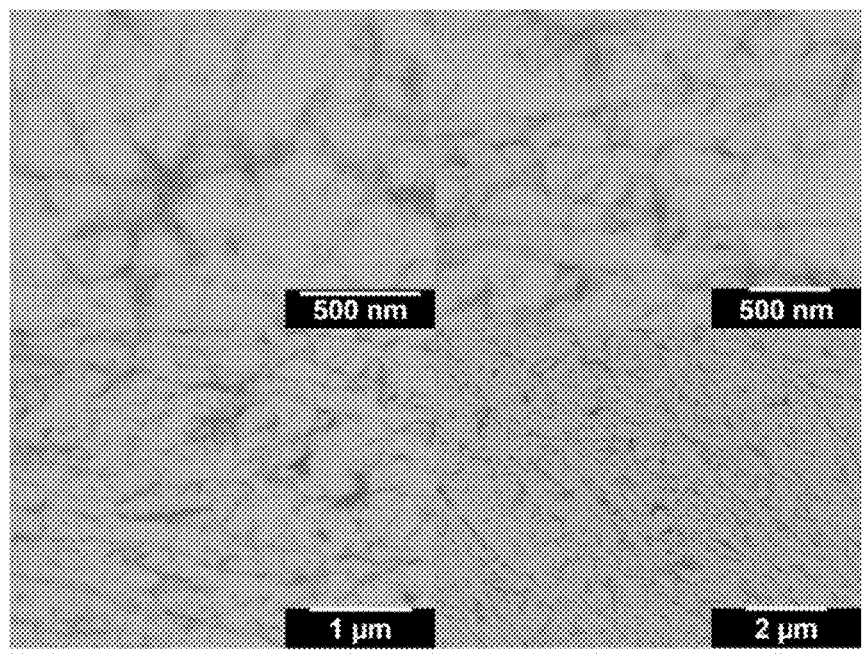
Figure 29A:
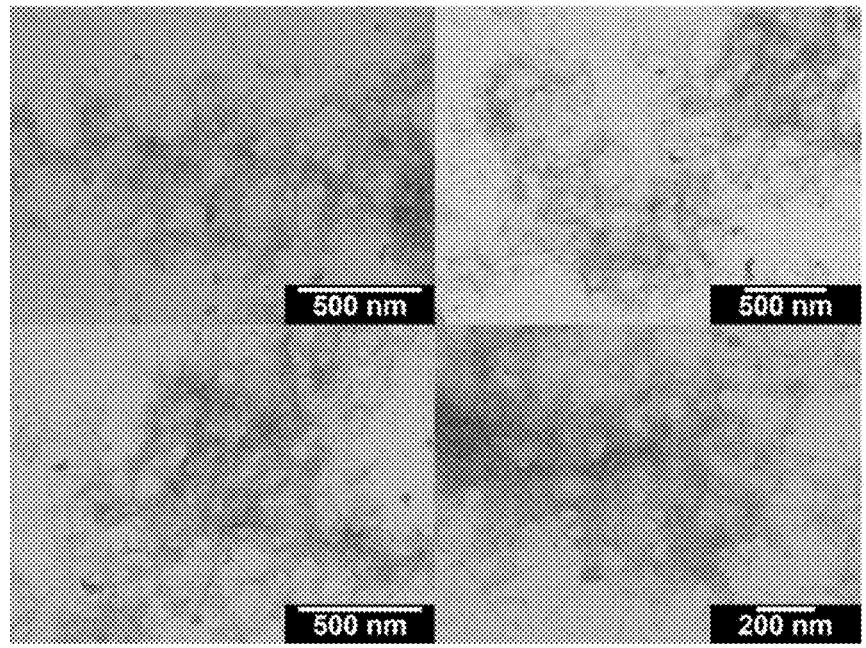
Figure 29B:
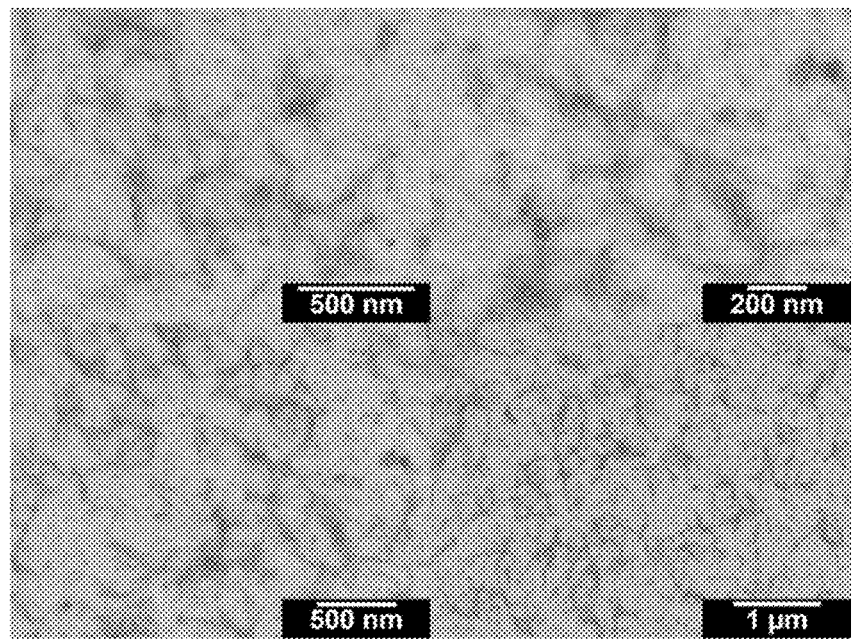
Figure 30A:
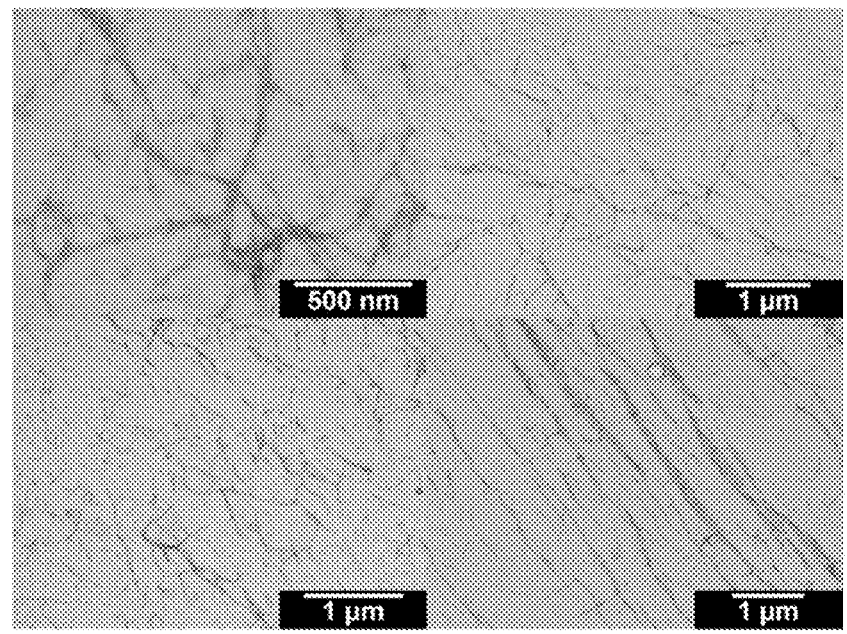
Figure 30B:
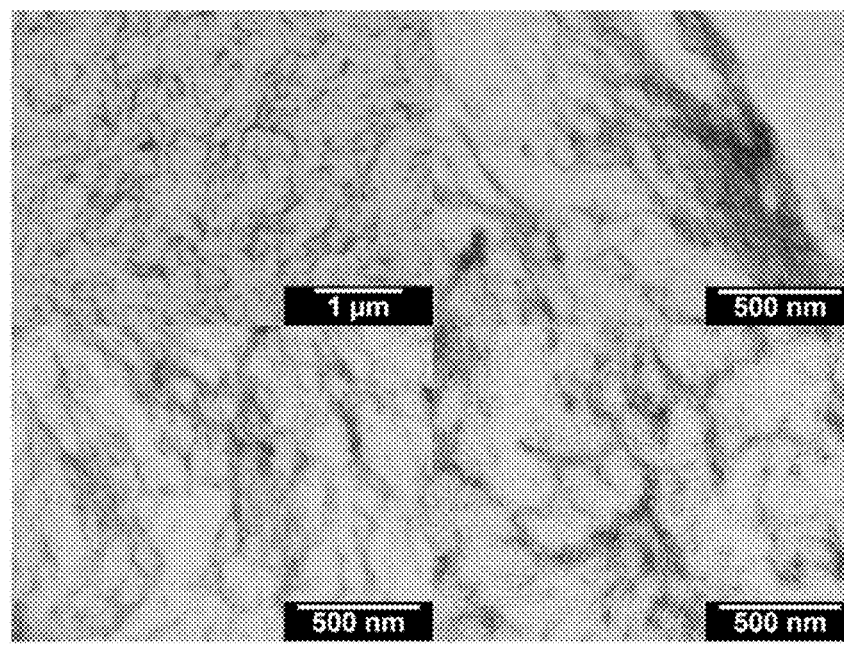
Figure 32:
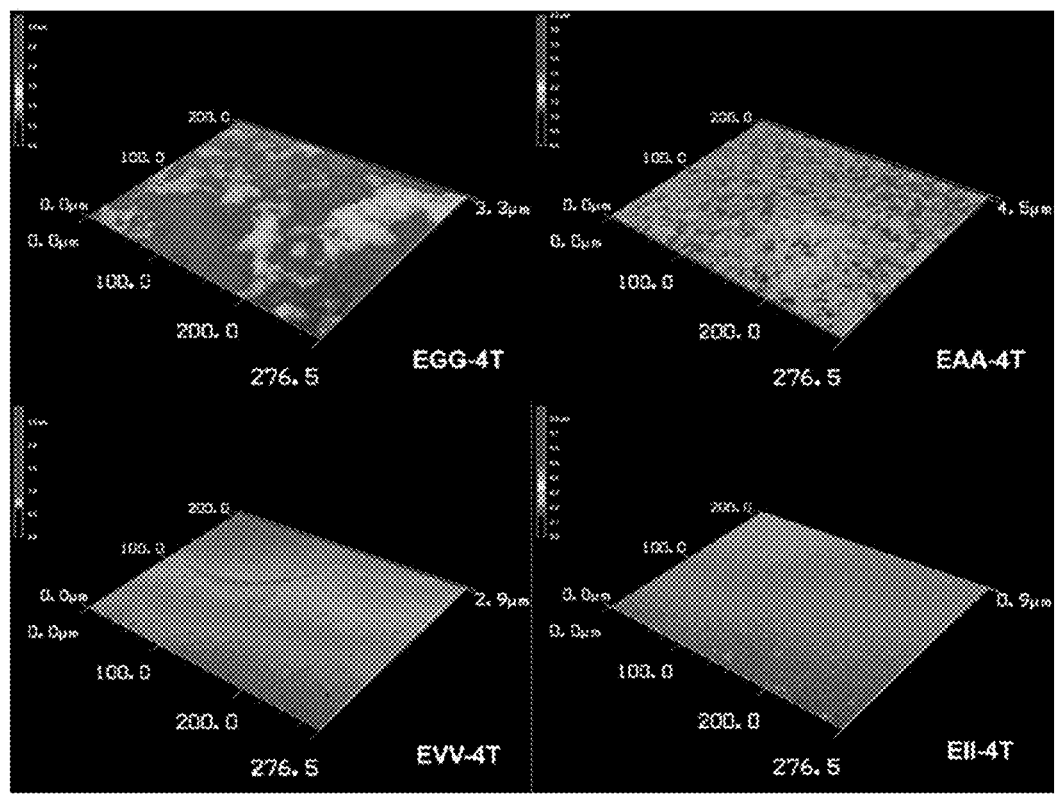
Figure 35A:
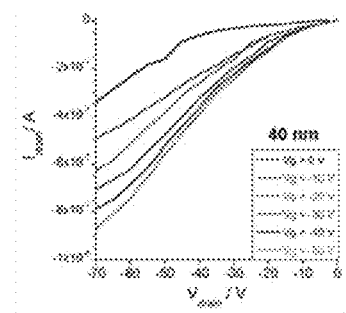
Figure 35B:
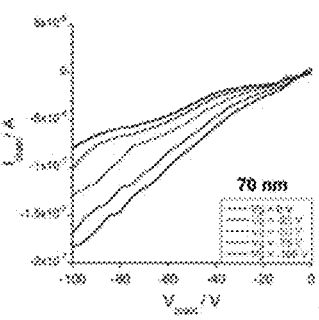
Figure 35C:
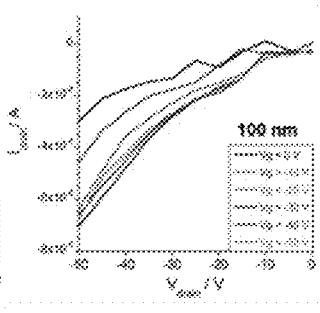
Figure 35D:
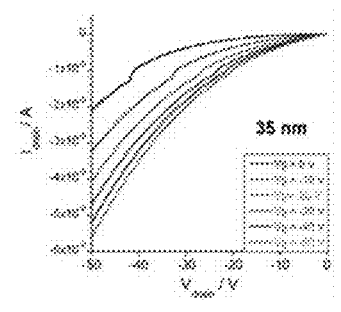
Figure 35E:
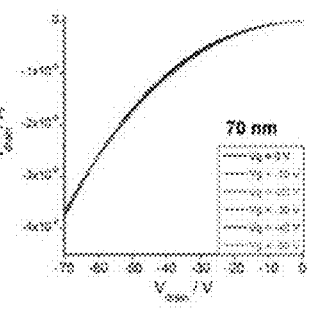
Figure 35F:
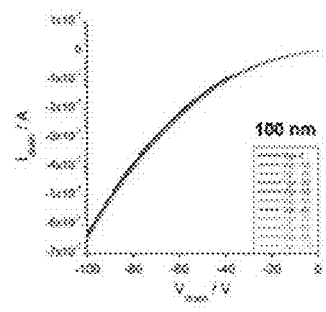
Figure 36A:
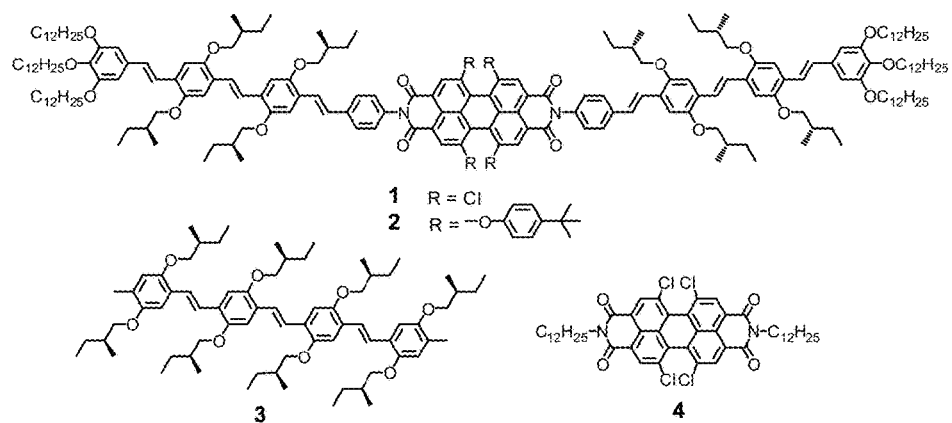
Figure 36B:
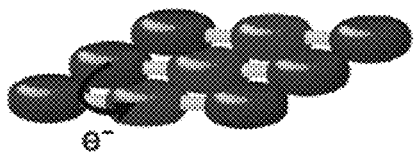
Figure 36C:
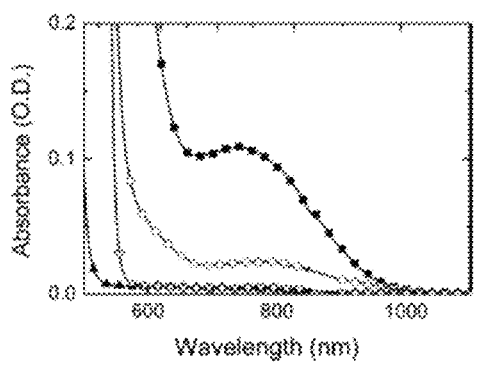
Figure 37A:
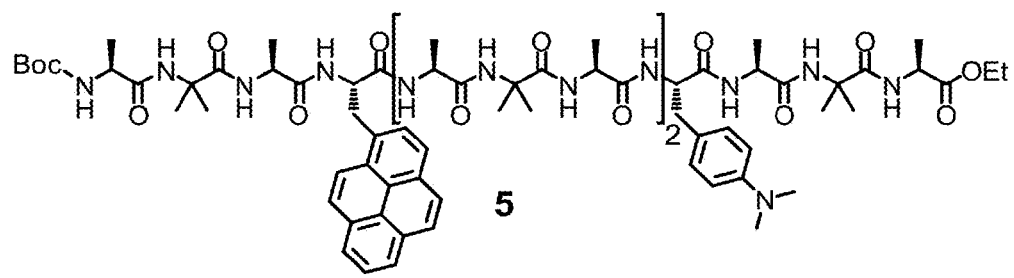
Figure 37B:
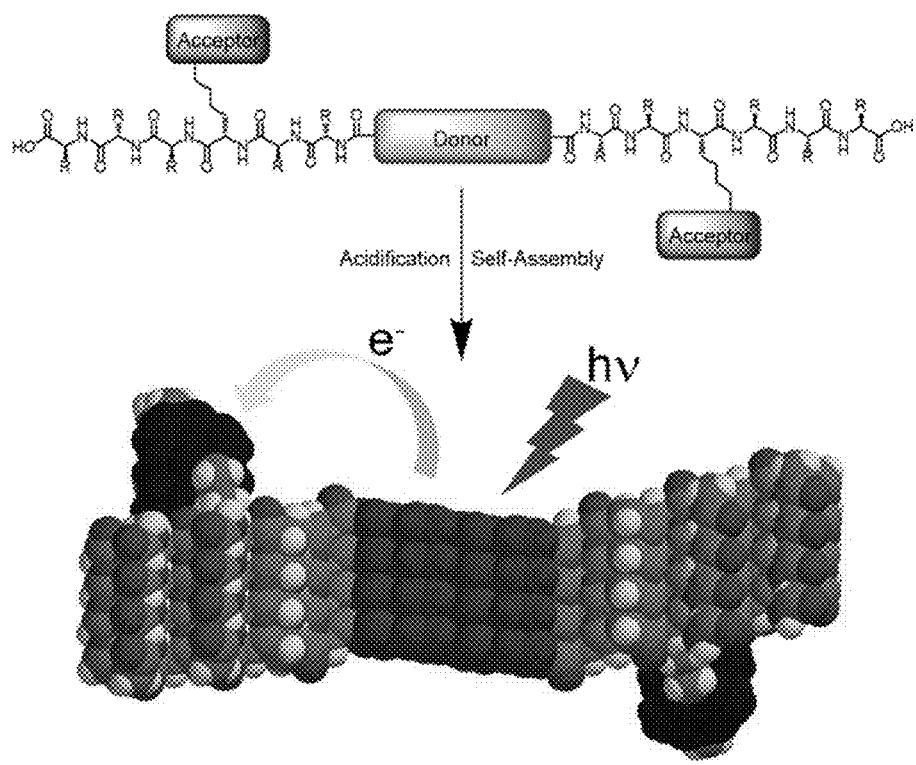
Figure 39:
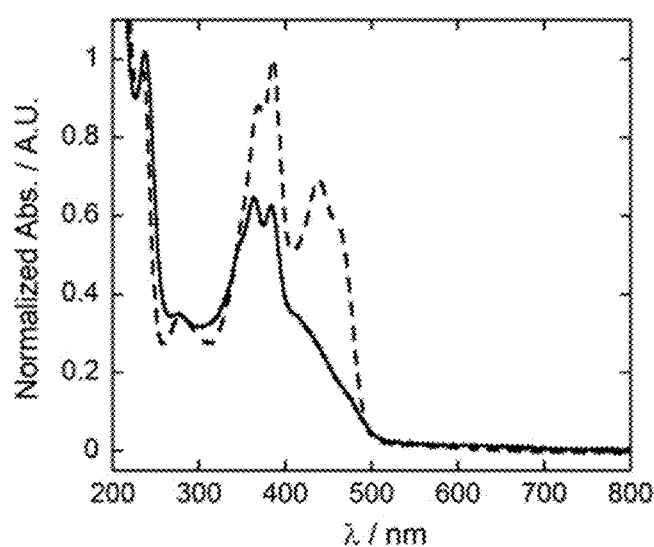
Figure 41A:
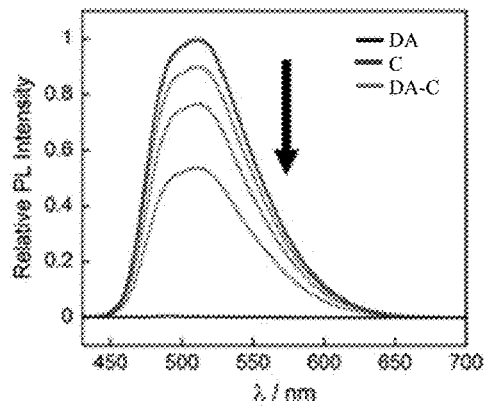
Figure 41B:
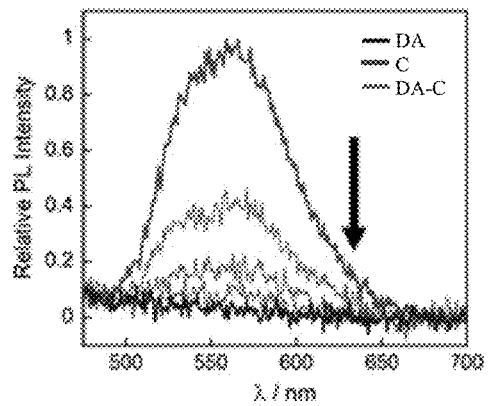
Figure 41C:
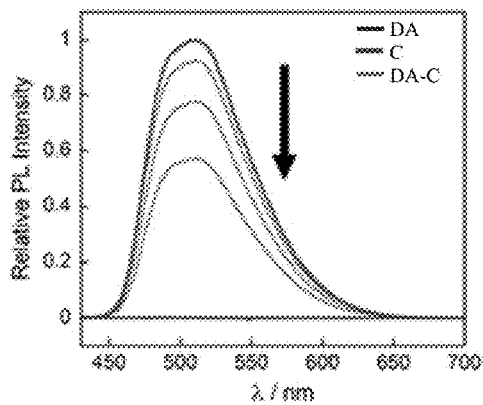
Figure 41D:
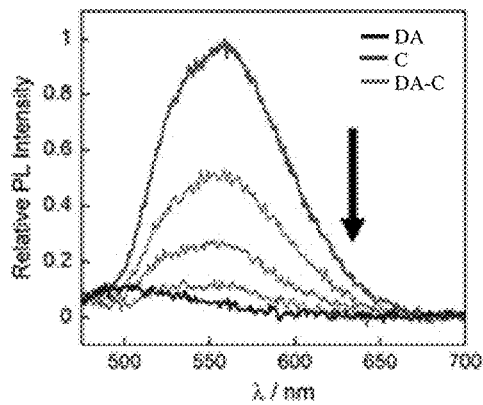
Figure 44:
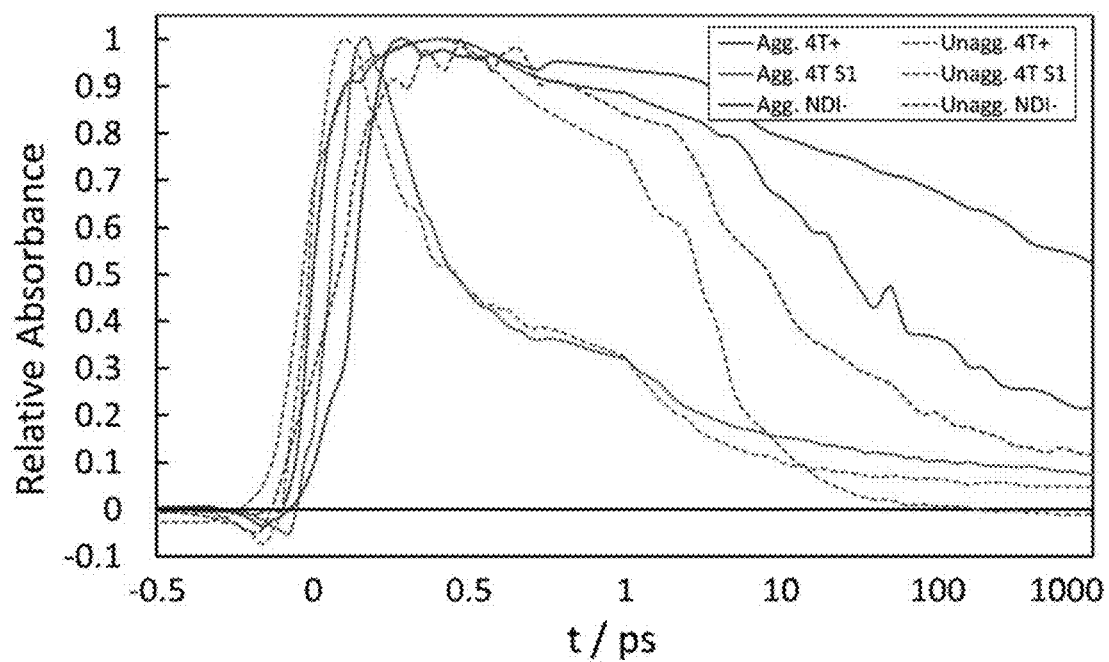
Figure 45A:
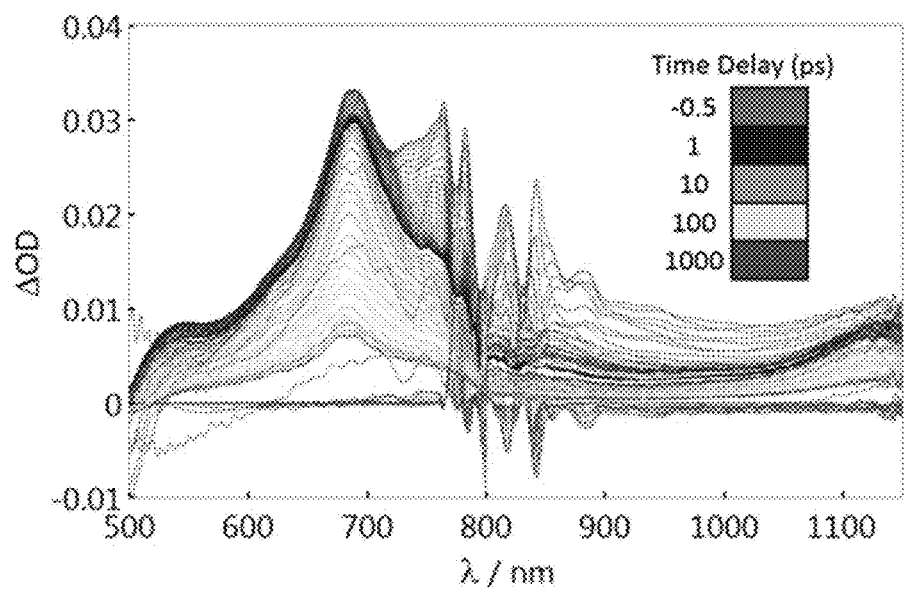
Figure 46:
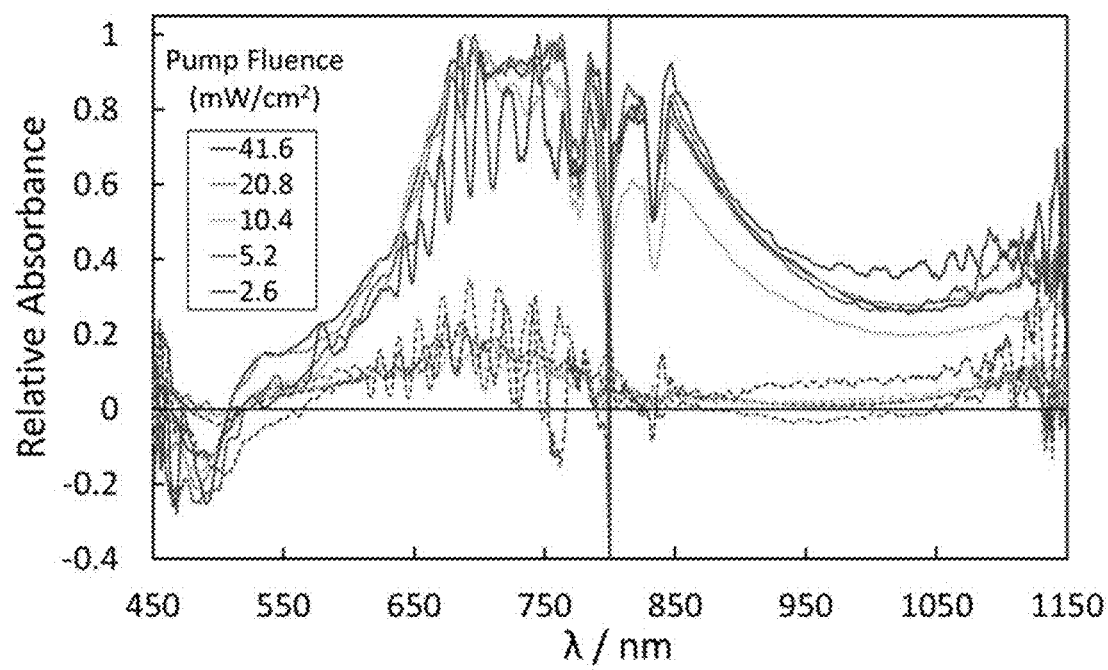
Figure 47A:
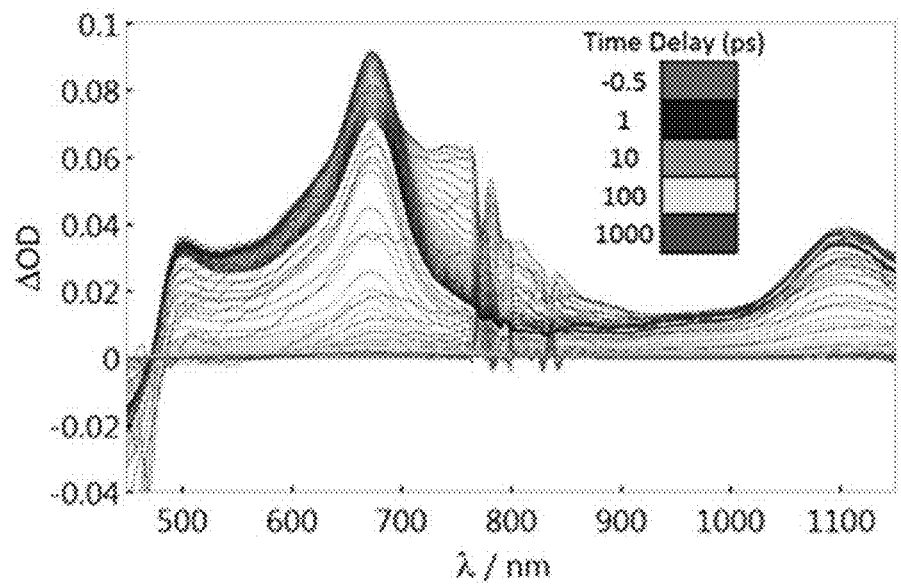
Figure 47B:
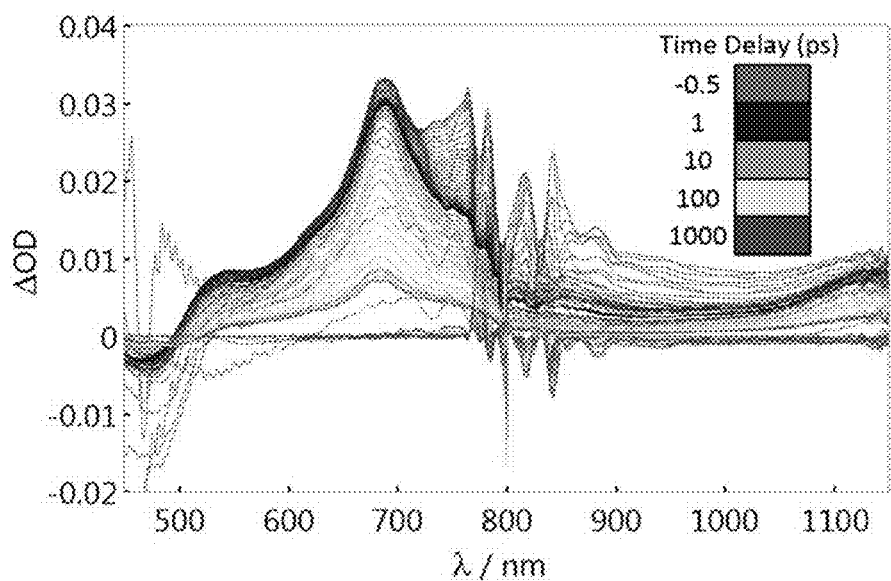
Figure 48A:
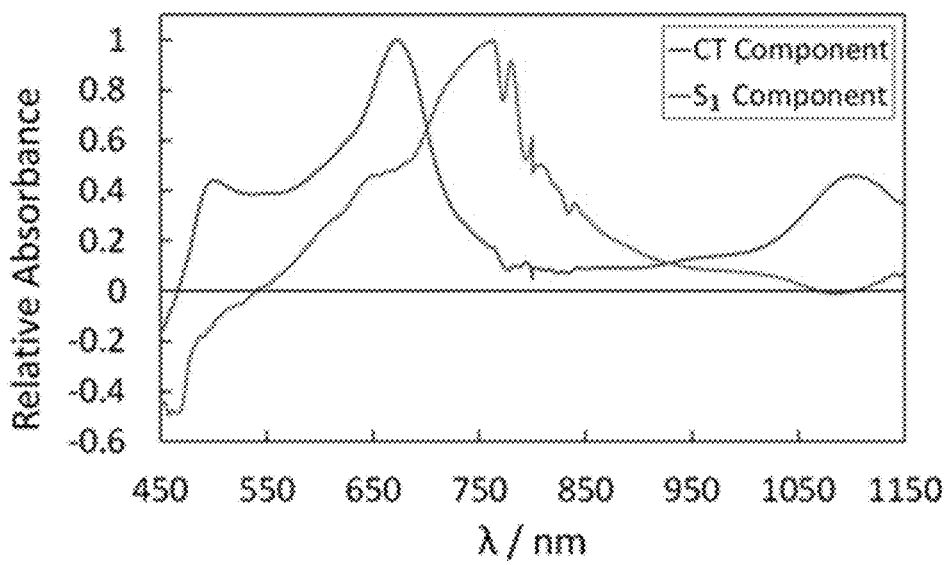
Figure 48B:
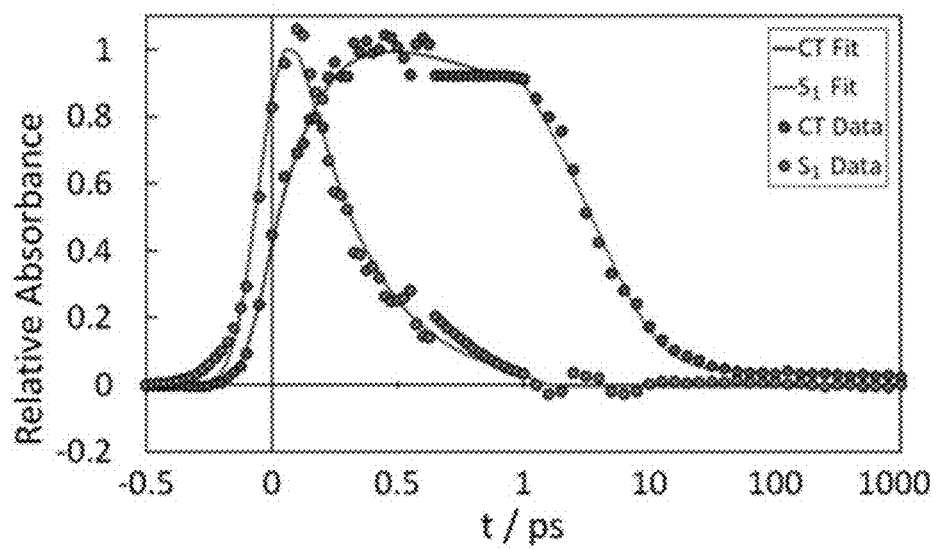
Figure 49A:
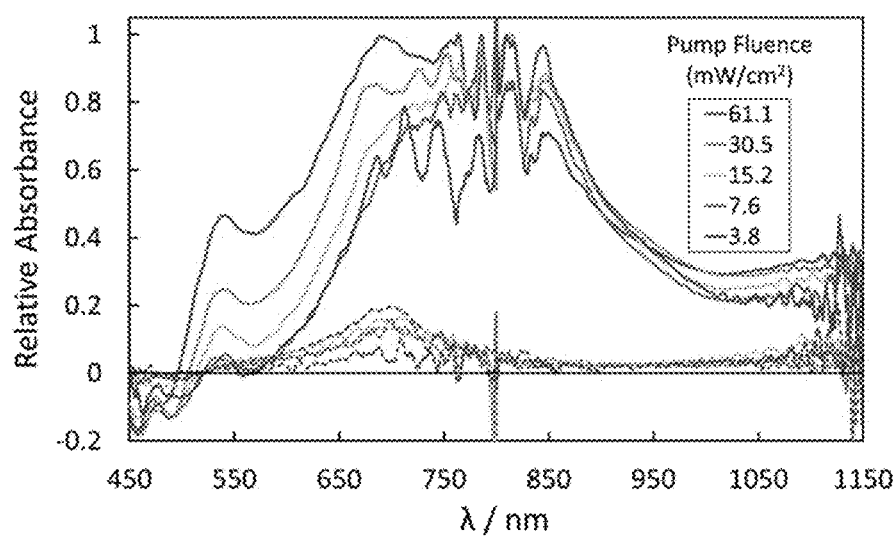
Figure 49B:
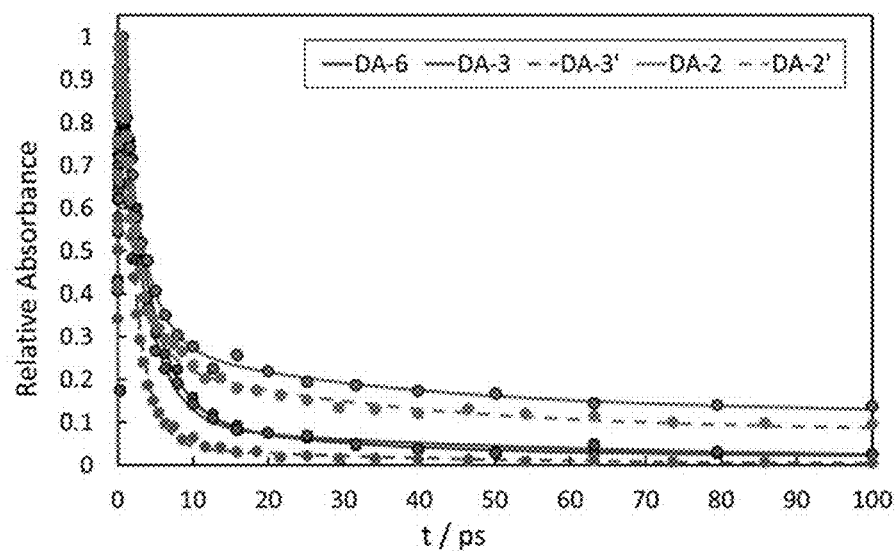
Figure 50A:
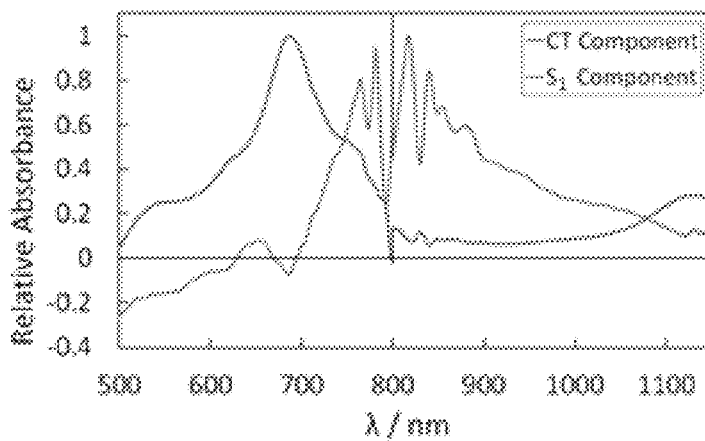
Figure 50B:
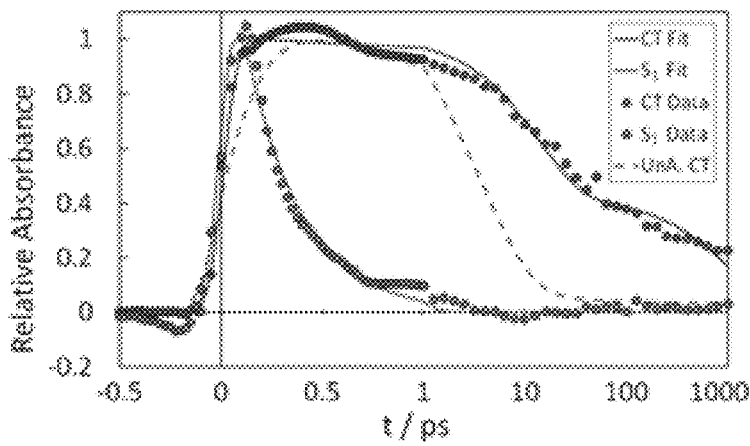
Figure 50C:
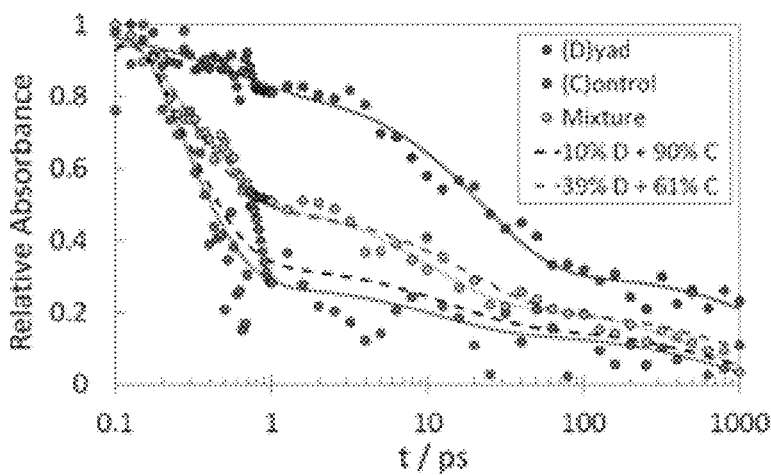

Having thus described the presently disclosed subject matter in general terms, reference will now be made to the accompanying Figures, which are not necessarily drawn to scale, and wherein:

FIG. 1 shows molecular structures of the DFAA-based OPV3 and 4T peptides disclosed herein;

FIG. 2A, FIG. 2B and FIG. 2C are: (A) energy-minimized assembly model for a hypothetical portion of an OPV3-4T heterostructure with a single isolated 4T unit within the OPV3 majority aggregate; TEM images (stained with 2% uranyl acetate) along with the observed widths of nanostructures formed from 0.1 wt % acidic, coassembled OPV3-4T solutions: (B) 1 mol % (5.6±0.64 nm) and (C) 9 mol % 4T (13.6±2.3 nm);

FIG. 3A, FIG. 3B, FIG. 3C, and FIG. 3D show dynamic light scattering data for 50 μM basic and acidic solutions of OPV3 and 4T;

FIG. 4A, FIG. 4B, FIG. 4C, FIG. 4D, FIG. 4E, FIG. 4F, FIG. 4G, FIG. 4H, FIG. 4I, FIG. 4J, FIG. 4K and FIG. 4L show dynamic light scattering data for 50 μM basic and acidic solutions of OPV3-4T coassemblies (x mol % 4T);

FIG. 5A, FIG. 5B and FIG. 5C show (A) energy-minimized assembly model for a hypothetical portion of a HO-(DFAA)$_2$-OPV3 assembly; (left) space-filling model and (right) wire structure showing H-bonds (---); (B) energy-minimized assembly model for a hypothetical portion of a HO-(DFAA)$_2$-4T assembly; (left) space-filling model and (right) wire structure showing H-bonds (---); (C) energy-minimized assembly model for a hypothetical portion of HO-(DFAA)$_2$-4T and -OPV3 heterostructure with multiple 4T units within the OPV3 majority aggregate; (left) space-filling model and (right) wire structure showing H-bonds (---);

FIG. 6A, FIG. 6B and FIG. 6C show ATR-IR spectra of lyophilized acidic solutions of (A) OPV3, 4T, and (B), (C) coassemblies;

FIG. 7A, FIG. 7B, FIG. 7C, and FIG. 7D are absorption spectra of OPV3, 4T, and their co-mixtures under basic (A) and acidic (B) conditions. Emission spectra (C) recorded at pH=10 (---, $\lambda_{exc}$=320 nm) and pH=2 (—, $\lambda_{exc}$=330 nm). For comparison, a direct excitation of 4T molecules and assemblies at 450 nm is shown in (C). [OPV3]=3.2 µM, [4T]=0.03-3.2 µM; arrows show trends as mol % 4T is increased. Relative quantum yields (D) of the OPV3-4T mixtures at pH=2 ($\lambda_{exc}$=330 nm);

FIG. 8A and FIG. 8B show representative TEM images showing the nanostructures from a 0.1 wt % acidic solution of 4T;

FIG. 9A and FIG. 9B show representative TEM images of the nanostructures from a 0.1 wt % acidic solution of coassembled OPV3-4T at different mol % 4T (widths: 5 mol % 4T=10.8±1.6 nm; 25 mol % 4T=13.0±2.3 nm);

FIG. 10A and FIG. 10B show representative TEM images of the nanostructures from a 0.1 wt % acidic solution of (A) coassembled OPV3-4T (1:1) and a solution wherein (B) 4T was added to pre-assembled OPV3 solution (1:1);

FIG. 11A, FIG. 11B, FIGS. 11C and 11D are photoluminescence (PL) spectra for OPV3 and 4T coassemblies (arrows indicate increasing mol % 4T) at different excitation wavelengths; solutions in (A) and (C) are at pH=10 (---), (B) and (D) at pH=2 (—);

FIG. 12A, FIG. 12B, FIGS. 12C, 12D and 12E show emission spectra (pH=10, $\lambda_{exc}$=320 nm (A); pH=2, $\lambda_{exc}$=330 nm, 4T at 450 (B) of OPV3, 4T, and their coassemblies; these are the same solutions used in FIG. 7A, FIG. 7B, FIG. 7C and FIG. 7D, showing all OPV3:4T coassembly ratios considered; arrow indicates the general trend as mol % 4T increases; UV-Vis (C,D) and PL (E) spectra for OPV3:4T mixtures, keeping the overall chromophore concentration constant under (C) acidic and (D) basic conditions; pH=10 (---), (D) and (C) at pH=2 (—); arrow indicates the general trend as mol % 4T increases;

FIG. 13 is a space-filling, energy-minimized model of 4T coassembled within 1D-stacks of OPV3, illustrating the possible energy transfer processes;

FIG. 14A, FIG. 14B, FIG. 14C, FIG. 14D and FIG. 14E are (A) PL spectra ($\lambda_{exc}$=330 nm) of resulting solutions from titrating 4T to a pre-assembled OPV3 acidic solution (arrows indicate increasing mol % 4T); (B) their corresponding relative quantum yields with respect to the pure OPV3 donor; (C,D,E) emission spectra of acidic and annealed* HO-(DXX)$_2$-4T hydrophobic peptides;

FIG. 15A, FIG. 15B, FIG. 15C and FIG. 15D are UV-Vis (A,B) and PL (C,D) spectra of (A,C) re-basified ($\lambda_{exc}$=320 nm) and (B,D) reacidified solutions used in FIG. 7A and FIG. 7C ($\lambda_{exc}$=330 nm); pH=10 (---), pH=2 (—); arrows indicate increasing mol % 4T;

FIG. 16A, FIG. 16B, FIG. 16C and FIG. 16D show emission spectra of coassembled OPV3-4T acidic solutions, excited at 370 nm (A) and 450 nm (B); arrows indicate increasing mol % 4T; these are the same acidic solutions used in FIG. 11, showing the absorption and emission spectra of all OPV3:4T coassembly ratios considered; plots showing the spectral overlap between the donor emission and acceptor absorbance for basic (C) and (D) acidic solutions;

FIG. 17A, FIG. 17B, FIG. 17C, FIG. 17D, and FIG. 17E show monitoring of the emission $\lambda_{exc}$=330 nm during the thermal cycling process for acidic samples of (A) OPV3 and (B) 9 mol % 4T solutions; acidic samples (bold line) were heated to 80° C. for 30 minutes, readings taken at ca. 60-70° C. and then cooled back to room temperature (thin line); arrows indicate increasing time of cooling within 4 hours; base was then added to these annealed samples and were then reacidified (broken line); [OPV3]=3.2 µM; lifetime decay profile of OPV3 and coassemblies under (C) basic (pH 10) and (D), (E) acidic (pH 2) conditions;

FIG. 18A, FIG. 18B, and FIG. 18C show CD spectra of (A) acidic (—; pH 2), basic (---; pH 10), and (B) annealed OPV3-4T coassembled solutions [OPV3]=3.2 µM; arrows indicate increasing mol % 4T; (C) the emission spectra ($\lambda_{exc}$=330 nm) of a solution wherein 4T was titrated with acidic, pre-assembled OPV3; arrow indicates increasing mol % 4T; these are the same acidic solutions used in FIG. 14A and FIG. 14B, showing all OPV3:4T coassembly ratios considered;

FIG. 19A, FIG. 19B, FIG. 19C, and FIG. 19D show reversibility of structure formation using pH control, different $\lambda_{exc}$; emission spectra when the re-basified (A,C) and reacidified (B,D) solutions are excited at different wavelengths; these are the same solutions used in FIG. 15A, FIG. 15B, FIG. 15C and FIG. 15D, showing all OPV3:4T coassembly ratios considered; arrows indicate increasing mol % 4T;

FIG. 20 shows titration with annealed samples; PL spectra ($\lambda_{exc}$=375 nm) of annealed, acidic samples ([OPV3]=7.4 µM); arrow indicates the trend as mol % 4T increases;

FIG. 21A FIG. 21B, and FIG. 21C show PL monitoring of acidic OPV3, 9 mol % 4T and 4T solutions during the thermal cycling process ($\lambda_{exc}$=(A) 370 nm; (B) 450 nm); (C) showing 4T emission when excited at 450 nm, including multiple time points during the 4 h-cooling process;

FIG. 22A and FIG. 22B show (A) molecular structures of the 4T bis(peptides) used for OFET devices reported herein; and (B) representative OFET devices reported herein;

FIG. 23A, FIG. 23B, FIG. 23C and FIG. 23D show (A) schematic of the OFET architecture used to measure the hole mobilities within the peptide nanostructures; (B) control compounds used as the active layer replacing 4T-peptides in the configuration shown in (A); (C) and (D) schematic diagrams of the OFET devices with peptide nanostructures as the gate;

FIG. 24A and FIG. 24B are (A) output curves of a presently disclosed OFET with DAA-4T as the Gate electrode in the configuration shown in FIG. 23C and FIG. 23D; (B) output curves of a presently disclosed OFET with control peptide 2 as the Gate electrode;

FIG. 25A, FIG. 25B and FIG. 25C show (A) Absorption, (B) emission ($\lambda_{exc}$=nm) (~14 µM), and (C) circular dichroism spectra (~6 µM) of 4T-peptides in basic (ca. pH 10, ---) and acidic solutions (ca. pH 2, —); for the emission spectra, peptides were normalized with respect to EVV and the basic spectrum was arbitrarily set to the same intensity as EVV;

FIG. 26A, FIG. 26B, FIG. 26C and FIG. 26D show AFM image of 0.1 mg/mL dropcast film of assembled EAA-4T peptide, (A) height and (B) phase profiles; (C) TEM image of 1 mg/mL solution of acidified EAA-4T solution (width=8.9±2.4 nm); (D) surface profile of a 10 mg/mL dropcast film of EAA-4T under a laser microscope;

FIG. 27A and FIG. 27B show (A) TEM images of 1 wt % DGG-4T peptide gel; (B) TEM images of 1 wt % DAA-4T peptide gel;

FIG. 28A and FIG. 28B show (A) TEM images of 1 wt % DVV-4T peptide gel; (B) TEM images of 1 wt % DII-4T peptide gel;

FIG. 29A and FIG. 29B show (A) TEM images of 1 wt % EGG-4T peptide gel; (B) TEM images of 1 wt % EAA-4T peptide gel;

FIG. 30A and FIG. 30B show (A) TEM images of 1 wt % EVV-4T peptide gel; (B) TEM images of 1 wt % EII-4T peptide gel;

FIG. 31A, FIG. 31B and FIG. 31C show representative AFM image for acidified 0.1 mg/mL EVV-4T dropcast film; height (A) and phase (B) profiles; (C) 3D surface profiles of 1 wt % DXX-4T peptide films generated from laser microscopy observations;

FIG. 32 shows 3D surface profiles of 1 wt % EXX-4T peptide films generated from laser microscopy observations;

FIG. 33A, FIG. 33B and FIG. 33C show (A) TEM images of 0.1 wt % solution of DVV C10 peptide; output curves for devices with 1 wt % EAA-4T as gate, 40-nm pentaerythritol as dielectric; (B) PQT-12 (poly(3,3'''-didodecylquaterthiophene)) and (C) pentacene as the semiconducting layer;

FIG. 34A, FIG. 34B, FIG. 34C, FIG. 34D, FIG. 34E and FIG. 34F shows output curves for OFET devices with the 4T bis(peptides) as the semiconductor active layers;

FIG. 35A, FIG. 35B, FIG. 35C, FIG. 35D, FIG. 35E and FIG. 35F show output curves showing the effect of varying the dielectric thickness of an OFET configuration with (A-C) DAA-4T and (D-F) EAA-4T as the gate, pentacene as the semiconductor, and $C_{44}H_{90}$ as the dielectric layer;

FIG. 36A FIG. 36B, and FIG. 36C show (A) the donor-acceptor-donor triads 1 and 2 and controls 3 and 4 studied by Janssen and coworkers (Beckers et al., 2006); (B) Schematic of J-like assembly and (C) absorption spectra of 1 (black squares), 3 (black triangles) and 4 (white triangles); adapted with permission from Beckers et al., 2006;

FIG. 37A and FIG. 37B show (A) structures of peptide-based donor-acceptor system studied by Fox and coworkers (Fox et al., 1997; Galoppini et al., 1996); (B) illustration of self-assembly and electron transfer of proposed donor-acceptor peptide-π hybrids;

FIG. 38A, FIG. 38B, FIG. 38C, FIG. 38D, FIG. 38E, FIG. 38F, FIG. 38G, FIG. 38H and FIG. 38I show transmission electron micrographs of (A) DA-6; (B) DA-3; (C) DA-2; (D) 25% DA-6:75% C-6; (E) 25% 7:75% C-3; (F) 25% DA-2: 75% C-2; (G) C-6; (H) C-3; and (I) C-2;

FIG. 39 is UV-vis spectra of 5 in water at pH 8 (unassembled, dashed lines), and pH 6 (assembled, solid lines);

FIG. 40A, FIG. 40B, FIG. 40C, FIG. 40D, FIG. 40E, and FIG. 40F, show steady-state absorption spectra of donor-acceptor (DA line) and control peptides (C line) and mixtures (10:90, 25:75, and 50:50 DA:C (DA-C line); (A) DA-6 and C-6, unassembled (pH 8), (B) DA-6 and C-6, assembled (pH 4); (C) 7 and 10, unassembled (pH 8); (D) DA-3 and C-3, assembled (pH 4); (E) DA-2 and C-2, unassembled (pH 8); (F) DA-2 and C-2, assembled (pH 8);

FIG. 41A, FIG. 41B, FIG. 41C, FIG. 41D, FIG. 41E, FIG. 41F, FIG. 41G, and FIG. 41H show steady-state emission spectra of donor-acceptor (DA line) and control peptides (C line) and mixtures (10:90, 25:75, and 50:50 DA:C (DA-C line)); (A) DA-6 and C-6, unassembled (pH 8), (B) DA-6 and C-6, assembled (pH 4), (C) DA-3 and C-3, unassembled (pH 8), (D) DA-3 and C-3, assembled (pH 4), (E) DA-2 and C-2, unassembled (pH 8), (F) DA-2 and C-2, assembled (pH 8); plots of relative (to 100% C) quantum yield vs mol % DA for each donor-acceptor and control pair (DA-6 and C-6—solid lines, DA-3 and C-3—dashed lines, DA-2 and C-2—dotted lines) while (G) unassembled and (H) assembled;

FIG. 42A, FIG. 42B, FIG. 42C, FIG. 42D, FIG. 42E, FIG. 42F, FIG. 42G, FIG. 42H and FIG. 42I show circular dichroism spectra of donor-acceptor (A, B, C,) and control (D, E, F,) peptides under assembled (pH 4, solid lines) and unassembled (pH 8, dashed lines) conditions; (A) DA-6; (B) DA-3; (C) DA-2; (D) C-6; (E) C-3; (F) C-2; and circular dichroism spectra of donor-acceptor (DA line) and control peptides (C line) and mixtures (10:90 DA:C (DA-C line)) under assembled conditions (pH 4); (G) DA-6 and C-6; (H) DA-3 and C-3; (I) DA-2 and C-2;

FIG. 43A, FIG. 43B, FIG. 43C, and FIG. 43D show transient absorption spectra and peak assignments of donor-acceptor peptide DA-2 (A,B) and acylated control peptide C-3 (C, D) under unassembled (A,C) and assembled (B,D) conditions;

FIG. 44 shows prototypical transient traces for integrated regions centered about three of the major features of an assembled (solid lines) and unassembled dyad (dashed lines); the OT4 singlet transient (850-900 nm) traces show similar kinetics independent of assembly; on the other hand, both the OT4 oxidized polaron (660-700 nm) and reduced NDI (1050-1125 nm) exhibit a 1-2 order of magnitude increase in lifetime upon assembly;

FIG. 45A and FIG. 45 B show waterfall plots comparing excitation of DA-2 using 400 (A) and 480 nm (B) excitation pulses of similar fluence. Both plots exhibit matching spectral features and similar kinetics; of note, (B) exhibits NIR features with greater intensity than in (A) though some of this may be due to scaling inconsistencies between the 450-800 and 800+ nm segments;

FIG. 46 shows spectra collected for assembled DA-2 photoexcited at 400 nm using the indicated excitation fluences; the solid lines represent spectra collected shortly after excitation (approximately 0.15 ps) scaled relative to their peak heights; dashed lines display the spectra remaining 1 ns after excitation and scaled by the same factors; the similarities in both sets indicate little to no fluence dependence to the dynamics of assembled dyads and the absence of two-photon processes at higher fluences as observed for the acylated control below;

FIG. 47A and FIG. 47B show spectral dynamics following photoexcitation of (A) unassembled DA-2 at 400 nm; (B) assembled DA-2; spectra were collected in 50 fs increments from −0.5 ps to 1 ps and then logarithmically dispersed delays between 1 and 1000 ps;

FIG. 48A and FIG. 48B show principal spectral (A) and kinetic (B) components from the global analysis of time-dependent spectra from 400-nm excitation of DA-2 presented in FIG. 47A; here, the CT traces correspond with charge-separated species and the $S_1$ traces correspond the OT4 excited singlet;

FIG. 49A and FIG. 49B show (A) spectra collected for assembled C-2 photoexcited at 400 nm using the indicated excitation fluences; the solid and dashed lines have the same designations as in FIG. 24; dashed spectra were scaled by a factor of 2 to make their fluence dependence more apparent; at 0.15 ps, the OT4$^+$ signatures at 540 and 680 nm are most intense at high excitation fluences, while at lower fluences the broad OT4 $S_1$ absorption remains as the only significant feature; photo-induced formation of OT4$^+$ at high fluence excitation is apparent from spectra collected 1 ns after excitation; (B) relative decay traces of NIR (1075-1125 nm) NDI$^-$ signature for unassembled dyads of various separation lengths. All data sets were normalized to 1 and fit with multi-exponential models. DA-3' and DA-2' represent dyads with equivalent separation as DA-3 and DA-2 but slightly different structures. DA-2 and DA-2' show a larger proportion of longer lived charge separated state compared to their further separated counterparts, and a similar trend is found in the assembled progressions as well; and FIG. 50A, FIG. 50B and FIG. 50C show principal spectral (A) and kinetic (B) components from the global analysis of time-dependent spectra presented in FIG. 47B; here, the CT traces correspond with charge-separated species and the $S_1$ corresponds with the OT4 excited singlet; the kinetic progression (B) is similar to that observed for unassembled aggregates (FIG. 48B) for the $S_1$ components, but about 1-2 orders of magnitude longer for the charge separated state; (C) relative time-dependent spectral intensity (1100-1150 nm) of the NIR absorption of NDI$^-$ and excited OT4 for assemblies of DA-2, C-2, and a 10:90 mixture; mixture data is compared to the anticipated 10:90 and fitted 39:61 combinations of dyad and control traces, revealing a disproportionate dependence on dyad concentration—a manifestation of energy migration through the assembly.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. ENERGY TRANSFER WITHIN PI-CONJUGATED PEPTIDE HETEROSTRUCTURES IN AQUEOUS ENVIRONMENTS

Due to the intrinsic ability of peptides to self-assemble, several types of conjugated I-systems have been functionalized with peptides to further control specific intermolecular interactions that give rise to distinct assembly architectures and electronic delocalization. Zelzer, M.; Ulijn, R. V. *Chem. Soc. Rev.* 2010, 39, 3351-3357; Diegelmann, S. R., et al., *J. Am. Chem. Soc.* 2008, 130, 13840-13841; Matmour, R., et al., *J. Am. Chem. Soc.* 2008, 130, 14576-14583; Shao, H., et al., *J. Am. Chem. Soc.* 2009, 131, 16374-16376; Schillinger, E.-K., et al., *Adv. Mater.* 2009, 21, 1562-1567; Stone, D. A.; et al., *Soft Matter* 2009, 5, 1990-1993; Jahnke, E., et al., *Angew. Chem. Int. Ed.* 2006, 45, 5383-5386. In some embodiments, the presently disclosed subject matter provides a two-component nanostructure comprising π-conjugated peptides containing donor and acceptor semiconducting π-units that upon self-assembly exhibit energy transport in completely aqueous media. The energy transport can be excitonic, i.e., a bound state of an electron and an electron hole which are attracted to each other by an electrostatic Coulomb force, electronic, or any form of energy transport known in the art. Further, in some embodiments, radical ions or radical cations can be formed from excited states to promote electronic energy transfer.

Previous studies on self-assembling peptides exhibiting energy transfer involve fluorescent dyes conjugated to peptide ends, showing efficient energy transfer in organic media or within hydrogels once a suitable acceptor dye has intercalated within the assembly network. Chen, L., et al., *Chem. Commun.* 2010, 46, 4267-4269; Nalluri, S. K. M.; Ulijn, R. V. *Chem. Sci.* 2013, 4, 3699-3705; Channon, K. J., et al., *J. Am. Chem. Soc.* 2009, 131, 12520-12521; Channon, K. J., et al., *J. Am. Chem. Soc.* 2008, 130, 5487-5491. Furthermore, the dyes often used in contemporary studies are chosen for their molecular photophysical properties rather than for their abilities to promote semiconductive electronic behavior.

In contrast, the presently disclosed subject matter provides pH-responsive self-assembling peptide systems conjugated to two different semiconducting π-electron units that also exhibit temperature-dependent aggregation behaviors. The presently disclosed subject matter discloses OPV-containing peptides, for which Meijer and co-workers who established that the fast exciton diffusion processes and energy transfer processes were possible within these types of organic-based nanomaterials. Hoeben, F. J. M., et al., *Angew. Chem. Int. Ed.* 2004, 116, 2010-2013; Hoeben, F. J. M., et al., *Chem Phys Chem* 2005, 6, 2337-2342; Herz, L., et al., *Phys. Rev. B* 2003, 68, 045203; Schmid, S. A., et al., *Philos. Trans. R. Soc. Math. Phys. Eng. Sci.* 2012, 370, 3787-3801; Spano, F. C. *J. Chem. Phys.* 2002, 116, 5877. In some embodiments, the pH and/or temperature responsiveness of the presently disclosed self-assembling peptide systems allows them to be used for pH and/or temperature sensing.

Accordingly, in some embodiments, the presently disclosed subject matter generally provides a peptide-based nanomaterial platform that is capable of supporting broadly defined energy transport processes, wherein such energy transport can be photonic or electrical in nature, and wherein the excitation energy transport can perturb or stimulate material associated with the nanomaterial.

More particularly, the presently disclosed subject matter provides heterostructure nanomaterials having energy donor units and energy acceptor units that exhibit photonic transfer of energy to the acceptor units or the photo-induced separation of charge, thus serving as a way to funnel excitation energy to specific sites or otherwise create localized electric fields within the nanomaterial composition.

In other embodiments, the presently disclosed subject matter demonstrates the use of electrical energy transport to influence organic semiconductor units deposited on the nanomaterials.

The presently disclosed subject matter provides the first examples of a biologically adhesive nanomaterial platform that can be formed in aqueous environments and remains capable for energy transport within nanoscale confinement, leading to the possibilities for the localization of energy that can then be harnessed for external perturbation of materials associated with the nanomaterial, be it biological or artificial in nature. Many "energy transfer" materials are known, but the properties of these examples are usually photonic in nature with no further discussion of the functional fate of the final state to which the energy has been transferred.

Peptide-based optoelectronic nanomaterials disclosed in International PCT Patent Application Publication No. WO/2014/066326 for "Palladium Catalyzed Reactions Executed on Solid-Phase Peptide Synthesis Supports for the Production of Self-Assembling Peptides Embedded with Complex Organic Electronic Subunits," to Tovar et al., published May 1, 2014; U.S. Patent Application Publication No. 2014/0114052, published Apr. 24, 2014, now U.S. Pat. No. 8,871,903, issued Oct. 28, 2014, each directed to the same subject matter; and U.S. Patent Application Publication No. 2012/0101022 for "Self-Assembling Peptides Bearing Organic Electronic Functionality and Applications Employing the Same," to Tovar et al., published Apr. 26, 2012, each of which is incorporated herein by reference in its entirety.

In contrast to previous disclosures, the presently disclosed subject matter demonstrates how this platform can be used not just as a scaffold for organizing organic semiconductors, but how energy transport can be achieved within them. The presently disclosed subject matter demonstrates how photonic transport can localize photonic emissions at the nanoscale (to an acceptor chromophore), how photoinduced charge separation can be used to achieve electron transfer within a molecular scaffold and thus achieve nanoscale electric field generation, and how electrical stimulation can be used to influence the transistor behavior of organic semiconductors adhered to the nanomaterial surface, wherein the nanomaterial is acting as the gate electrode. Further, coassemblies of semiconductors having different bandgaps can be used to create defined trap states that would localize electrical energy at specific segments of the nanomaterial scaffold.

In some embodiments, the presently disclosed nanomaterials can have cell-receptor-specific ligands attached thereto to encourage specific biological recognition events. Accordingly, the presently disclosed nanomaterials can be used to bring photonic or electrical energy to biological environments at a scale unavailable to standard biomaterials. Such "circuitry" could be used for in situ assembled energy/ power sources, external stimulation of biological media, or to influence cell physiology with spatial and temporal control. Further, in some embodiments, the presently disclosed subject matter provides conductive bio-compatible wire materials that can be formed and manipulated under in vivo conditions.

Accordingly, in some embodiments, the presently disclosed subject matter provides a nanostructure comprising two or more π-conjugated peptide units that upon self-assembly exhibits energy transport in a completely aqueous or physiological medium, wherein the energy transport can be photonic or electrical in nature. In some embodiments, the energy transport is photonic in nature.

In some embodiments, the two or more π-conjugated peptides have a structure of peptide-[(organic electronic unit)-peptide], wherein each peptide can be the same or different and comprises from 2 to 15 naturally occurring amino acid residues or a variant thereof.

In particular embodiments, the organic electronic unit is selected from the group consisting of an α-oligothiophene, an oligophenylene, an oligo(p-phenylene vinylene), a rylene, and diimides and diacids, thereof. In yet more particular embodiments, the α-oligothiophene is selected from the group consisting of bithiophene, terthiophene, and quaterthiophene.

In some embodiments, the diimide is selected from the group consisting of a naphthalene diimide and a perylene diimide. In other embodiments, the diacid is selected from the group consisting of an oligothiophene diacid, an oligophenylene diacid, and an oligophenylene vinylene diacid.

In certain embodiments, the amino acid residue can be the same or different and is selected from the group consisting of alanine, arginine, asparagine, aspartate, cysteine, glutamate, glutamine, glycine, histidine, isoleucine, leucine, lysine, methionine, phenylalanine, proline, serine, threonine, tryptophan, tyrosine, valine, 5-hydroxylysine, 4-hydroxyproline, thyroxine, 3-methylhistidine, ∈-N-methyllysine, ∈-N,N,N-trimethyllysine, aminoadipic acid, γ-carboxyglutamic acid, phosphoserine, phosphothreonine, phosphotyrosine, N-methylarginine, and N-acetyllysine.

In particular embodiments the two or more π-conjugated peptide units are selected from the group consisting of:

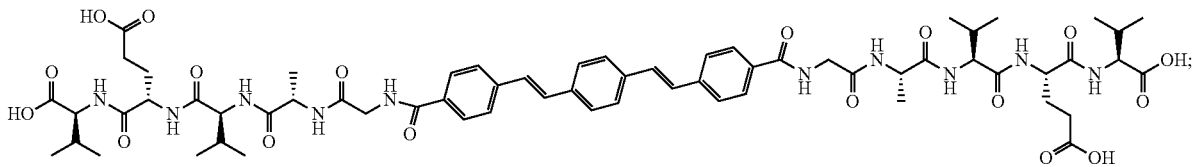

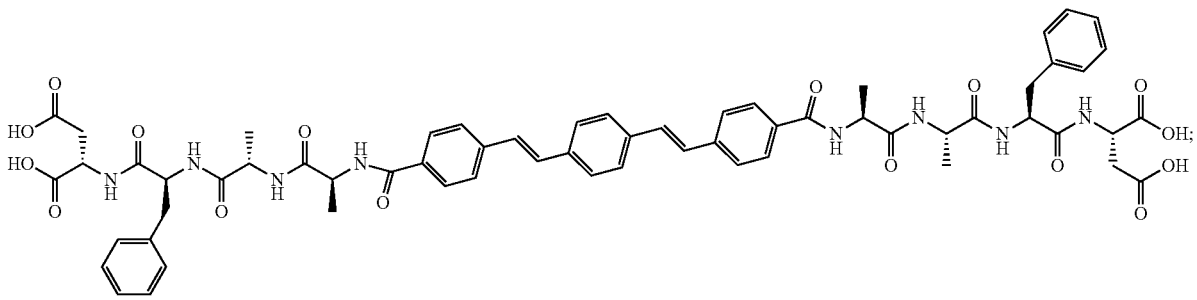

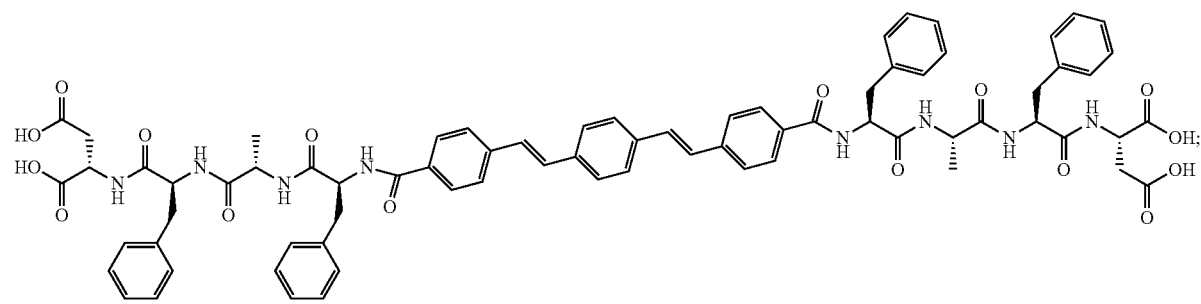
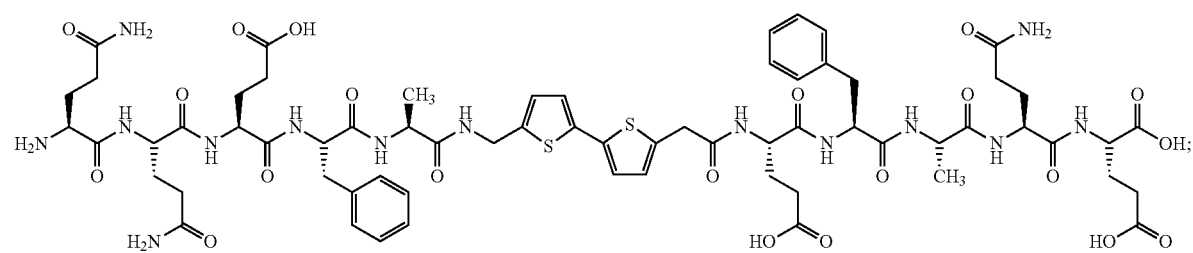
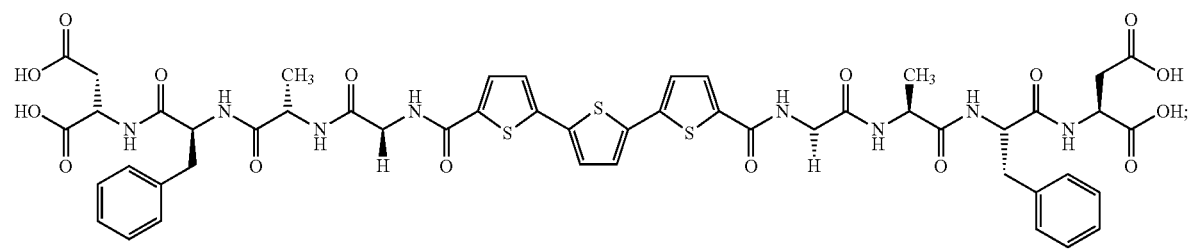
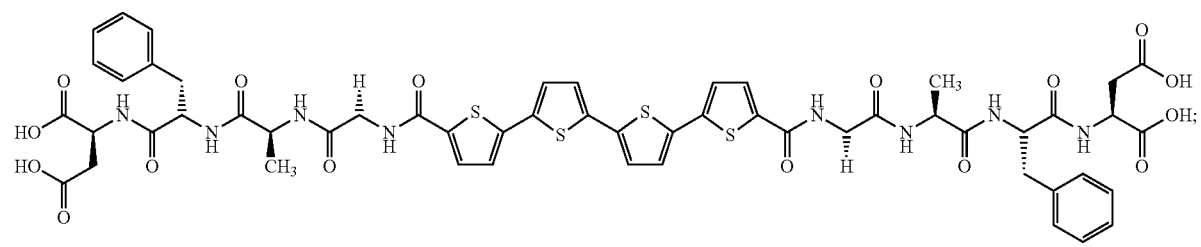
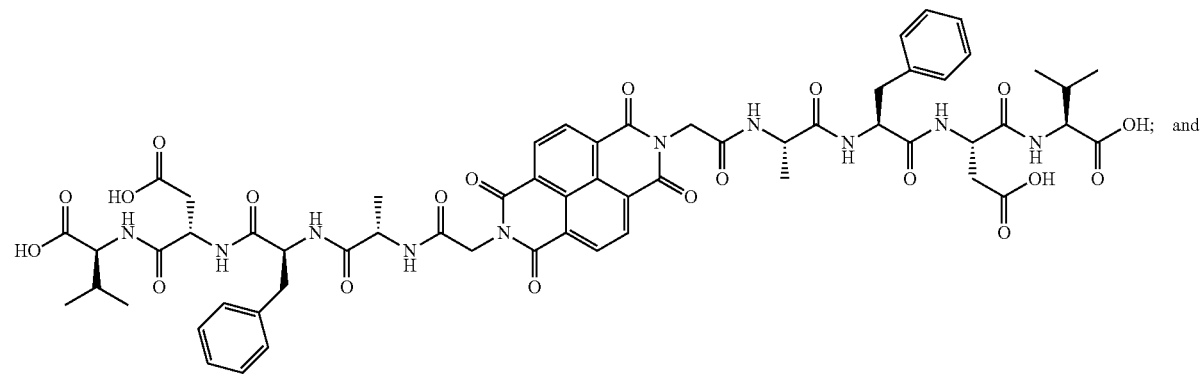

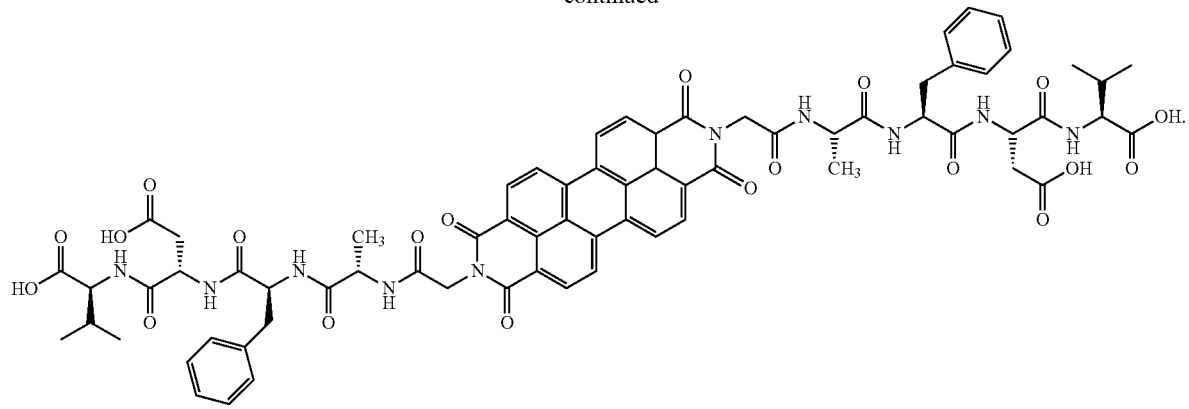

In particular embodiments, the two or more π-conjugated peptide units are:

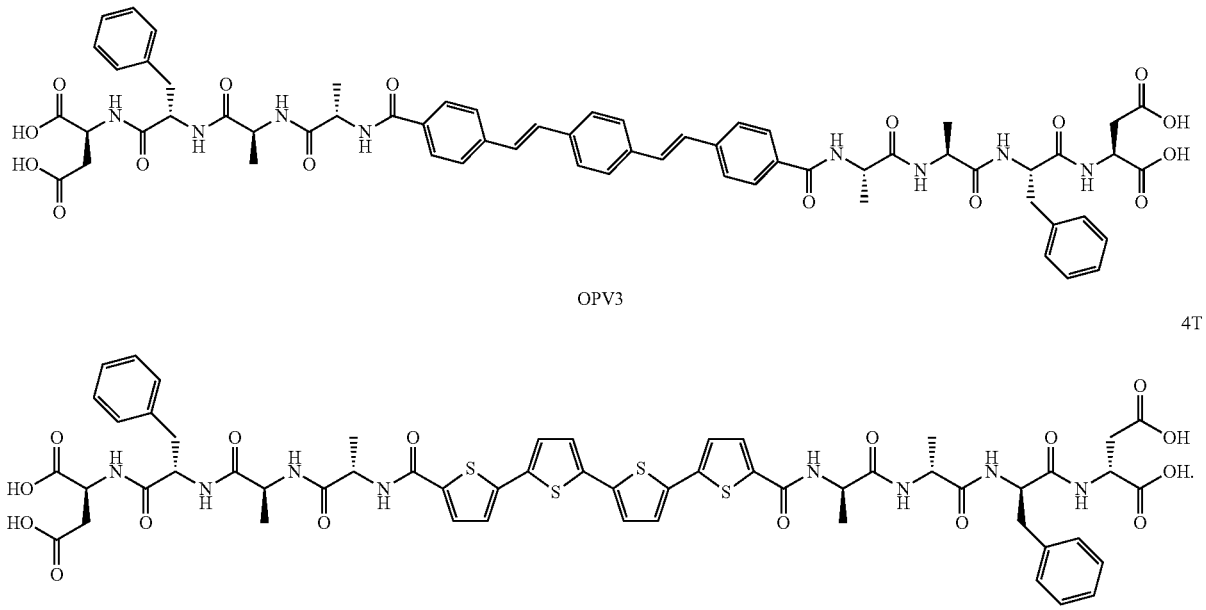

OPV3

4T

One of ordinary skill in the art would recognize that other donor or acceptor units would be suitable for use with the presently disclosed subject matter. Further, the donor and acceptor designation is relative. For example, a π-unit could be a donor in one two-component system, yet could be an acceptor in another two-component system depending on the particular donor/acceptor unit present in the system. In yet more particular embodiments, the two-component nanostructure further comprises one or more cell-receptor-specific ligands attached thereto.

II. HOLE TRANSPORT AND VOLTAGE EQUILIBRATION IN SELF-ASSEMBLED PI-CONJUGATED PEPTIDE NANOSTRUCTURES USING FIELD-EFFECT TRANSISTOR ARCHITECTURES

In other embodiments, the presently disclosed subject matter provides tripeptide-π-tripeptide constructs as switchable semiconducting layers or alternatively as the gate electrodes of bottom-gate OFETs. This type of π-conjugated peptide presents the bioactive peptide segments at the termini with a semiconducting π-system unit embedded in the core. Quaterthiophene (4T) has been chosen a hole-transporting organic semiconductor, as the central π-system (Horowitz, 1998). For the tripeptide segment, a negatively charged amino acid (aspartic acid, D, or glutamic acid, E) has been placed at the distal termini and aliphatic dipeptides (glycine, G; alanine, A; valine, V; isoleucine, I) near the π-core. This design allows for pH-triggered interconnected nanostructure assembly under acidic aqueous conditions while basic conditions generally result in essentially molecular solutions. In earlier studies, these peptide-π-peptide constructs were incorporated as active layers of OFETs, with hole mobility values of $1.4 \times 10^{-3}$ $cm^2$ $V^{-1}$ $s^{-1}$ for a 4T core (Wall et al., 2011). The previous study with Glu-Ala-Ala peptides conjugated to a 4T core is the first report of gate field conductance modulation for nanostructured π-conjugated units embedded within insulating peptide moieties assembled under aqueous conditions. In contract, the presently disclosed subject matter provides the incorporation of various sequences of 4T-bound tripeptide nanomaterials as both the active semiconducting layers and for the first time, as gates in a bottom-gate top-contact OFET configuration. Different peptide sequences attached to a 4T semiconductor have been investigated to determined whether sequence variation is a feasible way to modulate field-effect electronic properties since this strategy has been previously shown to rationally modulate excited-state photophysics (Wall et al., 2014) and the sheet resistance of π-conjugated peptide films (Ardona et al., 2015). The presently disclosed subject matter focuses on the electronic device properties of this hydrogel-forming material, building on the fundamental understanding of carrier transport and voltage equilibration of π-conjugated peptides for future biological applications.

Accordingly, in some embodiments, the presently disclosed subject matter provides a conductive material comprising the nanostructure described hereinabove. In other embodiments, the conductive material is a hole transporting material. In some other embodiments, the conductive material is an electron transporting material.

In further embodiments, the conductive material is used as a semiconducting layer in a field-effect transistor. In yet further embodiments, the conductive material are used as a gate layer in a field-effect transistor. Non-limiting examples of field-effect transistors are provided below, along with accompanying figures.

In specific embodiments, the π-conjugated peptides units have the following structure:

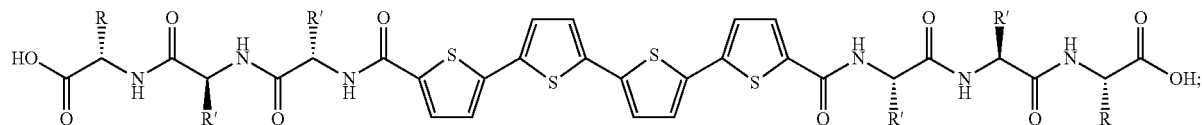

wherein R is —$(CH_2)_m$—$COR_1$, m is an integer selected from the group consisting of 0, 1, 2, 3, and 4, and $R_1$ is selected from the group consisting of —OH and —$NH_2$; R' is selected from the group consisting of H, straight-chain alkyl, branched alkyl, and benzyl. In yet more specific embodiments the π-conjugated peptides units are selected from the group consisting of:

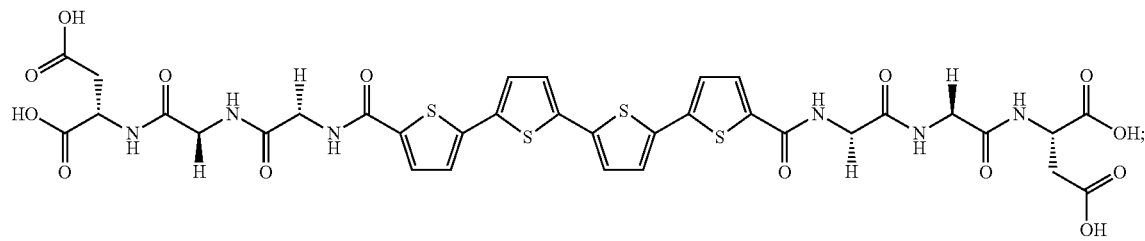

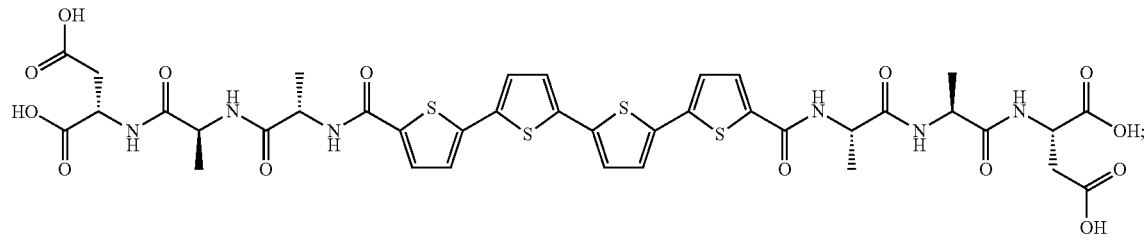

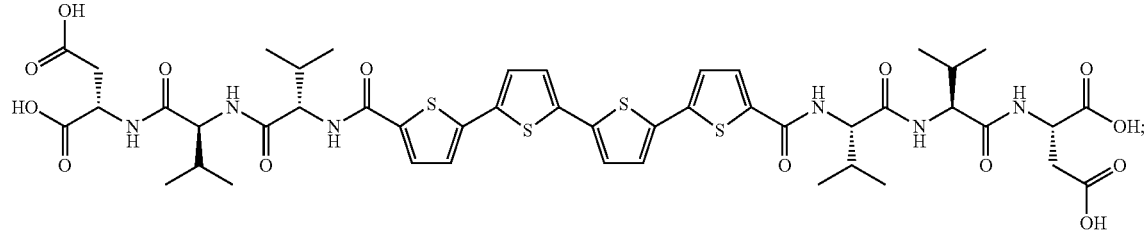

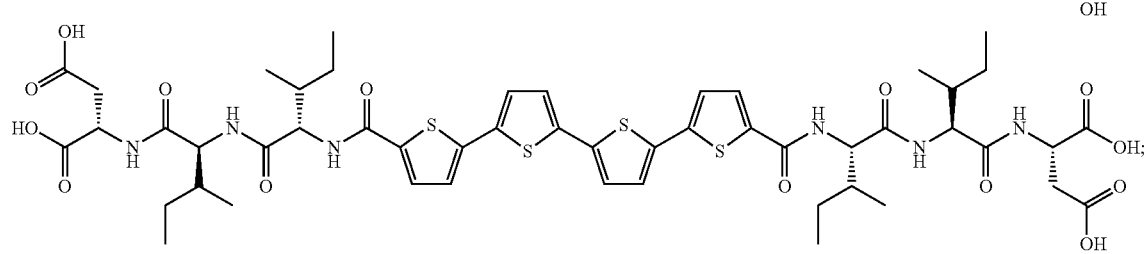

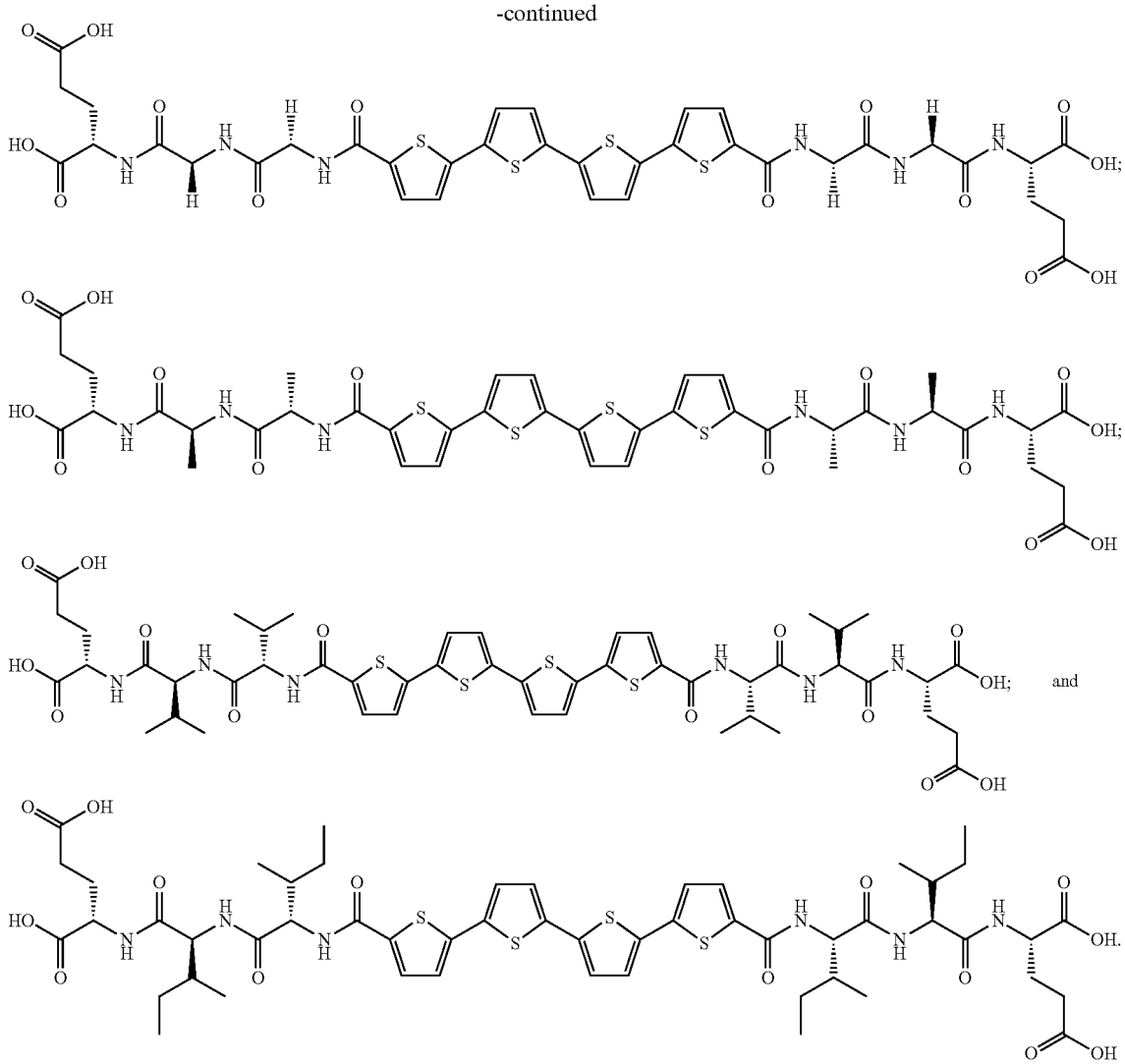

One of ordinary skill in the art would appreciate that an architecture including a nanowire as a gate, wherein the nanowire comprises a two-component nanostructure as disclosed herein, allows for the possibility of a phototransistor, wherein the gate could be photopolarized so that it maintains an "on" state as a type of memory element. In such embodiments, the "acceptor" units could be configured to be under the dielectric and carriers could be shuttled to them from outside the device.

III. DONOR-ACCEPTOR PEPTIDE-Π HYBRIDS NANOMATERIALS FOR PHOTO-INDUCED CHARGE SEPARATION

Previous studies have focused on creating functional semiconducting peptides with tunable electronic, assembly, and materials properties. Sanders, A. M., et al., *ACS Macro Lett.* 2012, 1, 1326; Sanders, A. M.; Tovar, J. D. *Supramol. Chem.* 2014, 26, 259; Vadehra, G. S.; Wall, B. D.; Diegelmann, S. R.; Tovar, J. D. *Chem. Commun.* 2010, 46, 3947. The functionality of the systems, however, namely the ability to create charge-carriers and generate electric fields, has so far relied on the use of external electronics. An interesting next step in the development of these materials, specifically to aid in their potential future uses in regenerative medicinal applications, is to investigate a means to create charge-separation in the absence of external electronics. One possible means to achieve this is to design peptidic donor-acceptor systems capable of photoinduced charge transfer.

Photoinduced electron transfer is a method that nature uses to perform redox reactions, particularly in the process of photosynthesis. Much work has been done to mimic this process, typically through the design of covalently bound donor-acceptor diads, triads, and tetrads. Wasielewski, M. R. *Acc. Chem. Res.* 2009, 42, 1910; Ahrens, M. J., et al., *J. Am. Chem. Soc.* 2004, 126, 8284; Rybtchinski, B., et al., *J. Am. Chem. Soc.* 2004, 126, 12268; Schenning, A. P. H. J., et al., *J. Am. Chem. Soc.* 2002, 124, 10252; Bheemaraju, A., et al., *J. Macromol. Sci, Pure Appl. Chem.* 2011, 48, 986; Wasielewski et al., 1992; Imahori, Guldi et al., 2001; Imahori, Tamaki et al., 2001; Liddell et al., 1994; Kuciauskas et al., 1996; Liddell et al., 1997; Kuciauskas et al., 1999; Liddell et al., 2002).

The covalent connection of the two redox-active chromophores allows for charge transfer to not be limited by diffusion. Furthermore, additional work has been done to study the self-assembly of these donor-acceptor systems into supramolecular arrays, facilitated by π-stacking or peptide assembly, and the effect of this on the charge transfer processes. Beckers, E. H. A., et al., *J. Am. Chem. Soc.* 2006, 128, 649-657; Galoppini, E.; Fox, M. A. *J. Am. Chem. Soc.* 1996, 118, 2299; Fox, M. A.; Galoppini, E. *J. Am. Chem. Soc.* 1997, 119, 5277; Wasielewski, 2009; Ahrens et al., 2004; Rybtchinski et al., 2004; Schenning et al., 2002). One particular study by Janssen investigates both of these concepts (Beckers et al., 2006). Two donor-acceptor-donor triads were studied, each containing two oligophenylenevinylene units covalently attached to a perylene diimide moiety (FIG. 36A). The triads differed by the substitution of the perylene subunit at the bay positions, ranging from chloride (1) to tert-butyl phenoxide (2). Donor and acceptor controls (3 and 4, respectively) were also prepared for comparison.

The absorption spectra of the systems were studied in methylcyclohexane at concentrations that allowed for aggregation of the compounds. It was deduced that the systems tended to form J-like aggregates upon assembly (FIG. 36B) due to the hindrance of the bay substituents preventing face-to-face stacking of the perylene units. A low energy absorbance in the range of 800 nm was seen for compound 1 (FIG. 36C black squares), which was determined to correspond to a charge transfer band, because this low energy peak was absent in the spectra for the isolated donor and acceptor controls 3 and 4 (black and white triangles, respectively). A solution of both controls (1:1) gave rise to only a weak charge transfer band (white squares), illustrating the importance of the covalent attachment of the donor and acceptor moieties. Furthermore, the charge transfer kinetics of the assemblies were compared to the molecularly dissolved triads by changing the solvent. It was found, in the case of compound 2, that electron transfer occurs nearly an order of magnitude faster for the assemblies in methylcyclohexane ($1.2 \times 10^{12}$ s$^{-1}$) than for the molecularly dissolved samples in toluene ($2.7 \times 10^{11}$ s$^{-1}$), presumably due to the closer proximity of the donor and acceptor moieties in the J-like aggregated state.

Utilizing peptide assembly to organize donor and acceptor moieties in space has also been investigated (Home et al., 2005; Jones et al., 2000), including work performed by Fox and coworkers (Fox et al., 1997; Galoppini et al., 1996). They synthesized peptide 5 shown in FIG. 37A, which contains unnatural amino acids containing pyrene and dimethylaniline groups. The peptide was designed to assemble into an α-helical structure, thus placing the chromophore substituents within appropriate distances to facilitate charge transfer. It was found that electron transfer occurred nearly 25 times faster when the peptide was dissolved in a solvent that encouraged its self-assembly (acetonitrile), in comparison to solvents that disrupted assembly (2,2,2-trifluoroethanol) (Fox et al., 1997). These examples illustrate that self-assembling peptide-based pi-electron molecules (and their resulting nanomaterials) are promising targets to realize the photonic creation of charge-separated states. Several groups have validated the ability of an oligopeptide assembly paradigm to be directly applicable to the supramolecular organization of pi-electron structures (Ardona et al., 2015). These types of peptide-pi-electron hybrids typically lead to static electronic structures whose photophysical properties are dictated by local geometries imposed on the pi-electron moieties within the supramolecular assembly. More recently, complex peptide co-assemblies have validated the encouragement of excitonic energy migration within nanoscopic materials (Gao et al., 2015). Indeed, an energy donor-acceptor pair of peptidic pi-electron molecules that co-assembled under aqueous conditions and subsequently fostered energy migration to a low-energy "dopant" has been recently reported (Ardona et al., 2012), in line with other recent studies on intercalated donor-acceptor peptide nanomaterials (Chen et al., 2010; Nalluri et al., 2013).

The presently disclosed subject matter provides a new direction in peptide-driven supramolecular polymerization of pi-conjugated nanomaterials whereby electron-accepting groups are positioned pendant to a pi-stacked electron donor core. These materials are a conceptual advance from the pi-peptide hybrid systems that we previously studied (Vadehra et al., 2010; Sanders et al., 2012; Sanders et al., 2014), in which solid-phase synthetic procedures were used to create novel peptides embedded with semiconducting pi-conjugated subunits that could self-assemble in aqueous environments. To create pi-stacked peptidic platforms capable of photoinduced electron transfer, acceptor units were incorporated onto amino acid side chains along peptide backbones that comprise a general self-assembling peptide-pi-electron hybrid as illustrated in FIG. 37B. These molecules undergo a well-established pH assembly trigger, whereby changes in solution pH (in this case, a decrease in pH) allow for supramolecular self-assembly via the establishment of favorable intermolecular hydrogen bonding, ultimately creating noncovalent 1-D nanostructures. Upon excitation of the internal donor moiety, energy migration and subsequent electron transfer to the peripheral acceptors can occur.

Accordingly, in some embodiments, the presently disclosed subject matter provides a supramolecular assembly comprising covalently-bound electron donor-acceptor chromophores in which either electron acceptor semiconducting π-units are incorporated into amino acid side chains on peptides embedded with an electron donor semiconducting π-unit or electron donor semiconducting π-units are incorporated into amino acid side chains on peptides embedded with an electron acceptor semiconducting π-unit.

In other embodiments, the π-conjugated peptides units have the following structures:

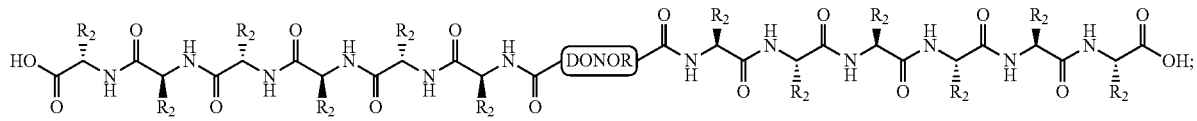

wherein each $R_2$ is independently selected from the group consisting of H, straight-chain alkyl, branched alkyl, benzyl, —$(CH_2)_n$-A and —$(CH_2)_p$—$COR_3$, wherein A is an electron acceptor, n is an integer selected from the group consisting of, 2, 3, and 4, p is an integer selected from the group consisting of 0, 1, 2, 3, and 4, and $R_3$ is selected from the group consisting of —OH and —$NH_2$; or

wherein each $R_2$ is independently selected from the group consisting of H, straight-chain alkyl, branched alkyl, benzyl, —$(CH_2)_n$-D and —$(CH_2)_p$—$COR_3$, wherein D is an electron donor, n is an integer selected from the group consisting of, 2, 3, and 4, p is an integer selected from the group consisting of 0, 1, 2, 3, and 4, and $R_3$ is selected from the group consisting of —OH and —$NH_2$.

In further embodiments, the π-conjugated peptide units are selected from the group consisting of:

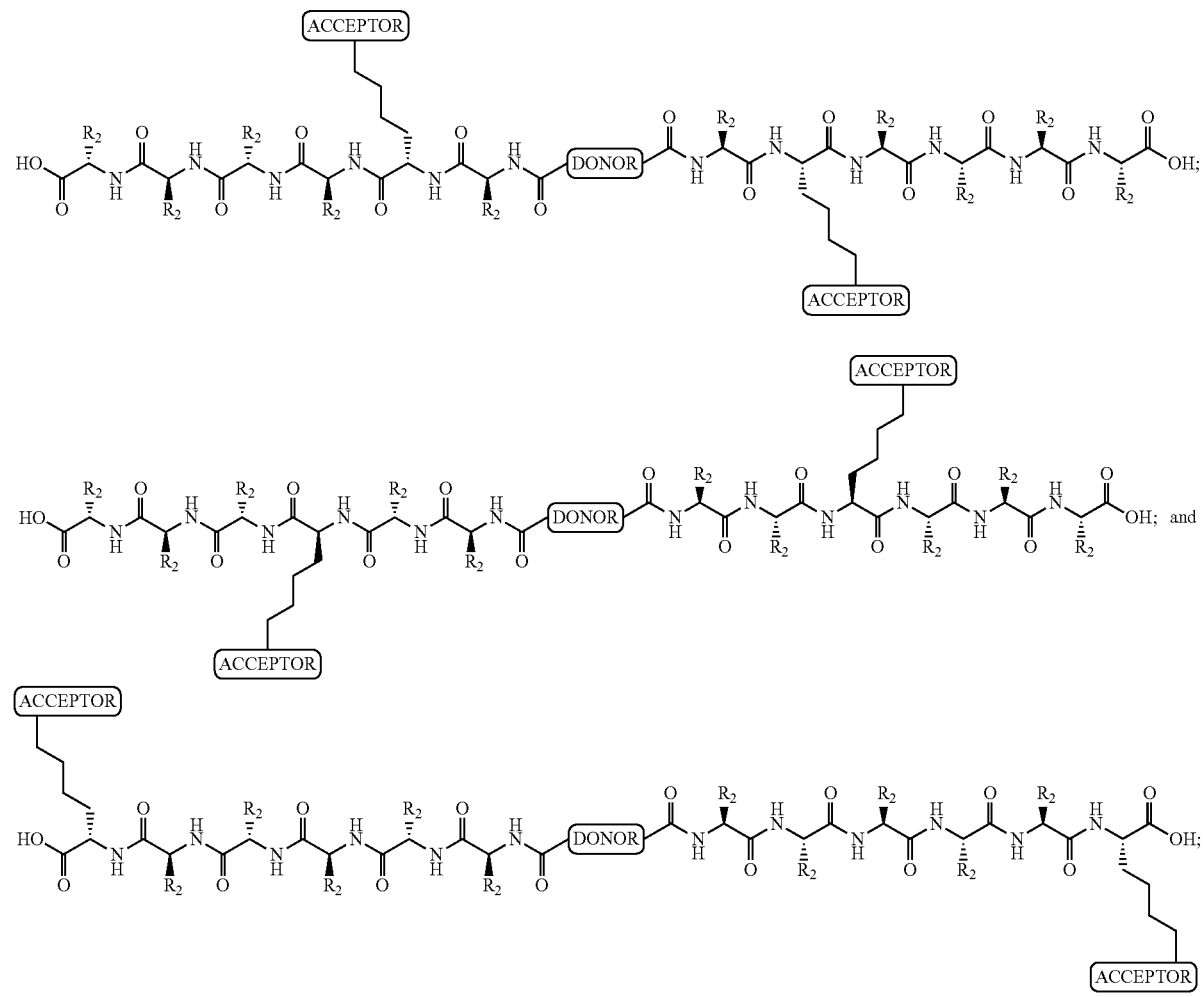

wherein each $R_2$ is independently selected from the group consisting of H, straight-chain alkyl, branched alkyl, benzyl, and —$(CH_2)_p$—$COR_3$, wherein p is an integer selected from the group consisting of 0, 1, 2, 3, and 4, and $R_3$ is selected from the group consisting of —OH and —$NH_2$.

In the presently disclosed subject matter, a quaterthiophene (OT4)/naphthalene diimide (NDI) donor-acceptor system was chosen as a representative example. Venkataraman and coworkers have previously used this donor-acceptor pair and found it to be an ideal system for electron transfer due to the lack of spectral overlap between the emission wavelengths of OT4 and absorption wavelengths of NDI (to discourage non-polar energy transfer) and beneficial LUMO level positioning (to encourage transfer of excited electrons). Bheemaraju, A., et al., *J. Macromol. Sci, Pure Appl. Chem.* 2011, 48, 986. Furthermore, the synthesis of peptides embedded with OT4 subunits has been optimized, Sanders, A. M., et al., *ACS Macro Lett.* 2012, 1, 1326; Sanders, A. M.; Tovar, J. D. *Supramol. Chem.* 2014, 26, 259, and the NDI acceptor moiety can be easily incorporated onto the side chain of a lysine residue.

Accordingly, in some embodiments, the electron donor semiconducting π-unit is a quaterthiophene and the electron acceptor semiconducting π-unit is a naphthalene diimide.

In particular embodiments, the π-conjugated peptide units are selected from the group consisting of:

33 34
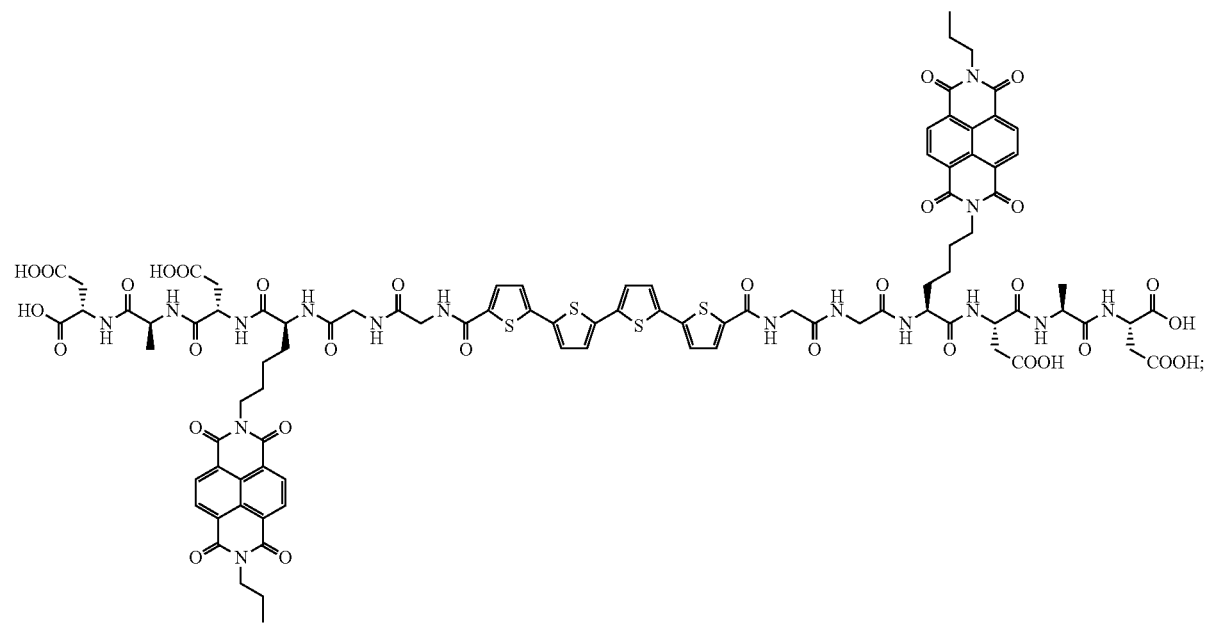
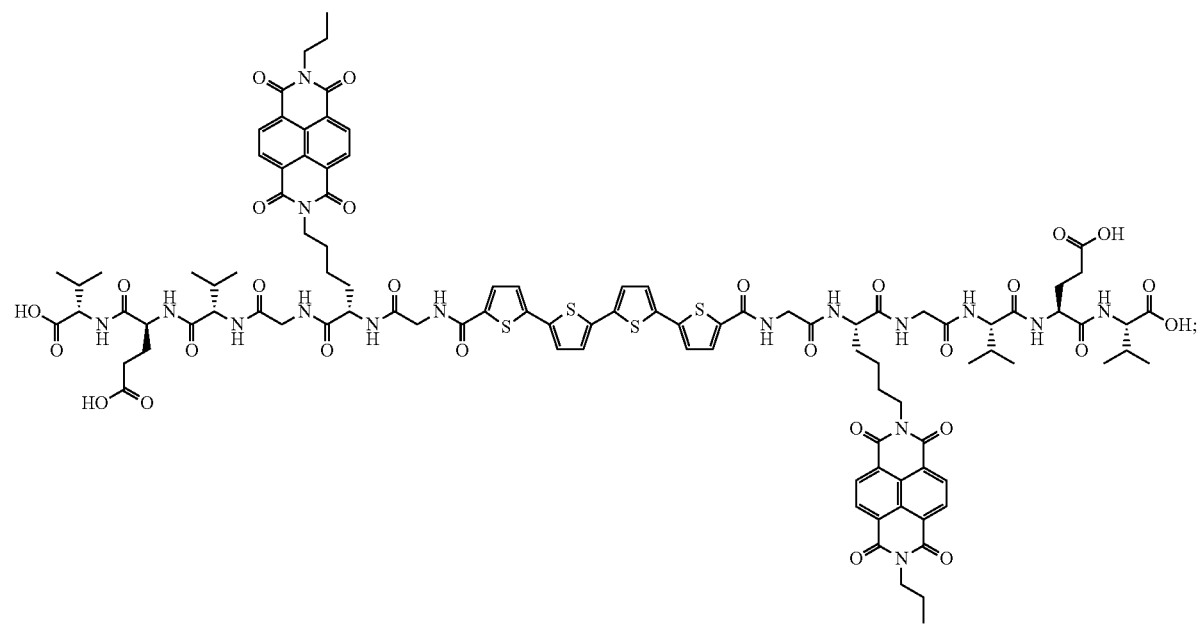
DA-2

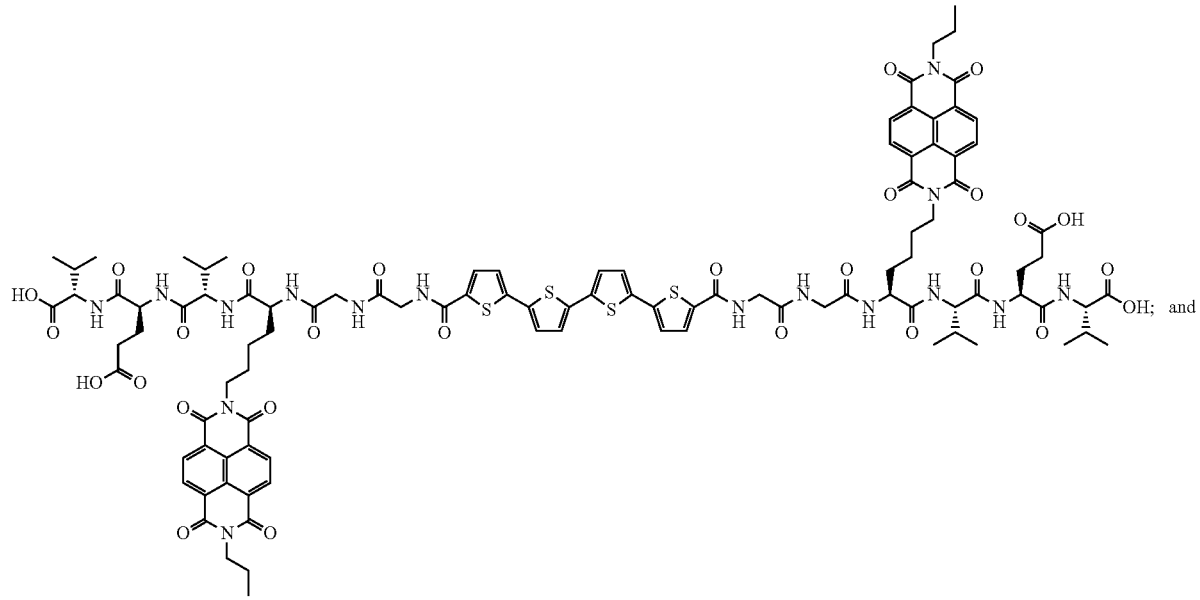

DA-3

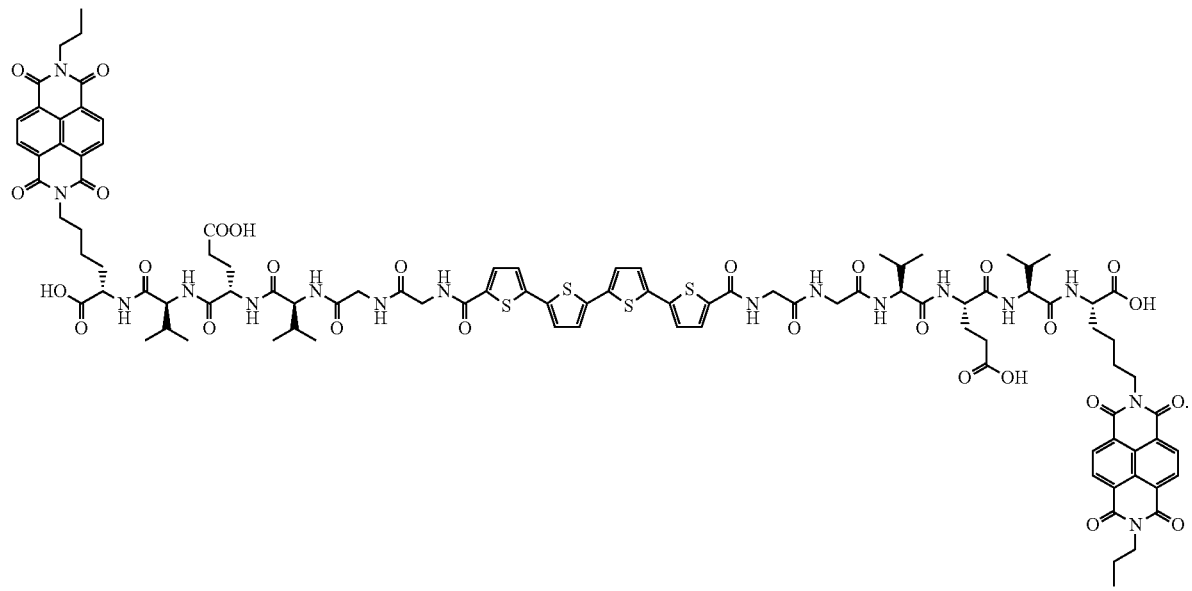

DA-6

IV. DEFINITIONS

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

As used herein, the term "organic electronic unit" is used interchangeably with the terms "π-conjugated segment," "π-conjugated oligomer," and "π-conjugated unit" and is intended to mean a molecule, a portion of a molecule or a chemical moiety comprising one or more conjugated linkages of arenes, heteroarenes, and other unsaturated groups, such alkenes, alkynes, and the like, having delocalized i-electron properties as will be understood by those of skill in the art.

As used herein, the term "arene" includes monocyclic and polycyclic aromatic hydrocarbons. Representative arenes include benzene and substituted benzenes, biphenylene, and substituted biphenylenes. Representative polycyclic aromatic hydrocarbons include naphthalene, acenaphthylene, acenaphthene, fluorene, phenanthrene, anthracene, fluoranthene, pyrene, perylene, benz[a]anthracene, chrysene, benzo[b]fluoranthene, benzo[k]fluoranthene, benzo[a]pyrene, dibenz[a,h]anthracene, benzo[g,h,i]perylene, and indeno[1,2,3-cd]pyrene.

As used herein the term "heteroarene" includes heterocyclic compounds derived from arenes by replacement of one or more methine (—C=) and/or vinylene (—CH=CH—) groups by trivalent or divalent heteroatoms, e.g., oxygen, nitrogen, and sulfur, respectively, in such a way as to maintain the π-electron system characteristic of aromatic systems. Thiophene is an example of a heteroarene.

Alkenes include acyclic branched or unbranched hydrocarbons having at least one carbon-carbon double bond and the general formula $C_nH_{2n}$. Alkynes include acyclic branched or unbranched hydrocarbons having a carbon-carbon triple bond and the general formula $C_nH_{2n-2}$, RC≡CR. One of ordinary skill in the art would recognize that hydrocarbon radicals can be derived from the hydrocarbon moieties defined hereinabove by removal of one or more hydrogen atoms such that all valencies are satisfied when the radical is included in one or more of the presently disclosed compounds and materials.

As used herein, an "oligomer" includes a few monomer units, for example, in contrast to a polymer that potentially can comprise an unlimited number of monomers. Dimers, trimers, and tetramers are non-limiting examples of oligomers.

The organic electronic units can be varied, for example, to include fluorescent materials, electroactive materials, and/or materials that might have environmentally sensitive optoelectronic properties. Such organic electronic units include, for example, the α-oligothiophenes (bithiophene, terthiophene, quaterthiophene, and the like) used for p-channel (hole-transporting) organic semiconductors, oligophenylenes, the rylene diimides (naphthalene and perylene diimides, and the like) used for dyestuffs and for n-channel (electron-transporting) organic semiconductors, and the oligo(p-phenylene vinylenes) used as intense fluorophores for light emission and as dyes for photovoltaics. Other suitable examples of organic electronic units will be evident to those of skill in the art.

As used herein, the term "peptide segment," "oligopeptide," or "peptide" is intended to mean in some embodiments a peptide of 2 to 100 amino acid residues, including any integer from 2 to 100, and in some embodiments, 2 to 15 amino acid residues, including 2, 3, 4, 5, 6, 7, 8, 9, 10, 11, 12, 13, 14, and 15 amino acid residues, which are obtainable by standard peptide synthesis protocols known in the art. In other embodiments, a "peptide" can mean a protein comprising more than 100 amino acids, such as from about 100 to about 150 amino acids, from about 150 to about 200 amino acids, and the like.

As used herein, an "amino acid residue" is a residue of a naturally occurring amino acid or a variant thereof, including but not limited to alanine (A), arginine (R), asparagine (N), aspartate (D), cysteine (C), glutamate (E), glutamine (Q), glycine (G), histidine (H), isoleucine (I), leucine (L), lysine (K), methionine (M), phenylalanine (F), proline (P), serine (S), threonine (T), tryptophan (W), tyrosine (Y), valine (V), 5-hydroxylysine, 4-hydroxyproline, thyroxine, 3-methylhistidine, ∈-N-methyllysine, ∈-N,N,N-trimethyllysine, aminoadipic acid, γ-carboxyglutamic acid, phosphoserine, phosphothreonine, phosphotyrosine, N-methylarginine, and N-acetyllysine. Naturally occurring amino acid residues are preferred.

In addition to naturally occurring amino acids and variants thereof, other residues that are compatible with standard solid-phase peptide synthesis protocols can be used to form the compounds described herein, as will be appreciated by those of skill in the art. Representative residues include, but are not limited to, moieties such as .beta.-amino acids and longer chain amino alkanoic acids, peptide nucleic acids, and amino benzoic acids.

Peptide segments can be varied, for example, to encourage specific cellular adhesion through integrin mediated binding (RGD tripeptide as fibronectin mimic, IKVAV as a laminin mimic, and the like) or to encourage other molecular recognition events (carboxylates to sequester metal ions, defined entities of a natural or unnatural origin to promote a chemical interaction).

As used herein, "self-assembly" is intended to mean the process by which molecules adopt a defined arrangement without guidance from an outside source.

As used herein, "supramolecular" is intended to mean relating to or denoting structures composed of several or many molecules.

As used herein, "semiconductor nanomaterials" are those materials that have electrical conductivity intermediate to that of a conductor and an insulator and have structured components with at least one dimension less than 100 nm.

As used herein, "bioelectronic nanomaterials" are those biological materials that have electronic characteristics and have structured components with at least one dimension less than 100 nm.

As used herein, a "field-effect transistor" is a transistor that uses an electric field to control the shape and hence the conductivity of a channel of one type of charge carrier in a semiconductor material.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments±50%, in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Peptidic Nanomaterial for Directed Energy Transport

Overview

Steady-state and time-resolved photophysical measurements demonstrate energy transfer within aqueous π-conjugated peptide nanostructures comprising oligo-(p-phenylenevinylene)-based donor units and quaterthiophene-based acceptor units. These peptide-based assemblies encourage energy migration along the stacking axis, thus resulting in the quenching of donor emission peaks along with the development of new spectral features reminiscent of acceptor emission. These spectral changes were observed even at minute amounts of the acceptor (starting at 1 mol %), suggesting that exciton migration is involved in energy transport and supporting a funnel-like energy transduction mechanism. The reversibility of nanostructure formation and the associated photophysical responses under different conditions (e.g., pH, temperature) also are disclosed. The presently disclosed material design offers a platform for the engineering of energy migration through bioelectronics materials in aqueous environments.

Material and Methods

General Experimental Procedures.

The chemicals used for 9-fluorenylmethoxycarbonyl (Fmoc)-based solid phase peptide synthesis (N-methylpyrrolidone (NMP), O-(benzotriazol-1-yl)-N,N,N',N'-tetramethyluronium hexafluorophosphate (HBTU), benzotriazol-1-yl-oxytripyrrolidinophosphonium hexafluorophosphate (PyBOP), N,N-diisopropylethylamine (DIPEA), Wang resin, and Fmoc-protected amino acids) were obtained from Oakwood Products, Inc. or Advanced ChemTech. Tetrahydrofuran (THF) was obtained from an Innovative Technologies PureSolv solvent purification system and stored over 4 Å molecular sieves (Sigma-Aldrich). N,N-dimethylformamide (DMF) was obtained from either Sigma-Aldrich or EMD Millipore Chemicals. DIPEA, THF and DMF were degassed by sparging with nitrogen ($N_2$) gas for one hour prior to use.

Tetrakis(triphenylphosphine)palladium ($Pd(PPh_3)_4$) was obtained from Strem Chemicals. The Biotech-grade cellulose ester dialysis tubings (MWCO 500-1000), with flat widths of either 16-mm or 31-mm were obtained from Spectrum Labs. All other reagents and starting materials were obtained from Sigma-Aldrich and were used as received. 5-bromothiophene-2-carboxylic acid, 5,5'-bis-tributylstannyl-[2,2']-bithiophene and 4,4'-((1E,1'E)-1,4-phenylenebis(ethene-2,1-diyl))dibenzoic acid were prepared using literature procedures. Sanders, A. M., et al., *ACS Macro Lett.* 2012, 11, 1326-1329; Guo, X.; Watson, M. D. *Org. Lett.* 2008, 10, 5333-5336; Vadehra, G. S., et al., *Chem. Commun.* 2010, 46, 3947-3949. $^1$H-NMR spectra were obtained using a Bruker Avance 400 MHz and the data were processed using Bruker Topsin 1.3. Chemical shifts are reported in parts per million relative to residual protio solvent [$d_6$-DMSO δ: 2.50].

General Solid Phase Peptide Synthesis (SPPS).

All peptides were synthesized using the standard Fmoc solid-phase technique with Wang resin preloaded with the terminal amino acid (Wang-Asp=0.6 mmol/g). To the resin in a peptide chamber, Fmoc-deprotection was accomplished by adding a (1:4) piperidine/DMF solution twice (successive 5- and 10-minute treatment) and then washing with NMP, methanol and dichloromethane (DCM). For the amino acid couplings, 3.0 eq. of the Fmoc-protected amino acid (1.0 eq of the Fmoc-deprotected peptide bound to the resin) underwent external activation with 2.9 eq. of HBTU and 10 eq. DIPEA. The activated amino acid mixture was mixed for one minute prior to addition in the peptide chamber. The reaction mixture was allowed to mix for 60-120 minutes, after which was rinsed with NMP, methanol and DCM. The completion of all couplings was monitored using a Kaiser test on a few dry resin beads, repeating same amino acid coupling as needed. The general procedure for amino acid coupling was repeated until the desired peptide sequence was obtained.

General N-Acylation Procedure for Peptides.

Following a procedure reported in the literature, Sanders, A. M., et al., *ACS Macro Lett.* 2012, 11, 1326-1329, a solution containing 2.1 eq. of 5-bromothiophene-2-carboxylic acid that was activated by HBTU (2.0 eq.) with DIPEA (10 eq.) was mixed for 180 minutes with the resin containing the completed peptide sequence. The resin was rinsed with NMP, methanol and DCM. The resin was treated again with 1.1 eq. of 5-bromothiophene-2-carboxylic acid that was activated by HBTU (1.0 eq.) with DIPEA (10 eq.) for 60 minutes. After rinsing the resin with the standard wash cycle (NMP-methanol-DCM), completion was assessed using a Kaiser test on a few dry resin beads. Treatment with 1.1 eq. of the activated 5-bromothiophene-2-carboxylic acid was repeated as needed.

General On-Resin Stille Coupling Procedure.

Following a procedure reported in the literature, Sanders, A. M., et al., *ACS Macro Lett.* 2012, 11, 1326-1329, the N-acylated peptide made by following the general procedures described above were transferred to a Schlenk flask topped with a reflux condenser. The dried resin with $Pd(PPh_3)_4$ (4.0 mol % relative to the amino acid loading in the resin) was kept in the Schlenk flask under a nitrogen ($N_2$) atmosphere (approximately 10-20 mTorr). In a separate vessel, an approximately 15 mM solution of 5,5'-bis-tributylstannyl-[2,2']-bithiophene was prepared in DMF. This was then added to the reaction flask via syringe. The reaction mixture was heated up to 80° C. while agitating by constantly bubbling nitrogen ($N_2$) gas in the solution. The said conditions were maintained for 16 hours, and then the reaction mixture was allowed to cool to room temperature. The resin was washed with DMF (3×) in a peptide chamber, followed by the standard wash cycle. The synthesized π-conjugated peptides were then subjected to cleavage procedure.

General Cleavage Procedure for Peptides.

The cleavage cocktail was prepared with 9.5 mL of trifluoroacetic acid, 250 μL Milli-Q water, and 250 μL of triisopropylsilane. The resin was treated with 10 mL of cleavage cocktail in a peptide chamber for 3 hours. The filtrate was drained and the resin was washed with DCM (3×). The filtrate was concentrated under reduced pressure. The crude peptide was precipitated out of the filtrate by adding 90 mL of cold $Et_2O$, allowing the suspension to sit for 5 minutes at 4° C. The pellet formed was isolated by centrifugation, followed by decanting the solvent and drying the solid formed. The pellet was redissolved in Milli-Q water with a few drops of ammonium hydroxide (to completely dissolve the solid) and was subjected to lyophilization. All peptides (both crude and purified) were stored as lyophilized solids at 4° C.

Reverse Phase High-Performance Liquid Chromatography (RP-HPLC).

Peptides that underwent Stille coupling were dialyzed prior to HPLC purification in order to completely remove any excess Pd. The HPLC samples were prepared from lyophilized peptide solids after the dialysis procedure and were dissolved in Milli-Q water as basic samples by adding μL amounts of 1 M KOH until the pH reached 8 to 9. Purification and analysis were performed using an Agilent SD1 PrepStar System with a Phenomenex C8 column (Luna 5 μm, 250×21.20 mm and 250×4.60 mm) The mobile phase used consists of an ammonium formate aqueous buffer (pH 8) and acetonitrile.

Electrospray Ionization Mass Spectrometry (ESI-MS).

Samples for ESI-MS analyses were prepared in a 1:1 methanol and water solution with 1.0% (v/v) ammonium hydroxide. Mass spectra were collected using a Thermo Finnigan LCQ Deca Ion Trap Mass Spectrometer in negative mode.

Attenuated Total Reflection-Fourier Transform Infrared (ATR-FTIR) Spectroscopy.

All data were obtained on dry peptides using a ThermoSci Nicolet iD5 ATR-IR.

UV-Vis and Photoluminescence (PL).

All samples for absorption and emission scans were prepared by dissolving lyophilized peptides in degassed Milli-Q water. The pH of the samples was adjusted accordingly (pH 2 to 3 for acidic samples and pH 8 to 9 for basic samples) using 1 M HCl or 1 M KOH. Acidic and basic samples were separately prepared from a neutral peptide stock solution (ca. pH 7; 100 μM), keeping the final concentration for both samples the same and having an optical density of 0.1 to 0.2 for the acidic samples. Reacidified samples were prepared from acidic samples, wherein we added μL amounts of 1 M KOH and mixed (re-basified), then added μL amounts of 1 M HCl and mixed. Annealed samples were prepared from acidic solutions that were heated to 80° C. for 30 mins and cooled down to room temperature. The absorption spectra in the UV-Vis region were obtained using a Varian Cary 50 Bio UV-Vis spectrophotometer. The photoluminescence spectra were obtained using a PTi Photon S2 Technology International Fluorometer with an Ushio Xenon short arc lamp.

Circular Dichroism (CD).

Samples for CD analyses were dissolved in Milli-Q water with pH values adjusted accordingly (pH 2 to 3 for acidic samples and pH 8 to 9 for basic samples) using 1 M HCl or 1 M KOH. The spectra were collected using a Jasco J-810 spectropolarimeter at approximately 20° C. (unless otherwise stated), taking the final spectrum from the average of three scans.

Transmission Electron Microscopy (TEM).

Peptide nanostructures were imaged by preparing 0.1 wt % (1 mg/mL) peptide solutions in Milli-Q water. Samples were adsorbed for 5 minutes at 25° C. onto 200 mesh copper grids coated with Formvar in carbon film. All samples were stained with a 2% uranyl acetate solution. The grids were allowed to dry prior to imaging. Images were acquired using a Philips EM 420 transmission electron microscope equipped with an SIS Megaview III CCD digital camera, at an accelerating voltage of 100 kV.

OPV3 Peptide.

HO-DFAA-OPV3-AAFD-OH. Prepared according to a literature procedure; Wall, B. D., et al., *Langmuir* 2014, 30, 5946-5956, characterization data matches that of the literature. Crude peptide obtained was observed as a yellow powder ($\lambda_{max}$=367 nm, pH=8; HPLC purified, 52.6 mg, 18%). MS (ESI−) 1177.7 (M-1H)⁻ (calc. 1177.46), m/z 588.3 (M-2H)$^{2-}$ (calc. 588.2). $^1$H NMR (400 MHz, $d_6$-DMSO) δ: 8.51 (d, 1H, 7.3 Hz), 8.03 (d, 1H, J=6.4 Hz), 8.02 (d, 1H, J=7.1 Hz), 7.92 (d, 2H, J=8.4 Hz), 7.71 (t, 3H, J=8.4 Hz), 7.41 (m, 2H), 7.23 (d, 4H, J=4.4 Hz), 7.21-7.13 (m, 1H), 4.50-4.42 (m, 2H), 4.28-4.20 (m, 1H), 3.07 (dd, 1H, J=15.2, 4.3 Hz), 2.82 (dd, 1H, J=16.8, 11.0 Hz), 2.44-2.36 (m, 1H), 1.31 (d, 3H, J=7.2 Hz), 1.21 (d, 3H, J=7.0 Hz).

4T Peptide.

HO-DFAA-4T-AAFD-OH. Solid-supported Wang-DFAA-$NH_2$ peptide N-acylated with 5-bromothiophene-2-carboxylic acid was prepared (0.5 mmol). The peptide was coupled with 5,5'-bis-tributylstannyl-[2,2']-bithiophene (0.25 mmol, 0.186 g) in the presence of $Pd(PPh_3)_4$ (0.02 mmol, 0.023 g) using the general on-resin Stille coupling procedure for 13 hours. Resin was then subjected to the general cleavage procedure. Crude peptide obtained was observed as an orange powder (HPLC purified, 43.5 mg, 14%). MS (ESI−) m/z 1225.5 (M-1H)⁻ (calc. 1225.3), m/z 1247.5 (M-2H+Na)⁻ (calc. 1247.3), m/z 1291.5 (M-4H+3Na) (calc. 1291.3), m/z 612.4 (M-2H)$^{-2}$ (calc. 612.2), m/z 311.2 (M-5H+Na)$^{-4}$ (calc. 311.1) m/z 325.2 (M-6H+2K) (calc. 324.6). $^1$H NMR (400 MHz, $d_6$-DMSO) δ: 8.62 (d, 1H, J=7.8 Hz), 8.34 (br s, 1H), 8.05 (dd, 2H, J=16.0, 7.9 Hz), 7.86 (d, 1H, J=4.0 Hz), 7.76 (d, 1H, J=6.2 Hz), 7.43 (d, 1H, J=3.8 Hz), 7.38 (d, 2H, J=3.8 Hz), 7.22 (d, 4H, J=4.3 Hz), 7.18-7.14 (m, 1H), 4.45-4.41 (m, 2H), 4.27-4.19 (m, 1H), 4.11-4.03 (m, 1H), 3.06 (dd, 2H, J=14.6, 4.2 Hz), 2.86-2.78 (dd, 2H, J=16.0, 8.7 Hz), 2.44 (m, 1H), 2.36 (dd, 1H, J=15.8, 2.4 Hz), 1.28 (d, 3H, J=7.2 Hz), 1.21 (d, 3H, J=7.1 Hz).

Results and Discussion

Design considerations.

The presently disclosed system involves two peptide-π-peptide triblock systems that have pH-dependent assembly, generally resulting in molecularly dissolved structures under basic conditions (ca. pH 10) and 1D-nanostructures under acidic (ca. pH 2) conditions. Two widely investigated π-conjugated molecules with known semiconducting properties were used as π-electron cores within the triblock system: 1,4-distyrylbenzene (OPV3) as the donor unit, an oligo(p-phenylenevinylene), which is known to facilitate efficient exciton migration and has well-studied spectroscopic behavior, and quaterthiophene (4T) as the acceptor unit, which is a known hole-transporting organic semiconductor and low-energy dye (FIG. 1). Both of these chromophores have separately been incorporated into peptide-π-peptide molecules that undergo self-assembly to form nanofibrillar structures with high aspect ratios in aqueous environments.

Vadehra, G. S., et al., *Chem. Commun.* 2010, 46, 3947-3949; Wall, B. D., et al., *Adv. Mater.* 2011, 23, 5009-5014. These two particular π-conjugated units also were chosen because they have comparable molecular lengths and thus can be reasonably expected to encourage intermolecular hydrogen-bonding interactions within a coassembled nanostructure. The aspartic acid-phenylalanine-alanine-alanine (DFAA) tetrapeptide sequence was chosen because the OPV3-assemblies derived from the DFAA peptide sequence were shown previously to generate high-aspect ratio nanostructures with vibronic photoluminescence features associated with high-energy exciton-like emission, making it easier to differentiate the emission of the OPV3 donor from the 4T donor. Wall, B. D., et al., *Langmuir* 2014, 30, 5946-5956; Marciel, A. B., et al., *Adv. Mater.* 2013, 25, 6398-6404.

1D-assembly structure/morphology.

FIG. 2A shows an energy-minimized model generated from low-level equilibrium geometry calculations of a portion of 1D-assembly structure whereby the internal hydrogen-bonding networks deviate from ideal β-sheet architectures yet still allow for enthalpic stabilization. Past molecular dynamics simulations on OPV3-embedded peptides found that the deviations of these assemblies from ideal β-sheet conformations can be attributed to the entropic mixing within the stacks and internal deformations that are brought by a combination of various stabilizing hydrogen-bonding interactions that do not solely rely on strict interpretations β-sheet interactions. Wall, B. D., et al., *Langmuir* 2014, 30, 5946-5956. The quadrupole associated with the central π-conjugated structure presents a distinctly non-natural intermolecular interaction that further skews these oligopeptide assemblies from ideal protein secondary structures. This deviation is observed even in pure OPV3 or 4T assemblies (FIG. 3A, FIG. 3B, FIG. 3C, FIG. 3D, FIG. 4A, FIG. 4B, FIG. 4C, FIG. 4D, FIG. 4E, FIG. 4F, FIG. 4G, FIG. 4H, FIG. 4I, FIG. 4J, FIG. 4K and FIG. 4L), but is more pronounced in the coassemblies (FIG. 2A and FIG. 5A). Nevertheless, the generated structural models support the formation of 1D-stacks stabilized by intermolecular hydrogen-bonding interactions that place the donor and acceptor units into intimate intermolecular electronic contact. Transmission electron microscopy (TEM) was used to image the morphologies of the nanostructures formed in acidic OPV3-4T mixtures. Unlike the previously reported high-aspect ratio morphology of OPV3, the TEM images of pure 4T show irregularly-shaped nanostructures under acidic conditions (FIG. 5B). However, TEM indicates that the addition of acceptor 4T did not significantly perturb the self-assembling ability of the donor OPV3 as shown by the 1D-nanostructure formation observed at different coassembly ratios up to 50 mol % 4T (FIG. 2B, FIG. 2C, FIG. 5C, FIG. 6A, FIG. 6B and FIG. 6C). The only obvious difference was the change in the widths of each nanostructure as the 4T component was increased, suggesting a change in the bundling behavior within each nanostructure upon coassembly.

Steady-State Photophysical Characterization.

The steady-state absorption and photoluminescence (PL) spectra of the donor and acceptor solutions (both molecularly dissolved and assembled) were recorded as baseline points (FIG. 7A, FIG. 7B, AND FIG. 7C). Under basic (molecularly dissolved) conditions, OPV3 has an absorption $\lambda_{max}$ at 367 nm and emission $\lambda_{max}$ at 448 nm while 4T absorbs at 416 nm and emits at 510 nm. Upon initiating assembly under acidic conditions, both OPV3 and 4T show a blue-shift in absorbance with respect to their basic counterparts, having $\lambda_{max}$ at 339 and 400 nm, respectively. A broad, featureless emission peak with a $\lambda_{max}$ at 561 nm was observed for the assembled 4T solution. For the assembled OPV3 solution, vibronic features suggesting an excitonic emission were observed, with distinct peaks appearing at 431, 460 and 490 nm. These steady-state spectral properties are consistent with those found previously for OPV3 Wall, B. D., et al., *Langmuir* 2014, 30, 5946-5956, and for a peptide sequence variant of 4T Wall, B. D., et al., *Adv. Mater.* 2011, 23, 5009-5014, with the blue-shift in absorption and PL quenching and red-shift observed in acidic samples indicating the formation of "H-like" aggregates. The differences in PL inherent to these two chromophores allow spectral signatures originating from the OPV3 donor and the 4T acceptor to be distinguished.

As for the coassembled heterostructures, UV-Vis and PL spectra of the OPV3-4T mixtures were recorded during titration experiments where OPV3 concentration was held constant ([OPV3]=3.2 µM) in order to monitor the photophysical events during the coassembly process. The emission spectra of the mixtures shown in FIG. 7C correspond to solutions that were excited at 320 nm (basic) and 330 nm (acidic), the wavelengths at which OPV3 has reasonable absorption but 4T has minimum absorption. The absorption profile consistently shows a blue-shifted absorption of acidic against the basic solutions in all mol % 4T, indicating the fidelity of the "H-like" aggregation (FIG. 7B). In the molecularly dissolved state (ca. pH 10), discrete spectral peaks for OPV3 and 4T in the absorption spectra (FIG. 7A) and peaks characteristic of molecularly dissolved OPV3 in the emission spectra (FIG. 8A) were observed for mixtures of OPV3 and 4T wherein [OPV3] was kept constant. When the overall chromophore concentration is kept constant (FIG. 9A and FIG. 9B), discrete spectral peaks for OPV3 and 4T emission were observed for the basic solutions, further illustrating the absence of interactions (e.g., collisional quenching) and energy transfer between the donor-acceptor pair in their molecularly dissolved state.

For the acidic mixtures, where nanostructure formation is expected to occur, the emission peaks characteristic of the donor OPV3 became quenched along with the decrease in quantum yield (FIG. 7D) upon the addition of the acceptor 4T, giving rise to a new spectral feature ($\lambda_{em}$ approximately 540 nm) reminiscent of 4T emission. The progressively red-shifted PL spectral features of the coassembled solutions as the acceptor concentration increases are also indicative of energy transfer. The donor peak quenching was observed even by adding 1 mol % of the acceptor 4T, leading to the decrease in the PL peak area down to 46%. This suggests that during the lifetime of the OPV3 excited state, a significant fraction of the photogenerated excitons has the ability to migrate to the 4T acceptor dopant. In an analogous study by Adams and coworkers, where donor and acceptor π-systems were conjugated to dipeptides within a hydrogel, only a 15% decrease in the emission intensity of the donor at 0.8 mol % acceptor was observed. Chen, L., et al., *Chem. Commun.* 2010, 46, 4267-4269. Ulijn and coworkers were able to increase the efficiency by using a related dipeptide that formed a gelator system using an enzymatic assembly trigger and observed complete quenching of donor PL at an acceptor concentration of about 3 mol %. Nalluri, S. K. M.; Ulijn, R. V. *Chem. Sci.* 2013, 4, 3699-3705. Both of these examples demonstrated energy transfer using end-functionalized peptide hydrogelators with alkoxy naphthalene donor combined with a dansyl derivative acceptor whereas in the presently disclosed subject matter, a peptide-based donor-acceptor pair with a comparable energy transfer efficiency occurring between the semiconductor units that are buried within peptide-π-peptide nanostructures is provided.

At 9 mol % 4T, complete quenching of the higher energy vibronic features characteristic to aggregated OPV3 emission peak was observed. In parallel studies involving more hydrophobic peptide sequences attached to the quaterthiophene core, similar PL profiles under acidic, self-assembling conditions as observed with the 9 mol % 4T acidic solution were observed (FIG. 10). The broad, featureless peak observed from 33 to 50 mol % 4T (FIG. 7C and FIG. 8B) exhibits a red shift as the mol % 4T increases within this range, and can be attributed to the contribution of 4T emission due to the absence of spectral features characteristic of assembled OPV3. This broad peak is an apparent superposition of the emission $\lambda_{max}$ peaks associated with molecularly dissolved (510 nm) and aggregated (561 nm) 4T, and suggests the coexistence of "isolated" and "aggregated" 4T exciton traps diluted within the aggregated OPV3 π-stacked nanostructures.

The emission spectra were then recorded after excitation at other wavelengths (FIG. 11 and FIG. 12A): one at a higher energy wherein both OPV3 and 4T strongly absorbs (380 nm for basic and 370 nm for acidic) and one at a lower energy wherein 4T absorbs, but OPV3 does not (450 nm). With the higher energy excitation, the resulting emission spectral features of both the basic and acidic solutions are similar to that excited at 320 nm or 330 nm, only varying in intensities due to the higher extinction coefficient of the system at the latter longer wavelengths. The extent of quenching at 1 mol % 4T also was similar (peak area decreased down to 47%) when the solutions are excited at 320 nm and 330 nm. On the other hand, having the excitation at 450 nm, wherein only 4T strongly absorbs, the resulting emission profiles for the basic solutions only correspond to 4T. The PL peaks for the coassemblies are blue-shifted with respect to pure 4T emission that is possibly due to the less planar 4T conformation when locked within the stacks of OPV3 than within 4T units as observed in the energy-minimized models. Note that at 9 mol % 4T, the PL intensity when the acidic solution is excited at 330 nm is about 25-fold higher than when the solution is excited at 450 nm, thereby confirming the contributions of energy transfer from OPV3 to 4T in the coassembled nanostructures.

In general, a Førster-like energy transfer that is governed by dipole-dipole interactions requires the donor-acceptor system to have strong spectral overlap between the donor emission and acceptor absorbance. Such requirement is achieved in both the molecularly dissolved and aggregated states of OPV3 and 4T donor-acceptor pair (FIG. 12B). This shows that the chosen donor-acceptor pair can foster a direct resonance energy transfer, but the significant changes in the emission spectra features observed even at very low loadings of the 4T acceptor within the coassemblies and the fact that OPV-based stacks are known to facilitate fast exciton migration implies that other mechanisms are potentially involved for the overall transport process (FIG. 13). In addition, increasing the proximity between donor-acceptor units by trapping them within the 1D-nanostructures potentially allows shorter-range energy transfer processes that result from direct wavefunction overlap between the interacting chromophores to occur, which are generally known to increase transport within a chain of conjugated polymers as compared to those solely dictated by dipole-dipole interactions. Rose, A., et al., *Philos. Trans. R. Soc. Math. Phys. Eng. Sci.* 2007, 365, 1589-1606.

Lifetime Measurements.

To further support that the spectral changes observed above are consequences of the funneling of energy from OPV3 to 4T via exciton migration, fluorescence lifetime measurements were recorded at different OPV3 and 4T mixture ratios (Table 1). The PL decay profiles for pure OPV3 and 4T assemblies, as well as their coassemblies can be fit to a two-component exponential while a single component fit was suitable for the decay profiles of basic solutions. The decrease in the average lifetime, similar to the observation in energy-transporting OPV gels studied by Ajayaghosh and coworkers, Ajayaghosh, A., et al., *Angew. Chem. Int. Ed.* 2007, 46, 6260-6265, and the progressively decreasing fraction of the long-lived component upon increasing the mol % of the acceptor under acidic conditions supports the energy transfer within the coassemblies. This observation also supports the minimal contributions from OPV3 excimer formation, which would result in a low-energy charge transfer band that would overlap with the 4T emission profile, but has a longer-lived lifetime. Wall, B. D., et al., *Langmuir* 2014, 30, 5946-5956; Sherwood, G. A., et al., *J. Phys. Chem. C* 2009, 113, 18851-18862. The absence of energy transfer in the molecularly dissolved solutions and the need for nanostructure formation to initiate the energy transfer within an ordered matrix, which also is found important in the systems studied by Meijer and coworkers Hoeben, F. J. M., et al., *Angew. Chem. Int. Ed.* 2004, 116, 2010-2013; Hoeben, F. J. M., et al., *Chem Phys Chem* 2005, 6, 2337-2342, is further verified by the unchanging lifetime decay values of the OPV3-4T basic mixtures with respect to pure, basic OPV3 solution.

TABLE 1

Fluorescence lifetimes of OPV3, 4T, and their coassemblies in acidic (pH 2) and basic (pH 10) solutions ($\lambda_{exc}$ = 375 nm).

| | | τ/ns | |
|---|---|---|---|
| | | pH 2 | |
| mol % 4T | pH 10 | τ (%) | avg |
| 0% | 1.06 | 1.10 (69.8); 5.28 (30.2) | 2.03 |
| 1% | 1.06 | 0.968 (78.6); 4.84 (21.4) | 1.79 |
| 5% | 1.06 | 0.767 (94.6); 3.39 (5.44) | 0.91 |
| 13% | 1.05 | 0.720 (98.0); 6.71 (2.00) | 0.84 |
| 26% | 1.06 | 0.664 (99.2); 4.13 (0.78) | 0.69 |
| 33% | 1.06 | 0.631 (99.6); 4.02 (0.36) | 0.64 |
| 100% | 0.55 | 0.528 (82.0); 1.67 (18.0) | 0.73 |

Effect of 1D-Heterostructure Formation on the Energy Transfer Efficiency.

The potential mechanisms of energy transfer proposed for this system involve exciton migration along intimately stacked donor chromophores within a 1D-assembly that is trapped by the acceptor. To further investigate how this nanoscale ordering improves energy transfer, the emission spectra of donor-acceptor mixtures wherein a pre-assembled OPV3 was separately prepared as an acidic solution and then titrated against neutral 4T were monitored. The TEM images for a 1:1 coassembled OPV3-4T mixture under this condition (FIG. 6B) shows that this forms two different aggregate morphologies that are indicative of the favored separate aggregation of OPV3 and 4T, potentially generating nanomaterial interfaces similar to p-n heterojunctions Sugiyasu, K., et al., *Chem. Mater.* 2008, 20, 2863-2865; Morris, K. L., et al., *Nat. Commun.* 2013, 4, 1480, for the semiconductor chromophores. Unlike in the coassembled mixtures used in FIG. 7A, FIG. 7B, FIG. 7C, FIG. 7D, FIG. 11A, FIG. 11B, FIG. 11C, and FIG. 11D, wherein 4T can serve as a local trap for diffusing excitons along the 1D-nanostructures, assemblies from the solution wherein 4T was titrated with a pre-assembled OPV3 is expected to foster an energy transfer process that would mostly rely on non-specific dipole interactions or diffusive encounters. Although the dynamic nature of these assemblies opens the possibility of the intercalation 4T units in pre-assembled OPV3 stacks, these non-specific electronic interactions are expected because majority of 4T units are likely to have separately aggregated from the 1D-stacks of OPV3 as supported by the observations under TEM. At 1 mol % 4T, the peak area of the emission profile of assemblies (FIG. 14A and FIG. 14B) generated from this condition only decreased down to 82% with respect to pure OPV3, showing a much less efficient energy transfer than when the OPV3 and 4T are intimately coassembled. Moreover, the complete quenching of the donor vibration features at approximately 430 nm and 460 nm, which was observed at 9 mol % for the coassembled mixtures, was only observed starting at 33 mol % 4T (FIG. 14C, FIG. 14D and FIG. 14E) when 4T is titrated against pre-assembled OPV3 nanostructures.

Reversibility of Heterostructure Formation.

The dynamic nature of these heterostructures when exposed to different environmental stimuli, such as pH and temperature, also was explored. These conditions allowed different kinetic regimes for nanostructure formation beyond the kinetically-trapped state obtained upon initial solution acidification to be investigated. The pH-dependence of nanostructure formation for these π-conjugated peptides is already well-established, but its reversibility and the underlying consequences of pH switching to the energy transfer within our peptide heterostructure system are not yet explored. Similarly, an effort also was made to explore the thermal response of both nanostructure formation and efficiency of energy transfer due to the temperature-dependent assembly mechanisms existing in the related energy-transporting oligo(p-phenylenevinylene)-based systems studied by Meijer and co-workers. Hoeben, F. J. M., et al., *Angew. Chem. Int. Ed.* 2004, 116, 2010-2013; Hoeben, F. J. M., et al., *Chem Phys Chem* 2005, 6, 2337-2342.

Variation of pH.

Interestingly, energy transfer was observed to be reversible within a pH-controlled assembly-dissolution cycle (FIG. 15A, FIG. 15B, FIG. 15C and FIG. 15D). From the acidic coassembled samples, whether pH could be used as a "switch" that could turn on or off the occurrence of energy transfer within the assemblies was tested. Upon adding base, the solution immediately goes back to the molecularly dissolved state that does not demonstrate energy transfer as confirmed by the absorption and emission spectra (FIG. 15A and FIG. 15C). After reacidifying these samples, quenching of the OPV3 donor emission peaks, along with the development of new spectral peaks reminiscent of 4T emission, suggests that the re-assembled structure still fosters the energy transfer process (FIG. 15 B and FIG. 15D). Comparing the emission spectra shown in FIG. 7C, an enhancement in the intensity with corresponding blue-shift in central vibronic feature at 455 nm as compared to 430 nm and 490 nm shoulder intensities was observed. However, the intensity of this 455 nm decreased by approximately 25% as compared to the 460 nm peak of the initial acidic OPV3, which can be attributed to environmental degradation. Note that the nearly complete quenching of the 430 nm and 455 nm peaks still occurred at 9 mol % 4T. The observed trends in the changes of the emission signals also were the same as that of the initial acidic solution when excited at 380 nm and 450 nm (FIG. 16A and FIG. 16B). These observations show an important characteristic of these 1D-nanostructures, that although these are kinetically-trapped states formed from rapid (re)acidification, the ensemble photophysics remain reproducible.

Variation of Temperature.

In general, an efficient energy transfer occurs in a state wherein the assembled structure of the donor-acceptor pair represents a local thermodynamic minimum within the free energy landscape. Nalluri, S. K. M.; Ulijn, R. V. *Chem. Sci.* 2013, 4, 3699-3705; Hirst, A. R., et al., *Nat. Chem.* 2010, 2, 1089-1094. By subjecting the acidic samples to a heating-cooling cycle (25° C. to 80° C. to 25° C.) as a form of annealing, thermodynamic minima that are potentially different from the initial trapped state formed after rapid sample acidification could be accessed. The emission spectra of the annealed, acidic samples (FIG. 16C and FIG. 16D) were observed to have vibronic features similar to the reacidified sample in FIG. 15D. The existence of quenched vibronic features at 430 nm and 460 nm observed for the annealed 9 mol % 4T solution, which deviates from the observed complete quenching of these signals for the initial 9 mol % 4T acidic samples at 25° C. in FIG. 7C, suggests that the annealed aggregate has an assembly structure that results in excitons being trapped easier within the donor matrix rather than reaching the acceptor site—leading to the appearance of donor emission features even up to 25 mol % 4T. It is possible that exposure at high temperatures and subsequent cooling leads to more local disorder at the donor-acceptor interface, thus allowing for more excitons to be trapped within the donor matrix.

To obtain more information about the assembly dynamics and energy transfer as the temperature increases, the emission spectra of high temperature samples (ca. 60-70° C.) for OPV3, 4T, and 9 mol % 4T coassembly were collected and the signals were monitored as the solutions cool down (FIG. 17A, FIG. 17B, FIG. 17C, FIG. 17D and FIG. 17E). At a high temperature, the emission signature is still reminiscent of an exciton-coupled structure instead of the molecularly dissolved state reported in previous studies of oligo(p-phenylenevinylene)-based systems at higher temperatures in organic solvents. Hoeben, F. J. M., et al., *Angew. Chem. Int. Ed.* 2004, 116, 2010-2013. This reflects the resistance towards nanostructure disassembly of these peptide-bound π-systems in aqueous environments, even at biologically "extreme" temperatures. At 9 mol % 4T, wherein the complete quenching of donor emission was observed for the acidic samples, quenched signals were also observed for the heated samples but the approximately 430 nm and 460 nm peaks associated with the OPV3 vibronic couplings were still present. This indicates that energy transfer is still facilitated in the potentially new aggregate structure formed by heating, however, the efficiency of the transfer decreased. Moreover, the PL spectra of both OPV3 and 9 mol % 4T both showed blue-shifted signals (approximately 10 nm) as compared to the acidic samples at 25° C., which is maintained throughout the cooling period. This unchanging emission profile upon cooling is consistent with the recent report by Stupp and coworkers about the hysteresis effect upon heating and cooling back their peptide amphiphiles under different solvent conditions Korevaar, P. A., et al., *J. Am. Chem. Soc.* 2014, 136, 8540-8543. It also is interesting to note that following the addition of base to the annealed samples and subsequently reacidifying, the signal recovers back to the initial acidic emission profile. The persistence of self-assembled structures under extreme conditions is important because it is generally addressed that the development of supramolecular polymers that do not break apart at high temperatures remains as a challenge in the field. Krieg, E., et al., *J. Am. Chem. Soc.* 2014, 136, 9443-9452.

In the presently disclosed peptide-π-peptide triblock system, this structure stability can be attributed to the contributions of the hydrogen-bonding networks among the peptide segments. The CD spectrum (FIG. 18A) of pure OPV3 under acidic conditions shows a large negative Cotton effect and a high-energy minimum at approximately 220 nm, indicative of β-sheet formation of the peptide moiety. On the other hand, the CD spectrum of pure 4T under acidic conditions shows weak Cotton effect with no signals in the high-energy region. The CD spectra of the molecularly dissolved basic samples showed no low energy features, but a bisignate Cotton effect within the chromophore absorption region for the coassembled acidic samples was observed at all mol % 4T, indicating the existence of exciton-coupled chromophores held within a chiral environment. This supports that the occurrence of 1D-stacking of π-units in a chiral environment is maintained during the coassembly process. Upon annealing the acidic solutions, the high-energy signature indicative of β-sheet formation in the CD spectra for acidic OPV3 and the coassemblies (FIG. 18B) became more pronounced. Since the energy-minimized structures previously discussed do not show an ideal β-sheet assembly, the enhanced high-energy spectral signature in CD supports the possibility that heating of the 1D-nanostructures leads to a more thermodynamically favored "β-sheet-like" motif that subsequently alters the spatial orientation of the transition dipoles of the chromophores within the aggregate, and thus, their corresponding photophysics as observed in FIG. 17A and FIG. 17B.

In summary, the presently disclosed subject matter demonstrates energy transport within a donor-acceptor system based on π-conjugated peptide nanostructures in water. This system shows an energy transfer process that involves multiple mechanisms, such as exciton migration and resonance energy transfer. The presently disclosed subject matter also supports the importance of nanoscale order to obtain an efficient energy transport as mediated by the funneling of excitons to the acceptor sites and how these processes are impacted by thermal annealing and repetitive changes in pH. The nanostructures do not result in complete dissolution upon increasing the temperature to approximately 70° C., but reflects the formation of another rearranged structure that exhibits hysteresis, indicating nanostructure stability. The interesting assembly features can be attributed to the dynamic and stable nature of hydrogen bonds and side chain interactions of the peptide segments that stabilizes the anisotropic π-π interactions between the monomers. Although the heterostructure reversibility provides insights to the dependence of energy transfer efficiency into appropriately assembled donor-acceptor pair and the stability of this system, a more accurate elucidation of energy transfer mechanism within the annealed 1D-heterostructures requires further investigation of the temperature-dependent nanostructure morphology changes. Overall, this strategy to design bioelectronic materials that utilize peptide interactions to enhance chromophore interactions and energy transfer efficiency is applicable to a range of emerging bio-relevant optoelectronic devices, such as artificial photonic antenna systems and other photosynthetic unit mimics.

Example 2

Hole Transport and Voltage Equilibration in Self-Assembled Pi-Conjugated Peptide Nanostructures Using Field-Effect Transistor Architectures Overview Pi-conjugated peptide materials are attractive for bioelectronics due to their unique photophysical characteristics, biofunctional interfaces, and processability under aqueous conditions. In order to be relevant for electrical applications, these types of materials must be able to support the passage of current and the transmission of applied voltages. Presented herein is an investigation of both the current- and voltage-transmission activities of one-dimensional π-conjugated peptide nanostructures. Observations of the nanostructures as both semiconducting and gate layers in organic field-effect transistors were made, and the effect of systematic changes in amino acid composition on the semiconducting/conducting functionality of the nanostructures was investigated. These molecular variations directly impacted the hole mobility values observed for the nanomaterial active layers over three orders of magnitude (~0.02 to $5\times10^{-5}$ cm$^2$ V$^{-1}$ s$^{-1}$) when the nanostructures had quaterthiophene cores and the assembled peptide materials spanned source and drain electrodes. Peptides without the quaterthiophene core were used as controls, and did not show field-effect currents, verifying that the transport properties of the nanostructures rely on the semiconducting behavior of the π-electron core and not just ionic rearrangements. It also have been showed that the nanomaterials could act as gate electrodes and assessed the effect of varying the gate dielectric layer thickness in devices where the conventional organic semiconductor pentacene spanned the source and drain electrodes in a top-contact OFET, showing an optimum performance with 35-40 nm dielectric thickness. This study shows that these peptides that self-assemble in aqueous environments can be used successfully to transmit electronic signals over biologically relevant distances.

Material and Methods

General Considerations.

The chemicals used for 9-fluorenylmethoxycarbonyl (Fmoc)-based solid phase peptide synthesis (N-methylpyrrolidone (NMP), O-(benzotriazol-1-yl)-N,N,N',N'-tetramethyluronium hexafluorophosphate (HBTU), benzotriazol-1-yl-oxytripyrrolidinophosphonium hexafluorophosphate (PyBOP), N,N-diisopropylethylamine (DIPEA), Wang resin, and Fmoc-protected amino acids) were obtained from Oakwood Products, Inc. or Advanced ChemTech. Tetrahydrofuran (THF) was obtained from an Innovative Technologies PureSolv solvent purification system and stored over 4 Å molecular sieves (Sigma-Aldrich). N,N-dimethylformamide (DMF) was obtained from either Sigma-Aldrich or EMD Millipore Chemicals. DIPEA, THF and DMF were degassed by sparging with nitrogen (N$_2$) gas for one hour prior to use.

Tetrakis(triphenylphosphine)palladium (Pd(PPh$_3$)$_4$) was obtained from Strem Chemicals. The Biotech-grade cellulose ester dialysis tubings (MWCO 500-1000), with flat widths of either 16-mm or 31-mm were obtained from Spectrum Labs. All other reagents and starting materials were obtained from Sigma-Aldrich and were used as received. 5-bromothiophene-2-carboxylic acid and 5,5'-bis-tributylstannyl-[2,2']-bithiophene were prepared using literature procedures (Sanders et al., 2012). The $^1$H-NMR spectra were obtained using a Bruker Avance 400 MHz (unless otherwise stated) and the data was processed using Bruker Topsin 1.3. Chemical shifts are reported in parts per million relative to residual protio solvent [d$_6$-DMSO δ: 2.50, D$_2$O δ: 4.79 ($^1$H NMR)]. The tabulated values for NMR peaks may not reflect the theoretical number of protons expected due to some aggregation previously observed for these materials under basic to neutral conditions (Ardona et al., 2015).

General Solid Phase Peptide Synthesis (SPPS).

All peptides were synthesized using the standard Fmoc solid-phase technique with Wang resin preloaded with the terminal amino acid (Wang-Asp=0.6 mmol/g). To the resin in a peptide chamber, Fmoc-deprotection was accomplished by adding a (1:4) piperidine/DMF solution twice (successive 5- and 10-minute treatment) and then washing with NMP, methanol and dichloromethane (DCM). For the amino acid couplings, 3.0 eq. of the Fmoc-protected amino acid (1.0 eq of the Fmoc-deprotected peptide bound to the resin) underwent external activation with 2.9 eq. of HBTU and 10 eq. DIPEA. The activated amino acid mixture was mixed for one minute prior to addition in the peptide chamber. The reaction mixture was allowed to mix for 60-120 minutes, after which was rinsed with NMP, methanol and DCM. The completion of all couplings was monitored using a Kaiser test on a few dry resin beads, repeating same amino acid coupling as needed. The general procedure for amino acid coupling was repeated until the desired peptide sequence was obtained.

General N-Acylation Procedure for Peptides.

Following a procedure reported in the literature (Sanders et al., 2012), a solution containing 2.1 eq. of 5-bromothiophene-2-carboxylic acid that was activated by HBTU (2.0 eq.) with DIPEA (10 eq.) was mixed for 180 minutes with the resin containing the completed peptide sequence. The resin was rinsed with NMP, methanol and DCM. The resin was treated again with 1.1 eq. of 5-bromothiophene-2-carboxylic acid that was activated by HBTU (1.0 eq.) with DIPEA (10 eq.) for 60 minutes. After rinsing the resin with the standard wash cycle (NMP-methanol-DCM), completion was assessed using a Kaiser test on a few dry resin beads. Treatment with 1.1 eq. of the activated 5-bromothiophene-2-carboxylic acid was repeated as needed.

General on-Resin Stille Coupling Procedure.

Following a procedure reported in the literature (Sanders et al., 2012), the N-acylated peptide made by following the general procedures described above were transferred to a Schlenk flask topped with a reflux condenser. The dried resin with Pd(PPh$_3$)$_4$ (4.0 mol % relative to the amino acid loading in the resin) was kept in the Schlenk flask under a nitrogen (N$_2$) atmosphere (~10-20 mTorr). In a separate vessel, a ~15 mM solution of 5,5'-bis-tributylstannyl-[2,2']-bithiophene was prepared in DMF. This was then added to the reaction flask via syringe. The reaction mixture was heated up to 80° C. while agitating by constantly bubbling nitrogen (N$_2$) gas in the solution. The said conditions were maintained for 16 hours, and then the reaction mixture was allowed to cool to room temperature. The resin was washed with DMF (3×) in a peptide chamber, followed by the standard wash cycle. The synthesized π-conjugated peptides were then subjected to cleavage procedure.

General Cleavage Procedure for Peptides.

The cleavage cocktail was prepared with 9.5 mL of trifluoroacetic acid, 250 μL Milli-Q water, and 250 μL of triisopropylsilane. The resin was treated with 10 mL of cleavage cocktail in a peptide chamber for 3 hours. The filtrate was drained and the resin was washed with DCM (3×). The filtrate was concentrated under reduced pressure. The crude peptide was precipitated out of the filtrate by adding 90 mL of cold Et$_2$O, allowing the suspension to sit for 5 minutes at 4° C. The pellet formed was isolated by centrifugation, followed by decanting the solvent and drying the solid formed. The pellet was redissolved in Milli-Q water with a few drops of ammonium hydroxide (to completely dissolve the solid) and was subjected to lyophilization. All peptides (both crude and purified) were stored as lyophilized solids at 4° C.

DGG-4T Peptide (HO-DGG-4T-GGD-OH).

Prepared according to literature procedure (Ardona et al., 2015); characterization matched that of literature.

DAA-4T Peptide (HO-DAA-4T-AAD-OH).

Prepared according to literature procedure (Ardona et al., 2015); characterization matched that of literature.

DVV-4T Peptide (HO-DVV-4T-VVD-OH).

Prepared according to literature procedure (Ardona et al., 2015); characterization matched that of literature.

DII-4T Peptide (HO-DII-4T-IID-OH).

Prepared according to literature procedure (Ardona et al., 2015); characterization matched that of literature.

EGG-4T Peptide (HO-EGG-4T-GGE-OH).

Solid-supported Wang-EGG-NH$_2$ peptide N-acylated with 5-bromothiophene-2-carboxylic acid was prepared (0.5 mmol). The peptide was coupled with 5,5'-bis-tributylstannyl-[2,2']-bithiophene (0.25 mmol, 0.186 g) in the presence of Pd(PPh$_3$)$_4$ (0.02 mmol, 0.023 g) using the general on-resin Stille coupling procedure for 14 hours. Resin was then subjected to the general cleavage procedure. Crude peptide obtained was observed as an orange powder (0.077 g, 34%). MS (ESI−) m/z 925.3 (M-2H$^+$+Na$^+$) (calc. 925.1), m/z 903.3 (M-H$^+$) (calc. 903.1), m/z 451.3 (M-2H$^+$) (calc. 451.1). $^1$H NMR (600 MHz, D$_2$O) δ, ppm: 8.37 (d, 1H, J=3.6 Hz), 7.53 (s, 1H), 7.21 (s, 1H), 7.14 (d, 2H, J=15.6 Hz), 4.11-4.08 (m, 1H), 4.05 (d, 1H, J=3.0 Hz), 3.93 (d, 1H, J=3.0 Hz), 2.20-2.17 (m, 1H), 2.05-2.00 (m, 1H), 1.89-1.84 (m, 1H).

EAA-4T Peptide (HO-EAA-4T-AAE-OH).

The synthesis for EAA-4T peptide was adapted from Wall et al., 2011, with the exception that the resin was not washed with DMF, isopropanol, water, THF, acetonitrile, ether and hexanes prior to cleavage. Crude peptide obtained was observed as an orange powder; characterization matched that of literature.

EVV-4T Peptide (HO-EVV-4T-VVE-OH).

Solid-supported Wang-EVV-NH$_2$ peptide N-acylated with 5-bromothiophene-2-carboxylic acid was prepared (0.5 mmol). The peptide was coupled with 5,5'-bis-tributylstannyl-[2,2']-bithiophene (0.25 mmol, 0.186 g) in the presence of Pd(PPh$_3$)$_4$ (0.02 mmol, 0.023 g) using the general on-resin Stille coupling procedure for 15 hours. Resin was then subjected to the general cleavage procedure. Crude peptide obtained was observed as an orange powder (0.102 g, 38%). MS (ESI−) m/z 1109.5 (M-2H$^+$+K$^+$) (calc. 1109.3), m/z 1071.7 (M-H$^+$) (calc. 1071.3), m/z 535.5 (M-2H$^+$) (calc. 535.2). $^1$H NMR (600 MHz, D$_2$O) δ, ppm: 8.37 (dd, 1H, J=1.2 Hz), 7.59 (d, 1H, J=3.6 Hz), 7.25 (s, 1H), 7.19 (m, 2H), 4.20 (dd, 2H, J=8.4 Hz, 2.7 Hz), 4.13 (dd, 2H, J=7.8 Hz, 2.7 Hz), 4.09-4.07 (m, 2H), 2.12 (t, 6H, J=8.1 Hz), 2.07-2.03 (m, 5H), 1.96-1.94 (m, 3H), 1.84-1.80 (m, 3H), 0.95 (d, 8H, J=3.0 Hz), 2.12 (t, 24H, J=6.6 Hz).

EII-4T Peptide (HO-EII-4T-IIE-OH).

Solid-supported Wang-EII-NH$_2$ peptide N-acylated with 5-bromothiophene-2-carboxylic acid was prepared (0.5 mmol). The peptide was coupled with 5,5'-bis-tributylstannyl-[2,2']-bithiophene (0.25 mmol, 0.186 g) in the presence of Pd(PPh$_3$)$_4$ (0.02 mmol, 0.023 g) using the general on-resin Stille coupling procedure for 16 hours. Resin was then subjected to the general cleavage procedure. Crude peptide obtained was observed as yellow/orange powder (0.055 g, 19%). MS (ESI−) m/z 1149.6 (M-2H$^+$+Na$^+$) (calc. 1150.4), m/z 1127.7 (M-H$^+$) (calc. 1127.4), m/z 5-63.5 (M-2H$^+$) (calc. 563.2). $^1$H NMR (400 MHz, d$_6$-DMSO) δ, ppm: 8.48 (d, 1H, J=8.8 Hz), 8.00 (d, 1H, J=8.8 Hz), 7.96 (d, 1H, J=7.2

Hz), 7.92 (d, 1H, J=4.0 Hz), 7.42 (d, 1H, J=4.0 Hz), 7.38 (dd, 2H, J=4 Hz, 2.6 Hz), 4.35 (t, 1H, J=9.00 Hz), 4.20-4.14 (m, 2H), 2.28-2.23 (m, 2H), 1.91-1.74 (m, 4H), 1.49-1.44 (m, 2H), 1.23-1.04 (m, 2H), 0.87-0.78 (m, 12H).

DVV-C10 Peptide (HO-DVV—$(CH_2)_{10}$—VVD-OH).

0.0288 g (0.125 mmol) of dodecanedioic acid and 0.0650 g (0.125 mmol) of PyBOP was dissolved in 10-mL of 2:1 NMP:DCM solution, after which 0.522 mL of DIPEA was gradually added then mixed for one minute. This solution was added to the solid-supported Wang-DVV-$NH_2$ (0.25 mmol) in a peptide chamber and mixed for 12 h. Resin was rinsed using the standard wash cycle. The general cleavage procedure was followed, only that the cleavage cocktail was diluted in a 1:1 ratio DCM and was mixed with the resin for 2 h. Crude peptide was obtained as a white powder (0.0565 g, 53%). MS (ESI−) m/z 893.5 ($M-2H^++K^+$) (calc. 893.6), m/z 427.2 ($M-2H^+$) (calc. 427.3). $^1$H NMR (400 MHz, $d_6$-DMSO) δ, ppm: 7.83 (m, 2H), 7.72 (br), 7.71 (br), 4.24-4.12 (ddd, 4H, J=32.4 Hz, 8.8 Hz, 7.2 Hz), 2.17-2.10 (m, 2H), 2.03-1.97 (m, 2H), 1.47 (t, 2H, J=9.2 Hz), 1.22 (s, 6H), 0.85-0.81 (m, 12H).

Transmission Electron Microscopy (TEM).

Nanostructures were prepared by acidifying 1 mg/mL (ca. 1 mM) solutions of peptides in Milli-Q water. Samples were adsorbed for 5 minutes (at 25° C.) onto 300 mesh copper grids coated with Formvar in carbon film (Electron Microscopy Sciences). All samples were stained with a 2% uranyl acetate solution. The grids were allowed to dry prior to imaging. Images were acquired using a Philips EM 420 transmission electron microscope equipped with SIS Megaview III CCD digital camera, at an accelerating voltage of 100 kV. ImageJ 1.47 (National Institutes of Health, Bethesda, Md., USA) was used to approximate the widths of the nanostructures (at least n=25 per TEM image).

Atomic Force Microscopy (AFM).

Acidified peptide solutions (0.1 mg/ml, 0.1 mM) were dropcasted into $SiO_2$ substrates. AFM topography images are taken in tapping mode using the Dimensional V scanning probe microscope. The images are visualized using VECCO's software, Nanoscope.

3D Laser Scanning Microscopy.

In order to characterize the surface roughness and height profile of the dried, acid-assembled peptide films on glass, all samples were observed under a Keyence Color 3R Laser Microscope VK-X100K/X200K.

Device Fabrication.

The OFET devices with π-conjugated peptide nanostructure films used as the semiconductor active layers (FIG. 23A) were fabricated on silicon wafers (with 300 nm silicon dioxide; capacitance per area=11.5 $nF/cm^2$). The wafers were cut into 1-inch by 1-inch square samples, which were cleaned by keeping them in piranha solution (3:1 ratio of concentrate concentrated sulfuric acid to hydrogen peroxide) for 3-4 hours followed by sonication in acetone and isopropanol for 30 minutes. The samples were blown dry using dry nitrogen flow. To each Si/$SiO_2$ substrate, 5 μL of 1 wt % (ca. 10 mM) peptide solution was dropcast and then exposed to an acid chamber (closed chamber with concentrated HCl vapor) for 5 minutes prior to drying at ambient temperature and pressure. The Au electrodes (50 nm-thick) were deposited using a TEM grid as the shadow mask (W/L=10) by physical vapor deposition while keeping the chamber temperature below 60° C.

For the OFET devices with the π-conjugated peptide nanostructures used as the gate (FIG. 23C and FIG. 23D), microscopic glass slides were cut into 1-inch by 1-inch squares and then subsequently cleaned by sonication in acetone followed by sonication in isopropanol. The glass substrate was blown dry by using dry nitrogen flow. Then, 2-cm by 3-mm rectangle Novec wells were painted on the glass substrates. The 1 wt % peptide solutions were dropcast on these wells and acidified as described earlier. The dielectric layer was then vapor-deposited on top of the assembled peptide films. Two different compounds were used to function as dielectric material: tetratetracontane ($C_{44}H_{90}$, $C_{44}$), and pentaerythritol. They were chosen to observe the effects of varying polarites of groups present (with tetratetracontane being a wax and pentaerythritol having a large number of hydroxyl groups, approaching a solid form of "water"). The thickness of the dielectric was varied from 20 nm to 100 nm. For these devices with assembled peptides as the gates, 25 nm of pentacene was vapor-deposited as the active semiconductor layer as it has been widely studied and is a very reliable organic semiconductor. As the nanomaterial dropcast films are hardly only ½ cm wide, TEM grid mask was used to deposit 50 nm-thick gold electrodes.

Measurements.

All the OFET measurements were done using an Agilent 4155C semiconductor analyzer under ambient conditions. The conjugate nanowire or control peptide gate layer was probed with an indium-gallium liquid electrode. It can be seen from the schematic in FIG. 23C and FIG. 23D that there is no other path for voltage transfer from the gate contact to the gate dielectric except for the nanowire or peptide layer, since the glass substrate is completely insulating. The results here demonstrate that the conjugated nanowire and the control peptide are both able to transmit the voltage from the gate contact to the C44 layer, where it is then capacitively coupled to the PQT-12 layer and thus modulates the current of the OFET.

In the plots shown in FIG. 24A and FIG. 24B, the current on the y-axes is plotted versus the source-drain voltages. Curves for different values of gate voltage are shown. The source is set to zero volts and the currents and other voltages are negative quantities. Currents of larger absolute magnitude are associated with larger absolute magnitude source and gate voltages. Furthermore, it can be clearly seen from the data that DAA (a conjugated nanowire) is much more effective than the control peptide in transmitting the voltage from the gate contact to the rest of the transistor since the currents obtained at particular gate voltages are about three times higher in the DAA case than for the control peptide.

Results and Discussion

The peptide-π-peptide triblock units (FIG. 22A) investigated in this study were all observed to have pH-triggered assembly behavior, wherein the protonation of carboxylates under acidic conditions mitigates Coulombic repulsion thus allowing for more intermolecular hydrogen bonding among the peptide backbones and π-electron interactions among the embedded 4T units. The 4T system was selected as the π-electron core in this study because it is a well-established p-channel semiconductor subunit. The spectroscopic investigations from previous report (Ardona et al., 2015) for DXX-4T peptides along with the findings for EXX-4T peptides here show that these 4T bis(peptides) have maximum absorption at 418 nm under basic conditions (ca. pH 10) which blue-shifts under acidic conditions (ca. pH 2) ranging from ~360 nm to 410 nm as the amino acid bulk adjacent to the chromophore increases (Table 2, FIG. 25A). The emission profiles of these π-conjugated peptides under basic conditions have a maximum at 510 nm, which redshifts to ~540 nm under acidic conditions (FIG. 25B). The circular dichroism (CD) spectra also shows varied bisignate exciton-coupled π-π* signals (i.e., different intensities and signs of the Cotton bands) among the peptides that have crossovers near the absorption maximum of each peptide, suggesting the differences in the extent of interactions between the 4T units held in local chiral environments (FIG. 25C). Varying the amino acid termini from glutamic acid residues to aspartic acid residues does not dramatically change the observed spectral profiles. These spectroscopic features support that these peptides form "H-like" aggregates upon assembly under acidic conditions.

TABLE 2

Absorption maxima of DXX- (Ardona et al., 2015) and EXX-4T peptides.

| Peptide-4T | $\lambda_{max}$/nm |
|---|---|
| DGG | 362 |
| DAA | 366 |
| DVV | 403 |
| DII | 408 |
| EGG | 361 |
| EAA | 374 |
| EVV | 406 |
| EII | 409 |

Nanostructure and Film Morphology.

Figure 26A:
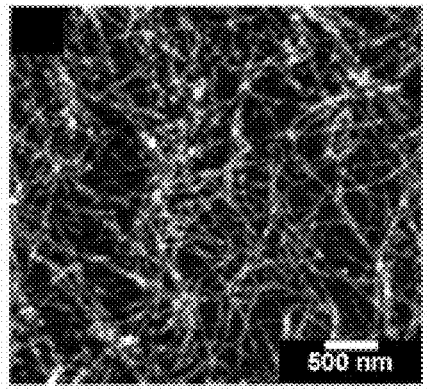
Figure 26C:
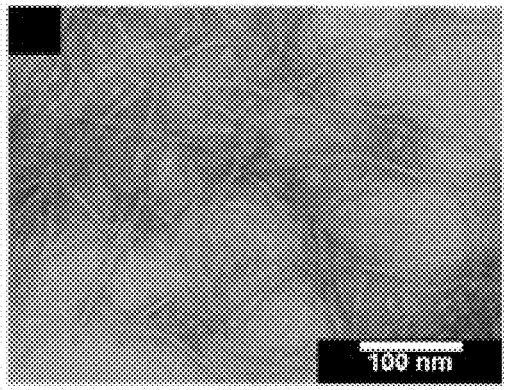
Figure 26B:
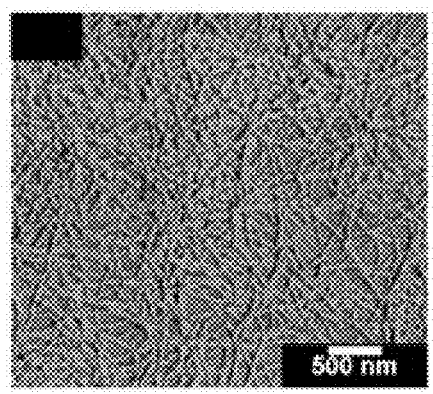
Figure 26D:
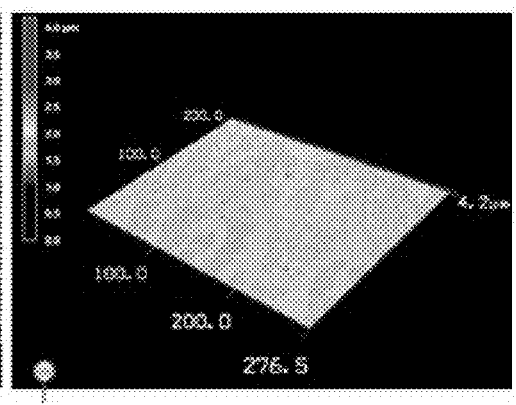

The formation of 1D-nanostructures from 0.01 to 1 wt % peptide solutions under acidic conditions were consistently observed for all the eight 4T peptides studied in solution and in dropcast films, with the alanine-containing peptides having the largest nanostructure widths (FIG. 26A, FIG. 26B, and FIG. 26C). The nanostructure lengths span up to micrometers, while the widths for 0.1 wt % acidified solutions of DXXpeptides were previously reported to range from 3 nm to 12 nm (i.e., DAA nanostructures have ~12 nm width, while DGG, DVV and DII are around 3-4 nm) (Ardona et al., 2015). All peptide sequences show well-connected nanostructures in the gel form, as shown in the TEM images (FIG. 27A, FIG. 27B, FIG. 28A, FIG. 28B, FIG. 29A, FIG. 29B, FIG. 30A, and FIG. 30B). It is interesting to note that the VV- and II-containing peptide hydrogels seem to have regions with local alignment, which could be attributed to high beta-sheet propensities within the peptide backbones based upon these sequences (FIG. 28A, FIG. 28B, FIG. 30A, and FIG. 30B). Even though nanostructure bundling is evident for these cases, the hydrogel fiber network seems to be less dense than for GG- and AA-containing peptides in the gel state. The dropcast film topography was investigated using AFM and the film roughness/thickness was measured using a laser profilometer (FIG. 26A, FIG. 26B, FIG. 26D, FIG. 31A, FIG. 31B and FIG. 32). The AFM images for EAA- and EVV-4T peptides show that the 1D-nanostructures are still microns in length in the dropcast films that were used for device fabrication. The microscopic surface profiles show varied surface roughness among the peptides that can be attributed to the different nanostructure aggregation behaviors upon drying of dropcast films of the peptides with different hydrophobicities. These surface profiles for the dropcast films (<10 µm-thick) support the network characteristics observed in hydrogel TEM, wherein GG- and AA-containing peptides show islands of dense networks of assembled nanostructures while VV- and II-containing peptides show more uniform films. Both AFM and surface profile characterizations were conducted on silicon surfaces and therefore can be reasonably extrapolated to the surfaces upon which these nanomaterials would be deposited for device fabrication. As thoroughly investigated in previous studies (Wall et al., 2014; Ardona et al., 2015), which are also supported by the recorded absorption and emission profiles for the eight 4T-peptides studied herein, such systematic variations of the amino acid bulk adjacent to the π-electron core result in varied photophysical properties due to the differences in the local packing order and contact of π-electron units within each assembled nanostructure. The effects of sequence variation were also previously observed for macroscopic material properties such as mechanical properties, due to the differences in the "bundling" interactions between the 1D-nanostructures (Wall et al., 2012; Ardona et al., 2015). Due to the observed variations in the surface roughness and local aggregation patterns of the films of the sequence-varied peptides, it was expected that this would have implications for the macroscopic connectivity of the semiconducting units, and thus, the currents passing through the films in device structures, as discussed below.

The organic field effect transistor is the foundational structure for technical applications like RFID (radio frequency detection), roll-up light emitting displays and different sensor platforms that possess attractive attributes such as printability, low cost production, and mechanical flexibility (Braga et al., 2009; Martinez-Hardigree et al., 2014; Malachowski et al., 2010). Film morphologies are closely related to device output currents (Generali et al., 2011; Kline et al., 2005; Himmelberger et al., 2014; Kwiatkowski et al., 2009; Wong et al., 2010; Fei et al., 2014). Specific morphological factors include grain size, connectivity, orientation or packing disorder and traps (chemical or interfacial) in the films (Noriega et al., 2013). For the present self-assembling peptides, the nanostructure assembly and the macroscopic film morphology are both crucial features for determining electronic signal transmission. All the eight peptides studied herein form 1D-nanostructures that are microns in length, 3-12 nm in width, varied network connectivities in gel and solution state, and varied surface roughness in the microscale (for dropcast films). In the presently disclosed subject matter the OFET architecture is used as an analytical tool to indicate effects of different nanostructure assembly morphologies on charge carrier mobility and electrical conductivity.

OFETs with π-Conjugated Peptides as the Semiconducting Layer.

In order to characterize the semiconducting behavior of the 4T cores bound within peptide environments with different hydrophobicities, thin films of peptide nanomaterials were deposited as semiconducting layers in bottom-gate OFET configurations (FIG. 23A). There have been a few isolated reports on the carrier mobilities of biomolecule-containing oligothiophene nanomaterials with π-electron function, revealing mobilities on the order of $10^{-7}$-$10^{-6}$ cm$^2$ V$^{-1}$ s$^{-1}$ (Tsai et al., 2010). One goal of the present work is to reveal how molecular variation impacts nanostructure-dependent transport properties. Controls without the semiconducting unit were used (FIG. 23B and FIG. 23C) (Lin et al., 2013). These two peptide nanomaterials were chosen as the control samples because they form similar one-dimensional nanostructures (Lin et al., 2013) (FIG. 33A) under aqueous conditions that would be geometrically relevant for the pi-conjugated peptides studied herein. Control sample 1 is a direct analog of peptide-4T-peptide, with the 4T substituted by —(CH$_2$)$_{10}$ units, while control sample 2 has an amphiphilic design with more charged residues in the peptide backbone than 1. When the controls were used as the semiconducting layer, no apparent gating effects were observed. This supports the premise that the 4T-containing nanostructures in the film are providing to charge transport pathways that do not merely rely on ionic effects and in fact require the presence of hole-transporting 4T subunits.

All the peptide-4T nanowires gave semiconductor characteristics but the mobility values (Table 3) were observed to vary by three orders of magnitude upon varying the amino acids adjacent to the 4T semiconductor. The corresponding output curves (FIG. 34A, FIG. 34B, FIG. 34C, FIG. 34D, FIG. 34E and FIG. 34F) show the gate-modulated field conductance for all the peptides. The peptides with -GG and -AA sequences, which have the most blue-shifted absorption and most quenched emission upon assembly thereby suggesting the strongest electronic coupling (Ardona et al., 2015), gave the highest mobility values. Those nanostructures with the bulky -VV sequences, which have photophysical properties for the assembly that are least shifted from the dissolved π-conjugated peptide under basic conditions (Ardona et al., 2015), showed the lowest mobility values. Apparently, even bulkier hydrophobic isoleucine residues perturb the assembly such that the charge-transporting properties within the assembly (as represented by hole mobilities) are inferior to the other peptides studied herein. Such trends can also be correlated to the importance of local packing order (nanostructure helicity, packing homogeneity, propensity to form ordered structures) and intermolecular distances of the semiconducting oligomers within the self-assembled nanostructures on the charge transport behavior of the resulting films (Wall et al., 2014; Ardona et al., 2015); both of which affect intermolecular π-electron delocalization.

TABLE 3

Mobility values for different 4T-containing π-conjugated peptides.

| Peptide-4T | $\mu_h/cm^2\ V^{-1}\ s^{-1}$ |
|---|---|
| DGG | 0.017 ± 0.006 |
| DAA | 0.004 ± 0.003 |
| DVV | $6.9 \times 10^{-5} \pm 2.1 \times 10^{-5}$ |
| EGG | 0.002 ± 0.0006 |
| EAA | 0.005 ± 0.004 |
| EVV | $4.7 \times 10^{-5} \pm 6.2 \times 10^{-5}$ |

* DII and EII are not included because no measurable hole mobility was obtained.

The DAA and EAA peptides show approximately three times greater nanostructure width than the six other peptides (Wall et al., 2012; Ardona et al., 2015). While this suggests a general correlation of nanostructure width and mobility, DGG is an exception, where the intermolecular interactions leading to the blue-shifted spectra are apparently dominant. The DVV and EVV samples, on the other hand, were observed to have more dispersed nanostructures within their dropcast films or in their gel state (Figure FIG. 28A and FIG. 30A). Considering the mobility data in Table 1 and the nanostructure characteristics that comprise the dropcast films, it could be deduced that nanostructure connectivity (i.e., network formation) and the individual nanostructure morphology are the major factors to be considered for performance of these devices. Another factor that might be affecting the huge variations of mobility values between the devices of same peptide is the local alignment of nanowires within the device. It was previously reported that having the electrodes parallel to the alignment of the nanostructures led to better charge transport as compared to when the electrodes are perpendicular to the direction of material alignment (Wall et al., 2011). Ideally, the films reported here should have randomly aligned nanowires distributed within the layer. However, it is possible that there are areas with local alignment where the probes are directed, and hence leading to higher mobility values as compared to other area. Moreover, the different chemical and interfacial traps could also be unevenly distributed within the semiconducting film that is mainly comprised of non-conducting peptide moieties, leading to variations for the calculated mobility values per device. When these devices are tested over a period of time, a continuous increase in drain current was observed with or without light irradiation, which indicates that there are low-lying traps being filled. No photoconductive response was observed in this geometry, although there are reports about photoconductive effects for other semiconductor-containing peptide gels (Ardona et al., 2015; Draper et al., 2014). The two effects (field effect and photoconductivity) likely target the same energy level, so they are very closely intertwined and, in this particular device structure, it was not possible to decouple these effects. It was also observed that there is a significant off-current—free ionic current in the material that is not related to gate leakage.

OFETs with π-Conjugated Peptides as the Gate Layer.

Because the -AA sequences yielded the nanostructures with the largest widths and seemed to result in films with good connectivities between nanostructures, these nanostructures were chosen to also function as gates for OFET devices (FIG. 23A) in order to assess the capability for these nanomaterials to support voltage transmission from an electrode contact and thus serve as an electrical extension of this contact. In this configuration, pentacene was used as the semiconductor while $C_{44}H_{90}$ (tetratetracontane) and pentaerythritol were chosen as the materials for gate dielectric layers because they form continuous films and bracket the extremes of hydrophobicity and hydrophilicity. The hydrocarbon has a dielectric constant of about 2.5 (Kraus et al., 2010). Pentaerythritol will have a dielectric constant on the order of 10, depending on the degree of hydration, by analogy to dextran, a solid with similar density of polar oxy-functional groups (Nishinari et al., 1985). With its high density of OH groups, pentaerythritol begins to model the OH-rich environment around cells. To determine whether the conjugated core and the nanowire self-assembly were necessary for gate voltage equilibration, devices with control samples 1 and 2 (FIG. 23B) as the gate material were also fabricated. Control sample 2 gave very similar results to the DAA sample, although the drain current in the pentacene channel was slightly lower 2 than for DAA, while 1 does not give any working OFET data. This indicates that the free ions present in the materials are partially responsible for the voltage transmission properties regardless of the composition of the internal cores (the hydrogels formed from peptides with and without π-electron cores are acidic).

Moreover, the thickness of the dielectric layer was varied between 20 nm and 100 nm in order to establish the maximum thickness through which the nanowire materials can transmit modest voltage that could be needed to stimulate a biological structure (e.g., cell membranes, <10 nm). It would be expected that by increasing the dielectric thickness over which the voltage has to be transmitted, the gating effect would be weaker as interfacial dipole could compensate the voltage applied through the dielectric. It has been noticed that 35-40 nm dielectric allows the maximum electric field to drop across the dielectric layer without undue leakage current (FIG. 35). Consistent with previous observation it was found that 20 nm was too low thickness for forming well connected films because of island growth morphology of tetratetracontane (Kraus et al., 2010). Related π-conjugated peptides have been previously found to have both protons and electrons as contributors to the conduction, with the dominating carrier being dependent on the humidity because of its effect on peptide folding (Amit et al., 2014). These results imply that the materials studied herein can impart an electrical field over approximately 35-40 nm effectively. It has been noticed that DAA does demonstrate the expected trend with the increasing dielectric thickness but the gating behavior is still apparent, while in EAA, the gating behavior almost ceases to exist above 70 nm dielectric thickness. This strengthens the claim that terminal charged groups indeed have a contribution in the overall gating effect. It is interesting to note that upon testing control sample 1, with less charged residues and is mainly comprised of hydrophobic valine residues, no gating effect was observed for this geometry.

In summary, properties of 4T bis(tripeptide)-based nanostructure OFETs were investigated it has been found that this type of material can show mobility values as high as ~0.02 $cm^2 V^{-1} s^{-1}$ and can be tuned within a range of three orders of magnitude by simply changing the amino acid sequence and keeping the same semiconducting unit. The materials were also sufficiently ionically conductive to serve as OFET gate electrodes. The success in incorporating assembled nanostructures in OFETs with clearly observable field-effect modulation when serving both as OFET semiconductors and gates for pentacene semiconductors is the key finding of this study. The modulation of nanostructures as semiconductors required the presence of the conjugated core, even though it was a small fraction of the total nanostructure mass. This demonstration of hole transport, above and beyond ionic conductivity, is crucial for the ultimate goal of electronically or photonically stimulating these materials to influence cell growth and behavior.

Example 3

Donor-Acceptor Nanomaterials for Photo-Induced Charge Separation

Overview

The synthesis, self-assembly, and electron transfer capabilities of peptide-based electron donor-acceptor molecules and supramolecular nanostructures has been reported. These modified peptides contain pi-conjugated oligothiophene electron donor cores that are peripherally substituted with naphthalene diimide electron acceptors installed via imidation of site-specific lysine residues. These molecules self-assemble into one-dimensional nanostructures in aqueous media, as shown through steady-state absorption, photoluminescence, and circular dichroism spectra, as well as transmission electron microscopy. Excitation of the oligothiophene donor moieties results in electron transfer to the acceptor units, ultimately creating polar, charge-separated states that persist for over a nanosecond as observed with transient absorption spectroscopy. This study demonstrates how transient electric fields can be engineered into aqueous nanomaterials of biomedical relevance through external, temporally-controlled photonic inputs.

Material and Methods

General Considerations:

DMF was purchased from Sigma-Aldrich and dried over 4 Å molecular sieves. Solvents were degassed by sparging with nitrogen for 30 to 90 minutes before use. Tetrakis (triphenylphosphine)palladium was obtained from Strem Chemicals. Wang-Lys(Mtt)-Fmoc was purchased from Chem-Impex International. N-Methylpyrrolidone (NMP), Wang-Val-Fmoc resin, Wang-Lys-Fmoc resin, and Fmoc-protected amino acids were obtained from Advanced ChemTech. O-(Benzotriazol-1-yl)-N,N,N',N'-tetramethyluronium hexafluorophosphate (HBTU) was purchased from Oakwood Products Inc. All other reagents and starting materials were obtained from Sigma-Aldrich and were used as received. Wang-Lys-Fmoc resin was acylated via treatment with acetic anhydride. 5,5'-bis-tributylstannyl-[2,2']-bithiophene, and 5-bromothiophene-2-carboxylic acid were prepare using literature procedures (Guo et al., 2008; Sanders et al., 2012).

NMR Spectroscopy:

$^1$H-NMR spectra were obtained using a Bruker Avance 400 MHz FT-NMR spectrometer, and processed with Bruker Topspin 1.3. Peptide $^1$H NMR spectra were acquired using a 1 second presaturation pulse to suppress water.

Electrospray Ionization Mass Spectrometry (ESI-MS):

ESI samples were collected using a Thermo Finnigan LCQ Deca Ion Trap Mass Spectrometer in negative mode. Samples were prepared in a 1:1 MeOH:water solution with 0.1% ammonium hydroxide.

UV-Vis and Photoluminescence:

UV-Vis spectra were obtained using a Varian Cary 50 Bio UV-Vis spectrophotometer. Photoluminescence spectra were obtained using a PTi Photon Technology International Fluorometer with an Ushio Xenon short arc lamp. Spectroscopic samples were prepared at 2.2 μM in Millipore water. The pH was then adjusted by adding 10 μL of either 1M KOH (basic) or 1M HCl (acidic).

Circular Dichroism (CD):

CD spectra were obtained using an AVIV 420 CD spectropolarimeter. Spectroscopic samples were prepared at 44 μM in Millipore water. The pH was then adjusted by adding 10 μL of either 1M KOH (basic) or 1M HCl (acidic).

Reverse-Phase HPLC:

HPLC purification was performed on an Agilent 1100 series (semi-preparative/analytical) and a Varian PrepStar SD-1 (preparative) instruments using Luna 5 μm particle diameter C8 with TMS endcapping columns with silica solid support. An ammonium formate aqueous buffer (pH 8) and acetonitrile were used as the mobile phase.

Transmission Electron Microscopy (TEM):

Imaging was performed on a Philips EM 420 transmission electron microscope equipped with an SIS Megaview III CCD digital camera. The samples were prepared by pipetting a drop of 1 mg/mL solution of assembled peptide in water onto 200 mesh Formvar coated copper grids and incubated for 5 minutes at 25° C. Excess solution was wicked off by touching the side of the grid to filter paper. The sample was then stained with a 2% uranyl acetate solution and excess moisture was wicked off. The grid was allowed to dry in air before imaging.

Ultrafast Transient Absorption (TA) Spectroscopy.

Ultrafast spectroscopic characterization was accomplished using an amplified Ti:Sapphire system as described in previous works. 3,4 Ultrafast laser pulses (~35-fs duration, 800-nm center wavelength) were generated with an amplified Ti:sapphire laser system (Coherent Legend Elite), producing approximately 4.0 W at a repetition rate of 990 Hz. A small fraction of the beam (<1 mW) was focused into a sapphire crystal to generate a broadband white-light continuum covering a range of 450-1150 nm. Another fraction of the amplifier output was passed through a Type I BBO, SHG crystal or used to pump a femtosecond optical parametric amplifier (Coherent, OPerA Solo) to generate 400 nm and 480 nm photoexcitation pulses, respectively. Optical delay of the photoexcitation pulse relative to the probe continuum was controlled with a translation stage (Newport). Excitation pulses were focused to diameters of 0.5-1.0 mm that ensured complete coverage of the white light spot (~100 micron) and prevented effects due to spatial chirp. The dispersed spectrum of the probe beam was collected after the sample using an Acton SP 2360 spectrograph outfitted with a Pixis 100BR CCD-array detector.

Each set of spectra was collected in two parts, 450-800 and 800-1150 nm, with each near-infrared measurement conducted immediately after the visible measurement without altering sample position or alignment conditions. All samples were studied at the same concentration unless otherwise indicated. Assembled samples were stirred to maintain a homogeneous distribution of aggregates. Collected spectra were smoothed, chirp-corrected, and combined to make the sets plotted in FIG. 47A and FIG. 47B. Time zero was uniformly set to the point at which the primary peak reached 50% of its maximum intensity. The time resolution given by the half-rise of the instrument response was found to be 90 fs for measurements using 400 and 480 nm excitation pulses. None of the samples suffered degradation due to laser exposure or storage over the timeframe of the conducted measurements.

Kinetic Models.

Principal kinetic components obtained through global analysis were fitted to exponential decay functions convoluted with the temporal instrument response, namely:

$$S(t) = S\exp(-t/\tau_{S1}) \quad (S1)$$

$$CS(t) = f_{CS1}\exp(-t/\tau_{CS1}) + f_{CS2}\exp(-t/\tau_{CS2}) \quad (S2)$$

Here $S(t)$ corresponds with the short-lived $S_1$ state of OT4, whereas $CS(t)$ corresponds with the charge-separated state (OT4+/NDI−). Values of fitting parameters are presented in Table 4. The rise in the CS signal for assembled DA-2 was fit with the 270-fs rise observed from the decay of $S_1$ OT4.

TABLE 4

| Parameter | Unassembled | 95% CI | Assembled | 95% CI |
|---|---|---|---|---|
| $f_{X\Sigma1}$ | 0.958 | 0.893-1.057 | 0.585 | 0.461-0.709 |
| $\tau_{X\Sigma1}$ | 4.84 | 3.35-6.35 | 13.7 | 6.4-26.2 |
| $f_{X\Sigma2}$ | 0.042 | −0.012-0.097 | 0.415 | 0.286-0.544 |
| $\tau_{X\Sigma2}$ | Constant | — | 1106 | 461-Constant |
| $\tau_{\Sigma1}$ | 0.269 | 0.203-0.305 | 0.276 | 0.228-0.330 |

Spectral Global Analysis.

A variation of global analysis (GA) was performed in order to isolate the various components contributing to the progression in FIG. 47A. Ordinarily, global analysis involves applying a loosely defined, pre-conceived kinetic model to tease out components spectrally based on adherence to that model. Validation of the model stems from evaluating how well the component spectra represent a plausible demarcation of the transient populations with reasonable and justifiable spectral features. Instead of making an assumption about the specific kinetic model, the approach utilized here involves limiting the kinetic progressions extracted via singular value decomposition (SVD) to those of populations (positive intensities). Briefly, SVD parses a matrix of data, A, into three other matrices based on Equation S3 below:

$$A = USV^T \quad (S3)$$

In this case, U is a matrix that contains information about the components' kinetics, $V^T$ their spectral profiles, and S the relative weights of each that will yield linear combinations that reconstruct the original data. The nomenclature U(n), etc. will be used to indicate the $n^{th}$ row/component of each. Examination of either U or $V^T$ without a model often yields negative kinetics, derivative spectral features, and other unassignable or illogical regions and trends. This occurs because SVD delineates the input matrix into the fundamental vectors of the system; these are defined as much by shifting, broadening/narrowing, and exchange between states over time as they are by the absolute spectra of component populations. Thus, the goal here is to linearly combine components of $V^T$ until non-negative (absolute) kinetics are obtained from U, as an attempt to elicit pure component spectra.

Examination of FIG. 47A and FIG. 47B validates an initial assumption that only two significant components contribute to the resulting progressions. $V^T(1)$ and $V^T(2)$ give spectra that are clearly contaminated by one another due to their spectral overlap and the presence of timescales on which both populations are significantly changing. This causes an over-representation of component 2 within component 1, leading to U(2) behaving more as a derivative function than an absolute one and leading to negative intensities at longer times. Since this is not possible for an absolute population, a small fraction of $V^T(2)$ is linearly combined with $V^T(1)$ in varying ratios as shown in Equation S4 with $|b_X| \approx 0.05$-0.4. X is then fit to the original data in a region where $V^T(1)$ is the most intense (preferably only) spectral contributor. SVD can then be reapplied to the residual matrix left after subtracting out this spectrum fitted to each spectrum in A ($c_iX$), as shown in Equation S5.

$$X = V^T(1) + b_X V^T(2) \quad (S4)$$

$$(A - c_iX) = U_X S_X V_X^T \quad (S5)$$

This yields a component, $V_X^T(1)$, that is nearly identical to $V^T(2)$. However, its resulting kinetic progression, $U_X(1)$, behaves very differently as a function of time compared to U(2). The scalar $b_X$ is selected to be the value with the smallest absolute value that generates a $U_X(1)$ progression in which an exponential model fit through it will always be greater than or equal to zero. This procedure yields a two component system with X and $V_X^T(1)$ as the spectral progressions and U(1) and $U_X(1)$ as the corresponding kinetic traces and could be extended iteratively in some cases for systems with more than two components. A notable limitation to the technique is that the components must be sufficiently isolatable either spectrally or kinetically for adequate separation.

N-propyl-1,4,5,8-naphthalenetetracarboxylic acid monoanhydride

Adapted from the literature as follows (Shao et al., 2009): 1,4,5,8-Naphthalenetetracarboxylic acid dianhydride (10.7 g, 40.0 mmol) was added to a three neck round bottomed flask equipped with a condenser and dissolved in DMF (300 mL). The mixture was heated to 140° C. Propylamine (3.28 mL, 40.0 mmol), was diluted in DMF (25 mL) and added dropwise over 2.5 hours to the reaction flask via syringe pump. The mixture was further heated to reflux for 15 hours, then allowed to return to room temperature. 500 mL of a saturated $NH_4Cl$ aqueous solution was added. The light brown solid was collected by filtration, then washed with water. The crude solid was suspended in boiling chloroform, and the suspension was filtered. The solvent was removed from the mother liquor to give the desired product as an off-white solid (5.26 g, 17.0 mmol, 43%) that was used without further purification. $^1$H NMR (400 MHz, $CDCl_3$) δ: 8.82 (s, 4H), 4.21-4.15 (m, 2H), 1.78 (sext, 2H, J=7.6 Hz), 1.03 (t, 3H, J=7.4 Hz). $^{13}$C NMR (100 MHz, CDCl$_3$) δ: 162.4, 159.0, 133.3, 131.4, 129.0, 128.1, 122.9, 42.8, 21.5, 11.6.

General Solid Phase Peptide Synthesis (SPPS), N-terminus-acylation, and On-Resin Stille Coupling procedure:

Peptides were synthesized via standard SPPS using Fmoc-protected amino acids, starting from Wang resin pre-loaded with the first amino acid (Wang-Val=0.7 or 0.4 mmol/g, Wang-Lys(Mtt)=0.47 mmol/g, Wang-Lys(Ac)=0.37 mmol/g), acylated with 5-bromothiophene-2-carboxylic acid and subjected to Stille cross-coupling conditions in the presence of 5,5'-bis-tributylstannyl-[2,2']-bithiophene as previously described in Chapter 2 and ref 29.

General On-Resin Deprotection and Imidation Procedure:

Following SPPS, N-terminus-acylation, and On-Resin Stille coupling procedures, the resin was dried and placed in a Schlenk tube equipped with a reflux condenser. N-propyl-1,4,5,8-naphthalenetetracarboxylic acid monoanhydride (3 eq.) and DMF (10 mL) was added and the mixture was heated to 50° C. for 1 hour, with continuous N$_2$ bubbling through the solution. The suspension was then heated to 110° C. for 22 hours. The mixture was allowed to cool, then the resin was transfer to a peptide chamber and subjected to a wash cycle (3×NMP, 3×DMF, 2× iPrOH, 2× H$_2$O, 2× (2×THF, 2× iPrOH), 2× acetonitrile, 2× diethylether, 2× hexanes).

General Cleavage, Work-Up Procedure of Peptides:

Following solid-phase cross-coupling and imidation (if applicable), the peptide was cleaved from the resin with a 95% TFA cocktail, isolated, and HPLC purified as previously described (Sanders et al., 2012)

HO-K(NDI)VEVGG-OT4-GGVEVK(NDI)-OH peptide (DA-6):

Solid supported Wang-K(MtOVEVGG-NH$_2$ peptide N-acylated with 5-bromothiophene-2-carboxylic acid was prepared (0.46 mmol) and subjected to the standard Stille coupling procedure in the presence of 5,5'-bis-tributylstannyl-[2,2']-bithiophene (0.23 mmol, 0.17 g) and Pd(PPh$_3$)$_4$ (0.018 mmol, 0.021 g) for 19 hours. The lysine residues of the resulting solid-supported peptide were then subjected to the deprotection and imidation procedure with N-propyl-1,4,5,8-naphthalenetetracarboxylic acid monoanhydride (1.4 mmol, 0.43 g) for 22 hours. Following general cleavage, work-up, and HPLC purification, the peptide was obtained as a light orange powder (0.0032 mmol, 0.0063 g, 1.3% yield). UV-Vis (H$_2$O) λ/nm (log ∈): 386 (4.32). MS (ESI) m/z 1068.8 (M-2H)−2 (calc. 1068.8), m/z 712.3 (M-3H)−3 (calc. 712.2), m/z 534.2 (M-3H)−3 (calc. 533.9).

HO-VEVK(NDI)GG-OT4-GGK(NDI)VEV-OH peptide (DA-3):

Solid supported Wang-VEVK(Mtt)GG-NH$_2$ peptide N-acylated with 5-bromothiophene-2-carboxylic acid was prepared (0.50 mmol) and subjected to the standard Stille coupling procedure in the presence of 5,5'-bis-tributylstannyl-[2,2']-bithiophene (0.25 mmol, 0.19 g) and Pd(PPh$_3$)$_4$ (0.020 mmol, 0.023 g) for 18 hours. The lysine residues of the resulting solid-supported peptide were then subjected to the deprotection and imidation procedure with N-propyl-1,4,5,8-naphthalenetetracarboxylic acid monoanhydride (1.5 mmol, 0.46 g) for 22 hours. Following general cleavage, work-up, and HPLC purification, the peptide was obtained as an orange powder (0.0068 mmol, 0.014 g, 2.7% yield). UV-Vis (H$_2$O) λ/nm (log ∈): 388 (4.54). MS (ESI) m/z 1068.8 (M-2H)-2 (calc. 1068.9), m/z 712.3 (M-3H)-3 (calc. 712.4), m/z 534.1 (M-3H)-3 (calc. 533.9).

HO-VEVGK(NDI)G-OT4-GK(NDI)GVEV-OH peptide (DA-2):

Solid supported Wang-VEVK(Mtt)GG-NH$_2$ peptide N-acylated with 5-bromothiophene-2-carboxylic acid was prepared (0.50 mmol) and subjected to the standard Stille coupling procedure in the presence of 5,5'-bis-tributylstannyl-[2,2']-bithiophene (0.25 mmol, 0.19 g) and Pd(PPh$_3$)$_4$ (0.020 mmol, 0.023 g) for 18 hours. The lysine residues of the resulting solid-supported peptide were then subjected to the deprotection and imidation procedure with N-propyl-1,4,5,8-naphthalenetetracarboxylic acid monoanhydride (1.5 mmol, 0.46 g) for 22 hours. Following general cleavage, work-up, and HPLC purification, the peptide was obtained as an orange-brown powder (0.010 mmol, 0.022 g, 4.1% yield). UV-Vis (H$_2$O) λ/nm (log ∈): 387 (4.60). MS (ESI) m/z 1068.9 (M-2H)-2 (calc. 1068.8), m/z 712.4 (M-3H)-3 (calc. 712.2), m/z 534.1 (M-3H)-3 (calc. 533.9).

HO-K(Ac)VEVGG-OT4-GGVEVK(Ac)-OH peptide (C-6):

Solid supported Wang-K(Ac)VEVGG-NH$_2$ peptide N-acylated with 5-bromothiophene-2-carboxylic acid was prepared (0.43 mmol) and subjected to the standard Stille coupling procedure in the presence of 5,5'-bis-tributylstannyl-[2,2']-bithiophene (0.22 mmol, 0.16 g) and Pd(PPh$_3$)$_4$ (0.017 mmol, 0.020 g) for 20 hours. Following general cleavage, work-up, and HPLC purification, the peptide was obtained as a light orange powder (0.0075 mmol, 0.012 g, 3.5% yield). UV-Vis (H$_2$O) λ/nm (log ∈): 420 (4.48). MS (ESI) m/z 819.7 (M-2H)-2 (calc. 819.3), m/z 546.2 (M-3H)-3 (calc. 545.9), m/z 409.5 (M-3H)-3 (calc. 409.1).

HO-VEVK(Ac)GG-OT4-GGK(Ac)VEV-OH peptide (C-3):

Solid supported Wang-VEVK(Ac)GG-NH$_2$ peptide N-acylated with 5-bromothiophene-2-carboxylic acid was prepared (0.5 mmol) and subjected to the standard Stille coupling procedure in the presence of 5,5'-bis-tributylstannyl-[2,2']-bithiophene (0.25 mmol, 0.19 g) and Pd(PPh$_3$)$_4$ (0.020 mmol, 0.023 g) for 20 hours. Following general cleavage, work-up, and HPLC purification, the peptide was obtained as a light orange powder (0.018 mmol, 0.029 g, 7.1% yield). UV-Vis (H$_2$O) λ/nm (log ∈): 417 (4.59). MS (ESI) m/z 819.7 (M-2H)-2 (calc. 819.3), m/z 546.2 (M-3H)-3 (calc. 545.9), m/z 409.5 (M-3H)-3 (calc. 409.1).

HO-VEVGK(Ac)G-OT4-GK(Ac)GVEV-OH peptide (C-2):

Solid supported Wang-VEVGK(Ac)G-NH$_2$ peptide N-acylated with 5-bromothiophene-2-carboxylic acid was prepared (0.5 mmol) and subjected to the standard Stille coupling procedure in the presence of 5,5'-bis-tributylstannyl-[2,2']-bithiophene (0.25 mmol, 0.19 g) and Pd(PPh$_3$)$_4$ (0.020 mmol, 0.023 g) for 20 hours. Following general cleavage, work-up, and HPLC purification, the peptide was obtained as a light orange powder (0.010 mmol, 0.016 g, 3.9% yield). UV-Vis (H$_2$O) λ/nm (log ∈): 420 (4.61). MS (ESI) m/z 819.8 (M-2H)-2 (calc. 819.3), m/z 546.2 (M-3H)-3 (calc. 545.9), m/z 409.5 (M-3H)-3 (calc. 409.1).

Results and Discussion

For the electron-donor unit, quaterthiophene (OT4) was chosen because the synthesis of peptides embedded with this pi-conjugated moiety has already been optimized (Sanders et al., 212; Sanders et al., 2014). Electron accepting naphthalene diimide (NDI) was selected for the acceptor, due to the option of facile incorporation via lysine side-chains. Venkataraman and coworkers have previously used this donor-acceptor pair in organic media and found it to be an ideal system for electron transfer due to the lack of spectral overlap between the emission wavelengths of OT4 and absorption wavelengths of NDI (to discourage non-polar energy transfer) and beneficial LUMO level positioning (to encourage transfer of excited electrons) (Bheemaraju et al., 2011). A series of electron donor-acceptor pairs was prepared with varied distance dependences alongside the analogous control molecules bearing the OT4 donor element only. These controls were used to dilute the donor-acceptor pair while at the same time being expected to foster exciton delocalization within the OT4 donor block prior to directing any excitations to the vicinity of the peptides with covalently-attached NDI electron acceptors.

Synthesis of Donor-Acceptor and Control Peptide-π Hybrids.

As outlined in Scheme 1 the synthesis of the OT4-NDI donor-acceptor peptides began with the synthesis of naphthalene monoanhride 1 through imidation with propylamine using a literature procedure (Scheme 1). Shao, H., et al., *J. Am. Chem. Soc.* 2009, 131, 16374-16376.

Scheme 1. Synthesis of naphthalene monoanhydride 5.

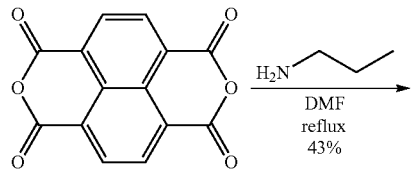

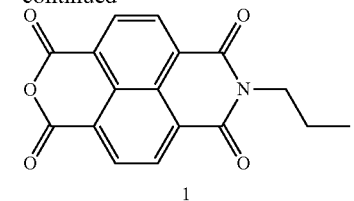

This monoimidation was performed to prevent the diimidation with two lysine residues on the peptide during later synthetic steps. Peptides consisting of sequence DADK(Mtt)GG-NH$_2$ were prepared and N-acylated with 5-bromothiophene-2-carboxylic acid, as previously described. Sanders, A. M., et al., *ACS Macro Lett.* 2012, 1, 1326; Sanders, A. M.; Tovar, J. D. *Supramol. Chem.* 2014, 26, 259.

The Mtt protecting group was chosen for the lysine residue, since it can be removed in a weakly acidic environment, making it an orthogonal protecting group in Fmoc peptide synthesis. The best method for constructing the donor and acceptor portions of the peptide were unclear, so two different methods were investigated simultaneously (Scheme 2). The first of these begins with the deprotection of the lysine residue by treatment with a TFA:TIPS:DCM cocktail, followed by imidation with 1. After washing the resin, the peptide is subjected to solid-phase Stille cross-coupling conditions in the presence of 5,5'-bis(tributylstannyl)-2,2'-bithiophene, as previously described, Sanders, A. M., et al., *ACS Macro Lett.* 2012, 1, 1326; Sanders, A. M.; Tovar, J. D. *Supramol. Chem.* 2014, 26, 259, then cleaved from the resin to give the final product 2. Alternatively, the second method first constructs the donor portion through the solid-phase Stille coupling, then installs the NDI moiety.

Scheme 2. Syntheses for donor-acceptor peptide 6.

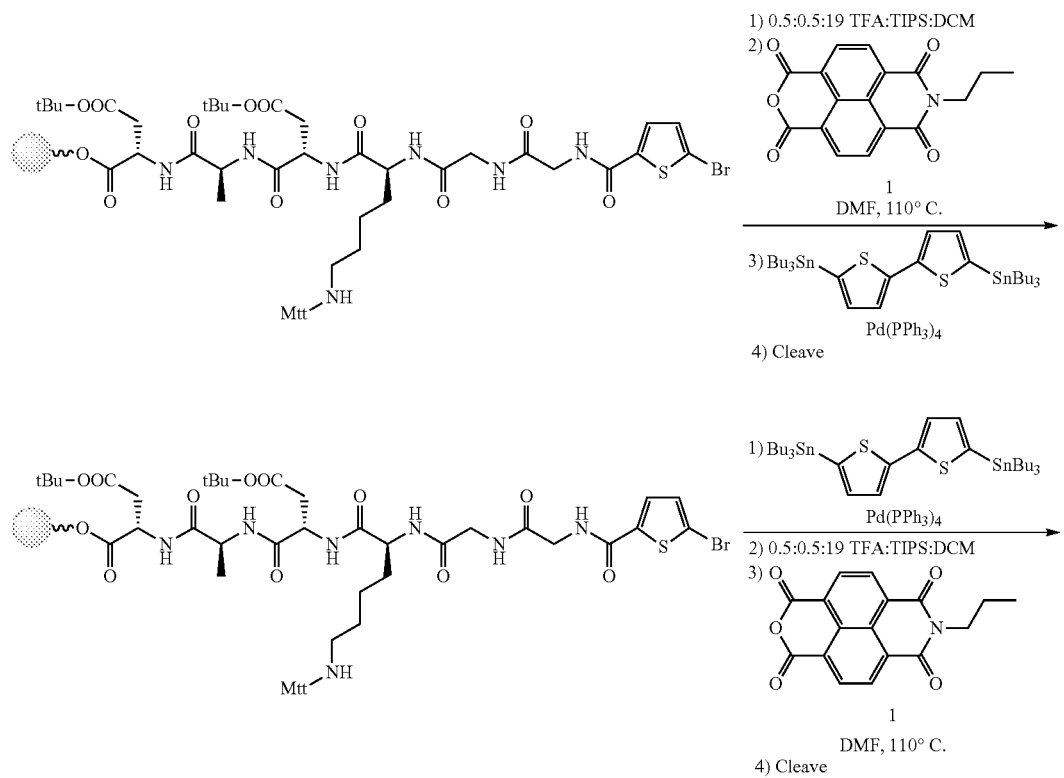

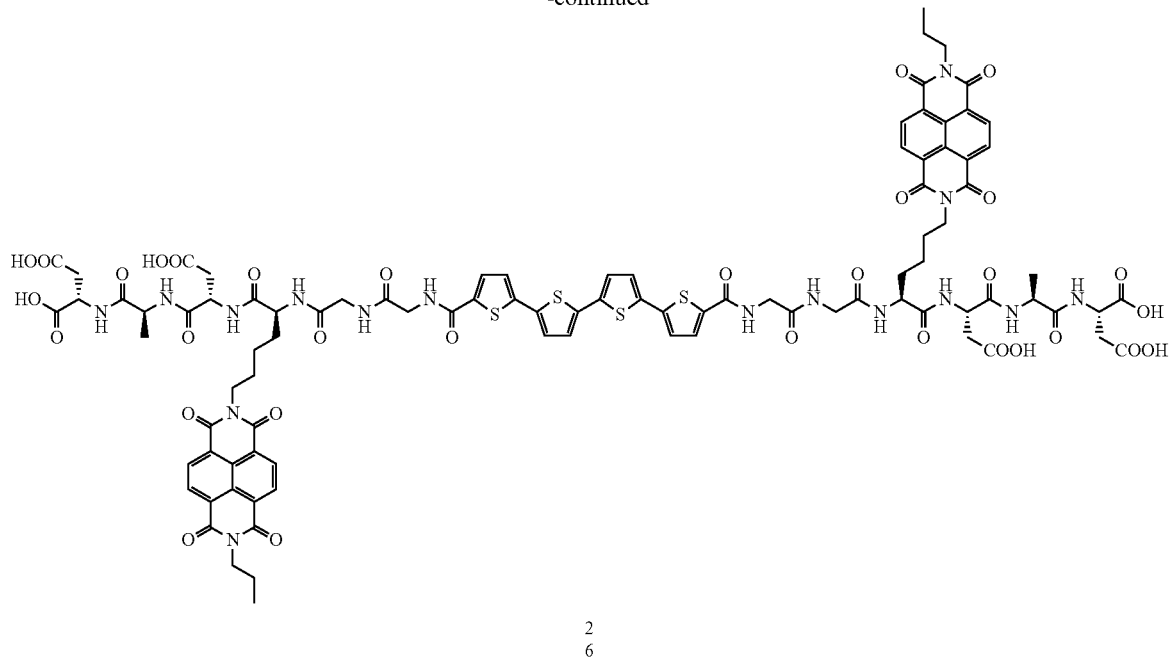

26

Using the second method, a series of key donor-acceptor dyads (DA) as well as the N-acylated control molecules (C) that vary in the spacing between the reactive lysine residues and the central OT4 core was synthetized, as shown in Scheme 3. The synthesis of the DA peptides (Scheme 4) began with the preparation of solid-supported oligopeptide sequences containing K(Mtt) residues (Mtt=4-methyltrityl) placed specifically at different positions along the backbones, which were then N-acylated with 5-bromothiophene-2-carboxylic acid, as previously described (Wasielewski, 2009; Ahren et al., 2004). Thus, three different regioisomers were prepared that vary by the position of the key K(Mtt) residue.

Scheme 3. Structures of donor-acceptor (DA-6, DA-3, and DA-2) and acylated control (C-6, C-3 and C-2) peptides.

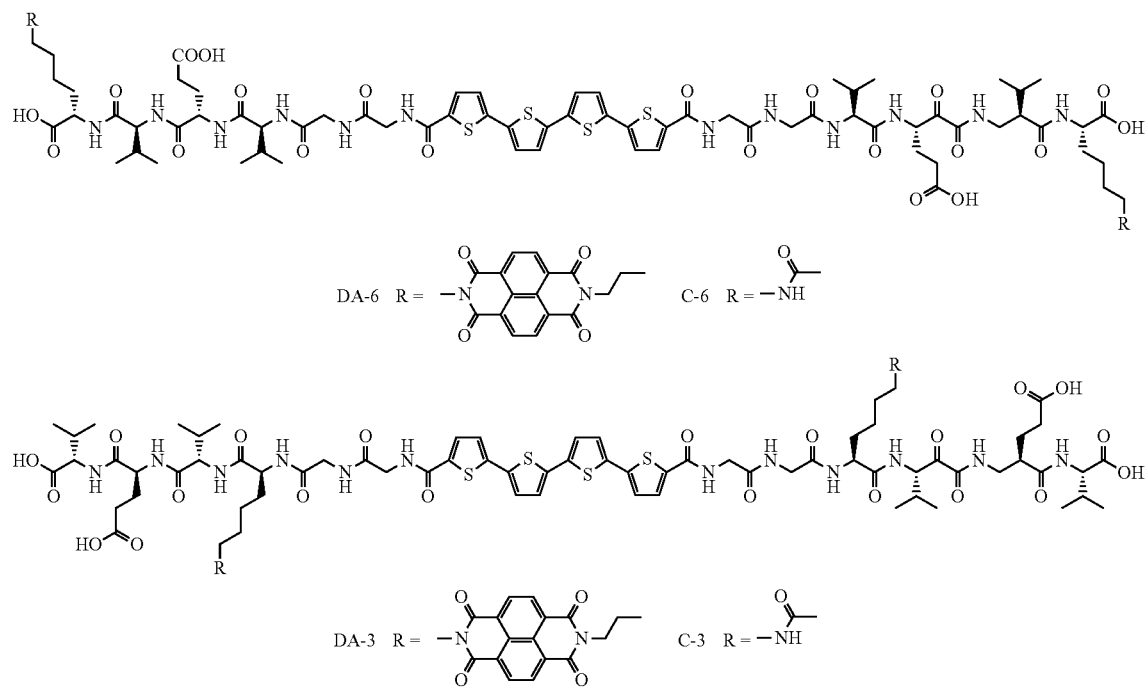

-continued

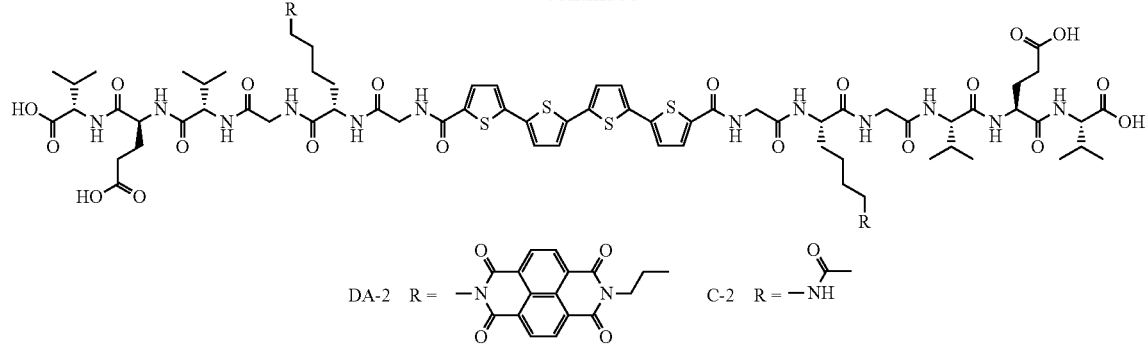

DA-2 R = [N-propyl naphthalenediimide group]   C-2 R = —NH—C(O)CH₃

Scheme 4. Synthesis of DA-6 via solid-phase Stille cross-coupling and imidation.

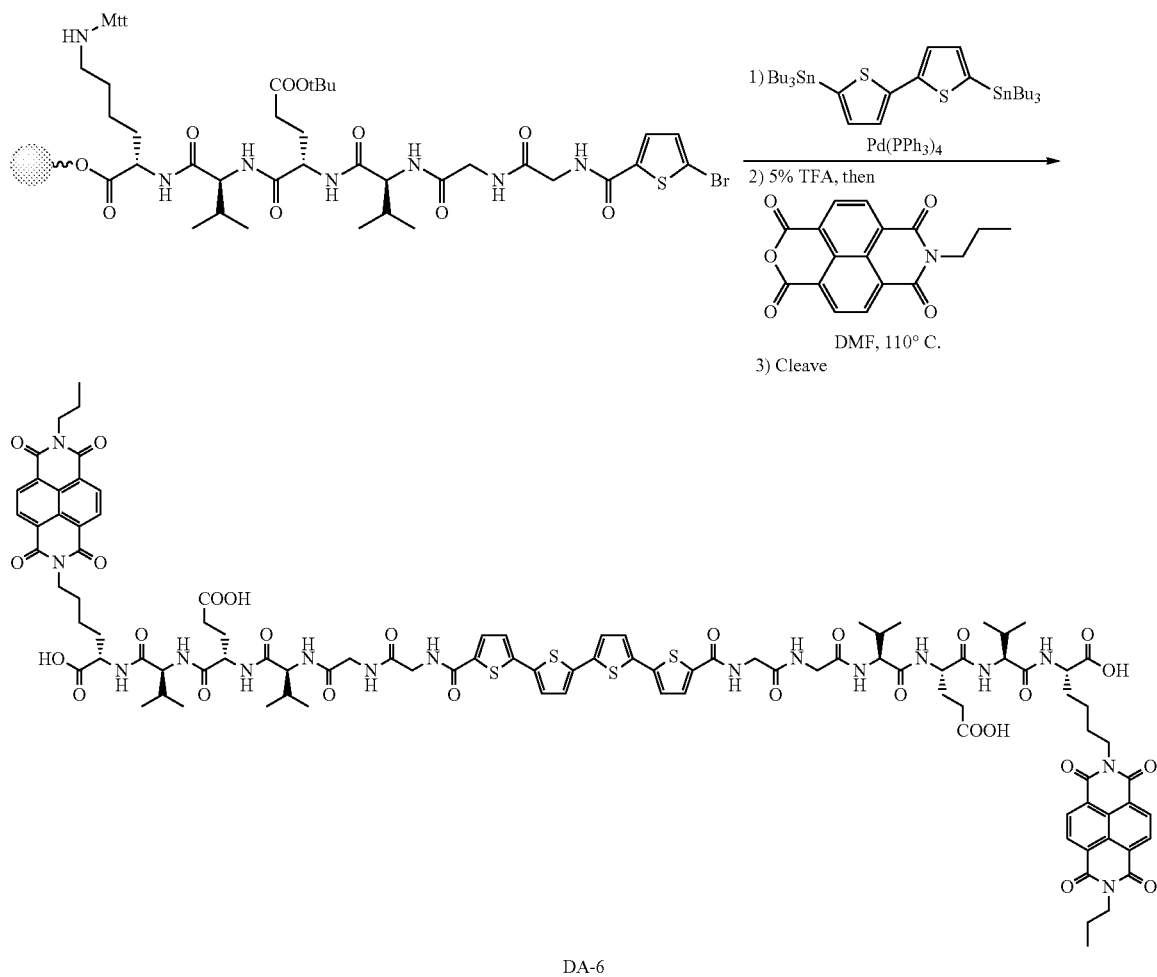

DA-6

The resin-bound peptides were subjected to solid-phase Stille cross-coupling conditions in the presence of 5,5'-bis (tributylstannyl)-2,2'-bithiophene, as previously described (Wasielewski, 2009). Next, the Mtt protecting groups were removed from the lysine residues by treatment with a 1% TFA cocktail, followed by imidation with N-propyl-1,4,5,8-naphthalenetetracarboxylic acid monoanhydride (to prepare the DA series) (Shao et al., 2009) or by N-acylation with acetic acid (to prepare the C series). The Mtt protecting group was chosen for the lysine residue because it can be removed in a weakly acidic environment, making it an orthogonal protecting group in Fmoc peptide synthesis. The resulting peptides were then cleaved from the resin (95% TFA) to give the final products. For example, the synthesis of DA-6, where the NDI acceptor is situated 6 amino acid residues away from the OT4 donor, is presented in Scheme 1.

To study the effect of donor-acceptor distance on the electron transfer capabilities of the peptides, DA-3 and DA-2 were synthesized using the same method, with donor-acceptor distances of 3 and 2 amino acids, respectively (Scheme 4). The valine-glutamic acid-valine sequence was maintained in each peptide to preserve similar overall hydrophilicity/hydrophobicity of the peptide chains. Analogous "donor-only" control peptides C-6, C-3, and C-2 were also prepared, where the NDI substituted lysine residues were replaced by N-acylated lysines (Scheme 3). The controls were used to determine the contribution of the NDI acceptor unit on the electron transfer and assembly behavior of the peptides and also as a means to "dilute" the acceptor moieties within self-assembled samples of donor-acceptor (DA-x) and control mixtures (C-x) through heterostructure assembly.

Microscopy of Donor-Acceptor and Control Peptide-π Hybrids.

The peptide-π hybrids are designed to maintain a relatively dissolved state in aqueous solution at high pH due to repulsion between negatively charged carboxylic acid groups. At low pH, the protonation of these groups reduces the Coulombic repulsion and triggers intermolecular self-assembly into 1-D nanostructures. TEM was employed to visualize these nanostructures and compare the assembly behavior of each donor-acceptor and control peptide. Micrographs of assembled samples of each peptide and mixtures of each donor-acceptor peptide with its analogous control (25% DA:75% C) are shown in FIG. 38A, FIG. 38B, FIG. 38C, FIG. 38D, FIG. 38E, FIG. 38F, FIG. 38G, FIG. 38H and FIG. 38I. Samples were prepared by acidification via acid vapor diffusion of the unassembled peptide or peptide mixture. In general, each peptide and mixture forms 1-D nanostructures displaying fairly uniform widths of 5-7 nm and significant intertwining of two or more structures is evident. The nanostructures formed by DA-6 are substantially thicker (at approximately 10-12 nm) suggesting that the positioning of the NDI moiety on the external amino acid side chain causes the peptide to exhibit a higher degree of hydrophobicity at its termini in comparison to the other peptides that alters its assembly. Furthermore, the donor-acceptor peptide structures appear to generally have lower aspect ratios in comparison to those of the acylated controls. The structures formed from a mixture of DA-2 and C-2 appear to be unique with less structure intertwining, slightly thicker diameters (8-10 nm), and relatively longer aspect ratios. These differences in nanostructure formation are common and unavoidable to these types of materials upon varying the amino acid sequence and introducing hydrophobic substituents to various positions on the peptide backbone. Importantly, all NDI-containing samples revealed the preference for 1-D assembly despite the added perturbation of the large aromatic diimide core.

Spectroscopy of Donor-Acceptor and Control Peptide-π Hybrids.

Following HPLC purification of compound 6, UV-vis was employed to characterize the assembly and potential charge transfer behavior of the system. Referring now to FIG. 39, spectra of were taken in water at pH 8 (dashed lines, unassembled) and pH 6 (solid lines, assembled). Unassembled samples showed distinct absorbances corresponding to the OT4 (450 nm) and NDI (390 nm) units. Upon acidification and assembly, an overall decrease in molar absorptivity is observed, accompanied by a blue shift of the absorbance corresponding to the OT4 subunit. This behavior suggests an H-like aggregation of these chromophores (Kasha, M., et al., *Pure Appl. Chem.* 1965, 11, 371-392, as has been previously seen. Sanders, A. M., et al., *ACS Macro Lett.* 2012, 1, 1326; Sanders, A. M.; Tovar, J. D. *Supramol. Chem.* 2014, 26, 259; Vadehra, G. S., et al., *Chem. Commun.* 2010, 46, 3947). A low energy charge transfer band, however, is not apparent in either the assembled or unassembled samples. Photoluminescence spectra have not yet been obtained for 6, but solutions of the peptide are non-fluorescent under a handheld UV lamp, while previously studied OT4-containing peptides without NDI acceptor units have been highly fluorescent when unassembled in solution. Sanders, A. M., et al., *ACS Macro Lett.* 2012, 1, 1326; Sanders, A. M.; Tovar, J. D. *Supramol. Chem.* 2014, 26, 259. This suggests that some type of excited state quenching is occurring that is potentially due to the proximity of the donor and acceptor units.

The acid-triggered self-assembly of the peptides simultaneously induces intimate π-electron interactions between the embedded OT4 moieties, thus encouraging exciton coupling between the transition dipoles of the chromophores. These interactions produce perturbations in the steady-state absorption spectra. Therefore, the data were acquired for each donor-acceptor peptide (DA), acylated control peptide (C), and various DA:C mixtures (10:90, 25:75, and 50:50 DA:C) in both basic and acidic aqueous environments, as shown FIG. 40A, FIG. 40B, FIG. 40C, FIG. 40D, FIG. 40E, and FIG. 40F. In general, each acylated control peptide displays a blue shift in the absorption $\lambda_{max}$ of the OT4 chromophore upon acid-triggered assembly, from 425 nm to 390-410 nm, which is indicative of cofacial H-like aggregation (Kasha et al., 1965). Interestingly, while control peptides C-6 and C-3 display larger blue shifts (32-34 nm), C-2 shifts only 13 nm and exhibits a low energy shoulder at 450 nm, reflecting the influence of the bulky acylated lysine residues in close proximity to the OT4 chromophore. Upon the addition of increasing amounts of the analogous donor-acceptor peptides, the absorptivity of the OT4 absorption at 420 nm decreases, while that of the NDI chromophore at 390 nm is enhanced. 100% DA peptide spectra shows minimal perturbation of the NDI absorption between basic and acidic environments and are similar for each peptide. The OT4 chromophore contribution to the absorption spectra is more varied for the series. From unassembled to assembled, DA-6 shows a slight perturbation of the OT4 absorption, while in DA-7, this absorption is essentially unperturbed, suggesting assembly is occurring even in a basic environment. DA-2 displays the most perturbation of the OT4 absorbance, showing a similar $\lambda_{max}$ blue shift and low energy shoulder as seen with control C-2.

The DA-C mixtures, under both molecular (basic pH) and assembled (acidic pH) conditions showed absorption features that were in essence additive superpositions of the ratio of the two components, indicating that the electronic interactions in the co-assemblies are not substantially different than those within the neat DA nanostructures. It should be noted that the extinction coefficient for the OT signature is reduced in the D-A peptides, so a constant OT4 absorption feature is not present.

Steady-state photoluminescence can also be perturbed upon interaction of emissive chromophores through self-assembly. As seen in FIG. 41A, FIG. 41B, FIG. 41C, FIG. 41D, FIG. 41E, and FIG. 41F, following excitation of the OT4 chromophore, each acylated control peptide displays nearly identical emission at 510 nm in a basic environment and dramatic (approx. 100 fold) quenching and red-shifting to 550-560 nm upon assembly, indicative of excimer formation (C line). Due to electron transfer occurring in the donor-acceptor peptides, radiative emission does not occur in unassembled or assembled samples (DA line). Therefore, increasing ratios of DA:C causes enhanced photoluminescence quenching (DA-C line), in both unassembled and assembled samples. Interestingly, more dramatic quenching of the photoluminescence occurs at the same mole percent of donor-acceptor peptide within assembled samples, as shown in the relative photoluminescence quantum yield vs mol % DA plots in FIG. 41G, and FIG. 41H. While minimal change occurs for the unassembled mixtures of 10% donor-acceptor to 90% acylated control relative to the 100% control samples, assembled 10:90 mixtures retain only 55%-46% relative quantum yield. Unassembled samples containing 50% donor-acceptor peptide are quenched to 87%-64% relative quantum yield, while assembled samples are much more dramatically reduced to 13%-11 These results not only suggest that electron transfer occurs in assemblies, but also that a greater fraction of excited donors are quenched by electron transfer when assembled. This likely reflects that excitons delocalize within the assembled arrays prior to electron transfer to the NDI acceptor units, a process that cannot occur within the unassembled mixtures.

Circular dichroism (CD) can be utilized to characterize electronic coupling between chromophores within a chiral environment. CD spectra for each donor-acceptor (DA-6, DA-3, and DA-2) and acylated control (C-6, C-3, and C-2) peptide in basic (pH 8) and acidic (pH 4) aqueous environments are shown in FIG. 42A, FIG. 42B, FIG. 42C, FIG. 42D, FIG. 42E, and FIG. 42F. While each control peptide displays minimal absorption within the wavelength range of the OT4 chromophore $\pi-\pi^*$ transition (dashed lines), upon acidification and assembly Cotton effects are evident (solid lines), suggesting chromophore interaction within the chiral environment created by the assembled peptide scaffolds. Control peptides C-6 and C-3 show similar behavior, each inducing a negative bisignate signal, although that for C-3 is over twice as intense. As was previously seen in the absorption studies, C-2 also exhibits much different behavior in its CD spectrum, suggesting a unique supramolecular assembly in comparison to the other acylated control peptides. Again, this could possibly be due to the relatively bulky lysine residue situated in close proximity to the embedded quaterthiophene chromophore. Each donor-acceptor peptide (DA-6, DA-3, and DA-2) displays vastly different CD behavior. While DA-6, shows no meaningful signal corresponding to the OT4 chromophore in either acidic or basic environments, weak signals consistent with the NDI subunit are evident. Alternatively, DA-3 exhibits a strong negative bisignate Cotton effect in the absorption range of the OT4 and NDI moieties while assembled in acidic solution. This signal is also still evident even at basic pH, as was predicted by the lack of perturbation of its absorption spectrum with pH change. DA-2 shows essential no meaningful signal in the chromophore absorbance range in acidic solution, but upon increasing the pH, a weak positive Cotton effect is revealed, suggesting that some aggregation may be occurring at high pH. This could be a consequence of the large, hydrophobic NDI subunit in the vicinity of the peptide core.

Figure 42A:
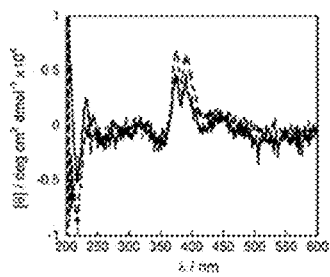
Figure 42B:
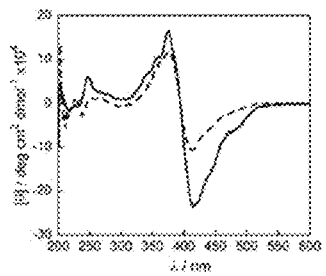
Figure 42C:
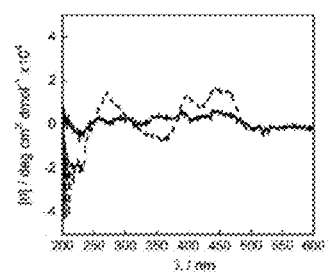
Figure 42D:
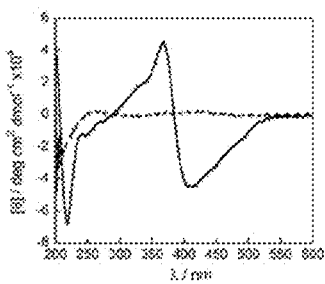
Figure 42E:
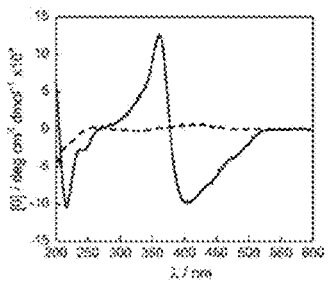
Figure 42F:
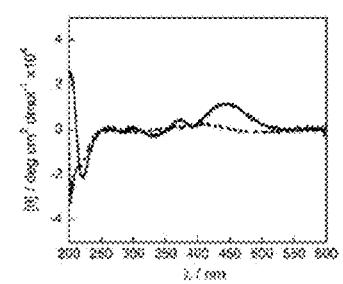
Figure 42G:
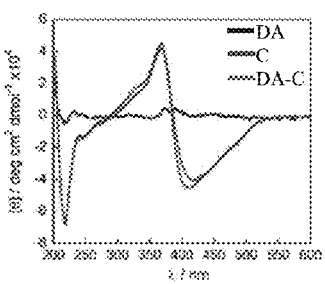
Figure 42H:
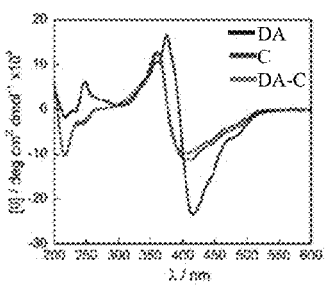
Figure 42I:
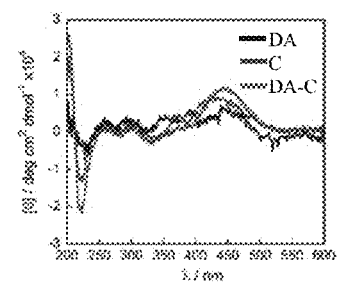
Figure 43A:
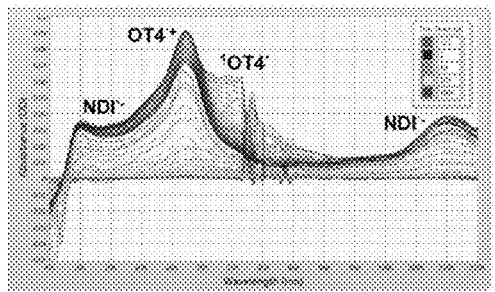
Figure 43B:
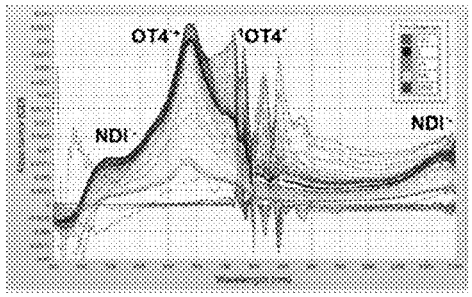
Figure 43C:
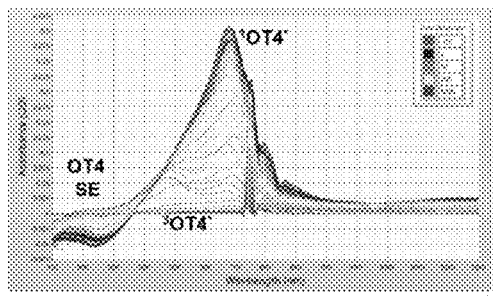
Figure 43D:
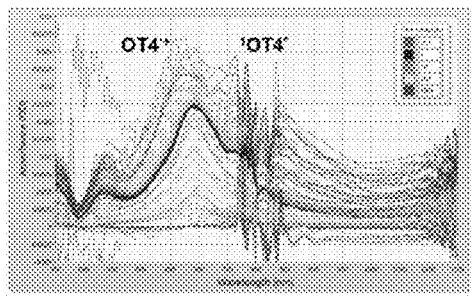

CD spectra of donor-acceptor/control mixtures in acidic solution (10:90 DA-C line) were also obtained and compared to those of the pure components (DA and C lines) (FIG. 42G, FIG. 42H and FIG. 42I). In the case of donor-acceptor/control pairs DA-6/C-6 and DA-2/C-2, addition of donor-acceptor peptide correlates with decreasing molar ellipticity. Alternatively, the mixture of DA-3 and C-3 causes a slight increase in signal intensity, due to the fact that the molar ellipticity of assembled DA-3 is significantly larger than that of C-3. These spectral studies demonstrate that, while the structure of each peptide is quite similar and each have been shown to form 1-D nanostructures by TEM, the position of the lysine residues elicit differences in aggregation at the molecular level, which is typical of related materials upon alteration of the amino acid sequence/substitution (Wall et al., 2014).

Dynamics of Charge Separation in Dyads and Dyad Assemblies.

As described above, the electron donor (OT4) and acceptor (NDI) moieties incorporated into the dyad structures were chosen specifically such that their relative HOMO and LUMO energies enable electron transfer from OT4 to NDI but not from NDI to OT4; furthermore, their HOMO-LUMO gaps inhibit energy transfer from photoexcited OT4 to NDI. Based on this design principle, any charge transfer that follows photoexcitation of OT4 moieties should only produce $NDI^-$ and $OT4^+$ radicals, which both have distinct spectroscopic signatures. There are many examples in the literature where the formation of these radicals within covalent or supramolecular donor-acceptor systems (upon donor excitation by laser pulse) is confirmed by transient absorption spectroscopy (Bhosale, 2006; van Hal et al., 2002; Rogers et al., 2000; Sessler et al., 1998). As formation of persistent charges could not be identified from steady-state UV-Vis measurements, broadband ultrafast transient absorption spectroscopy was used to probe the formation of charged species and assess how the properties of the dyad structures control charge separation and recombination kinetics when they are assembled and unassembled.

For these measurements the OT4 moiety was photoexcited at 400 nm, with resulting evolution in transient absorptivity probed between 450 and 1150 nm with an experimental time resolution of 90 fs. This excitation wavelength was chosen for convenience, but approaches the absorption onset for NDI. Control measurements were also made at 480 nm, at the red side of the steady-state OT4 spectrum (FIG. 45B) The similarity in the spectral dynamics observed at the two excitation wavelengths supports that the OT4 moiety is selectively excited at 400 nm. Variations in spectral dynamics with excitation fluence were also examined to ensure that spectral dynamics were not the effect of two-photon excitation or dynamics of biexcitations (FIG. 46), as described below.

FIG. 47A presents the spectral dynamics of unassembled DA-2 dyads in aqueous solution following excitation at 400 nm. Five transient spectral features can be identified from this spectral progression: a negative signal below 475 nm, which corresponds with bleach of the OT4 ground-state absorption band; three transient absorption bands at approximately 500, 670, and 1100 nm; and a broad absorption band centered around approximately 775 nm. All features appear almost immediately upon excitation, whereas the broad band around 775 nm disappears within a few hundred femtoseconds and the others disappear on a timescale of picoseconds.

FIG. 48A and FIG. 48B presents principal spectral (A) and kinetic (B) components obtained from a global analysis of this data; these indicate that the spectral dynamics observed following excitation is associated with two spectral patterns and two photoinduced responses. FIG. 48A reveals that the band centered near 775 nm that decays within the first picosecond after excitation resembles the spectrum of isolated OT4 photoexcited to its $S_1$ state as measured in previous works ((Zhou et al., 2015; Lap et al., 1997; Benincori et al., 1998). In contrast, the remaining features closely match signatures of reduced or oxidized components of the dyad: the bands at 500 and 1100 nm nm match spectra of reduced NDI (Bhosale, 2006; Invinski et al., 2014), whereas the band at 670 nm matches the well-known absorption band of oxidized OT4 (van Hal et al., 2002). The presence of these bands and their simultaneous decay with concomitant recovery of the OT4 bleach indicates that photoexcitation induces charge separation between the donor and acceptor moieties within the unassembled dyad; this photoinduced separation is followed by charge recombination on a timescale of several picoseconds.

There are no spectral or temporal signatures suggesting that peptide regions serve as charge acceptors or donors at any stage following excitation. However, principal kinetic components plotted in FIG. 48B demonstrate that charge separation occurs via two modes: (1) virtually instantaneously (within the time resolution of the experiment) and (2) on a delay of approximately 300 fs from the $S_1$ state of the OT4 moiety. The observation of two modes of charge separation suggests that conformation or charge of the bridging peptide impacts the electronic coupling between the OT4 and NDI moieties. The transients in FIG. 48B also reveal that charge separated species recombine predominantly on an approximately 5 ps timescale, with a small fraction persisting into the 100 s of ps to ns regime. Observation of two recombination timescales may reflect differences in the reorganization energy for charge recombination due to peptide conformation or charge, but may also arise from the presence of some assembled dyads in solution. Characteristic decay timescales of the local OT4 excitation and charge-separated pairs were obtained by fitting the temporal components obtained through global analysis to single or biexponential decay functions convoluted with the instrument response. Values of fitting parameters are presented in Table 4. Parameters for exponential fits to kinetic traces obtained from a global analysis of the unassembled and assembled DA-2 dyads. 95% confidence intervals were predicted using a non-linear least squares fitting error analysis. A single exponential decay was fit to the OT4 $S_1$ decay, whereas the decay of charge separated states (CS) were fit with a biexponential decay. For the latter, $F_{CTn}$ is the fraction of charge separated pairs with lifetime $\tau_{CTn}$.

FIG. 47B presents the transient spectral dynamics observed following 400-nm excitation of a suspension of assembled DA-2 dyads in aqueous solution. The shapes and positions of the transient spectra are qualitatively similar to those observed with unassembled dyads, except that the 500, 670, and 1100 nm transient bands associated with charge-separated species are red-shifted by 20-25 nm and also exhibit somewhat broader line shapes. Furthermore, the short-lived $S_1$ absorption of OT4 extends over 1100 nm and overlaps the absorption of NDI– in the near IR. This breadth and substantial redshift in the OT4 absorption are consistent with stacked chromophores in assemblies.

FIG. 50A and FIG. 50B present the corresponding principal spectral and kinetic components obtained through global analysis. Spectral components plotted in FIG. 50A are highly similar to those obtained with unassembled dyads. Furthermore, the signature of $S_1$ OT4 decays on comparable timescales for both cases (270 fs, Table 4), suggesting that charge-transfer dynamics are similar in the two environments and that any energy transfer along the OT4 core of an assembly may be limited by the rate of ultrafast charge separation. In contrast, the kinetics of charge recombination differs markedly: whereas recombination occurs on picosecond timescales in unassembled dyads, roughly 40% of separated charges persist for timescales of 100 s of ps to nanoseconds in assemblies. This observation indicates that stacking of the OT4 moieties (and potentially also NDI moieties) provides the ability for charge pairs to migrate or separate along the assemblies. Alternatively, assembly of the dyads may change the driving force or reorganization energy for charge recombination of proximal charge pairs. Nonetheless, the data demonstrate that an increase in the charge-separation lifetime is achieved through aggregation.

Figure 45B:
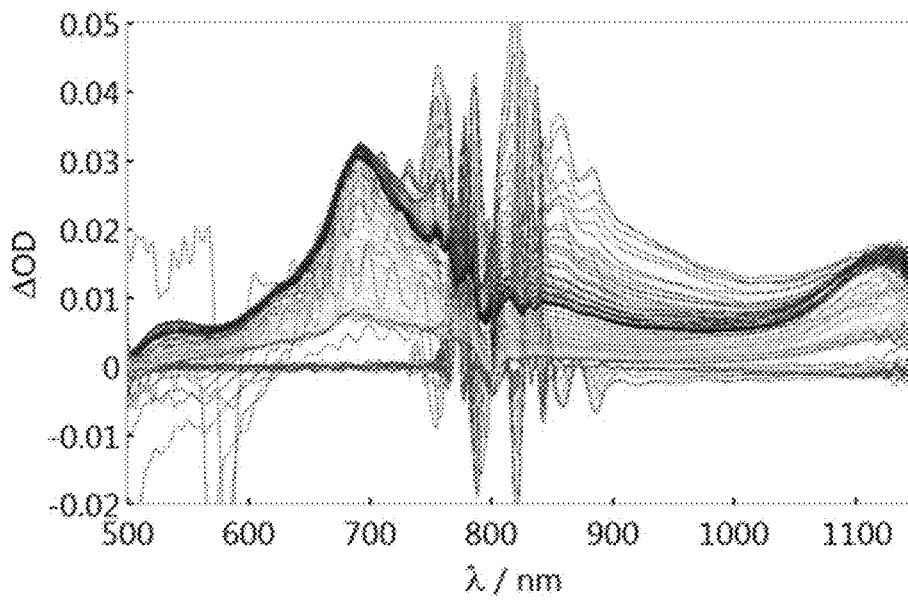

Only modest differences in the transient spectral dynamics are observed for both unassembled and assembled dyads upon increasing the excitation wavelength from 400 to 480 nm and with no appreciable change in excited-state and charge-pair lifetimes (FIG. 45A and FIG. 45B). Little fluence dependence is observed in the spectral dynamics measured with the unassembled or assembled dyads as well, confirming that charge separation observed here is not due to two-photon transitions or exciton annihilation. In contrast, the transient spectra of control assemblies exhibit signatures of OT4$^+$ at high fluence and long-lived OT4 $S_1$ signal at lower fluences (FIG. 49A). This demonstrates that donor-acceptor charge separation is highly competitive with multi-photon excitation and annihilation mechanisms along the OT4 core.

FIG. 50B presents absorption transients collected at 1100 nm under identical excitation fluences for control (C-2), dyad (DA-2), and mixed (C-2/DA-2) assemblies. Significantly different time-dependent behavior is observed at this probe wavelength for control and dyad assemblies (CT data symbols, $S_1$ data symbols, CT Fit line and $S_1$ Fit line, respectively). Transient absorption from an assembly of a 10%-90% DA:C mixture exhibits intermediate behavior (Mixture symbols and fit line). The intensity decay at this wavelength for mixed assemblies cannot be recovered through a proportionate combination of the control and dyad traces (dashed line, 10%-90%), but rather by a 39%-61% combination of these pure-assembly transients (dashed line 39%-61%). This comparison indicates that photoexcitation enables some degree of delocalization or energy transfer and supports observations from steady-state measurements (e.g. FIG. 42H). On statistical grounds, this suggests an effective delocalization over 3-4 donors (Herz et al., 2003; Spano et al., 2007).

Excitation Energy and Fluence Dependencies.

An assembled dyad sample was interrogated to explore excitation energy and fluence dependencies of excited-state dynamics and charge pair formation. Transient spectral signatures were found to be consistent for excitations at different energies along the OT4 visible absorbance band (FIG. 45A and FIG. 45B) and over the range of experimentally accessible fluences (FIG. 46). By contrast, a significant power dependence was observed for its acylated control, C-2, probed under similar conditions (FIG. 49A).

Variations in Time-Dependence with Peptide Length and Type.

The separation distance between the NDI and OT4 units also has a modest effect on the yields and kinetics for the charge separated states within the assembled and unassembled dyads. In either instance, a greater intensity due to charge-separated states was observed for shorter separation distances at similar excitation fluences. Dyads with spaced 2 peptide units apart displayed slightly longer relaxation lifetimes than the corresponding 3 and 6 unit separation dyads (FIG. 49B). This is consistent with the greater self-aggregation of DA-2 in basic solution.

In conclusion, a library of novel donor-acceptor π-peptide hybrids containing an OT4 donor core and NDI acceptor moieties peripherally attached to lysine residues were synthesized. The synthesis was completed by using the solid-phase Stille cross-coupling dimerization procedure previously developed in the lab, followed by the deprotection of the orgothonally protected lysine residues and solid-phase imidation with the naphthalene moiety. The three peptides differed in the spacial distance between the electron donor and acceptor subunits (6, 3, and 2 amino acids). Analogous "donor-only" control peptide-π hybrids were also prepared for comparison by replacing the NDI moiety with acyl groups.

The self-assembly of each peptide and mixtures of each donor-acceptor and control pair was investigated by TEM, absorption, photoluminescence, and circular dichroism. It was seen that each peptide and mixture formed 1-D nanostructures upon assembly via acidification, however the assembly and interaction of the embedded OT4 cores varied between peptides due to the different positioning of the lysine residues (either acylated or NDI-substituted).

These peptides undergo photoinduced electron transfer from the embedded OT4 donor moiety to the peripherally attached NDI acceptor units after excitation of the donor, as demonstrated explicitly with transient absorption spectroscopy. Electron transfer is observed to occur both instantaneously (<100 fs) and with a delay of 270 fs for assembled and unassembled dyads, suggesting that structural heterogeneities (e.g. conformation or peptide charge) likely impact charge-separation dynamics.

Furthermore, assembly of donor-acceptor hybrids results in a 10-100 fold increase in the charge-separation lifetime, with charges persisting into the nanosecond time regime. Through co-assembly the key donor-acceptor unit was diluted within a matrix of energy-harvesting donor peptides, thus offering the prospect for directed energy migration through this nanostructured matrix to the acceptor dopant site. Indeed, observations of both enhancements in the steady-state quenching of donor photoluminescence and transient spectral responses that are disproportionate with respect to dyad and donor-only composition indicate that such a process is operative. In general, this supramolecular platform offers the unique possibility of merging electric-field creation into biologically relevant nanomaterials, and future investigations will seek to understand how such fields can alter or impact cellular physiology.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Abidian, M. R.; Corey, J. M.; Kipke, D. R.; Martin, D. C. Conducting-Polymer Nanotubes Improve Electrical Properties, Mechanical Adhesion, Neural Attachment, and Neurite Outgrowth of Neural Electrodes. *Small* 2010, 6, 421-429;

Aida, T.; Meijer, E. W.; Stupp, S. I. *Science* 2012, 335, 813-817.

Ajayaghosh, A.; Praveen, V. K.; Vijayakumar, C.; George, S. J. *Angew. Chem. Int. Ed.* 2007, 46, 6260-6265;

Ahrens, M. J.; Sinks, L. E.; Tybtchinski, B.; Liu, W.; Jones, B. A.; Giaimo, J. M.; Gusev, A. V.; Goshe, A. J.; Tiede, D. M.; Wasielewski, M. R. *J. Am. Chem. Soc.* 2004, 126, 8284;

Amit, M.; Appel, S.; Cohen, R.; Cheng, G.; Hamley, I. W.; Ashkenasy, N., Hybrid Proton and Electron Transport in Peptide Fibrils. *Adv. Funct. Mater.* 2014, 24, 5873-5880;

Ardoña, H. A. M.; Besar, K.; Togninalli, M.; Katz, H. E.; Tovar, J. D. Sequence-Dependent Mechanical, Photophysical and Electrical Properties of Pi-Conjugated Peptide Hydrogelators. *J. Mater. Chem. C* 2015, 3, 6505-6514;

Ardoña, H. A. M.; Tovar, J. D., Energy Transfer within Responsive Pi-Conjugated Coassembled Peptide-Based Nanostructures in Aqueous Environments. *Chem. Sci.* 2015, 6, 1474-1484;

Ashkenasy, N.; Home, W. S.; Ghadiri, M. R. Design of Self-Assembling Peptide Nanotubes with Delocalized Electronic States. *Small* 2006, 2, 99-102;

Beckers, E. H. A.; Meskers, S. C. J.; Schenning, A. P. H. J.; Chen, Z.; Würthner, F.; Marsal, P.; Belionne, D.; Cornil, J.; Janssen, R. A. J. *J. Am. Chem. Soc.* 2006, 128, 649-657;

Benincori, T.; Bongiovanni, G.; Botta, C.; Cerullo, G.; Lanzani, G.; Mura, A.; Rossi, L.; Sannicolò, F.; Tubino, R. *Phys. Rev. B* 1998, 58 (14), 9082-9086;

Bheemaraju, A.; Pourmand, M.; Yang, B.; Surampudi, S. K.; Benanti, T. L.; Achermann, M.; Barnes, M. D.; Venkataraman, D. *J. Macromol. Sci, Pure Appl. Chem.* 2011, 48, 986-993;

Bhosale, S. *Science* 2006, 313 (5783), 84-86;

Bhosale, S. V; Jani, C. H.; Langford, S. J. *Chem. Soc. Rev.* 2008, 37 (2), 331-342;

Boekhoven, J; Stupp, S. I. *Adv. Mater.* 2014, 6, 1642-1659;

Botelho, A. L.; Shin, Y.; Liu, J.; Lin, X. *PLoS ONE* 2014, 9, e86370, doi: 10.1371/journal.pone.0086370;

Bradford, V. J.; Iverson, B. L. *J. Am. Chem. Soc.* 2008, 130, 1517-1524;

Braga, D.; Horowitz, G., High-Performance Organic Field-Effect Transistors. *Adv. Mater.* 2009, 21, 1473-1486;

Choi, M.-S.; Aida, T.; Yamazaki, T.; Yamazaki, I. A. *Angew. Chem. Int. Ed.* 2001, 40, 3194-3198;

Channon, K. J.; Devlin, G. L.; MacPhee, C. E. Efficient Energy Transfer within Self-Assembling Peptide Fibers: A Route to Light-Harvesting Nanomaterials. *J. Amer. Chem. Soc.* 2009, 131, 12520-12521;

Channon, K. J.; Devlin, G. L.; Magennis, S. W.; Finlayson, C. E.; Tickler, A. K.; Silva, C.; MacPhee, C. E. *J. Am. Chem. Soc.* 2008, 130, 5487-5491;

Chen, L.; Revel, S.; Morris, K.; Adams, D. J., Energy Transfer in Self-Assembled Dipeptide Hydrogels. *Chem. Commun.* 2010, 46, 4267-4269;

Chworos, A.; Severcan, I.; Koyfman, A. Y.; Weinkam, P.; Oroudjev, E.; Hansma, H. G.; Jaeger, L. Building Programmable Jigsaw Puzzles with RNA. *Science* 2004, 306, 2068-2072;

Cipriano, T.; Knotts, G.; Laudari, A.; Bianchi, R. C.; Alves, W. A.; Guha, S. Bioinspired Peptide Nanostructures for Organic Field-Effect Transistors. *ACS Appl. Mater. Interfaces* 2014, 6, 21408-21415;

Cornil, J.; Beljonne, D.; Calbert, J.-P.; Brédas, J.-L. *Adv. Mater.* 2001, 13, 1053-1067;

Diegelmann, S. R.; Gorham, J. M.; Tovar, J. D. One-Dimensional Optoelectronic Nanostructures Derived from the Aqueous Self-Assembly of Pi-conjugated Oligopeptides. *J. Am. Chem. Soc.* 2008, 130, 13840-13841;

Diegelmann, S. R.; Hartman, N.; Markovic, N.; Tovar, J. D. Synthesis and Alignment of Discrete Polydiacetylene-Peptide Nanostructures. *J. Amer. Chem. Soc.* 2012, 134, 2028-2031;

Draper, E. R.; Walsh, J. J.; McDonald, T. O.; Zwijnenburg, M. A.; Cameron, P. J.; Cowan, A. J.; Adams, D. J., Air-stable photoconductive films formed from perylene bisimide gelators. *J. Mater. Chem. C* 2014, 2, 5570-5575;

Fassioli, F.; Dinshaw, R.; Arpin, P. C.; Scholes, G. D. *J. R. Soc. Interface* 2013, 11, 20130901-20130901;

Fei, Z.; Pattanasattayavong, P.; Han, Y.; Schroeder, B. C.; Yan, F.; Kline, R. J.; Anthopoulos, T. D.; Heeney, M., Influence of Side-Chain Regiochemistry on the Transistor Performance of High-Mobility, All-Donor Polymers. *J. Am. Chem. Soc.* 2014, 136, 15154-15157;

Forciniti, L.; Guimard, N. K.; Lee, S.; Schmidt, C. E. *J. Mater. Chem.* 2010, 20 (40), 8865;

Fox, M. A.; Galoppini, E. *J. Am. Chem. Soc.* 1997, 119, 5277;

Frischmann, P. D.; Mahata, K.; Würthner, F. *Chem. Soc. Rev.* 2013, 42, 1847-1870;

Gallaher, J. K.; Aitken, E. J.; Keyzers, R. A.; Hodgkiss, J. M. *Chem. Commun.* 2012, 48 (64), 7961;

Galoppini, E.; Fox, M. A. *J. Am. Chem. Soc.* 1996, 118, 2299;

Gao, M.; Paul, S.; Schwieters, C. D.; You, Z.-Q.; Shao, H.; Herbert, J. M.; Parquette, J. R.; Jaroniec, C. P. *J. Phys. Chem. C* 2015, 119 (24), 13948-13956;

Generali, G.; Dinelli, F.; Capelli, R.; Toffanin, S.; di Maria, F.; Gazzano, M.; Barbarella, G.; Muccini, M., Correlation among Morphology, Crystallinity, and Charge Mobility in OFETs Made of Quaterthiophene Alkyl Derivatives on a Transparent Substrate Platform. *J. Phys. Chem. C* 2011, 115, 23164-23169;

Ghadiri, M. R.; Granja, J. R.; Milligan, R. A.; McRee, D. E.; Khazanovich, N. Self-Assembling Organic Nanotubes Based of a Cyclic Peptide Architecture. *Nature* 1994, 366, 324-327;

Guarino, V.; Alvarez-Perez, M. A.; Borriello, A.; Napolitano, T.; Ambrosio, L. *Adv. Healthc. Mater.* 2013, 2 (1), 218-227;

Gumus, A.; Califano, J. P.; Wan, A. M. D.; Huynh, J.; Reinhart-King, C. A.; Malliaras, G. G. *Soft Matter* 2010, 6 (20), 5138;

Guo, X.; Watson, M. D. *Org. Lett.* 2008, 10, 5333-5336;

Gust, D.; Moore, T. A.; Moore, A. L. *Acc. Chem. Res.* 2001, 34, 40-48.

Haycock, R. A.; Yartsev, A.; Michelsen, U.; Sundström, V.; Hunter, C. A. *Angew. Chem. Int. Ed.* 2000, 39, 3616-3619.

Herz, L.; Daniel, C.; Silva, C.; Hoeben, F. J. M., Schenning, A. P. H. J.; Meijer, E. W.; Friend, R. H.; Phillips, R. T. *Phys. Rev. B* 2003, 68, 045203;

Himmelberger, S.; Vandewal, K.; Fei, Z. P.; Heeney, M.; Salleo, A., Role of Molecular Weight Distribution on Charge Transport in Semiconducting Polymers. *Macromolecules* 2014, 47 (20), 7151-7157;

Hirst, A. R.; Roy, S.; Arora, M.; Das, A. K.; Hodson, N.; Murray, P.; Marshall, S.; Javid, N.; Sefcik, J.; Boekhoven, J.; van Esch, J. H.; Santabarbara, S.; Hunt, N. T.; Ulijn, R. V. *Nat. Chem.* 2010, 2, 1089-1094.

Hoeben, F. J. M.; Schenning, A. P. H. J.; Meijer, E. W. *Chem Phys Chem* 2005, 6, 2337-2342;

Hoeben, F. J. M.; Herz, L. M.; Daniel, C.; Jonkheijm, P.; Schenning, A. P. H. J; Silva, C.; Meskers, S. C. J.; Beljonne, D.; Philips, R. T.; Friend, R. H.; Meijer, E. W. *Angew. Chem. Int. Ed.* 2004, 116, 2010-2013;

Home, W. S.; Ashkenasy, N.; Ghadiri, M. R. *Chem. Eur. J.* 2005, 11 (4), 1137-1144;

Horowitz, G. Organic Field-Effect Transistors. *Adv. Mater.* 1998, 10, 365-377;

Imahori, H.; Guldi, D. M.; Tamaki, K.; Yoshida, Y.; Luo, C.; Sakata, Y.; Fukuzumi, S. *J. Am. Chem. Soc.* 2001, 123 (27), 6617-6628;

Imahori, H.; Tamaki, K.; Guldi, D. M.; Luo, C.; Fujitsuka, M.; Ito, O.; Sakata, Y.; Fukuzumi, S. *J. Am. Chem. Soc.* 2001, 123 (11), 2607-2617;

Ivnitski, D.; Amit, M.; Rubinov, B.; Cohen-Luria, R.; Ashkenasy, N.; Ashkenasy, G. *Chem. Commun.* 2014, 50 (51), 6733;

Jahnke, E.; Lieberwirth, I.; Severin, N.; Rabe, J. P.; Frauenrath, H. Topochemical Polymerization in Supramolecular Polymers of Oligopeptide-Functionalized Diacetylenes. *Angew. Chem. Int. Ed.* 2006, 45, 5383-5386;

Jatsch, A.; Schillinger, E. K.; Schmid, S.; Baeuerle, P., Biomolecule Assisted Self-Assembly of Pi-Conjugated Oligomers. *J. Mater. Chem.* 2010, 20, 3563-3578;

Jones, G.; Vullev, V.; Braswell, E. H.; Zhu, D. *J. Am. Chem. Soc.* 2000, 122 (2), 388-389;

Jurchescu, O. D.; Hamadani, B. H.; Xiong, H. D.; Park, S. K.; Subramanian, S.; Zimmerman, N. M.; Anthony, J. E.; Jackson, T. N.; Gundlach, D. J. Correlation Between Microstructure, Electronic Properties and Flicker Noise in Organic Thin Film Transistors. *Appl. Phys. Lett.* 2008, 92, 132103;

Kasha, M.; Rawls, H. R.; El-Bayoumi, M. A. *Pure Appl. Chem.* 1965, 11, 371-392;

Kawano, S.; Fujita, N.; Shinkai, S. Quater-, Quinque-, and Sexithiophene Organogelators: Unique Thermochromism and Heating-Free Sol-Gel Phase Transition. *Chem.-Eur. J.* 2005, 11, 4735-4742;

Kim, S. H.; Parquette, J. R. A Model for the Controlled Assembly of Semiconductor Peptides. *Nanoscale* 2012, 4, 6940-6947;

Kline, R. J.; McGehee, M. D.; Kadnikova, E. N.; Liu, J. S.; Frechet, J. M. J.; Toney, M. F., Dependence of Regioregular Poly(3-hexylthiophene) Film Morphology and Field-Effect Mobility on Molecular Weight. *Macromolecules* 2005, 38, 3312-3319;

Korevaar, P. A.; Newcomb, C. J.; Meijer, E. W.; Stupp, S. I. *J. Am. Chem. Soc.* 2014, 136, 8540-8543;

Kraus, M.; Richler, S.; Opitz, A.; Bruetting, W.; Haas, S.; Hasegawa, T.; Hinderhofer, A.; Schreiber, F., High-mobility copper-phthalocyanine field-effect transistors with tetratetracontane passivation layer and organic metal contacts. *J. Appl. Phys.* 2010, 107, 094503;

Krieg, E.; Weissman, H.; Shimoni, E.; Bar On (Ustinov), A.; Rybtchinski, B. *J. Am. Chem. Soc.* 2014, 136, 9443-9452;

Kuciauskas, D.; Lin, S.; Seely, G. R.; Moore, A. L.; Moore, T. A; Gust, D.; Drovetskaya, T.; Reed, C. A.; Boyd, P. D. W. *J. Phys. Chem.* 1996, 100 (39), 15926-15932;

Kuciauskas, D.; Liddell, P. A.; Lin, S.; Johnson, T. E.; Weghorn, S. J.; Lindsey, J. S.; Moore, A. L.; Moore, T. A.; Gust, D. *J. Am. Chem. Soc.* 1999, 121 (37), 8604-8614;

Kumar, R. J.; MacDonald, J. M.; Singh, T. B.; Waddington, L. J.; Holmes, A. B. Hierarchical Self-Assembly of Semiconductor Functionalized Peptide Alpha-Helices and Optoelectronic Properties. *J. Am. Chem. Soc.* 2011, 133, 8564-8573;

Kwiatkowski, J. J.; Frost, J. M.; Nelson, J., The Effect of Morphology on Electron Field-Effect Mobility in Disordered $C_{60}$ Thin Films. *Nano Lett.* 2009, 9, 1085-1090;

Lap, D. V; Grebner, D.; Rentsch, S. *J. Phys. Chem. A* 1997, 101 (2), 107-112;

Liddell, P. A.; Sumida, J. P.; Macpherson, A. N.; Noss, L.; Seely, G. R.; Clark, K. N.; Moore, A. L.; Moore, T. A.; Gust, D. *Photochem. Photobiol.* 1994, 60 (6), 537-541;

Liddell, P. A.; Kodis, G.; Moore, A. L.; Moore, T. A.; Gust, D. *J. Am. Chem. Soc.* 2002, 124 (26), 7668-7669;

Liddell, P. A.; Kodis, G.; Moore, A. L.; Moore, T. A.; Gust, D. *J. Am. Chem. Soc.* 2002, 124 (26), 7668-7669;

Lim, J. M.; Kim, P.; Yoon, M. C.; Sung, J.; Dehm, V.; Chen, Z.; Wiirthner, F.; Kim, D. *Chem. Sci.* 2013, 4, 388-397;

Lin, Y. A.; Ou, Y. C.; Cheetham, A. G.; Cui, H. G. Supramolecular Polymers Formed by ABC Miktoarm Star Peptides. *ACS Macro Letters* 2013, 2, 1088-1094;

Malachowski, M. J.; Zmija, J. Organic Field-Effect Transistors. *Opto-Electron. Rev.* 2010, 18, 121-136;

Marciel, A. B.; Tanyeri, M.; Wall, B. D.; Tovar, J. D.; Schroeder, C. M.; Wilson, W. L. *Adv. Mater.* 2013, 25, 6398-6404;

Martinez-Hardigree, J. F.; Katz, H. E. Through Thick and Thin: Tuning the Threshold Voltage in Organic Field-Effect Transistors. *Acc. Chem. Res.* 2014, 47, 1369-1377;

Matmour, R.; De Cat, I.; George, S. J.; Adriaens, W.; Leclere, P.; Bomans, P. H. H.; Sommerdijk, N. A. J. M.; Gielen, J. C.; Christianen, P. C. M.; Heldens, J. T.; van Hest, J. C. M.; Lowik, D. W. P. M.; De Feyter, S.; Meijer, E. W.; Schenning, A. P. H. J. Oligo(p-phenylenevinylene)-Peptide Conjugates: Synthesis and Self-Assembly in Solution and at the Solid-Liquid Interface. 2008, 130, 14576-14583;

Mawad, D.; Stewart, E.; Officer, D. L.; Romeo, T.; Wagner, P.; Wagner, K.; Wallace, G. G. *Adv. Funct. Mater.* 2012, 22 (13), 2692-2699;

Morris, K. L.; Chen, L.; Raeburn, J.; Sellick, O. R.; Cotanda, P.; Paul, A.; Griffiths P. C.; King, S. M.; O'Reilly, R. K.; Serpell, L. C.; Adams, D. J. *Nat. Commun.* 2013, 4, 1480;

Nakashima, T.; Kimizuka, N. *Adv. Mater.* 2002, 14, 1113-1116;

Nalluri, S. K. M.; Ulijn, R. V., Discovery of Energy Transfer Nanostructures Using Gelation-Driven Dynamic Combinatorial Libraries. *Chem. Sci.* 2013, 4, 3699-3705;

Neuteboom, E. E.; Beckers, E. H. A.; Meskers, S. C. J.; Meijer, E. W.; Janssen, R. A. J. *Org. Biomol. Chem.* 2003, 1, 198-203;

Nishinari, K.; Shibuya, N.; Kainuma, K., Dielectric-relaxation in solid dextran and pullulan. *Macromol. Chem. Phys.* 1985, 186, 433-438;

Noriega, R.; Rivnay, J.; Vandewal, K.; Koch, F. P. V.; Stingelin, N.; Smith, P.; Toney, M. F.; Salleo, A. A General Relationship Between Disorder, Aggregation and Charge Transport in Conjugated Polymers. *Nat. Mater.* 2013, 12, 1038-1044;

Prasanthkumar, S.; Gopal, A.; Ajayaghosh, A. Self-Assembly of Thienylenevinylene Molecular Wires to Semiconducting Gels with Doped Metallic Conductivity. *J. Am. Chem. Soc.* 2010, 132, 13206-13207;

Praveen, V. K.; Ranjith, C.; Bandini, E.; Ajayaghosh, A.; Armaroli, N. *Chem. Soc. Rev.* 2014, 43, 4222;

Reches, M.; Gazit, E., Casting Metal Nanowires Within Discrete Self-Assembled Peptide Nanotubes. *Science* 2003, 300, 625-627;

Rogers, J. E.; Weiss, S. J.; Kelly, L. A. *J. Am. Chem. Soc.* 2000, 122 (3), 427-436;

Roncali, J. *Macromol. Rapid Commun.* 2007, 28, 1761-1775;

Rose, A.; Tovar, J. D.; Yamaguchi, S.; Nesterov, E. E.; Zhu, Z.; Swager, T. M. *Philos. Trans. R. Soc. Math. Phys. Eng. Sci.* 2007, 365, 1589-1606;

Rybtchinski, B; Sinks, L. E.; Wasielewski, M. R. *J. Am. Chem. Soc.* 2004, 126, 12268;

Sakai, N.; Mareda, J.; Vauthey, E.; Matile, S. *Chem. Commun.* 2010, 46 (24), 4225;

Sakakibara, K.; Chithra, P.; Das, B.; Mori, T.; Akada, M.; Labuta; J.; Tsuruoka, T.; Maji, S.; Furumi, S.; Shrestha, L. K.; Hill, J. P.; Acharya, S.; Ariaga, K.; Ajayaghosh, A. *J. Am. Chem. Soc.* 2014, 136, 8548-8551;

Sanders, A. M.; Dawidczyk, T. J.; Katz, H. E.; Tovar, J. D., Peptide-Based Supramolecular Semiconductor Nanomaterials via Pd-Catalyzed Solid-Phase "Dimerizations". *ACS Macro Lett.* 2012, 1, 1326-1329;

Sanders, A. M.; Tovar, J. D., Solid-Phase Pd-Catalysed Cross-coupling Methods for the Construction of Pi-Conjugated Peptide Nanomaterials. *Supramol. Chem.* 2014, 26 (3-4), 259-266;

Schenning, A. P. H. J.; Herrikhuyzen, J. V.; Jonkheijm, P.; Chen, Z.; Würthner, F.; Meijer, E. W. *J. Am. Chem. Soc.* 2002, 124, 10252-10253;

Schillinger, E.-K.; Mena-Osteritz, E.; Hentschel, J.; Börner, H. G.; Bauerle, P. *Adv. Mater.* 2009, 21, 1562-1567;

Schmid, S.; Mena-Osteritz, E.; Kopyshev, A.; Bäuerle, P. Self-Assembling Carbohydrate-Functionalized Oligothiophenes. *Org. Lett.* 2009, 11, 5098-5101;

Schmid, S. A.; Abbel, R.; Schenning, A. P. H. J.; Meijer, E. W.; Herz, L. M. *Philos. Trans. R. Soc. Math. Phys. Eng. Sci.* 2012, 370, 3787-3801;

Schmidt, C. E.; Shastri, V. R.; Vacanti, J. P.; Langer, R. *Proc. Natl. Acad. Sci. U.S.A* 1997, 94 (17), 8948-8953;

Schulze, J.; Torbjörnsson, M.; Kühn, O.; Pullerits, T. *New J. Phys.* 2014, 16, 045010;

Seeman, N. C. DNA in a Material World. *Nature* 2003, 421, 427-431;

Serin, J. M.; Brousmiche, D. W.; Fréchet, J. M. J. *Chem. Commun.* 2002, 2605-2607;

Sessler, J. L.; Brown, C. T.; O'Connor, D.; Springs, S. L.; Wang, R.; Sathiosatham, M.; Hirose, T. *J. Org. Chem.* 1998, 63 (21), 7370-7374;

Shao, H.; Nguyen, T.; Romano, N. C.; Modarelli, D. A.; Parquette, J. R. Self-Assembly of 1-D n-Type Nanostructures Based on Naphthalene Diimide-Appended Dipeptides. *J. Am. Chem. Soc.* 2009, 131, 16374-16376;

Sherwood, G. A.; Cheng, R.; Smith, T. M.; Werner, J. H.; Shreve, A. P.; Peteanu, L. A.; Wilderman, J. *J. Phys. Chem. C* 2009, 113, 18851-18862;

Sirringhaus, H.; Brown, P. J.; Friend, R. H.; Nielsen, M. M.; Bechgaard, K.; Langeveld-Voss B. M. W.; Spiering, A. J. H.; Janssen, R. A. J.; Meijer, E. W.; Herwig, P.; de Leeuw, D. M. *Nature.* 1999, 401, 685-688;

Spano, F. C. *J. Chem. Phys.* 2002, 116, 5877;

Stone, D. A.; Hsu, L.; Stupp, S. I. Self-Assembling Quinquethiophene-Oligopeptide Hydrogelators. *Soft Matter* 2009, 5, 1990-1993;

Sugiyasu, K.; Kawano, S.; Fujita, N.; Shinkai, S. *Chem. Mater.* 2008, 20, 2863-2865;

Sugiyasu, K.; Fujita, N.; Shinkai, S. *Angew. Chem. Int. Ed.* 2004, 43, 1229-1233;

Sun, Y.; Jiang, L.; Schuermann, K. C.; Adriaens, W.; Zhang, L.; Boey, F. Y. C.; De Cola, L.; Brunsveld, L.; Chen, X. Semiconductive, One-Dimensional, Self-Assembled Nanostructures Based on Oligopeptides with Pi-Conjugated Segments. *Chem-Eur. J.* 2011, 17, 4746-4749;

Traina, C. A.; Bakus II, R. C.; Bazan, G. C. *J. Am. Chem. Soc.* 2011, 133 (32), 12600-12607;

Tsai, W.-W.; Tevis, I. D.; Tayi, A. S.; Cui, H.; Stupp, S. I. Semiconducting Nanowires from Hairpin-Shaped Self-Assembling Sexithiophenes. *J. Phys. Chem. B* 2010, 114, 14778-14786;

Vadehra, G. S.; Wall, B. D.; Diegelmann, S. R.; Tovar, J. D. *Chem. Commun.* 2010, 46, 3947-3949;
van Hal, P. A.; Beckers, E. H. A.; Meskers, S. C. J.; Jousselme, B.; Blanchard, P.; Roncali, *J. Chem. Eur. J.* 2002, 8 (23), 5415-5429;
Vijayakumar, C.; Praveen, V. K.; Kartha, K. K.; Ajayaghosh, A. *Phys. Chem. Chem. Phys.* 2011, 13, 4942-4949;
Wall, B. D.; Diegelmann, S. R.; Zhang, S.; Dawidczyk, T. J.; Wilson, W. L.; Katz, H. E.; Mao, H.-Q.; Tovar, J. D. Aligned Macroscopic Domains of Optoelectronic Nanostructures Prepared via Shear-Flow Assembly of Peptide Hydrogels. *Adv. Mater.* 2011, 23, 5009-5014;
Wall, B. D.; Zacca, A. E.; Sanders, A. M.; Wilson, W. L.; Ferguson, A. L.; Tovar, J. D. Supramolecular Polymorphism: Tunable Electronic Interactions within pi-Conjugated Peptide Nanostructures Dictated by Primary Amino Acid Sequence. *Langmuir* 2014, 30 (20) 5946-5956;
Wang, Y.; Corbitt, T. S.; Jett, S. D.; Tang, Y.; Schanze, K. S.; Chi, E. Y.; Whitten, D. G. *Langmuir* 2012, 28(1), 65-70.
Wasielewski, M. R. *Chem. Rev.* 1992, 92 (3), 435-461;
Wasielewski, M. R. *Acc. Chem. Res.* 2009, 42, 1910;
Whitten, D. G. *Langmuir* 2012, 28 (1), 65-70;
Wong, J. Y.; Langer, R.; Ingber, D. E. *Proc. Nati. Acad. Sci. U.S.A* 1994, 91 (8), 3201-3204;
Wong, L. Y.; Png, R. Q.; Silva, F. B. S.; Chua, L. L.; Repaka, D. V. M.; Shi, C.; Gao, X. Y.; Ke, L.; Chua, S. J.; Wee, A. T. S.; Ho, P. K. H. Interplay of Processing, Morphological Order, and Charge-Carrier Mobility in Polythiophene Thin Films Deposited by Different Methods: Comparison of Spin-Cast, Drop-Cast, and Inkjet-Printed Films. *Langmuir* 2010, 26, 15494-15507;
Zelzer, M.; Ulijn, R. V. *Chem. Soc. Rev.* 2010, 39, 3351-3357;
Zhao, H.; Zhu, B.; Sekine, J.; Luo, S. C.; Yu, H. H. *ACS Appl. Mater. Interfaces* 2012, 4 (2), 680-686;
Zhou, J.; Yu, W.; Bragg, A. E. *J. Phys. Chem. Lett.* 2015, 6, 3496-3502.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A supramolecular assembly comprising covalently-bound electron donor-acceptor chromophores in which either electron acceptor semiconducting π-units are incorporated into amino acid side chains on peptides embedded with an electron donor semiconducting π-unit or electron donor semiconducting π-units are incorporated into amino acid side chains on peptides embedded with an electron acceptor semiconducting π-unit, wherein the supramolecular assembly comprises π-conjugated peptides units having the following structures:

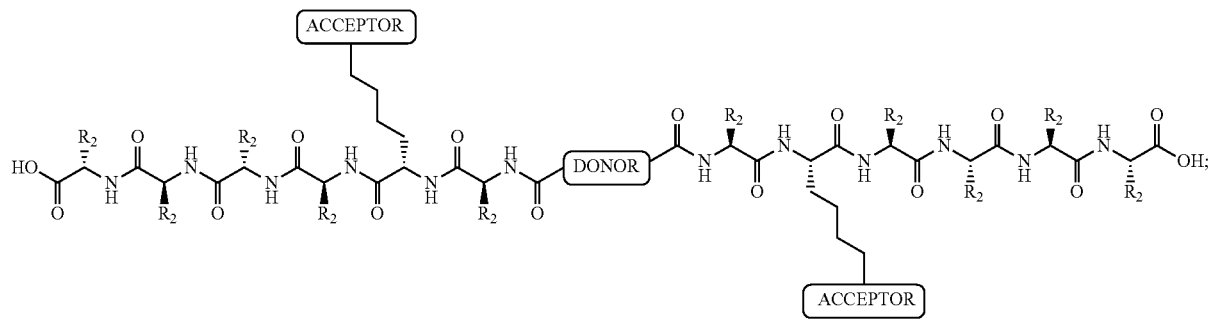

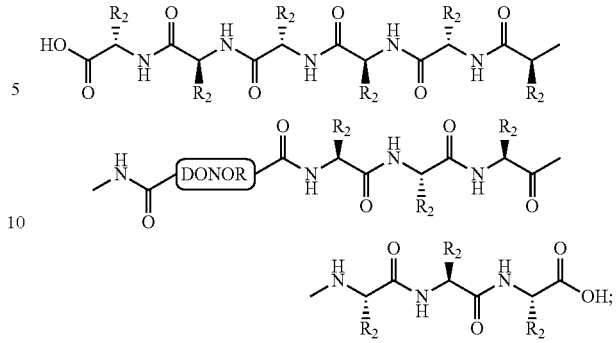

wherein each $R_2$ is independently selected from the group consisting of H, straight-chain alkyl, branched alkyl, benzyl, $-(CH_2)_n-A$ and $(CH_2)_p-COR_3$, wherein A is an electron acceptor, n is an integer selected from the group consisting of, 2, 3, and 4, p is an integer selected from the group consisting of 0, 1, 2, 3, and 4, and $R_3$ is selected from the group consisting of OH and $-NH_2$; or

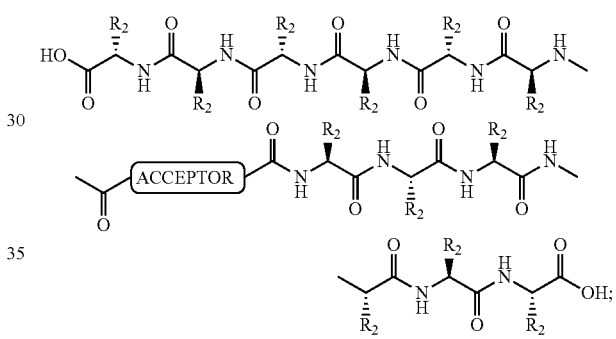

wherein each $R_2$ is independently selected from the group consisting of H, straight-chain alkyl, branched alkyl, benzyl, $-(CH_2)_n$-D and $-(CH_2)_p-COR_3$, wherein D is an electron donor, n is an integer selected from the group consisting of, 2, 3, and 4, p is an integer selected from the group consisting of 0, 1, 2, 3, and 4, and $R_3$ is selected from the group consisting of $-OH$ and $-NH_2$, wherein the supramolecular assembly self assembles into a one-dimensional nanostructure in an aqueous environment.

2. The supramolecular assembly of claim 1, wherein the π-conjugated peptide units are selected from the group consisting of:

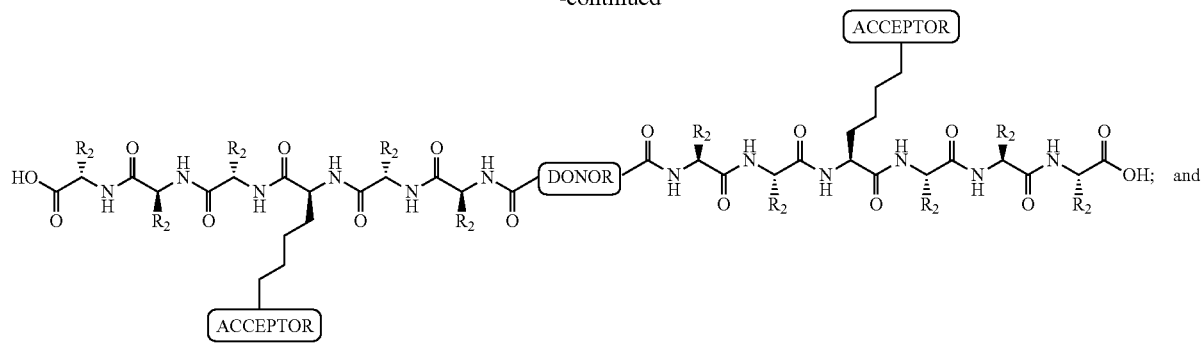

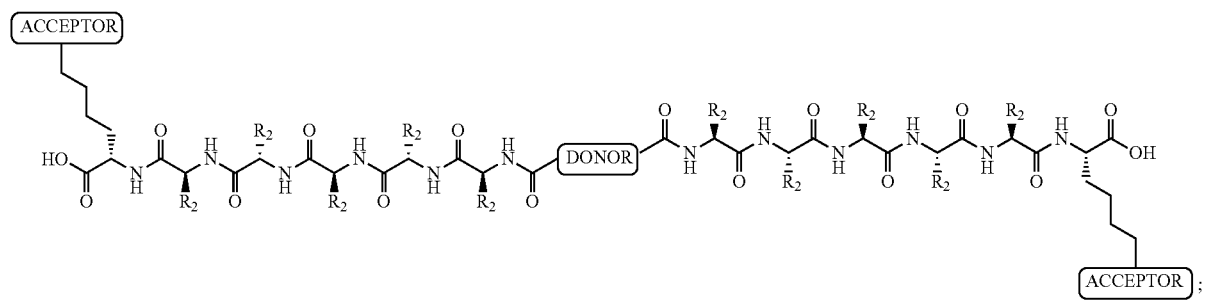

wherein each $R_2$ is independently selected from the group consisting of H, straight-chain alkyl, branched alkyl, benzyl, and —$(CH_2)_p$—$COR_3$, wherein p is an integer selected from the group consisting of 0, 1, 2, 3, and 4, and $R_3$ is selected from the group consisting of —OH and —$NH_2$.

3. The supramolecular assembly of claim 1, wherein the electron donor semiconducting π-unit is a quaterthiophene and the electron acceptor semiconducting π-unit is a naphthalene diimide.

4. The supramolecular assembly of claim 1, wherein the π-conjugated peptide units are selected from the group consisting of:

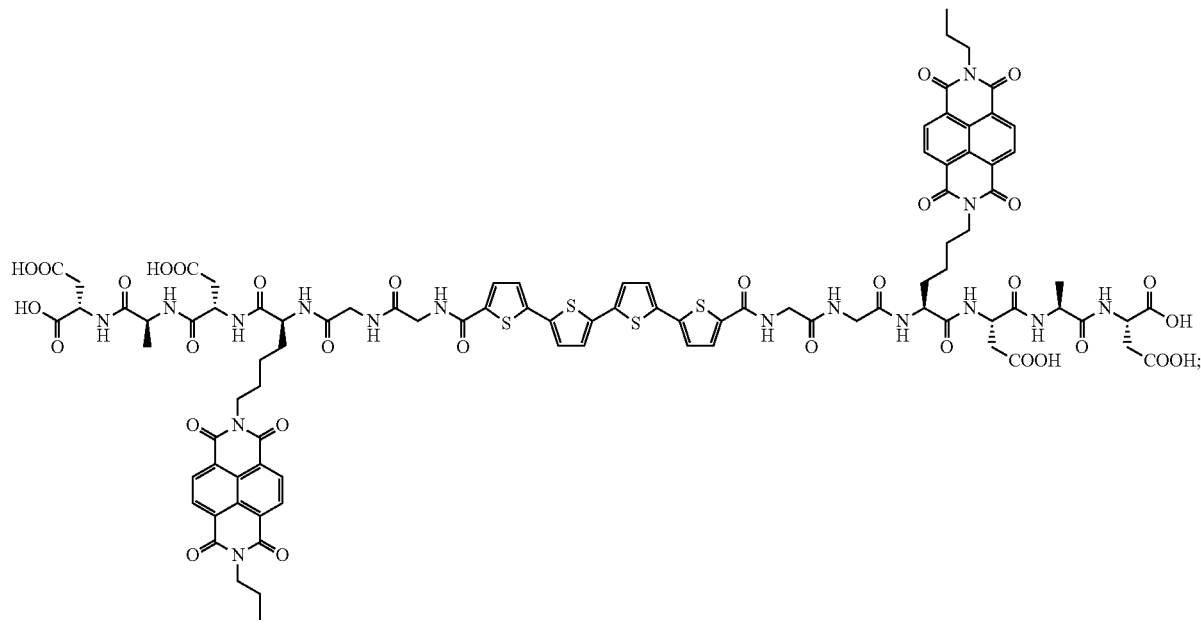

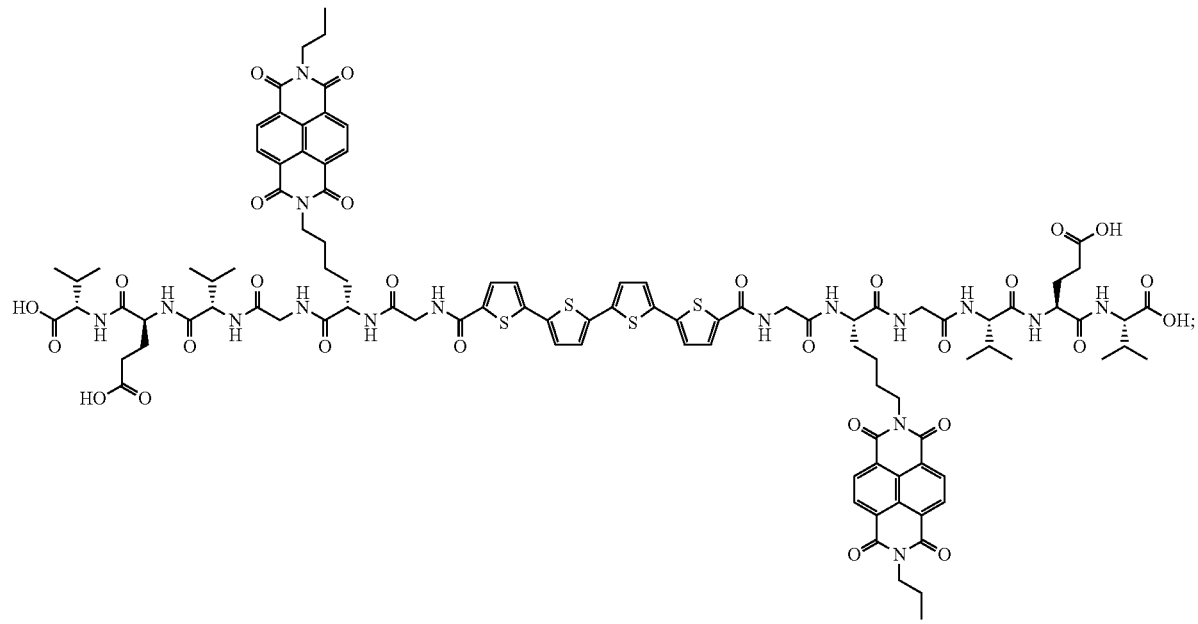
DA-2
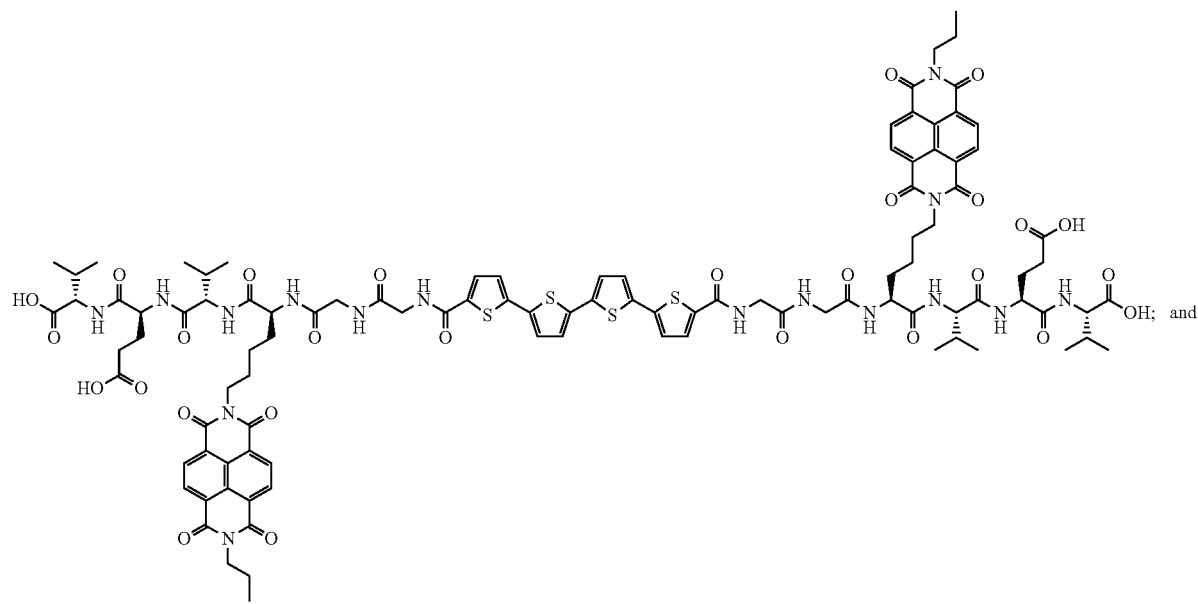
DA-3

DA-6
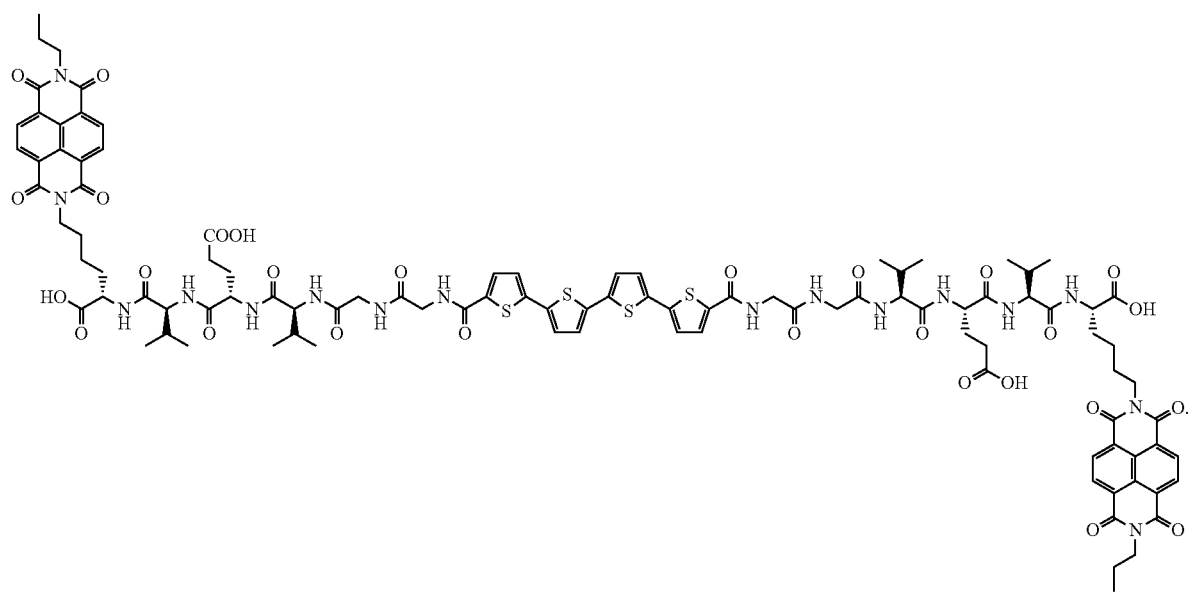
* * * * *